US012643886B2

(12) United States Patent
Al-Awar et al.

(10) Patent No.: US 12,643,886 B2
(45) Date of Patent: Jun. 2, 2026

(54) ISOINDOLINONE AMINOPYRIMIDINE COMPOUNDS AS INHIBITORS OF NUAK KINASES, COMPOSITIONS AND USES THEREOF

(71) Applicants: Ontario Institute for Cancer Research (OICR), Toronto (CA); The Governing Council of The University of Toronto, Toronto (CA); Sinai Health System, Toronto (CA)

(72) Inventors: Rima Al-Awar, Toronto (CA); Liliana Attisano, Toronto (CA); Methvin Isaac, Brampton (CA); Yong Liu, Oakville (CA); David Smil, Toronto (CA); David Uehling, Toronto (CA); Jeff Wrana, Toronto (CA)

(73) Assignee: Ontario Institute for Cancer Research (OICR), The Governing Council of the University of Toronto, Sinai Health System, Toronto (CA)

( * ) Notice: Subject to any disclaimer, the term of this patent is extended or adjusted under 35 U.S.C. 154(b) by 468 days.

(21) Appl. No.: 18/271,103

(22) PCT Filed: Jan. 7, 2022

(86) PCT No.: PCT/CA2022/050016

§ 371 (c)(1),
(2) Date: Jul. 6, 2023

(87) PCT Pub. No.: WO2022/147622

PCT Pub. Date: Jul. 14, 2022

(65) Prior Publication Data

US 2024/0092763 A1 Mar. 21, 2024

Related U.S. Application Data

(60) Provisional application No. 63/134,747, filed on Jan. 7, 2021.

(51) Int. Cl.

| | |
|---|---|
| *C07D 403/14* | (2006.01) |
| *A61P 35/00* | (2006.01) |
| *C07D 401/14* | (2006.01) |
| *C07D 403/12* | (2006.01) |
| *C07D 471/10* | (2006.01) |
| *C07D 487/04* | (2006.01) |
| *C07D 487/08* | (2006.01) |

(52) U.S. Cl.

CPC ............ *C07D 403/14* (2013.01); *A61P 35/00* (2018.01); *C07D 401/14* (2013.01); *C07D 403/12* (2013.01); *C07D 471/10* (2013.01); *C07D 487/04* (2013.01); *C07D 487/08* (2013.01)

(58) Field of Classification Search

None

See application file for complete search history.

(56) References Cited

FOREIGN PATENT DOCUMENTS

| | | | |
|---|---|---|---|
| CA | 2573371 | A1 | 3/2006 |
| CA | 2715658 | A1 | 8/2009 |
| CA | 2749837 | A1 | 8/2010 |
| CA | 2788450 | A1 | 7/2011 |
| CA | 2810900 | A1 | 4/2012 |
| CA | 3050239 | A1 | 8/2018 |
| WO | 2007072158 | A2 | 6/2007 |
| WO | 2008051547 | A1 | 5/2008 |
| WO | 2020180770 | A1 | 9/2020 |
| WO | 2020231806 | A1 | 11/2020 |
| WO | 2021239133 | A1 | 12/2021 |

OTHER PUBLICATIONS

International Search Report and Written Opinion dated Apr. 7, 2022 in respect of PCT/CA2022/050016.

Yang, "Optimization of WZ4003 as NUAK Inhibitors Against Human Colorectal Cancer", European Journal of Medicinal Chemistry, Dec. 4, 2020, vol. 210, pp. 113080.

Gill et al., "A feed forward loop enforces YAP/TAZ signaling during tumorigenesis", Nature Communications, DOI: 10.1038/s41467-018-05939-2, 2018, 9:3510, pp. 1-13.

Yuan et al., "NUAK2 is a critical YAP target in liver cancer", Nature Communications, DOI: 10.1038/s41467-018-07394-5, 2018, 9:4834, pp. 1-12.

*Primary Examiner* — Sarah Pihonak
*Assistant Examiner* — Donna M Nestor
(74) *Attorney, Agent, or Firm* — Smart & Biggar LP; Dominique Lambert

(57) ABSTRACT

The present application relates to compounds of Formula (I) or pharmaceutically acceptable salts, solvates and/or prodrugs thereof, to compositions comprising these compounds or pharmaceutically acceptable salts, solvates and/or prodrugs thereof, and various uses in the treatment of diseases, disorders or conditions that are treatable by inhibiting or blocking NUAK kinase, such as cancers and fibrosis.

(I)

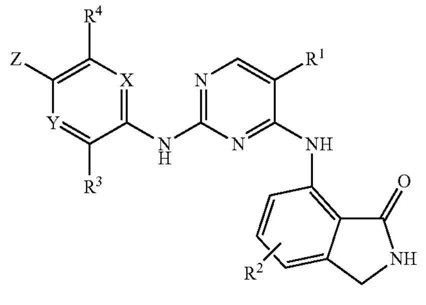

20 Claims, 1 Drawing Sheet

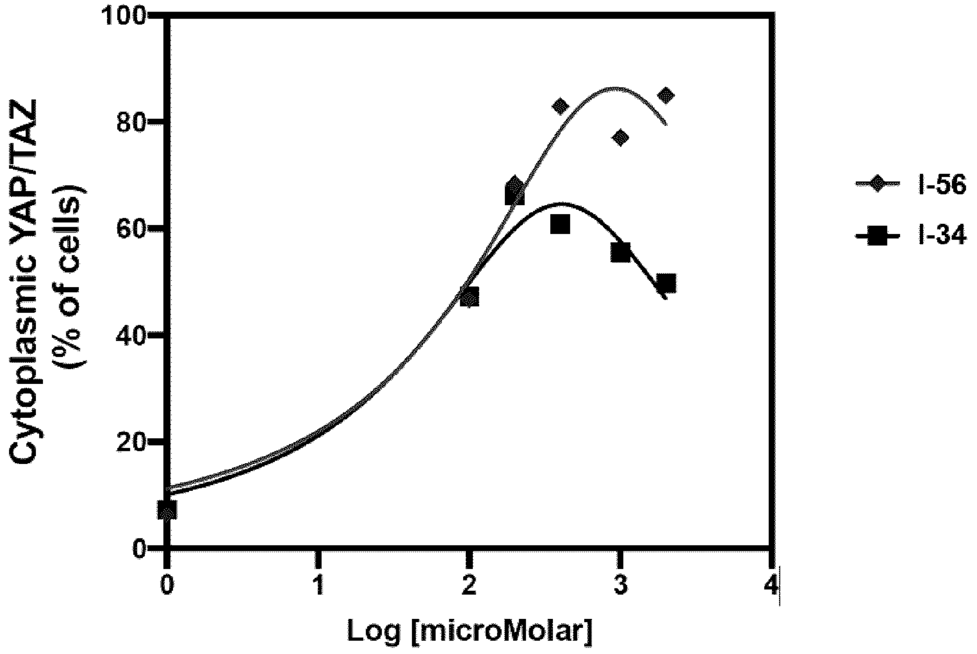
100
80
60
40
20
0
Cytoplasmic YAP/TAZ
(% of cells)
0
1
2
3
4
Log [microMolar]
I-56
I-34

ISOINDOLINONE AMINOPYRIMIDINE COMPOUNDS AS INHIBITORS OF NUAK KINASES, COMPOSITIONS AND USES THEREOF

CROSS-REFERENCE TO RELATED APPLICATION

The present application is a national stage application of International Application No. PCT/CA2022/050016 filed Jan. 7, 2022, which claims priority to U.S. Provisional Patent Application No. 63/134,747, which was filed Jan. 7, 2021, and the entire contents of each are incorporated herein by reference in their entirety.

TECHNICAL FIELD

The present application relates to isoindolinone aminopyrimidine compounds, to processes for their preparation, to compositions comprising them, and to their use in therapy. More particularly, the present application relates to isoindolinone aminopyrimidine compounds useful in the treatment of diseases, disorders or conditions treatable by inhibiting or blocking NUAK kinase such as cancers and fibrosis.

BACKGROUND

The Hippo signaling pathway, also known as the Salvador/Warts/Hippo pathway, controls organ size in animals through the regulation of cell proliferation and apoptosis. The pathway takes its name from one of its key signaling components identified in *Drosophila*—the protein kinase Hippo (Hpo), known as MST1/2 in vertebrates. Mutations in this gene lead to tissue overgrowth, or a "hippopotamus"-like phenotype. The Hippo signaling pathway responds to diverse extracellular cues including cell contact and cytoskeletal rearrangements to regulate tissue growth and organogenesis (*Cell* 2015, 163, 811*; Cancer Cell* 2016, 29, 783). Mechanistically, the transcriptional effectors YAP and TAZ are phosphorylated and thereby inhibited by a core cassette comprised of the tumour suppressor kinases MST and LATS. In most solid tumors, YAP/TAZ are uncoupled from the Hippo kinase cassette, and thus are constitutively nuclear and drive pro-oncogenic transcriptional programs. YAP/TAZ activity promotes proliferation, migration, invasion and maintenance of cancer stem cell traits (*Cell* 2015, 163, 811). Although active YAP/TAZ is a hallmark of cancer, mutations in pathway components are rare, thus there is a pressing need to identify new targetable nodes. Compounds that restore pathway activity in vitro or in vivo have not been previously described.

Using systematic physical and functional screens, NUAK2 (previously called SNARK), a poorly studied AMPK family kinase, most closely related to NUAK1, was identified as a cancer-relevant negative regulator of the Hippo pathway [*Nat Commun.* 2018, 9(1):3510*; Nat Commun.* 2018, 9(1):4834]. NUAK isoforms are ubiquitously expressed and possess an N-terminal kinase domain (residues 55-306, NUAK1), followed by a C-terminal region, which although similar between NUAK1 and NUAK2, possesses no obvious domains or homology with other proteins. Both NUAK1 and NUAK2 isoforms phosphorylate MYPT1 (myosin phosphate-targeting subunit 1) at Ser445. Abrogating NUAK2 expression using siRNA, shRNA and CRISPR or pharmacologically inhibiting NUAK activity using commercial tool compounds (WZ4003 or ON123300) in several cancer cell lines results in (1) a block of YAP/TAZ nuclear localization, as determined using manual or automated immunofluorescence confocal microscopy (IF) and (2) attenuates transcriptional function as measured by PCR analysis of target gene expression [*Nat Commun.* 2018, 9(1):3510*; Nat Commun.* 2018, 9 (1):4834]. Intriguingly, YAP/TAZ can transcriptionally activate NUAK2 expression, revealing a feedforward loop in which NUAK2 positively reinforces the pro-oncogenic activity of YAP/TAZ. Hence, disruption of this pro-oncogenic loop by inhibiting NUAK2 is thus an attractive therapeutic target.

Recently, it was also demonstrated that MYC-driven tumors are addicted to NUAK activity and full function of the spliceosome is relevant for their survival [*Mol Cell.* 2020, 77(6):1322-1339]. MYC drives gene expression needed for cell growth and division and is deregulated in many tumors. MYC itself has proven largely refractory to small molecule-based pharmacologic intervention, shifting much of the focus of drug discovery efforts to other potential targets-proteins or pathways contributing to survival in cancer cells with MYC amplification or otherwise deregulated MYC. Depletion of NUAK1 by RNA interference (RNAi) induced apoptosis specifically in osteosarcoma cells overexpressing MYC [*Nature.* 2012, 483(7391):608-12]. The decreased NUAK1 activity seems to impair splicing by deregulating PNUTS-PP1β, leading to accumulation of unspliced transcripts. These results suggest that deregulated MYC overrides a checkpoint control on transcript elongation, whereby splicing defects due to NUAK1 dysfunction that would otherwise trigger elongation arrest and/or premature termination are ignored, leading to the trapping of RNAPII in non-productive elongation complexes. Therefore, inhibition of NUAK activity, in addition to modulation the hippopathway in cancers, can also play a significant role in inhibiting the growth of MYC driven tumors.

Accumulating evidence also indicates that YAP/TAZ function in a cooperative manner with other established signaling pathways, in particular, crosstalking with TGFβ and Wnt signalling pathways (*Am. J. Physiol. Lung Cell. Mol. Physiol.* 2015, 309, L756-L767; Cell 2012, 151, 1443-1456). Importantly, in the context of immune-oncology, TGFβ has been demonstrated to have a key role in regulating antitumor immune response and contributes to resistance to anti-PD-1-PD-L1 treatment in cancer patients (*ACS Med. Chem. Lett.* 2018, 9, 1117). Therefore, targeting the TGFβ pathway (through NUAK-YAP/TAZ inhibition) in combination with anti-PD1 or anti-PD-L1 antibodies may help overcome resistance and produce a more effective antitumor response.

Another indication that can potentially benefit from inhibiting the NUAK-YAP/TAZ-TGFβ signaling axis is fibrosis. Fibrosis is a response to tissue or organ injury such as chronic inflammation or chemical and mechanical insults. In pathologic circumstances, fibrosis evolves into an uncontrolled process characterized by the progressive accumulation of extracellular matrix (ECM), mainly collagen, that ultimately disrupts normal organ architecture and leads to organ function loss. A key step in fibrosis is the conversion of quiescent fibroblasts into active myofibroblasts that deposit extracellular matrix (ECM) and secrete TGFβ which is a principal factor driving this activation process (Science 2002, 296: 1646-1647). Fibrosis, which impacts several organs such as the liver, lung, and kidney, is responsible for up to 45% of deaths in the industrialized world (*J. Clin. Invest.* 2007, 117, 524-529*; Front. Pharmacol.* 2017, 8, 855). Current therapeutics are mostly supportive rather than curative and there is an urgent need to identify drugs with a therapeutic potential to address this disease. NUAK inhibition, which modulates YAP/TAZ and TGFβ signaling, is a novel approach to treat fibrosis.

The previously reported NUAK inhibitor drugs lack potency and selectivity and are not ideal, suggesting that novel, potent and selective NUAK inhibitor drugs are needed. Design efforts to identify compounds that bind a specific kinase such as NUAK can result in inhibition of multiple kinase targets and can have a therapeutic impact on compound safety. One such off-target kinase is Aurora kinase A (AurA), whose inhibition results in undesired adverse effects such as neutropenia and hematological toxicities (*Semin. Oncol.* 2015, 42 (6), 832-848). Hence, identifying compounds that are potent at NUAK kinases and selective over AurA is a means of finding ligands with reduced side effects.

There remains a need to provide potent NUAK kinase inhibitors for the treatment of, for example, cancers and fibrosis. Also, there is a need to provide NUAK kinase inhibitors with selectivity over other kinases, such as the Aurora A kinase.

SUMMARY

The present application describes certain inhibitors of NUAK kinases (NUAK2 and/or NUAK1) and their use for treating cancer and fibrosis through modulation of the Hippo-pathway. Additionally, the present application describes NUAK inhibitors that are selective over Aurora A inhibitors and therefore have improved safety and therapeutic potential.

Accordingly, the present invention includes a compound of Formula I, or a pharmaceutically acceptable salt, solvate and/or prodrug thereof:

(I)

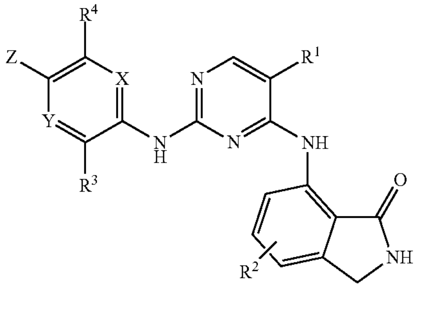

wherein

- $R^1$ is selected from H, halo, $C_{1-4}$alkyl, $OC_{1-4}$alkyl, $C_{1-4}$haloalkyl, $OC_{1-4}$haloalkyl, CN, $C_{1-4}$hydroxyalkyl and $OC_{1-4}$hydroxyalkyl;
- $R^2$ is selected from H, halo, CN, $C_{1-4}$alkyl, $C_{1-4}$haloalkyl, $OC_{1-4}$alkyl and $OC_{1-4}$haloalkyl;
- $R^3$ is selected from H, halo, $C_{1-4}$alkyl, $OC_{1-4}$alkyl, $C_{1-4}$haloalkyl, $OC_{1-4}$haloalkyl,
- X is selected from $CR^a$ and N;
- Y is selected from $CR^b$ and N;
- $R^a$ and $R^b$ are independently selected from H, halo, $C_{1-4}$alkyl and $C_{1-4}$haloalkyl;
- Z is selected from $C_{1-6}$alkyleneNR$^5$R$^6$, $OC_{1-6}$alkyleneNR$^5$R$^6$, NR$^7$C$_{1-6}$alkyleneNR$^5$R$^6$, NR$^7$C$_{1-6}$alkyleneOR$^5$ and NR$^5$R$^6$;
- $R^4$ is selected from H, halo, CN, $C_{1-4}$alkyl, $C_{1-4}$haloalkyl, $OC_{1-4}$alkyl and $OC_{1-4}$haloalkyl; or
- Z and $R^4$ are joined to form, together with the atoms therebetween a ring B which is selected from $C_{3-12}$cycloalkyl and $C_{3-12}$heterocycloalkyl, wherein the ring B is optionally substituted with one or more substituents selected from halo, =O, OH, $C_{1-6}$alkyl, $C_{3-6}$cycloalkyl, aryl, $C_{5-6}$heteroaryl, $C_{3-6}$heterocycloalkyl, $C_{1-6}$alkyleneC$_{3-6}$cycloalkyl, $C_{1-6}$alkylenearyl, $C_{1-6}$alkyleneC$_{5-6}$heteroaryl, $C_{1-6}$alkyleneC$_{3-6}$heterocycloalkyl, C(O)C$_{1-6}$alkyl, OC$_{1-6}$alkyl, OC$_{1-6}$alkyleneOC$_{1-6}$alkyl, C(O)NH$_2$, C(O)NH(C$_{1-6}$alkyl), C(O)N(C$_{1-6}$alkyl)(C$_{1-6}$alkyl), NHC(O)C$_{1-6}$alkyl, N(C$_{1-6}$alkyl)C(O)C$_{1-6}$alkyl, NH$_2$, NH(C$_{1-6}$alkyl), N(C$_{1-6}$alkyl)(C$_{1-6}$alkyl), SC$_{1-6}$alkyl, S(O)C$_{1-6}$alkyl and SO$_2$C$_{1-6}$alkyl, wherein all alkyl, alkylene, cycloalkyl, heterocycloalkyl, aryl and heteroaryl groups of the optional substituents on the ring B are also optionally substituted with one or more of halo, $C_{1-6}$alkyl, OC$_{1-6}$alkyl, $C_{1-6}$haloalkyl and OC$_{1-6}$haloalkyl;
- $R^5$ is selected from H, $C_{1-6}$alkyl, $C_{3-10}$cycloalkyl, $C_{3-10}$heterocycloalkyl, $C_{2-6}$alkenyl, $C_{2-6}$alkynyl, $C_{1-6}$alkyleneC$_{3-10}$cycloalkyl, $C_{1-6}$alkyleneC$_{3-10}$heterocycloalkyl, $C_{1-6}$alkylalkyleneOR$^8$ and $C_{1-6}$alkylalkyleneNR$^8$R$^9$, and all alkyl, alkenyl, alkynyl, alkylene, heterocycloalkyl and cycloalkyl groups of $R^5$ are optionally substituted with one or more of halo, $C_{1-6}$alkyl and $C_{1-6}$haloalkyl;
- $R^6$ is selected from H, $C_{1-6}$alkyl and $C_{1-6}$haloalkyl; or
- $R^5$ and $R^6$ are joined to form, together with the atom therebetween, $C_{3-12}$heterocycloalkyl, optionally containing one additional heteromoiety selected from NR$^{10}$, O, S, S(O) and SO$_2$, and optionally substituted with one or more substituents selected from halo, =O, OH, $C_{1-6}$alkyl, $C_{3-6}$cycloalkyl, aryl, $C_{5-6}$heteroaryl, $C_{3-6}$heterocycloalkyl, $C_{1-6}$alkyleneC$_{3-6}$cycloalkyl, $C_{1-6}$alkylenearyl, $C_{1-6}$alkyleneC$_{5-6}$heteroaryl, $C_{1-6}$alkyleneC$_{3-6}$heterocycloalkyl, C(O)C$_{1-6}$alkyl, OC$_{1-6}$alkyl, OC$_{1-6}$alkyleneOC$_{1-6}$alkyl, C(O)NH$_2$, C(O)NH(C$_{1-6}$alkyl), C(O)N(C$_{1-6}$alkyl)(C$_{1-6}$alkyl), NHC(O)C$_{1-6}$alkyl, N(C$_{1-6}$alkyl)C(O)C$_{1-6}$alkyl, NH$_2$, NH(C$_{1-6}$alkyl), N(C$_{1-6}$alkyl)(C$_{1-6}$alkyl), SC$_{1-6}$alkyl, S(O)C$_{1-6}$alkyl and SO$_2$C$_{1-6}$alkyl, wherein all alkyl, alkylene, cycloalkyl, heterocycloalkyl, aryl and heteroaryl groups of the optional substituents on the $C_{3-12}$heterocycloalkyl formed by $R^5$ and $R^6$ are also optionally substituted with one or more of halo, $C_{1-6}$alkyl, OC$_{1-6}$alkyl, $C_{1-6}$haloalkyl and OC$_{1-6}$haloalkyl; and
- $R^7$, $R^8$, $R^9$ and $R^{10}$ are independently selected from H, $C_{1-6}$alkyl and $C_{1-6}$haloalkyl.

The present invention also includes a composition comprising one or more compounds of the application and a carrier and/or diluent. In some embodiments, the composition is a pharmaceutical composition comprising one or more compounds of the application and a pharmaceutically acceptable carrier and/or diluent.

In some embodiments, the compounds of the application are used as medicaments. Accordingly, the application also includes one or more compounds of the application for use as a medicament.

The compounds of the application have been shown to inhibit or block NUAK2 and/or NUAK1, including the NUAK2 and/or NUAK1 promotion of a YAP/TAZ cytoplasmic localization and to attenuate the transcriptional function of YAP/TAZ target gene expression. Therefore, the compounds of the application are useful for inhibiting NUAK2 and/or NUAK1 (more specifically NUAK2). Accordingly, the present application also includes a method of inhibiting NUAK2 and/or NUAK1 comprising administering an effective amount of one or more compounds of the application to the cell or subject in need thereof.

The present application also includes a use of one or more compounds of the application for inhibiting NUAK2 and/or NUAK1 in a cell or subject. The application further includes one or more compounds of the application for use in inhibiting NUAK2 and/or NUAK1 in a cell or subject.

In some embodiments, the compounds of the application are useful for treating diseases, disorders or conditions that are treatable by inhibiting NUAK2 and/or NUAK1 (more specifically NUAK2). Accordingly, the present application also includes a method of treating a disease, disorder or condition that is treatable by inhibiting NUAK2 and/or NUAK1, comprising administering a therapeutically effective amount of one or more compounds of the application to a subject in need thereof.

The present application also includes a use of one or more compounds of the application for treatment of a disease, disorder or condition that is treatable by inhibiting NUAK2 and/or NUAK1, as well as a use of one or more compounds of the application for the preparation of a medicament for treatment of a disease, disorder or condition that is treatable by inhibiting NUAK2 and/or NUAK1. The application further includes one or more compounds of the application for use in treating a disease, disorder or condition that is treatable by inhibiting NUAK2 and/or NUAK1.

In some embodiments, the disease, disorder or condition that is treatable by inhibiting NUAK2 and/or NUAK1, is a neoplastic disorder. In some embodiments, the treatment comprises administration or use of an amount of one or compounds of the application that is effective to ameliorate at least one symptom of the neoplastic disorder, for example, reduced cell proliferation or reduced tumor mass in a subject in need of such treatment.

In some embodiments, the disease, disorder or condition that is treatable by inhibiting NUAK2 and/or NUAK1, is cancer. In some embodiments, the cancer is selected from solid cancers such as breast cancers, colon cancers, bladders, skin cancers, head and neck cancers, liver cancers, bone cancers and glioblastomas.

In some embodiments, the disease, disorder or condition that is treatable by inhibiting NUAK2 and/or NUAK1, is a fibrosis. Fibrosis is a response to tissue or organ injury such as chronic inflammation or chemical and mechanical insults. In pathologic circumstances, fibrosis evolves into an uncontrolled process characterized by the progressive accumulation of extracellular matrix (ECM), mainly collagen, that ultimately disrupts normal organ architecture and leads to organ function loss. A relevant step in fibrosis is the conversion of quiescent fibroblasts into active myofibroblasts that deposit extracellular matrix (ECM) and secrete TGFβ which is a principal factor driving this activation process (*Science* 2002, 296: 1646-1647). Fibrosis, which impacts several organs such as the liver, lung, and kidney.

In some embodiments, the fibrosis is selected from fibrotic disorders such as kidney fibrosis, lung (pulmonary) fibrosis and liver fibrosis.

In some embodiments, the treatment comprises administration or use of an amount of one or compounds of the application that is effective to ameliorate at least one symptom of the fibrosis, for example, reduced accumulation of extracellular matrix (ECM), such as collagen, in a subject in need of such treatment.

In some embodiments, the disease, disorder or condition that is treatable by inhibiting NUAK2 and/or NUAK1, is a disease, disorder or condition associated with an uncontrolled and/or abnormal cellular activity affected directly or indirectly by inhibiting NUAK2 and/or NUAK1. In another embodiment, the uncontrolled and/or abnormal cellular activity that is affected directly or indirectly by inhibiting NUAK2 and/or NUAK1 is proliferative activity in a cell.

In some embodiments, the application also includes a method of inhibiting proliferative activity in a cell, comprising administering an effective amount of one or more compounds of the application to the cell.

In some embodiments the disease, disorder or condition that is treatable by inhibiting NUAK2 and/or NUAK1, is cancer and/or fibrosis and the one or more compounds of the application are administered or used in combination with one or more additional cancer and/or anti-fibrotic treatments. In another embodiment, the additional treatment is selected from one or more radiotherapy, chemotherapy, targeted therapies such as antibody therapies (including anti-PD1 and/or anti-PD-L1 antibodies) and small molecule therapies such as tyrosine-kinase inhibitors therapies, immunotherapy, hormonal therapy and anti-angiogenic therapies.

The application additionally includes processes for the preparation of compounds of the application. General and specific processes are discussed in more detail and set forth in the Examples below.

In some embodiments, the application includes a process for preparing a compound of the application comprising:

(a) reacting a substituted dichloropyrimidine of Formula A, wherein $R^1$ is as defined in Formula I or a protected version thereof, with an 7-amino isoindolin-1-one of Formula B, wherein $R^2$ is as defined in Formula I or protected version thereof, under basic conditions to provide compounds of Formula D:

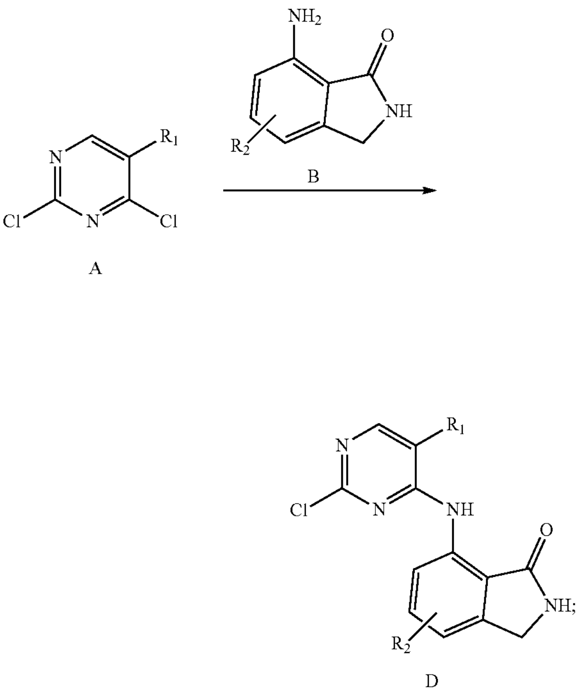
A
B
D (b) reacting compounds of Formula D with anilines of Formula E, wherein $R^3$, $R^4$, X, Y and Z are as defined in Formula I or protected versions thereof, under acidic or basic conditions to provide, after removal of any protecting groups if needed, compounds of Formula I:

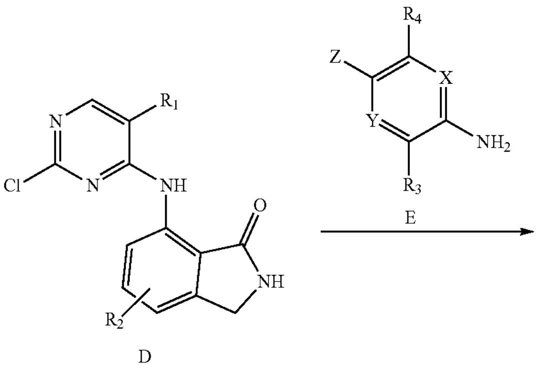

Formula I.

Other features and advantages of the present application will become apparent from the following detailed description. It should be understood, however, that the detailed description and the specific examples, while indicating embodiments of the application, are given by way of illustration only and the scope of the claims should not be limited by these embodiments but should be given the broadest interpretation consistent with the description as a whole.

BRIEF DESCRIPTION OF THE DRAWINGS

The present application will be described in greater detail with reference to the attached drawings in which:

FIG. 1 shows results of the YAP/TAZ nuclear localization in cells assay performed on exemplary compounds I-34 and I-56.

DETAILED DESCRIPTION

1. Definitions

Unless otherwise indicated, the definitions and embodiments described in this and other sections are intended to be applicable to all embodiments and aspects of the present application herein described for which they are suitable as would be understood by a person skilled in the art.

The present application refers to a number of chemical terms and abbreviations used by those skilled in the art. Nevertheless, definitions of selected terms are provided for clarity and consistency.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process/method steps.

As used herein, the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one compound or two or more additional compounds. In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

Unless otherwise specified within this application or unless a person skilled in the art would understand otherwise, the nomenclature used in this application generally follows the examples and rules stated in "Nomenclature of Organic Chemistry" (Pergamon Press, 1979), Sections A, B, C, D, E, F, and H. Optionally, a name of a compound may be generated using a chemical naming program: ACD/ChemSketch, Version 5.09/September 2001, Advanced Chemistry Development, Inc., Toronto, Canada.

The term "compound of the application" or "compound of the present application" and the like as used herein refers to a compound of Formula I, including pharmaceutically acceptable salts, solvates and/or prodrugs thereof.

The term "composition of the application" or "composition of the present application" and the like as used herein refers to a composition comprising one or more compounds the application and at least one additional ingredient.

The term "suitable" as used herein means that the selection of the particular compound or conditions would depend on the specific synthetic manipulation to be performed, and the identity of the species to be transformed, but the selection would be well within the skill of a person trained in the art. All chemical synthesis method steps described herein are to be conducted under conditions sufficient to provide the desired product. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compound may also contain certain amounts (for example, less than 20%, suitably less than 10%, more suitably less than 5%) of the same compound of the present application having alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form are included within the scope of the present application.

The compounds of the present application may further exist in varying polymorphic forms and it is contemplated that any polymorphs which form are included within the scope of the present application.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas).

The term "cell" as used herein refers to a single cell or a plurality of cells and includes a cell either in a cell culture or in a subject.

The term "subject" as used herein includes all members of the animal kingdom including mammals. Thus, the methods and uses of the present application are applicable to both human therapy and veterinary applications.

The term "pharmaceutically acceptable" means compatible with the treatment of subjects.

The term "pharmaceutically acceptable carrier" means a non-toxic solvent, dispersant, excipient, adjuvant or other material which is mixed with an active ingredient (for example, one or more compounds of the application) to permit the formation of a pharmaceutical composition, i.e., a dosage form capable of administration to a subject.

The term "pharmaceutically acceptable salt" means either an acid addition salt or a base addition salt which is suitable for, or compatible with the treatment of subjects.

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. Either the mono- or di-acid salts can be formed, or such salts can exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, EGFRaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. [See, for example, S. M. Berge, et al., "Pharmaceutical Salts," *J. Pharm. Sci.* 1977, 66, 1-19]. The selection of the appropriate salt may be useful so that an ester functionality, if any, elsewhere in a compound is not hydrolyzed. The selection criteria for the appropriate salt will be known to one skilled in the art.

Prodrugs of the compounds of the present application may be, for example, conventional esters formed with available hydroxy, thiol, amino or carboxyl groups. Some common esters which have been utilized as prodrugs are phenyl esters, aliphatic ($C_1$-$C_{24}$) esters, acyloxymethyl esters, carbamates and amino acid esters.

The term "solvate" as used herein means a compound, or a salt or prodrug of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "inert organic solvent" as used herein refers to a solvent that is generally considered as non-reactive with the functional groups that are present in the compounds to be combined together in any given reaction so that it does not interfere with or inhibit the desired synthetic transformation. Organic solvents are typically non-polar and dissolve compounds that are nonsoluble in aqueous solutions.

The term "alkyl" as used herein, whether it is used alone or as part of another group, means straight or branched chain, saturated alkyl groups. The number of carbon atoms that are possible in the referenced alkyl group are indicated by the prefix "$C_{n1\text{-}n2}$". For example, the term $C_{1\text{-}10}$alkyl means an alkyl group having 1, 2, 3, 4, 5, 6, 7, 8, 9 or 10 carbon atoms.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1\text{-}n2}$". For example, the term $C_{1\text{-}10}$alkylene means an alkylene group having 1, 2, 3, 4, 5, 6, 7, 8, 9 or 10 carbon atoms. All alkyl groups are optionally fluorosubstituted unless otherwise indicated.

The term "alkenyl" as used herein, whether it is used alone or as part of another group, means straight or branched chain, unsaturated alkyl groups containing at least one double bond. The number of carbon atoms that are possible in the referenced alkylene group are indicated by the prefix "$C_{n1-n2}$". For example, the term $C_{2-6}$alkenyl means an alkenyl group having 2, 3, 4, 5 or 6 carbon atoms and at least one double bond.

The term "alkynyl" as used herein, whether it is used alone or as part of another group, means straight or branched chain, unsaturated alkynyl groups containing at least one triple bond. The number of carbon atoms that are possible in the referenced alkyl group are indicated by the prefix "$C_{n1-n2}$". For example, the term $C_{2-6}$alkynyl means an alkynyl group having 2, 3, 4, 5 or 6 carbon atoms.

The term "cycloalkyl," as used herein, whether it is used alone or as part of another group, means a saturated carbocyclic group containing from 3 to 20 carbon atoms and one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "aryl" as used herein, whether it is used alone or as part of another group, refers to carbocyclic groups containing at least one aromatic ring and contains from 6 to 10 carbon atoms.

The term "heterocycloalkyl" as used herein, whether it is used alone or as part of another group, refers to cyclic groups containing at least one non-aromatic ring containing from 3 to 10 atoms in which one or more of the atoms are a heteroatom selected from O, S and N and the remaining atoms are C. Heterocycloalkyl groups are either saturated or unsaturated (i.e. contain one or more double bonds). When a heterocycloalkyl group contains the prefix $C_{n1-n2}$ this prefix indicates the number of carbon atoms in the corresponding carbocyclic group, in which one or more, suitably 1 to 5, of the ring atoms is replaced with a heteroatom as defined above. Heterocycloalkyl groups are optionally benzofused.

The term "heteroaryl" as used herein, whether it is used alone or as part of another group, refers to cyclic groups containing at least one heteroaromatic ring containing 5-10 atoms in which one or more of the atoms are a heteroatom selected from O, S and N and the remaining atoms are C. When a heteroaryl group contains the prefix $C_{n1-n2}$ this prefix indicates the number of carbon atoms in the corresponding carbocyclic group, in which one or more, suitably 1 to 5, of the ring atoms is replaced with a heteroatom as defined above. Heteroaryl groups are optionally benzofused.

All cyclic groups, including aryl, heteroaryl, heterocyclo and cycloalkyl groups, contain one (i.e. are monocyclic) or more than one ring (i.e. are polycyclic). When a cyclic group contains more than one ring, the rings may be fused, bridged or spirofused.

The term "benzofused" as used herein refers to a polycyclic group in which a benzene ring is fused with another ring.

A first ring being "fused" with a second ring means the first ring and the second ring share two adjacent atoms there between.

A first ring being "bridged" with a second ring means the first ring and the second ring share two non-adjacent atoms there between.

A first ring being "spirofused" with a second ring means the first ring and the second ring share one atom there between.

The term "fluorosubstituted" refers to the substitution of one or more, including all, available hydrogen atoms in a referenced group with fluoro.

The term "halosubstituted" refers to the substitution of one or more, including all, available hydrogen atoms in a referenced group with halo.

The term "hydroxysubstituted" refers to the substitution of one or more, including all, available hydrogen atoms in a referenced group with hydroxyl (OH).

The terms "halo" or "halogen" as used herein, whether it is used alone or as part of another group, refers to a halogen atom and includes fluoro, chloro, bromo and iodo.

The term "available", as in "available hydrogen atoms" or "available atoms" refers to atoms that would be known to a person skilled in the art to be capable of replacement by another atom or group.

The term "optionally substituted" as used herein means that the referenced group is unsubstituted or substituted.

The term "atm" as used herein refers to atmosphere.

The term "MS" as used herein refers to mass spectrometry.

The term "LCMS" as used herein refers to liquid chromatography-mass spectrometry.

The term "LRMS" as used herein refers to low resolution mass spectrometry.

The term "NMR" as used herein refers to nuclear magnetic resonance.

The term "aq." as used herein refers to aqueous.

The term "N" as used herein, for example in "4N", refers to the unit symbol of normality to denote "eq/L".

The term "M" as used herein, for example in 4M, refers to the unit symbol of molarity to denote "moles/L".

The term "DCM" as used herein refers to dichloromethane.

The term "DIPEA" as used herein refers to N,N-diisopropyl ethylamine.

The term "DMF" as used herein refers to dimethylformamide.

The term "THF" as used herein refers to tetrahydrofuran.

The term "DMSO" as used herein refers to dimethylsulfoxide.

The term "EtOAc" as used herein refers to ethyl acetate.

The term "MeOH" as used herein refers to methanol.

The term "EtOH" as used herein refers to ethanol.

The term "AcOH" as used herein refers to acetic acid.

The term "MeCN" or "ACN" as used herein refers to acetonitrile.

The term "HCl" as used herein refers to hydrochloric acid.

The term "TFA" as used herein refers to trifluoroacetic acid.

The term "TFAA" as used herein refers to trifluoroacetic anhydride.

The term "$Tf_2O$" as used herein refers to trifluoromethanesulfonic anhydride, also known as triflic anhydride.

The term "CV" as used herein refers to column volume.

The term "Hex" as used herein refers to hexanes.

The term "PBS" as used herein refers to phosphate-based buffer.

The term "IPA" as used herein refers to isopropyl alcohol.

The term "HATU" as used herein refers to 1-[Bis(dimethylamino)methylene]-1H-1,2,3-triazolo[4,5-b]pyridinium 3-oxide hexafluorophosphate, also known as Hexafluorophosphate Azabenzotriazole Tetramethyl Uronium.

The term "N-Boc" as used herein refers to tert-butoxycarbonyl protecting group.

The term "dba" as used herein refers to dibenzylideneacetone.

The term "dppf" as used herein refers to 1,1'-bis(diphenylphosphino)ferrocene.

The term "RT" as used herein refers to room temperature.

The term "DCE" as used herein refers to 1,2-dichloroethane.

The term "TPP" as used herein refers to triphenylphosphine.

The term "TLC" as used herein refers to thin-layer chromatography.

The term "HPLC" as used herein refers to high-performance liquid chromatography.

The term "PPA" as used herein refers to polyphosphoric acid.

The term "TEA" or "$Et_3N$" as used herein refer to triethylamine.

The term "DMAP" as used herein refers to 4-dimethylaminopyridine.

The term "MOPS" as used herein refers to 3-(N-morpholino)propanesulfonic acid.

The term "EDTA" as used herein refers to ethylenediaminetetraacetic acid.

The term "NMP" as used herein refers to N-methyl-2-pyrrolidone.

The term "ATP" as used herein refers to adenosine triphosphate.

The term "FBS" as used herein refers to fetal bovine serum.

The term "MEM" as used herein refers to Minimum Essential Medium.

The term "treating" or "treatment" as used herein and as is well understood in the art, means an approach for obtaining beneficial or desired results, including clinical results. Beneficial or desired clinical results can include, but are not limited to alleviation or amelioration of one or more symptoms or conditions, diminishment of extent of a disease, disorder or condition, stabilized (i.e. not worsening) state of a disease, disorder or condition, preventing spread of a disease, disorder or condition, delay or slowing of a disease, disorder or condition progression, amelioration or palliation of a disease, disorder or condition state, diminishment of the reoccurrence of a disease, disorder or condition, and remission (whether partial or total), whether detectable or undetectable. "Treating" and "treatment" can also mean prolonging survival as compared to expected survival if not receiving treatment. "Treating" and "treatment" as used herein also include prophylactic treatment.

"Palliating" a disease, disorder or condition means that the extent and/or undesirable clinical manifestations of the disease, disorder or condition are lessened and/or time course of the progression is slowed or lengthened, as compared to not treating the disease, disorder or condition.

The term "prevention" or "prophylaxis", or synonym thereto, as used herein refers to a reduction in the risk or probability of a subject becoming afflicted with a disease, disorder or condition treatable by inhibition of NUAK2 and/or NUAK1 or manifesting a symptom associated with a disease, disorder or condition treatable by inhibition of NUAK2 and/or NUAK1.

As used herein, the term "effective amount" or "therapeutically effective amount" means an amount of a compound, or one or more compounds, of the application that is effective, at dosages and for periods of time necessary to achieve the desired result.

The expression "inhibiting NUAK2 and/or NUAK1" as used herein refers to inhibiting, blocking and/or disrupting the kinase activity or function of NUAK2 and/or NUAK1 in a cell. The inhibiting, blocking and/or disrupting causes a therapeutic effect in the cell.

By "inhibiting, blocking and/or disrupting" it is meant any detectable inhibition, block and/or disruption in the presence of a compound compared to otherwise the same conditions, except for in the absence in the compound.

The term "NUAK" as used herein refers to NUAK family SNF1-like kinase 1 and 2 also known as AMPK-related protein kinase 5 (ARK5) or SNARK respectively, or any functional mutant or analogous forms thereof.

The term "administered" as used herein means administration of a therapeutically effective amount of a compound, or one or more compounds, or a composition of the application to a cell or a subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder. Neoplasms can be benign (such as uterine fibroids and melanocytic nevi), potentially malignant (such as carcinoma in situ) or malignant (i.e. cancer).

The term "fibrosis" as used herein refers to a disease, disorder or condition the thickening and scarring of connective tissue, usually as a result of injury.

I. COMPOUNDS

The present application includes a compound of Formula I, or a pharmaceutically acceptable salt, solvate and/or prodrug thereof:

(I)

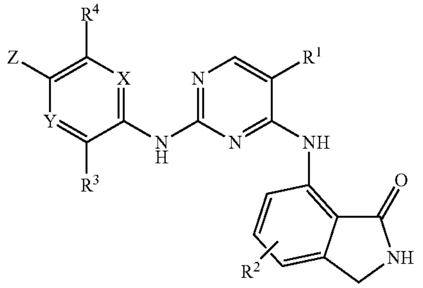

wherein

- $R^1$ is selected from H, halo, $C_{1-4}$alkyl, $OC_{1-4}$alkyl, $C_{1-4}$haloalkyl, $OC_{1-4}$haloalkyl, CN, $C_{1-4}$hydroxyalkyl and $OC_{1-4}$hydroxyalkyl;
- $R^2$ is selected from H, halo, CN, $C_{1-4}$alkyl, $C_{1-4}$haloalkyl, $OC_{1-4}$alkyl and $OC_{1-4}$haloalkyl;
- $R^3$ is selected from H, halo, $C_{1-4}$alkyl, $OC_{1-4}$alkyl, $C_{1-4}$haloalkyl, $OC_{1-4}$haloalkyl,
- X is selected from $CR^a$ and N;
- Y is selected from $CR^b$ and N;
- $R^a$ and $R^b$ are independently selected from H, halo, $C_{1-4}$alkyl and $C_{1-4}$haloalkyl;
- Z is selected from $C_{1-6}$alkyleneN$R^5R^6$, $OC_{1-6}$alkyleneN$R^5R^6$, N$R^7C_{1-6}$alkyleneN$R^5R^6$, N$R^7C_{1-6}$alkyleneO$R^5$ and N$R^5R^6$;

$R^4$ is selected from H, halo, CN, $C_{1-4}$alkyl, $C_{1-4}$haloalkyl, $OC_{1-4}$alkyl and $OC_{1-4}$haloalkyl; or Z and $R^4$ are joined to form, together with the atoms therebetween a ring B which is selected from $C_{3-12}$cycloalkyl and $C_{3-12}$heterocycloalkyl, wherein the ring B is optionally substituted with one or more substituents selected from halo, =O, OH, $C_{1-6}$alkyl, $C_{3-6}$cycloalkyl, aryl, $C_{5-6}$heteroaryl, $C_{3-6}$heterocycloalkyl, $C_{1-6}$alkyleneC$_{3-6}$cycloalkyl, $C_{1-6}$alkylenearyl, $C_{1-6}$alkyleneC$_{5-6}$heteroaryl, $C_{1-6}$alkyleneC$_{3-6}$heterocycloalkyl, $C(O)C_{1-6}$alkyl, $OC_{1-6}$alkyl, $OC_{1-6}$alkyleneOC$_1$-6alkyl, $C(O)NH_2$, $C(O)NH(C_{1-6}$alkyl), $C(O)N(C_{1-6}$alkyl)($C_{1-6}$alkyl), $NHC(O)C_{1-6}$alkyl, $N(C_{1-6}$alkyl)$C(O)C_{1-6}$alkyl, $NH_2$, $NH(C_{1-6}$alkyl), $N(C_{1-6}$alkyl)($C_{1-6}$alkyl), $SC_{1-6}$alkyl, $S(O)C_{1-6}$alkyl and $SO_2C_{1-6}$alkyl, wherein all alkyl, alkylene, cycloalkyl, heterocycloalkyl, aryl and heteroaryl groups of the optional substituents on the ring B are also optionally substituted with one or more of halo, $C_{1-6}$alkyl, $OC_{1-6}$alkyl, $C_{1-6}$haloalkyl and $OC_{1-6}$haloalkyl;

$R^5$ is selected from H, $C_{1-6}$alkyl, $C_{3-10}$cycloalkyl, $C_{3-10}$heterocycloalkyl, $C_{2-6}$alkenyl, $C_{2-6}$alkynyl, $C_{1-6}$alkyleneC$_{3-10}$cycloalkyl, $C_{1-6}$alkyleneC$_{3-10}$heterocycloalkyl, $C_{1-6}$alkylalkyleneOR$^8$ and $C_{1-6}$alkylalkyleneNR$^8$R$^9$, and all alkyl, alkenyl, alkynyl, alkylene, heterocycloalkyl and cycloalkyl groups of $R^5$ are optionally substituted with one or more of halo, $C_{1-6}$alkyl and $C_{1-6}$haloalkyl;

$R^6$ is selected from H, $C_{1-6}$alkyl and $C_{1-6}$haloalkyl; or $R^5$ and $R^6$ are joined to form, together with the atom therebetween, $C_3$-12heterocycloalkyl, optionally containing one additional heteromoiety selected from $NR^{10}$, O, S, S(O) and $SO_2$, and optionally substituted with one or more substituents selected from halo, =O, OH, $C_{1-6}$alkyl, $C_{3-6}$cycloalkyl, aryl, $C_{5-6}$heteroaryl, $C_{3-6}$heterocycloalkyl, $C_{1-6}$alkyleneC$_{3-6}$cycloalkyl, $C_{1-6}$alkylenearyl, $C_{1-6}$alkyleneC$_{5-6}$heteroaryl, $C_{1-6}$alkyleneC$_{3-6}$heterocycloalkyl, $C(O)C_{1-6}$alkyl, $OC_{1-6}$alkyl, $OC_{1-6}$alkyleneOC$_{1-6}$alkyl, $C(O)NH_2$, $C(O)NH(C_{1-6}$alkyl), $C(O)N(C_{1-6}$alkyl)($C_{1-6}$alkyl), $NHC(O)C_{1-6}$alkyl, $N(C_{1-6}$alkyl)$C(O)C_{1-6}$alkyl, $NH_2$, $NH(C_{1-6}$alkyl), $N(C_{1-6}$alkyl)($C_{1-6}$alkyl), $SC_{1-6}$alkyl, $S(O)C_{1-6}$alkyl and $SO_2C_{1-6}$alkyl, wherein all alkyl, alkylene, cycloalkyl, heterocycloalkyl, aryl and heteroaryl groups of the optional substituents on the $C_{3-12}$heterocycloalkyl formed by $R^5$ and $R^6$ are also optionally substituted with one or more of halo, $C_{1-6}$alkyl, $OC_{1-6}$alkyl, $C_{1-6}$haloalkyl and $OC_{1-6}$haloalkyl; and $R^7$, $R^8$, $R^9$ and $R^{10}$ are independently selected from H, $C_{1-6}$alkyl and $C_{1-6}$haloalkyl.

In some embodiments, $R^1$ is selected from Cl, F, Br, I, $CH_3$, $CH_2OH$, $OCH_3$, $OCF_3$, $OCF_2H$, $OCH_2F$, $CF_3$, $CF_2H$ and $CH_2F$. In some embodiments, $R^1$ is selected from $C_1$, F, $CF_3$, $CH_3$, $OCF_3$ and $OCH_3$.

In some embodiments, $R^2$ is selected from H, F, $CH_3$, $CF_3$, $OCH_3$ and $OCF_3$. In some embodiments, $R^2$ is H.

In some embodiments, $R^3$ is selected from H, $C_1$, iPr, $OCH_3$, $CF_3$, $OCF_3$, $OCHF_2$ and $OCH_2F$. In some embodiments, $R^3$ is $OCHF_2$.

In some embodiments, X is selected from N, CH, CF and $CCH_3$. In some embodiments, X is CH.

In some embodiments, Y is selected from N, CH, CF and $CCH_3$. In some embodiments, Y is CH.

In some embodiments, Z is selected from $C_{1-4}$alkyleneNR$^5$R$^6$, $OC_{1-4}$alkyleneNR$^5$R$^6$, $NR^7C_{1-4}$alkyleneNR$^5$R$^6$, $NR^7C_{1-4}$alkyleneOR$^5$ and $NR^5R^6$, and $R^5$ and $R^6$ are independently selected from H and $C_{1-6}$alkyl.

In some embodiments, Z is selected from $C_{1-4}$alkyleneNR$^5$R$^6$, $OC_{1-4}$alkyleneNR$^5$R$^6$, $NR^7C_{1-4}$alkyleneNR$^5$R$^6$, $NR^7C_{1-4}$alkyleneOR$^5$ and $NR^5R^6$, and $R^5$ and $R^6$ are joined to form, together with the atom therebetween, $C_{4-12}$heterocycloalkyl, optionally containing one additional heteromoiety selected from $NR^{10}$, O and S, and optionally substituted with one or more of halo and $C_{1-6}$alkyl.

In some embodiments, Z is $NR^5R^6$, and $R^5$ and $R^6$ are joined to form, together with the atom therebetween, $C_{4-12}$heterocycloalkyl, optionally containing one additional heteromoiety selected from $NR^{10}$, O and S, and optionally substituted with one or two substituents selected from halo, =O, $C_{1-6}$alkyl, $C_{3-6}$cycloalkyl, $C_{3-6}$heterocycloalkyl, $NH(C_{1-6}$alkyl), $N(C_{1-6}$alkyl)($C_{1-6}$alkyl), $SC_{1-6}$alkyl, $S(O)C_{1-6}$alkyl and $SO_2C_{1-6}$alkyl, wherein all alkyl, cycloalkyl, and heterocycloalkyl, groups of the optional substituents on the $C_4$-12heterocycloalkyl formed by $R^5$ and $R^6$ are also optionally substituted with one or more of halo, $C_{1-6}$alkyl, $OC_{1-6}$alkyl, $C_{1-6}$haloalkyl and $OC_{1-6}$haloalkyl.

In some embodiments, Z is $NR^5R^6$, and $R^5$ and $R^6$ are joined to form, together with the atom therebetween, $C_{5-11}$heterocycloalkyl, optionally containing one additional heteromoiety selected from $NR^{10}$ and O, and optionally substituted with one substituent selected from halo, =O, $C_{1-4}$alkyl, $C_{3-6}$cycloalkyl, $C_{3-6}$heterocycloalkyl, $NH(C_{1-4}$alkyl) and $N(C_{1-4}$alkyl)($C_{1-4}$alkyl), wherein all alkyl, cycloalkyl, and heterocycloalkyl, groups of the optional substituents on the $C_{5-11}$heterocycloalkyl formed by $R^5$ and $R^6$ are also optionally substituted with one to three of fluoro, $C_{1-4}$alkyl, $OC_{1-4}$alkyl, $C_{1-4}$fluoroalkyl and $OC_{1-4}$fluoroalkyl.

In some embodiments, Z is selected from:

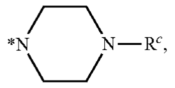,
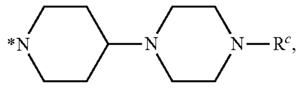,
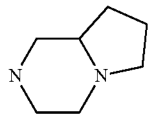,
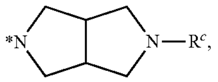,
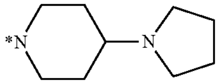,
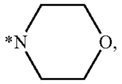,
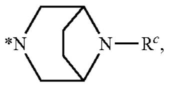,
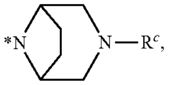,
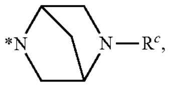,
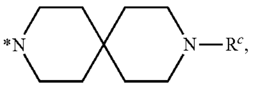,
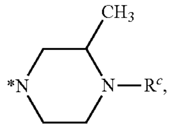,
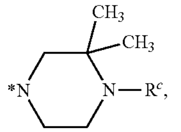,
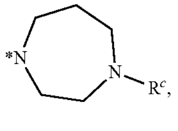,
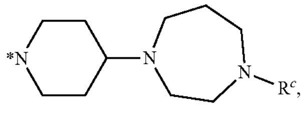,
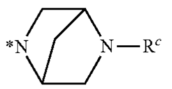
and -continued

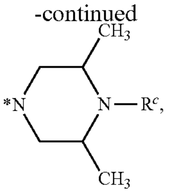

wherein $R^c$ is selected from H and $C_{1-6}$alkyl and * represents the point of attachment for Z in the compound of Formula I.

In some embodiments, $R^5$ is selected from H, $CH_3$, $CH_2CH_3$, $CH(CH_3)_2$, $C(CH_3)_3$, $CF_3$, $CH_2CF_3$, and $(CH_2)_2OCH_3$.

In some embodiments, $R^6$, $R^7$, $R^8$, $R^9$ and $R^{10}$ are independently selected from H and $CH_3$.

In some embodiments, Z and $R^4$ are joined to form, together with the atoms therebetween a ring B which is selected from $C_{5-7}$cycloalkyl and $C_{5-10}$heterocycloalkyl, wherein the ring B is optionally substituted with one or more substituents selected from halo, =O, OH, $C_{1-4}$ alkyl, $C_{3-6}$cycloalkyl, aryl, $C_{5-6}$heteroaryl, $C_{3-6}$heterocycloalkyl, $C_{1-5}$alkylene$C_{3-6}$cycloalkyl, $C_{1-4}$alkylenearyl, $C_{1-4}$alkylene$C_{5-6}$heteroaryl, $C_{1-4}$alkylene$C_{3-6}$heterocycloalkyl, C(O)$C_{1-4}$alkyl, O$C_{1-4}$alkyl, O$C_{1-4}$alkyleneO$C_{1-4}$alkyl, C(O)$NH_2$, C(O)NH($C_{1-4}$alkyl), C(O)N($C_{1-4}$alkyl)($C_{1-4}$alkyl), NHC(O)$C_{1-4}$alkyl, N($C_{1-4}$alkyl)C(O)$C_{1-4}$alkyl, $NH_2$, NH($C_{1-4}$alkyl), N($C_{1-4}$alkyl)($C_{1-4}$alkyl), S$C_{1-4}$alkyl, S(O)$C_{1-4}$alkyl and $SO_2C_{1-4}$alkyl, wherein all alkyl, alkylene, cycloalkyl, heterocycloalkyl, aryl and heteroaryl groups of the optional substituents on the ring B are also optionally substituted with one or more of halo, $C_{1-4}$alkyl, O$C_{1-4}$alkyl, $C_{1-4}$fluoroalkyl and O$C_{1-4}$fluoroalkyl.

In some embodiments, ring B is selected from $C_{5-7}$cycloalkyl and $C_{5-8}$heterocycloalkyl that is optionally substituted with one or more substituents selected from halo, =O and $C_{1-4}$alkyl. In some embodiments, ring B is selected from

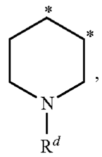,
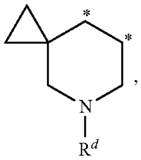,
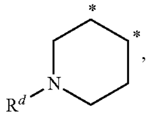,
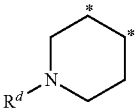,
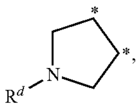
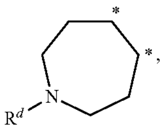
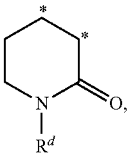
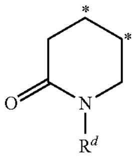,
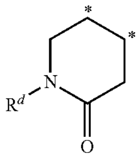
and
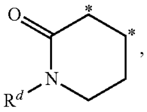

wherein $R^d$ is selected from H and $C_{1-6}$alkyl and * represents the points of attachment for ring B in the compound of Formula I.

In some embodiments, the compounds of Formula I are selected from:

| Compound I.D. | Structure | IUPAC Name |
|---|---|---|
| I-1 | 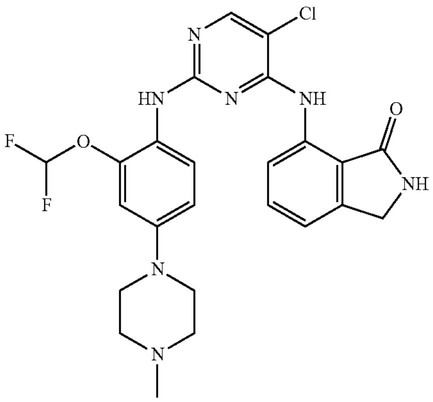 [SMILES: CN1CCN(c2ccc(Nc3ncc(Cl)c(Nc4cccc5c4C(=O)NC5)n3)c(OC(F)F)c2)CC1] | 7-((5-chloro-2-((2-(difluoromethoxy)-4-(4-methylpiperazin-1-yl)phenyl)amino)pyrimidin-4-yl)amino)isoindolin-1-one |

-continued

| Compound I.D. | Structure | IUPAC Name |
|---|---|---|
| I-2 | 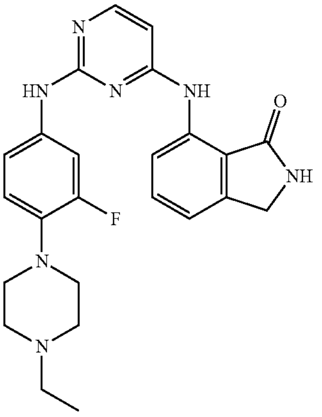 [SMILES: CCN1CCN(c2ccc(Nc3nccc(Nc4cccc5c4C(=O)NC5)n3)cc2F)CC1] | 7-((2-((4-(4-ethylpiperazin-1-yl)-3-fluorophenyl)amino)pyrimidin-4-yl)amino)isoindolin-1-one |
| I-3 | 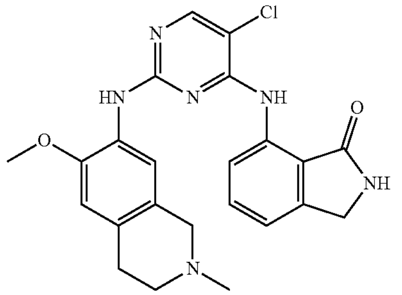 [SMILES: COc1cc2c(cc1Nc1ncc(Cl)c(Nc3cccc4c3C(=O)NC4)n1)CN(C)CC2] | 7-((5-chloro-2-((6-methoxy-2-methyl-1,2,3,4-tetrahydroisoquinolin-7-yl)amino)pyrimidin-4-yl)amino)isoindolin-1-one |
| I-4 | 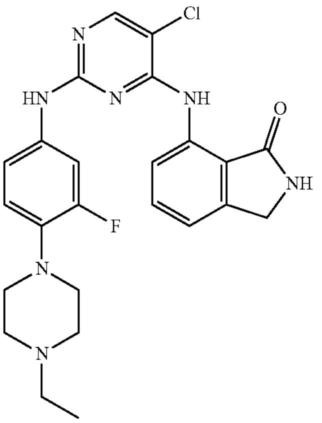 [SMILES: CCN1CCN(c2ccc(Nc3ncc(Cl)c(Nc4cccc5c4C(=O)NC5)n3)cc2F)CC1] | 7-((5-chloro-2-((4-(4-ethylpiperazin-1-yl)-3-fluorophenyl)amino)pyrimidin-4-yl)amino)isoindolin-1-one |
| I-5 | 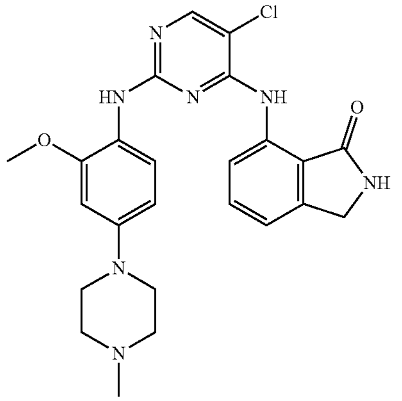 [SMILES: COc1cc(N2CCN(C)CC2)ccc1Nc1ncc(Cl)c(Nc2cccc3c2C(=O)NC3)n1] | 7-((5-chloro-2-((2-methoxy-4-(4-methylpiperazin-1-yl)phenyl)amino)pyrimidin-4-yl)amino)isoindolin-1-one |

-continued
| Compound I.D. | Structure | IUPAC Name |
|---|---|---|
| I-6 | 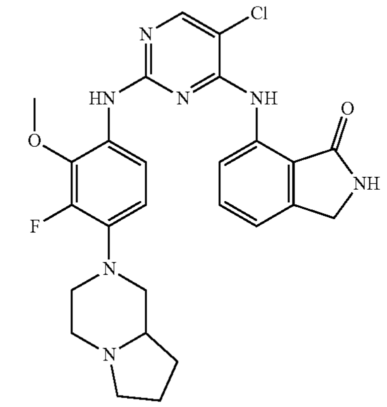 [SMILES: COc1c(Nc2ncc(Cl)c(Nc3cccc4c3C(=O)NC4)n2)ccc(N2CCN3CCCC3C2)c1F] | 7-((5-chloro-2-((3-fluoro-4-(hexahydropyrrolo[1,2-a]pyrazin-2(1H)-yl)-2-methoxyphenyl)amino)pyrimidin-4-yl)amino)isoindolin-1-one |
| I-7 | 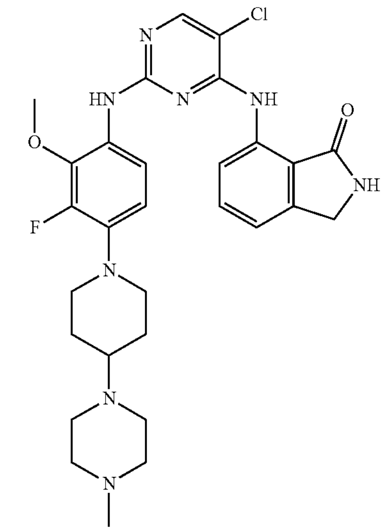 [SMILES: COc1c(Nc2ncc(Cl)c(Nc3cccc4c3C(=O)NC4)n2)ccc(N2CCC(N3CCN(C)CC3)CC2)c1F] | 7-((5-chloro-2-((3-fluoro-2-methoxy-4-(4-(4-methylpiperazin-1-yl)piperidin-1-yl)phenyl)amino)pyrimidin-4-yl)amino)isoindolin-1-one |
| I-8 | 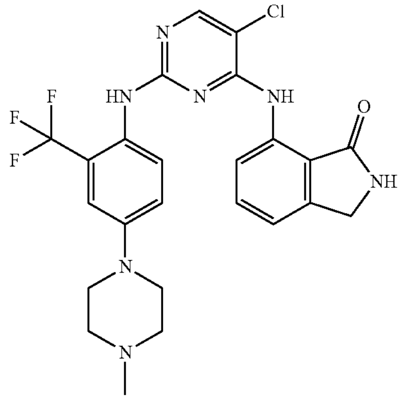 [SMILES: CN1CCN(c2ccc(Nc3ncc(Cl)c(Nc4cccc5c4C(=O)NC5)n3)c(C(F)(F)F)c2)CC1] | 7-((5-chloro-2-((4-(4-methylpiperazin-1-yl)-2-(trifluoromethyl)phenyl)amino)pyrimidin-4-yl)amino)isoindolin-1-one |

-continued

| Compound I.D. | Structure | IUPAC Name |
| --- | --- | --- |
| I-9 | 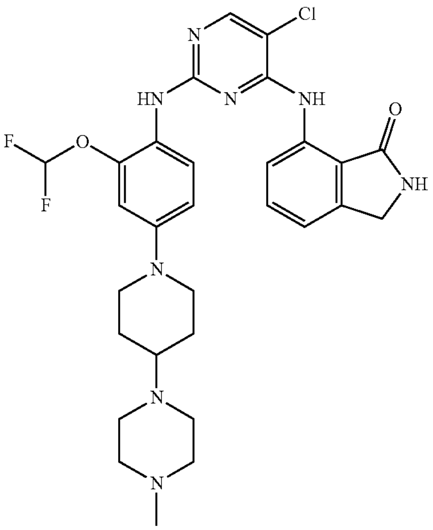 [SMILES: CN1CCN(C2CCN(c3ccc(Nc4ncc(Cl)c(Nc5cccc6c5C(=O)NC6)n4)c(OC(F)F)c3)CC2)CC1] | 7-((5-chloro-2-((2-(difluoromethoxy)-4-(4-(4-methylpiperazin-1-yl)piperidin-1-yl)phenyl)amino)pyrimidin-4-yl)amino)isoindolin-1-one |
| I-10 | 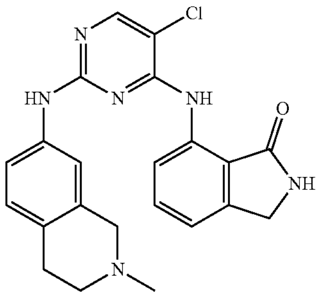 [SMILES: CN1CCc2ccc(Nc3ncc(Cl)c(Nc4cccc5c4C(=O)NC5)n3)cc2C1] | 7-((5-chloro-2-((2-methyl-1,2,3,4-tetrahydroisoquinolin-7-yl)amino)pyrimidin-4-yl)amino)isoindolin-1-one |
| I-11 | 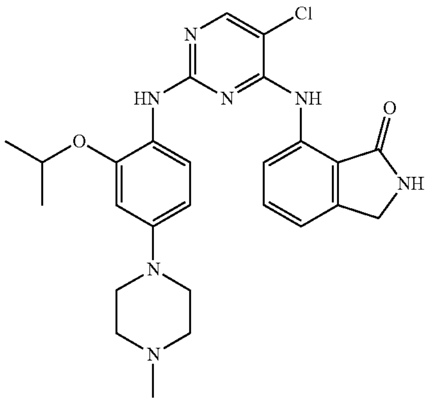 | 7-((5-chloro-2-((2-isopropoxy-4-(4-methylpiperazin-1-yl)phenyl)amino)pyrimidin-4-yl)amino)isoindolin-1-one |
| I-12 | 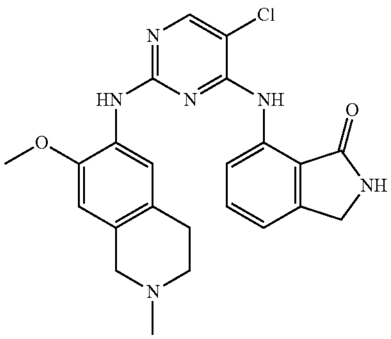 [SMILES: COc1cc2c(cc1Nc1ncc(Cl)c(Nc3cccc4c3C(=O)NC4)n1)CCN(C)C2] | 7-((5-chloro-2-((7-methoxy-2-methyl-1,2,3,4-tetrahydroisoquinolin-6-yl)amino)pyrimidin-4-yl)amino)isoindolin-1-one |

-continued
| Compound I.D. | Structure | IUPAC Name |
|---|---|---|
| I-13 | 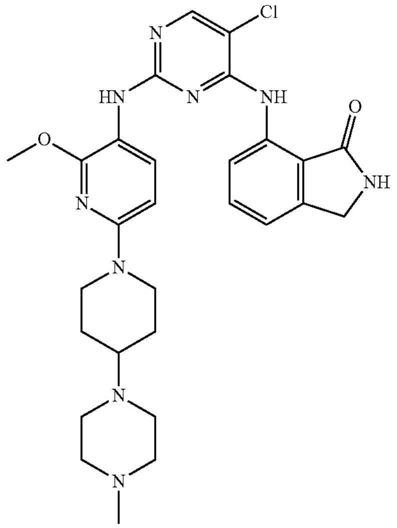 | 7-((5-chloro-2-((2-methoxy-6-(4-(4-methylpiperazin-1-yl)piperidin-1-yl)pyridin-3-yl)amino)pyrimidin-4-yl)amino)isoindolin-1-one |
| I-14 | 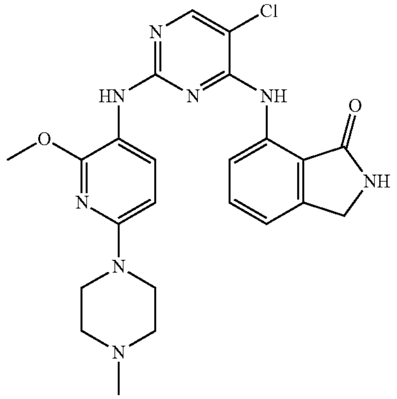 | 7-((5-chloro-2-((2-methoxy-6-(4-methylpiperazin-1-yl)pyridin-3-yl)amino)pyrimidin-4-yl)amino)isoindolin-1-one |
| I-15 | 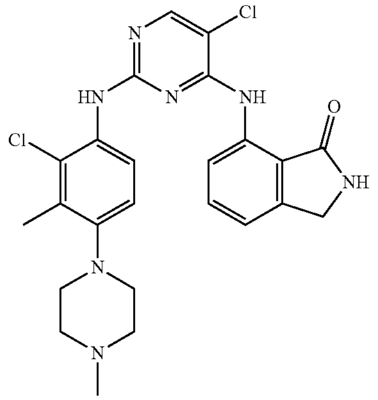 | 7-((5-chloro-2-((2-chloro-3-methyl-4-(4-methylpiperazin-1-yl)phenyl)amino)pyrimidin-4-yl)amino)isoindolin-1-one |

-continued

| Compound I.D. | Structure | IUPAC Name |
|---|---|---|
| I-16 | 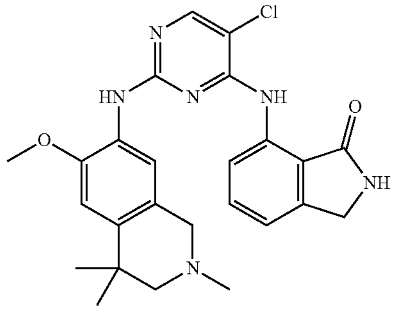 [SMILES: COc1cc2c(cc1Nc1ncc(Cl)c(Nc3cccc4c3C(=O)NC4)n1)CN(C)CC2(C)C] | 7-((5-chloro-2-((6-methoxy-2,4,4-trimethyl-1,2,3,4-tetrahydroisoquinolin-7-yl)amino)pyrimidin-4-yl)amino)isoindolin-1-one |
| I-17 | 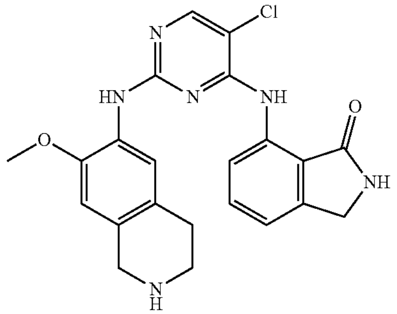 [SMILES: COc1cc2c(cc1Nc1ncc(Cl)c(Nc3cccc4c3C(=O)NC4)n1)CCNC2] | 7-((5-chloro-2-((7-methoxy-1,2,3,4-tetrahydroisoquinolin-6-yl)amino)pyrimidin-4-yl)amino)isoindolin-1-one |
| I-18 | 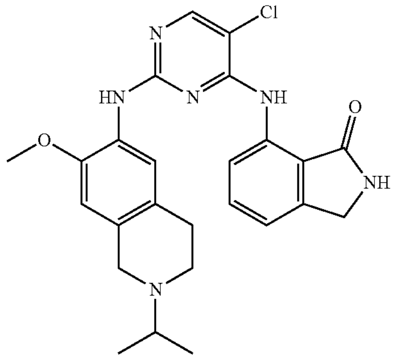 [SMILES: COc1cc2c(cc1Nc1ncc(Cl)c(Nc3cccc4c3C(=O)NC4)n1)CCN(C(C)C)C2] | 7-((5-chloro-2-((2-isopropyl-7-methoxy-1,2,3,4-tetrahydroisoquinolin-6-yl)amino)pyrimidin-4-yl)amino)isoindolin-1-one |
| I-19 | 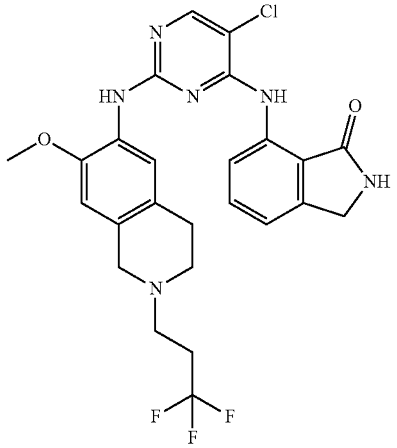 [SMILES: COc1cc2c(cc1Nc1ncc(Cl)c(Nc3cccc4c3C(=O)NC4)n1)CCN(CCC(F)(F)F)C2] | 7-((5-chloro-2-((7-methoxy-2-(3,3,3-trifluoropropyl)-1,2,3,4-tetrahydroisoquinolin-6-yl)amino)pyrimidin-4-yl)amino)isoindolin-1-one |

-continued

| Compound I.D. | Structure | IUPAC Name |
|---|---|---|
| I-20 | 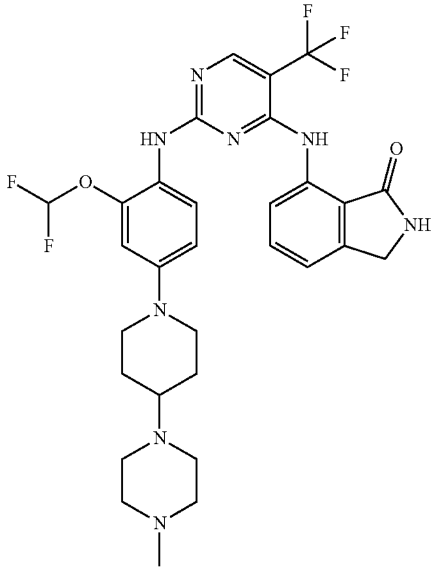 [SMILES: CN1CCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-methylpiperazin-1-yl)piperidin-1-yl)phenyl)amino)-5-(trifluoromethyl)pyrimidin-4-yl)amino)isoindolin-1-one |
| I-21 | 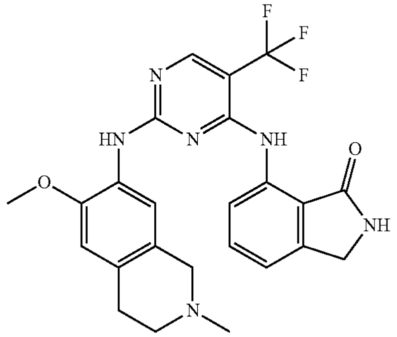 [SMILES: COc1cc2c(cc1Nc1ncc(C(F)(F)F)c(Nc3cccc4c3C(=O)NC4)n1)CN(C)CC2] | 7-((2-((6-methoxy-2-methyl-1,2,3,4-tetrahydroisoquinolin-7-yl)amino)-5-(trifluoromethyl)pyrimidin-4-yl)amino)isoindolin-1-one |
| I-22 | 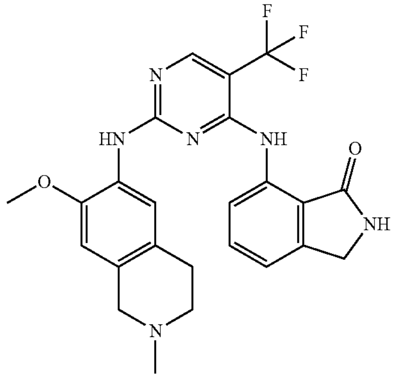 [SMILES: COc1cc2c(cc1Nc1ncc(C(F)(F)F)c(Nc3cccc4c3C(=O)NC4)n1)CCN(C)C2] | 7-((2-((7-methoxy-2-methyl-1,2,3,4-tetrahydroisoquinolin-6-yl)amino)-5-(trifluoromethyl)pyrimidin-4-yl)amino)isoindolin-1-one |

-continued

| Compound I.D. | Structure | IUPAC Name |
|---|---|---|
| I-23 | 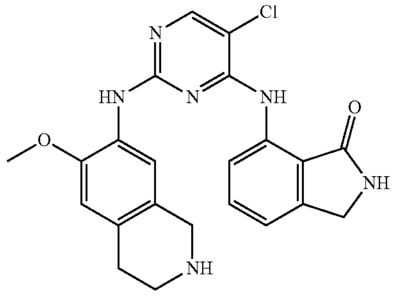 [SMILES: COc1cc2c(cc1Nc1ncc(Cl)c(Nc3cccc4c3C(=O)NC4)n1)CNCC2] | 7-((5-chloro-2-((6-methoxy-1,2,3,4-tetrahydroisoquinolin-7-yl)amino)pyrimidin-4-yl)amino)isoindolin-1-one |
| I-24 | 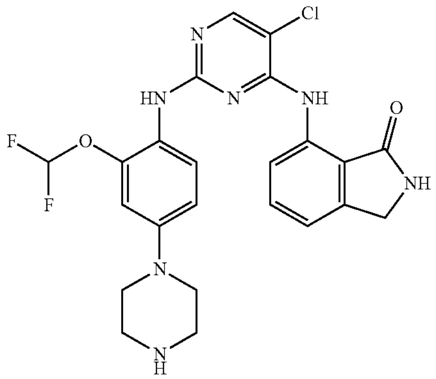 [SMILES: O=C1NCc2cccc(Nc3nc(Nc4ccc(N5CCNCC5)cc4OC(F)F)ncc3Cl)c21] | 7-((5-chloro-2-((2-(difluoromethoxy)-4-(piperazin-1-yl)phenyl)amino)pyrimidin-4-yl)amino)isoindolin-1-one |
| I-25 | 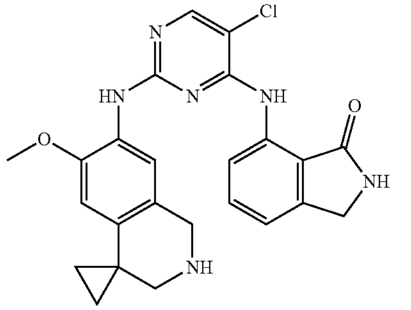 [SMILES: COc1cc2c(cc1Nc1ncc(Cl)c(Nc3cccc4c3C(=O)NC4)n1)CNCC21CC1] | 7-((5-chloro-2-((6'-methoxy-2',3'-dihydro-1'H-spiro[cyclopropane-1,4'-isoquinolin]-7'-yl)amino)pyrimidin-4-yl)amino)isoindolin-1-one |
| I-26 | 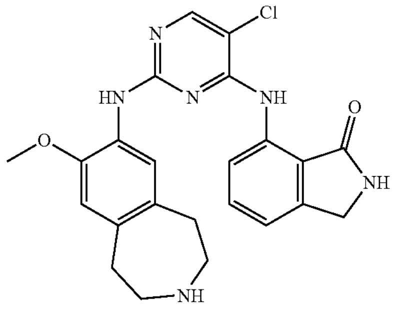 [SMILES: COc1cc2c(cc1Nc1ncc(Cl)c(Nc3cccc4c3C(=O)NC4)n1)CCNCC2] | 7-((5-chloro-2-((8-methoxy-2,3,4,5-tetrahydro-1H-benzo[d]azepin-7-yl)amino)pyrimidin-4-yl)amino)isoindolin-1-one |

-continued

| Compound I.D. | Structure | IUPAC Name |
|---|---|---|
| I-27 | 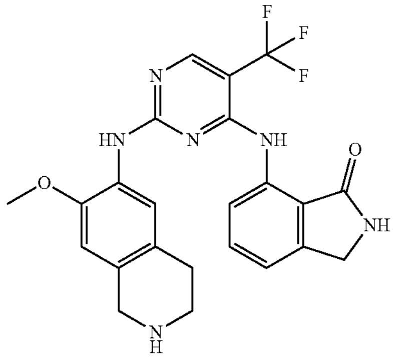 [SMILES: COc1cc2c(cc1Nc1ncc(C(F)(F)F)c(Nc3cccc4c3C(=O)NC4)n1)CCNC2] | 7-((5-chloro-2-((8-methoxy-2,3,4,5-tetrahydro-1H-benzo[d]azepin-7-yl)amino)pyrimidin-4-yl)amino)isoindolin-1-one |
| I-28 | 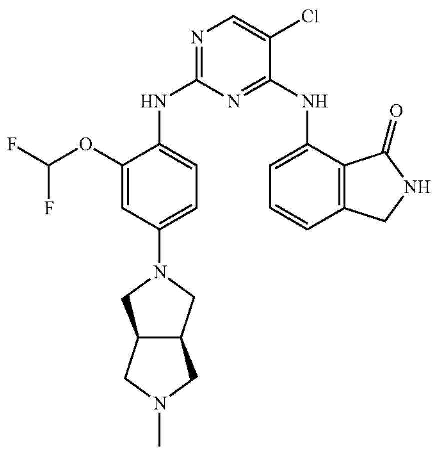 [SMILES: CN1C[C@@H]2CN(c3ccc(Nc4ncc(Cl)c(Nc5cccc6c5C(=O)NC6)n4)c(OC(F)F)c3)C[C@@H]2C1] | 7-((5-chloro-2-((2-(difluoromethoxy)-4-((3aR,6aS)-5-methylhexahydropyrrolo[3,4-c]pyrrol-2(1H)-yl)phenyl)amino)pyrimidin-4-yl)amino)isoindolin-1-one |
| I-29 | 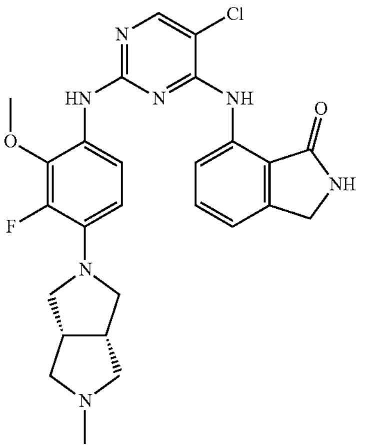 [SMILES: COc1c(Nc2ncc(Cl)c(Nc3cccc4c3C(=O)NC4)n2)ccc(N2C[C@H]3CN(C)C[C@H]3C2)c1F] | 7-((5-chloro-2-((3-fluoro-2-methoxy-4-((3aR,6aS)-5-methylhexahydropyrrolo[3,4-c]pyrrol-2(1H)-yl)phenyl)amino)pyrimidin-4-yl)amino)isoindolin-1-one |

-continued

| Compound I.D. | Structure | IUPAC Name |
| --- | --- | --- |
| I-30 | 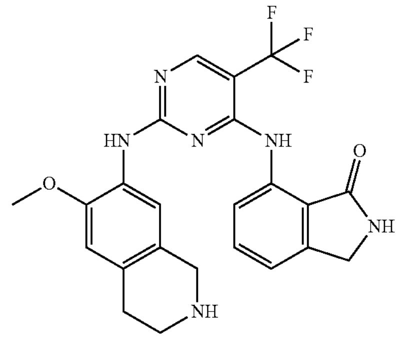 [SMILES: COc1cc2c(cc1Nc1ncc(C(F)(F)F)c(Nc3cccc4c3C(=O)NC4)n1)CNCC2] | 7-((2-((6-methoxy-1,2,3,4-tetrahydroisoquinolin-7-yl)amino)-5-(trifluoromethyl)pyrimidin-4-yl)amino)isoindolin-1-one |
| I-31 | 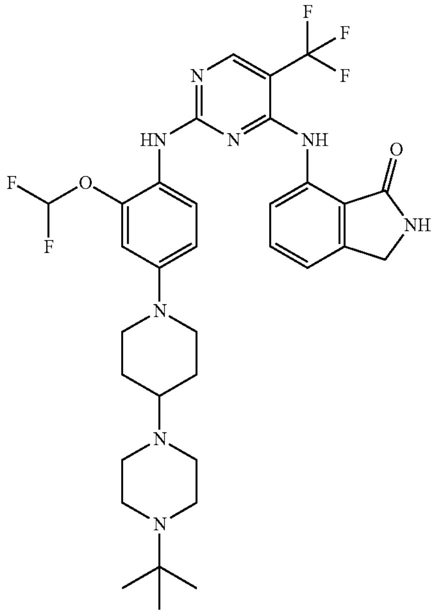 [SMILES: CC(C)(C)N1CCN(C2CCN(c3ccc(Nc4ncc(C(F)(F)F)c(Nc5cccc6c5C(=O)NC6)n4)c(OC(F)F)c3)CC2)CC1] | 7-((2-((4-(4-(4-(tert-butyl)piperazin-1-yl)piperidin-1-yl)-2-(difluoromethoxy)phenyl)amino)-5-(trifluoromethyl)pyrimidin-4-yl)amino)isoindolin-1-one |
| I-32 | 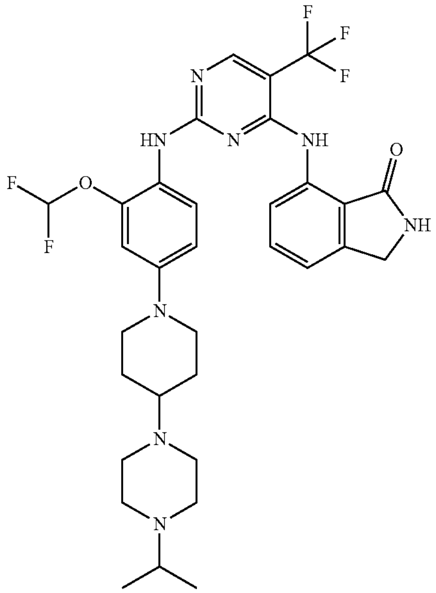 [SMILES: CC(C)N1CCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-isopropylpiperazin-1-yl)piperidin-1-yl)phenyl)amino)-5-(trifluoromethyl)pyrimidin-4-yl)amino)isoindolin-1-one |

-continued

| Compound I.D. | Structure | IUPAC Name |
|---|---|---|
| I-33 | 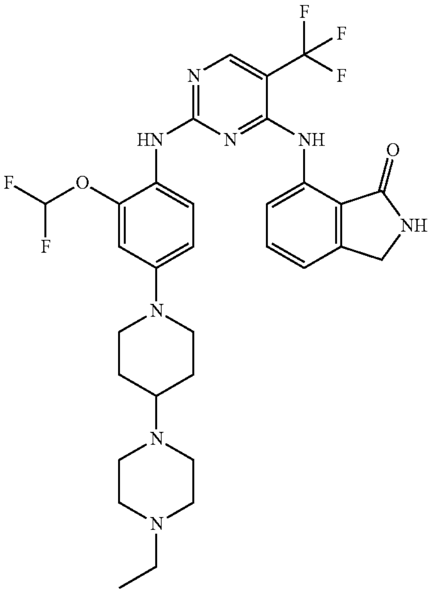 [SMILES: CCN1CCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-ethylpiperazin-1-yl)piperidin-1-yl)phenyl)amino)-5-(trifluoromethyl)pyrimidin-4-yl)amino)isoindolin-1-one |
| I-34 | 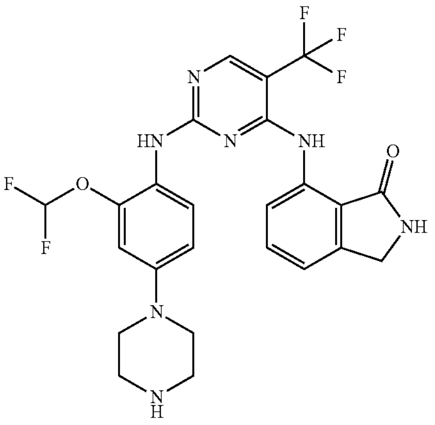 [SMILES: O=C1NCc2cccc(Nc3nc(Nc4ccc(N5CCNCC5)cc4OC(F)F)ncc3C(F)(F)F)c21] | 7-((2-((2-(difluoromethoxy)-4-(piperazin-1-yl)phenyl)amino)-5-(trifluoromethyl)pyrimidin-4-yl)amino)isoindolin-1-one |
| I-35 | 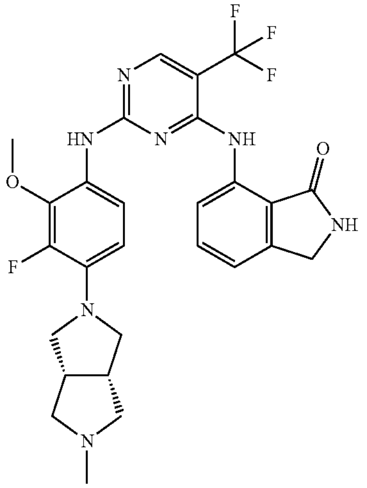 [SMILES: COc1c(Nc2ncc(C(F)(F)F)c(Nc3cccc4c3C(=O)NC4)n2)ccc(N2C[C@H]3CN(C)C[C@H]3C2)c1F] | 7-((2-((3-fluoro-2-methoxy-4-((3aR,6aS)-5-methylhexahydropyrrolo[3,4-c]pyrrol-2(1H)-yl)phenyl)amino)-5-(trifluoromethyl)pyrimidin-4-yl)amino)isoindolin-1-one |

-continued
| Compound I.D. | Structure | IUPAC Name |
|---|---|---|
| I-36 | 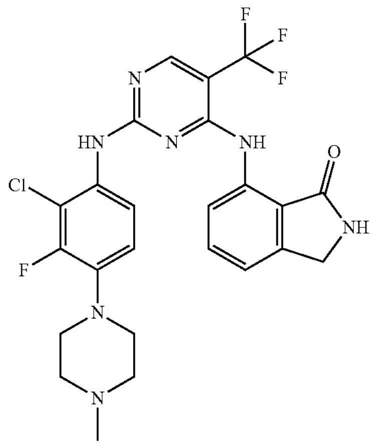 [SMILES: CN1CCN(c2ccc(Nc3ncc(C(F)(F)F)c(Nc4cccc5c4C(=O)NC5)n3)c(Cl)c2F)CC1] | 7-((2-((2-chloro-3-fluoro-4-(4-methylpiperazin-1-yl)phenyl)amino)-5-(trifluoromethyl)pyrimidin-4-yl)amino)isoindolin-1-one |
| I-37 | 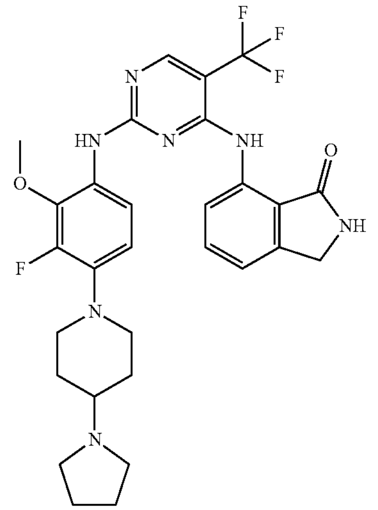 [SMILES: COc1c(Nc2ncc(C(F)(F)F)c(Nc3cccc4c3C(=O)NC4)n2)ccc(N2CCC(N3CCCC3)CC2)c1F] | 7-((2-((3-fluoro-2-methoxy-4-(4-(pyrrolidin-1-yl)piperidin-1-yl)phenyl)amino)-5-(trifluoromethyl)pyrimidin-4-yl)amino)isoindolin-1-one |
| I-38 | 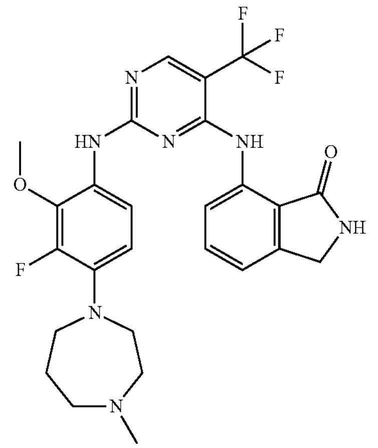 [SMILES: COc1c(Nc2ncc(C(F)(F)F)c(Nc3cccc4c3C(=O)NC4)n2)ccc(N2CCCN(C)CC2)c1F] | 7-((2-((3-fluoro-2-methoxy-4-(4-methyl-1,4-diazepan-1-yl)phenyl)amino)-5-(trifluoromethyl)pyrimidin-4-yl)amino)isoindolin-1-one |

-continued

| Compound I.D. | Structure | IUPAC Name |
|---|---|---|
| I-39 | 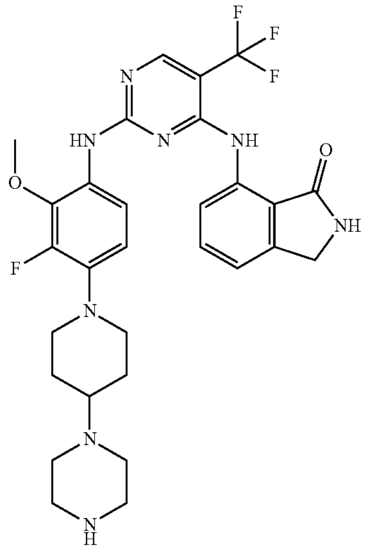 [SMILES: COc1c(Nc2ncc(C(F)(F)F)c(Nc3cccc4c3C(=O)NC4)n2)ccc(N2CCC(N3CCNCC3)CC2)c1F] | 7-((2-((3-fluoro-2-methoxy-4-(4-(piperazin-1-yl)piperidin-1-yl)phenyl)amino)-5-(trifluoromethyl)pyrimidin-4-yl)amino)isoindolin-1-one |
| I-40 | 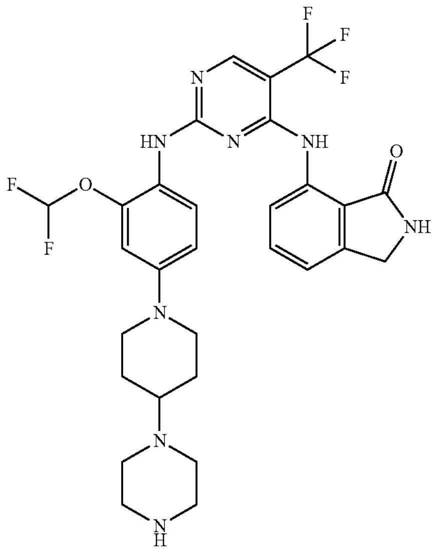 [SMILES: O=C1NCc2cccc(Nc3nc(Nc4ccc(N5CCC(N6CCNCC6)CC5)cc4OC(F)F)ncc3C(F)(F)F)c21] | 7-((2-((2-(difluoromethoxy)-4-(4-(piperazin-1-yl)piperidin-1-yl)phenyl)amino)-5-(trifluoromethyl)pyrimidin-4-yl)amino)isoindolin-1-one |
| I-41 | 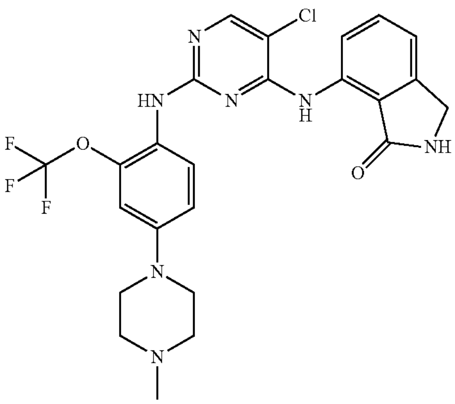 [SMILES: CN1CCN(c2ccc(Nc3ncc(Cl)c(Nc4cccc5c4C(=O)NC5)n3)c(OC(F)(F)F)c2)CC1] | 7-((5-chloro-2-((4-(4-methylpiperazin-1-yl)-2-(trifluoromethoxy)phenyl)amino)pyrimidin-4-yl)amino)isoindolin-1-one |

-continued
| Compound I.D. | Structure | IUPAC Name |
|---|---|---|
| I-42 | 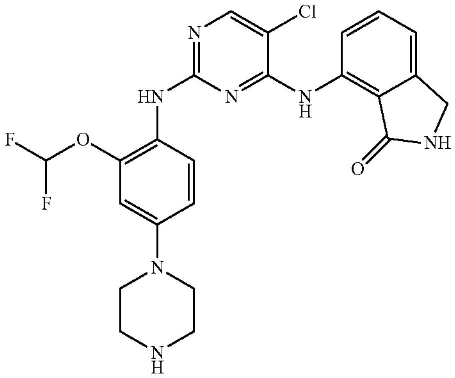 [SMILES: O=C1NCc2cccc(Nc3nc(Nc4ccc(N5CCNCC5)cc4OC(F)F)ncc3Cl)c21] | 7-((2-((2-(difluoromethoxy)-4-(piperazin-1-yl)phenyl)amino)-5-fluoropyrimidin-4-yl)amino)isoindolin-1-one |
| I-43 | 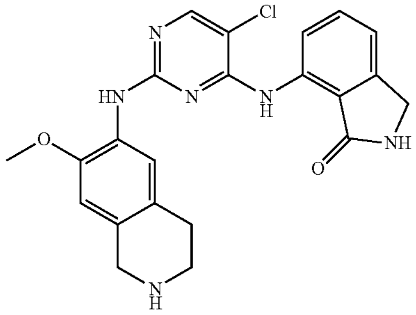 [SMILES: COc1cc2c(cc1Nc1ncc(Cl)c(Nc3cccc4c3C(=O)NC4)n1)CCNC2] | 7-((5-fluoro-2-((7-methoxy-1,2,3,4-tetrahydroisoquinolin-6-yl)amino)pyrimidin-4-yl)amino)isoindolin-1-one |
| I-44 | 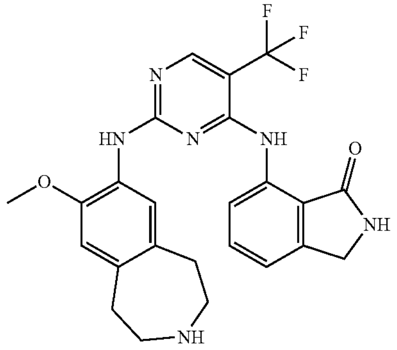 [SMILES: COc1cc2c(cc1Nc1ncc(C(F)(F)F)c(Nc3cccc4c3C(=O)NC4)n1)CCNCC2] | 7-((2-((8-methoxy-2,3,4,5-tetrahydro-1H-benzo[d]azepin-7-yl)amino)-5-(trifluoromethyl)pyrimidin-4-yl)amino)isoindolin-1-one |

-continued

| Compound I.D. | Structure | IUPAC Name |
|---|---|---|
| I-45 | 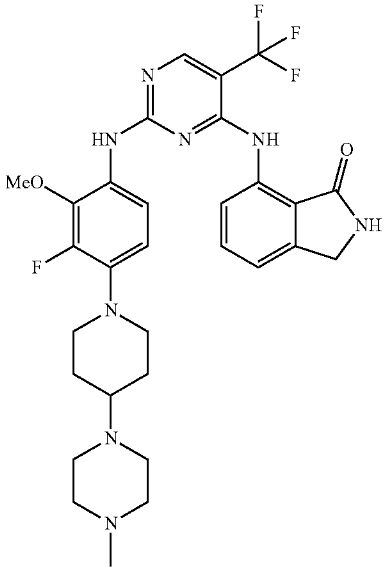 [SMILES: COc1c(Nc2ncc(C(F)(F)F)c(Nc3cccc4c3C(=O)NC4)n2)ccc(N2CCC(N3CCN(C)CC3)CC2)c1F] | 7-((2-((3-fluoro-2-methoxy-4-(4-(4-methylpiperazin-1-yl)piperidin-1-yl)phenyl)amino)-5-(trifluoromethyl)pyrimidin-4-yl)amino)isoindolin-1-one |
| I-46 | 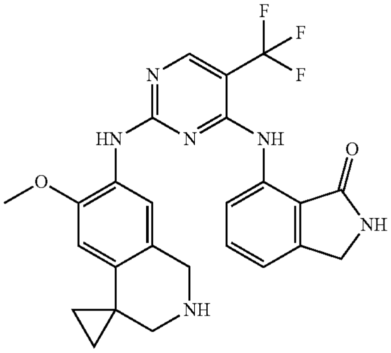 [SMILES: COc1cc2c(cc1Nc1ncc(C(F)(F)F)c(Nc3cccc4c3C(=O)NC4)n1)CNCC21CC1] | 7-((2-((6'-methoxy-2',3'-dihydro-1'H-spiro[cyclopropane-1,4'-isoquinolin]-7'-yl)amino)-5-(trifluoromethyl)pyrimidin-4-yl)amino)isoindolin-1-one |
| I-47 | 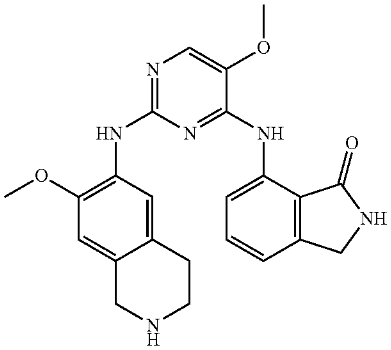 [SMILES: COc1cc2c(cc1Nc1ncc(OC)c(Nc3cccc4c3C(=O)NC4)n1)CCNC2] | 7-((5-methoxy-2-((7-methoxy-1,2,3,4-tetrahydroisoquinolin-6-yl)amino)pyrimidin-4-yl)amino)isoindolin-1-one |

-continued

| Compound I.D. | Structure | IUPAC Name |
|---|---|---|
| I-48 | 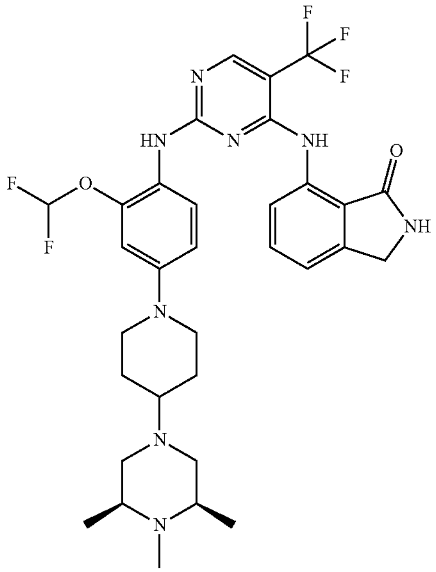 [SMILES: C[C@@H]1CN(C2CCN(c3ccc(Nc4ncc(C(F)(F)F)c(Nc5cccc6c5C(=O)NC6)n4)c(OC(F)F)c3)CC2)C[C@H](C)N1C] | 7-((2-((2-(difluoromethoxy)-4-(4-((3S,5R)-3,4,5-trimethylpiperazin-1-yl)piperidin-1-yl)phenyl)amino)-5-(trifluoromethyl)pyrimidin-4-yl)amino)isoindolin-1-one |
| I-49 | 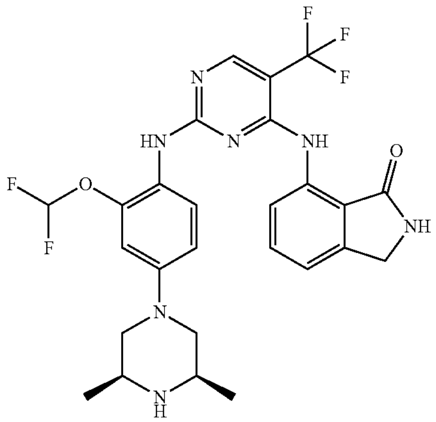 [SMILES: C[C@@H]1CN(c2ccc(Nc3ncc(C(F)(F)F)c(Nc4cccc5c4C(=O)NC5)n3)c(OC(F)F)c2)C[C@H](C)N1] | 7-((2-((2-(difluoromethxoy)-4-((3S,5R)-3,5-dimethylpiperazin-1-yl)phenyl)amino)-5-(trifluoromethyl)pyrimidin-4-yl)amino)isoindolin-1-one |
| I-50 | 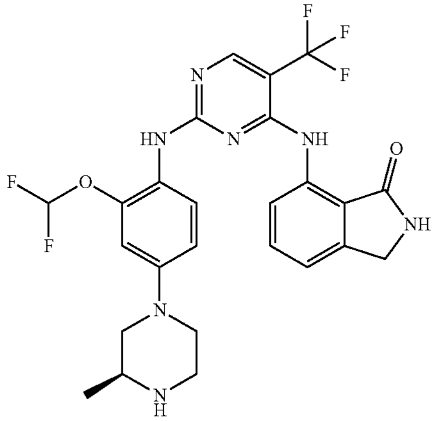 [SMILES: C[C@H]1CN(c2ccc(Nc3ncc(C(F)(F)F)c(Nc4cccc5c4C(=O)NC5)n3)c(OC(F)F)c2)CCN1] | (S)-7-((2-((2-(difluoromethoxy)-4-(3-methylpiperazin-1-yl)phenyl)amino)-5-(trifluoromethyl)pyrimidin-4-yl)amino)isoindolin-1-one |

-continued
| Compound I.D. | Structure | IUPAC Name |
|---|---|---|
| I-51 | 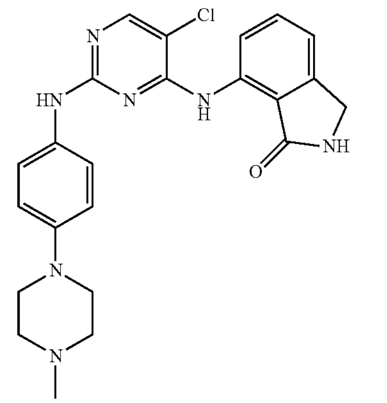 [SMILES: CN1CCN(c2ccc(Nc3ncc(Cl)c(Nc4cccc5c4C(=O)NC5)n3)cc2)CC1] | 7-((5-chloro-2-((4-(4-methylpiperazin-1-yl)phenyl)amino)pyrimidin-4-yl)amino)isoindolin-1-one |
| I-52 | 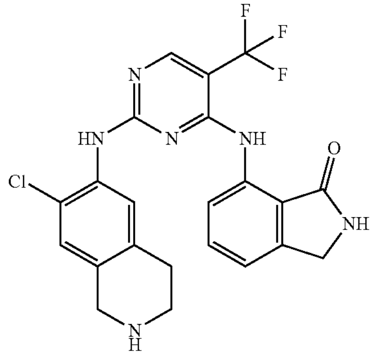 [SMILES: O=C1NCc2cccc(Nc3nc(Nc4cc5c(cc4Cl)CNCC5)ncc3C(F)(F)F)c21] | 7-((2-((7-chloro-1,2,3,4-tetrahydroisoquinolin-6-yl)amino)-5-(trifluoromethyl)pyrimidin-4-yl)amino)isoindolin-1-one |
| I-53 | 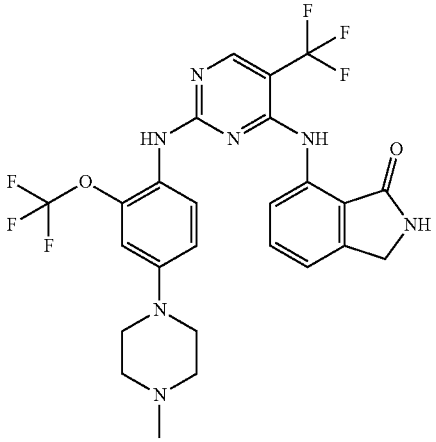 [SMILES: CN1CCN(c2ccc(Nc3ncc(C(F)(F)F)c(Nc4cccc5c4C(=O)NC5)n3)c(OC(F)(F)F)c2)CC1] | 7-((2-((4-(4-methylpiperazin-1-yl)-2-(trifluoromethoxy)phenyl)amino)-5-(trifluoromethyl)pyrimidin-4-yl)amino)isoindolin-1-one |

-continued

| Compound I.D. | Structure | IUPAC Name |
|---|---|---|
| I-54 | 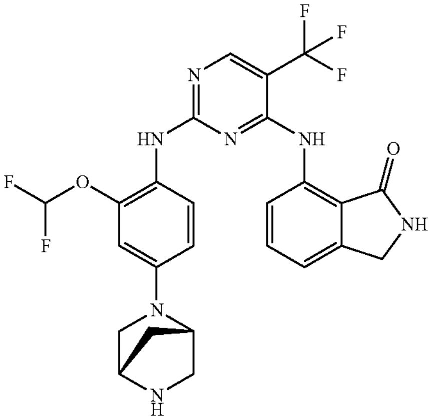 [SMILES: O=C1NCc2cccc(Nc3nc(Nc4ccc(N5C[C@@H]6C[C@H]5CN6)cc4OC(F)F)ncc3C(F)(F)F)c21] | 7-((2-((4-((1S,4S)-2,5-diazabicyclo[2.2.1]heptan-2-yl)-2-(difluoromethoxy)phenyl)amino)-5-(trifluoromethyl)pyrimidin-4-yl)amino)isoindolin-1-one |
| I-55 | 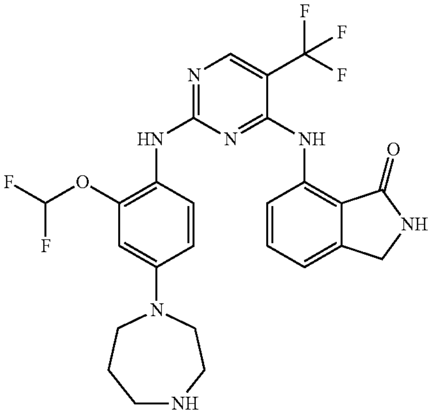 [SMILES: O=C1NCc2cccc(Nc3nc(Nc4ccc(N5CCCNCC5)cc4OC(F)F)ncc3C(F)(F)F)c21] | 7-((2-((4-(1,4-diazepan-1-yl)-2-(difluoromethoxy)phenyl)amino)-5-(trifluoromethyl)pyrimidin-4-yl)amino)isoindolin-1-one |
| I-56 | 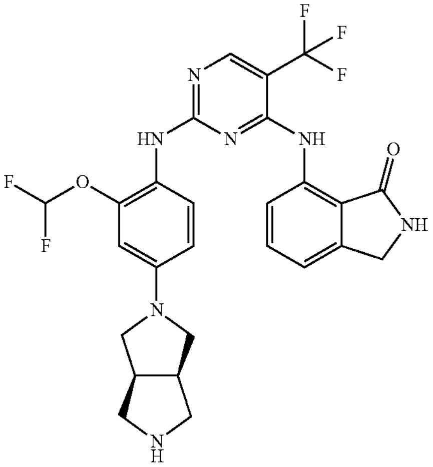 [SMILES: O=C1NCc2cccc(Nc3nc(Nc4ccc(N5C[C@H]6CNC[C@H]6C5)cc4OC(F)F)ncc3C(F)(F)F)c21] | 7-((2-((2-(difluoromethoxy)-4-((3aR,6aS)-hexahydropyrrolo[3,4-c]pyrrol-2(1H)-yl)phenyl)amino)-5-(trifluoromethyl)pyrimidin-4-yl)amino)isoindolin-1-one |

-continued

| Compound I.D. | Structure | IUPAC Name |
|---|---|---|
| I-57 | 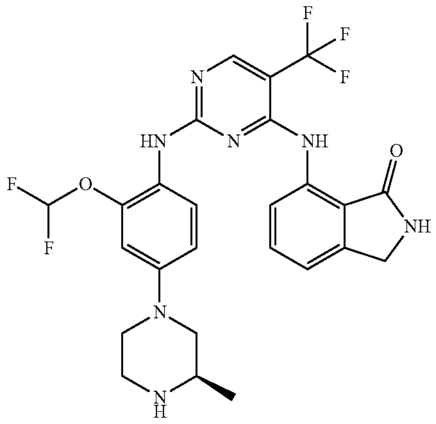 [SMILES: C[C@@H]1CN(c2ccc(Nc3ncc(C(F)(F)F)c(Nc4cccc5c4C(=O)NC5)n3)c(OC(F)F)c2)CCN1] | (R)-7-((2-((2-(difluoromethoxy)-4-(3-methylpiperazin-1-yl)phenyl)amino)-5-(trifluoromethyl)pyrimidin-4-yl)amino)isoindolin-1-one |
| I-58 | 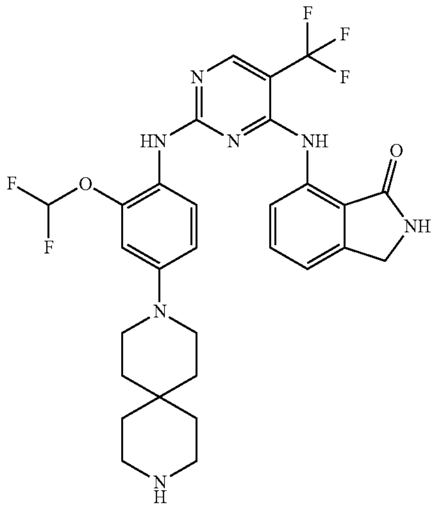 [SMILES: O=C1NCc2cccc(Nc3nc(Nc4ccc(N5CCC6(CCNCC6)CC5)cc4OC(F)F)ncc3C(F)(F)F)c21] | 7-((2-((2-(difluoromethoxy)-4-(3,9-diazaspiro[5.5]undecan-3-yl)phenyl)amino)-5-(trifluoromethyl)pyrimidin-4-yl)amino)isoindolin-1-one |
| I-59 | 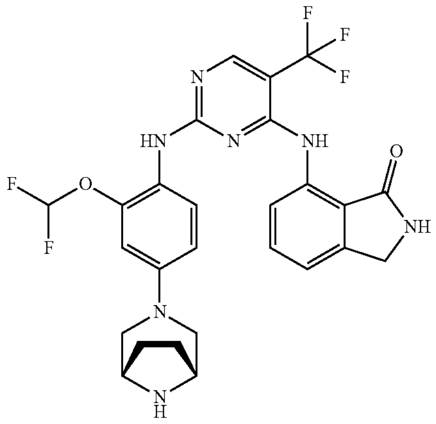 | 7-((2-((4-((1R,5S)-3,8-diazabicyclo[3.2.1]octan-3-yl)-2-(difluoromethoxy)phenyl)amino)-5-(trifluoromethyl)pyrimidin-4-yl)amino)isoindolin-1-one |

-continued
| Compound I.D. | Structure | IUPAC Name |
|---|---|---|
| I-60 | 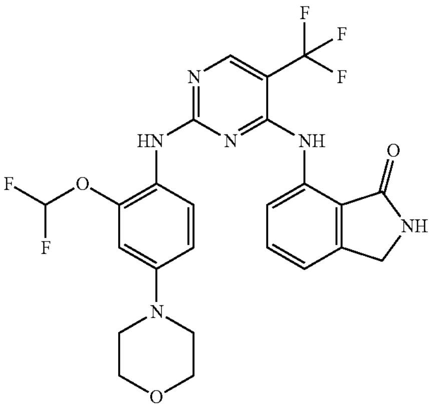 | 7-((2-((2-(difluoromethoxy)-4-morpholinophenyl)amino)-5-(trifluoromethyl)pyrimidin-4-yl)amino)isoindolin-1-one |
| I-61 | 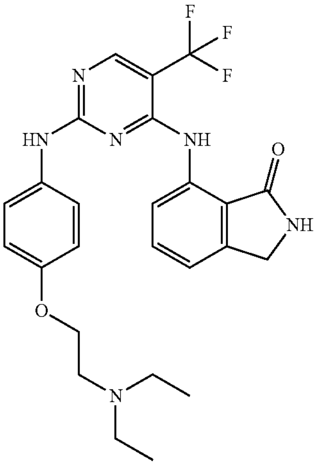 [SMILES: CCN(CC)CCOc1ccc(Nc2ncc(C(F)(F)F)c(Nc3cccc4c3C(=O)NC4)n2)cc1] | 7-((2-((4-(2-(diethylamino)ethoxy)phenyl)amino)-5-(trifluoromethyl)pyrimidin-4-yl)amino)isoindolin-1-one |
| I-62 | 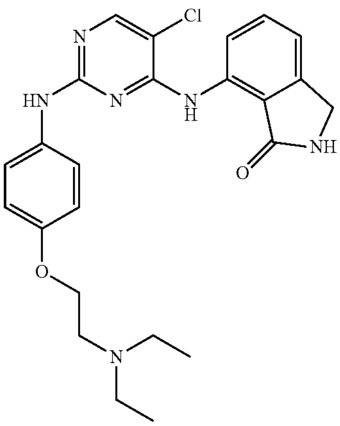 [SMILES: CCN(CC)CCOc1ccc(Nc2ncc(Cl)c(Nc3cccc4c3C(=O)NC4)n2)cc1] | 7-((5-chloro-2-((4-(2-(diethylamino)ethoxy)phenyl)amino)pyrimidin-4-yl)amino)isoindolin-1-one |

-continued

| Compound I.D. | Structure | IUPAC Name |
|---|---|---|
| I-63 | 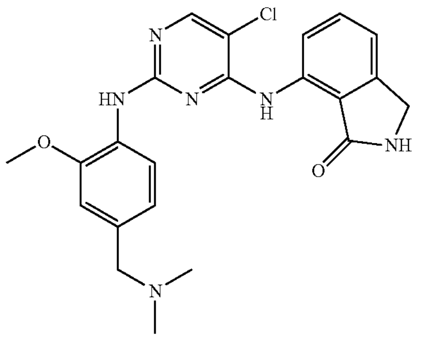 [SMILES: COc1cc(CN(C)C)ccc1Nc1ncc(Cl)c(Nc2cccc3c2C(=O)NC3)n1] | 7-((5-chloro-2-((4-((dimethylamino)methyl)-2-methoxyphenyl)amino)pyrimidin-4-yl)amino)isoindolin-1-one |
| I-64 | 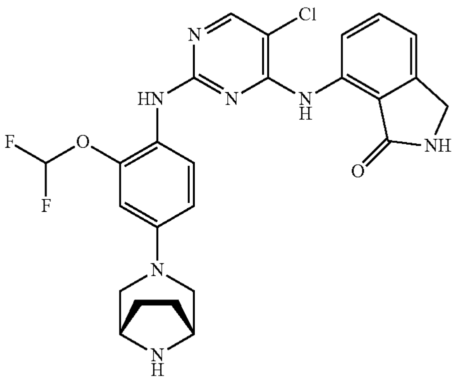 | 7-((2-((4-((1R,5S)-3,8-diazabicyclo[3.2.1]octan-3-yl)-2-(difluoromethoxy)phenyl)amino)-5-chloropyrimidin-4-yl)amino)isoindolin-1-one |
| I-65 | 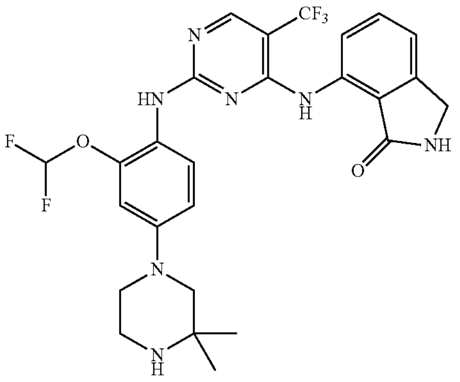 [SMILES: CC1(C)CN(c2ccc(Nc3ncc(C(F)(F)F)c(Nc4cccc5c4C(=O)NC5)n3)c(OC(F)F)c2)CCN1] | 7-((2-((2-(difluoromethoxy)-4-(3,3-dimethylpiperazin-1-yl)phenyl)amino)-5-(trifluoromethyl)pyrimidin-4-yl)amino)isoindolin-1-one |
| I-66 | 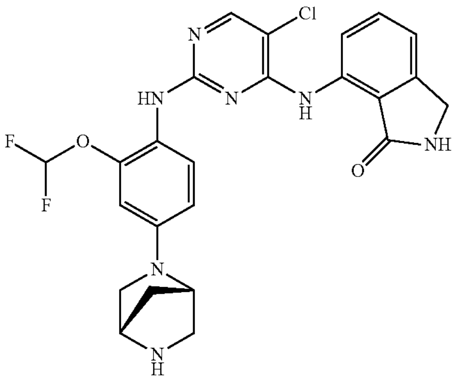 [SMILES: O=C1NCc2cccc(Nc3nc(Nc4ccc(N5C[C@@H]6C[C@H]5CN6)cc4OC(F)F)ncc3Cl)c21] | 7-((2-((4-((1S,4S)-2,5-diazabicyclo[2.2.1]heptan-2-yl)-2-(difluoromethoxy)phenyl)amino)-5-chloropyrimidin-4-yl)amino)isoindolin-1-one |

-continued

| Compound I.D. | Structure | IUPAC Name |
| --- | --- | --- |
| I-67 | 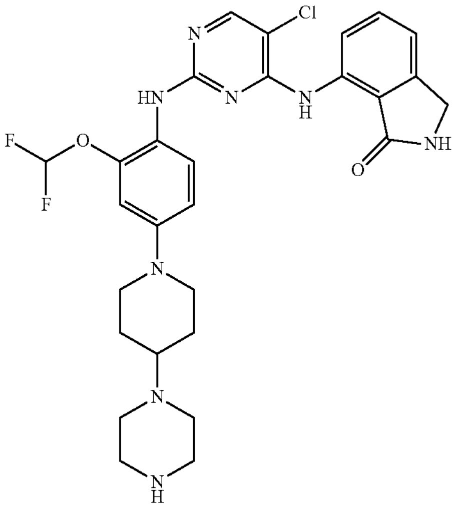 [SMILES: O=C1NCc2cccc(Nc3nc(Nc4ccc(N5CCC(N6CCNCC6)CC5)cc4OC(F)F)ncc3Cl)c21] | 7-((5-chloro-2-((2-(difluoromethoxy)-4-(4-(piperazin-1-yl)piperidin-1-yl)phenyl)amino)pyrimidin-4-yl)amino)isoindolin-1-one |
| I-68 | 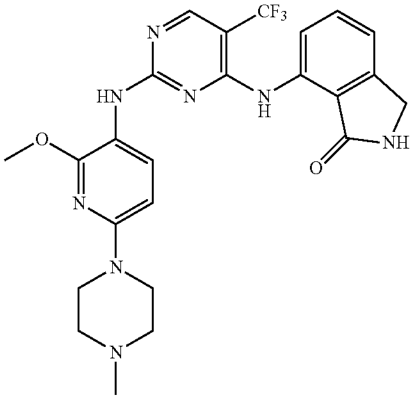 [SMILES: COc1nc(N2CCN(C)CC2)ccc1Nc1ncc(C(F)(F)F)c(Nc2cccc3c2C(=O)NC3)n1] | 7-((2-((2-methoxy-6-(4-methylpiperazin-1-yl)pyridin-3-yl)amino)-5-(trifluoromethyl)pyrimidin-4-yl)amino)isoindolin-1-one |
| I-69 | 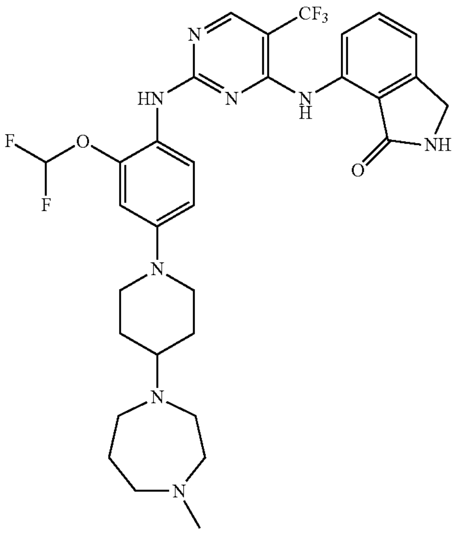 [SMILES: CN1CCCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-methyl-1,4-diazepan-1-yl)piperidin-1-yl)phenyl)amino)-5-(trifluoromethyl)pyrimidin-4-yl)amino)isoindolin-1-one |

-continued

| Compound I.D. | Structure | IUPAC Name |
| --- | --- | --- |
| I-70 | 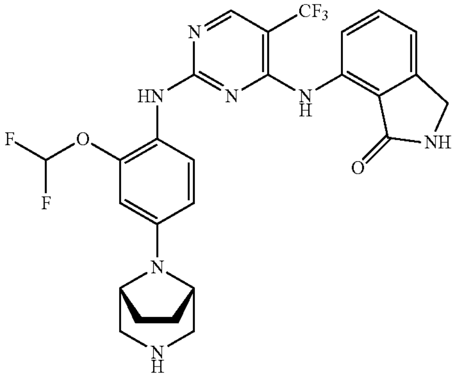 | 7-((2-((4-((1R,5S)-3,8-diazabicyclo[3.2.1]octan-8-yl)-2-(difluoromethoxy)phenyl)amino)-5-(trifluoromethyl)pyrimidin-4-yl)amino)isoindolin-1-one |
| I-71 | 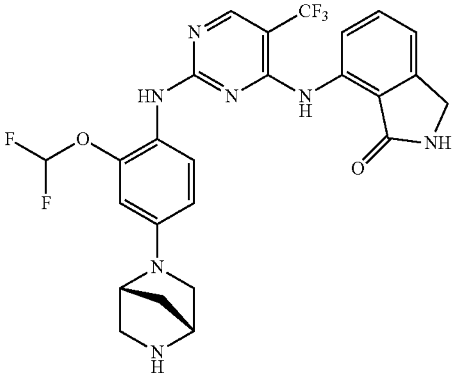 [SMILES: O=C1NCc2cccc(Nc3nc(Nc4ccc(N5C[C@H]6C[C@@H]5CN6)cc4OC(F)F)ncc3C(F)(F)F)c21] | 7-((2-((4-((1R,4R)-2,5-diazabicyclo[2.2.1]heptan-2-yl)-2-(difluoromethoxy)phenyl)amino)-5-(trifluoromethyl)pyrimidin-4-yl)amino)isoindolin-1-one |
| I-72 | 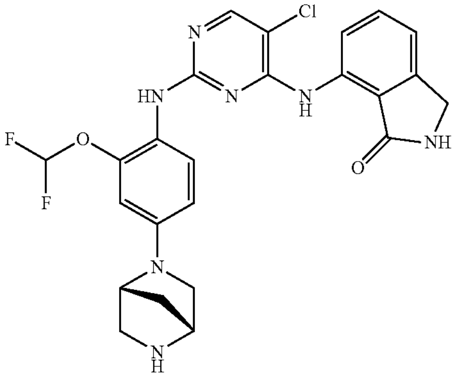 [SMILES: O=C1NCc2cccc(Nc3nc(Nc4ccc(N5C[C@H]6C[C@@H]5CN6)cc4OC(F)F)ncc3Cl)c21] | 7-((2-((4-((1R,4R)-2,5-diazabicyclo[2.2.1]heptan-2-yl)-2-(difluoromethoxy)phenyl)amino)-5-chloropyrimidin-4-yl)amino)isoindolin-1-one |
| I-73 | 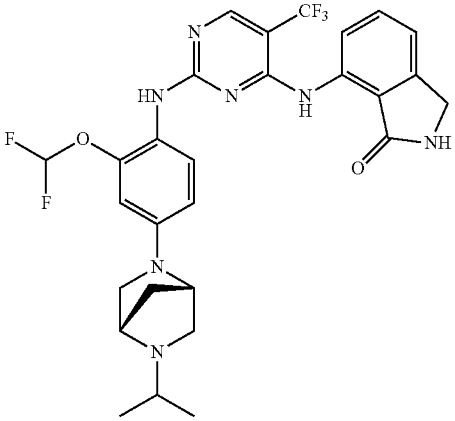 [SMILES: CC(C)N1C[C@@H]2C[C@H]1CN2c1ccc(Nc2ncc(C(F)(F)F)c(Nc3cccc4c3C(=O)NC4)n2)c(OC(F)F)c1] | 7-((2-((2-(difluoromethoxy)-4-((1S,4S)-5-isopropyl-2,5-diazabicyclo[2.2.1]heptan-2-yl)phenyl)amino)-5-(trifluoromethyl)pyrimidin-4-yl)amino)isoindolin-1-one |

-continued
| Compound I.D. | Structure | IUPAC Name |
| --- | --- | --- |
| I-74 | 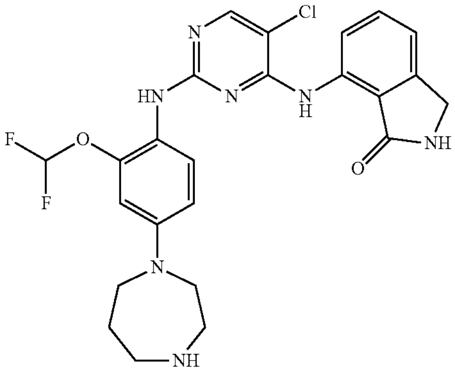 [SMILES: O=C1NCc2cccc(Nc3nc(Nc4ccc(N5CCCNCC5)cc4OC(F)F)ncc3Cl)c21] | 7-((2-((4-(1,4-diazepan-1-yl)-2-(difluoromethoxy)phenyl)amino)-5-chloropyrimidin-4-yl)amino)isoindolin-1-one |
| I-75 | 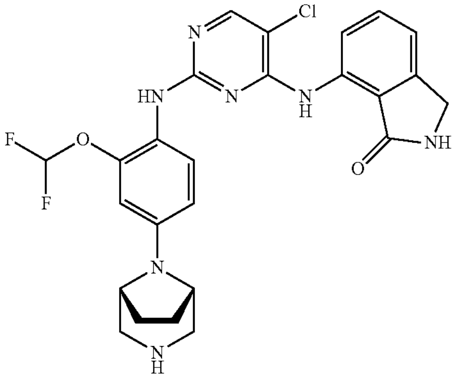 | 7-((2-((4-((1R,5S)-3,8-diazabicyclo[3.2.1]octan-8-yl)-2-(difluoromethoxy)phenyl)amino)-5-chloropyrimidin-4-yl)amino)isoindolin-1-one |
| I-76 | 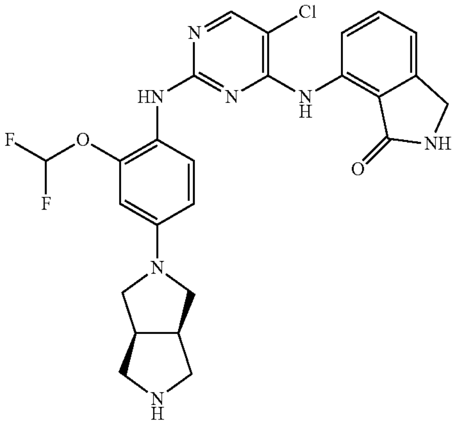 [SMILES: O=C1NCc2cccc(Nc3nc(Nc4ccc(N5C[C@H]6CNC[C@H]6C5)cc4OC(F)F)ncc3Cl)c21] | 7-((5-chloro-2-((2-(difluoromethoxy)-4-((3aR,6aS)-hexahydropyrrolo[3,4-c]pyrrol-2(1H)-yl)phenyl)amino)pyrimidin-4-yl)amino)isoindolin-1-one |

-continued
| Compound I.D. | Structure | IUPAC Name |
|---|---|---|
| I-77 | 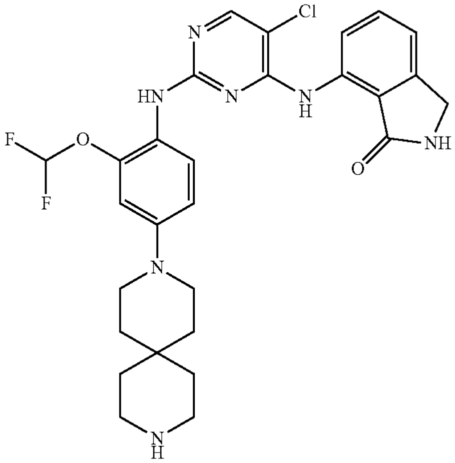 [SMILES: O=C1NCc2cccc(Nc3nc(Nc4ccc(N5CCC6(CCNCC6)CC5)cc4OC(F)F)ncc3Cl)c21] | 7-((5-chloro-2-((2-(difluoromethoxy)-4-(3,9-diazaspiro[5.5]undecan-3-yl)phenyl)amino)pyrimidin-4-yl)amino)isoindolin-1-one |
| I-78 | 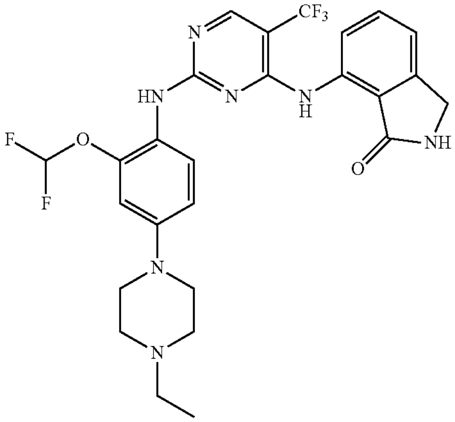 [SMILES: CCN1CCN(c2ccc(Nc3ncc(C(F)(F)F)c(Nc4cccc5c4C(=O)NC5)n3)c(OC(F)F)c2)CC1] | 7-((2-((2-(difluoromethxoy)-4-(4-ethylpiperazin-1-yl)phenyl)amino)-5-(trifluoromethyl)pyrimidin-4-yl)amino)isoindolin-1-one |
| I-79 | 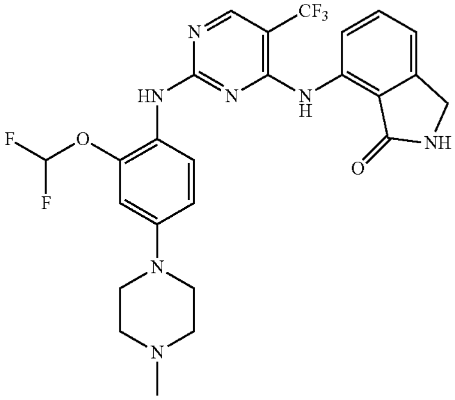 [SMILES: CN1CCN(c2ccc(Nc3ncc(C(F)(F)F)c(Nc4cccc5c4C(=O)NC5)n3)c(OC(F)F)c2)CC1] | 7-((2-((2-(difluoromethxoy)-4-(4-methylpiperazin-1-yl)phenyl)amino)-5-(trifluoromethyl)pyrimidin-4-yl)amino)isoindolin-1-one |

-continued

| Compound I.D. | Structure | IUPAC Name |
|---|---|---|
| I-80 | 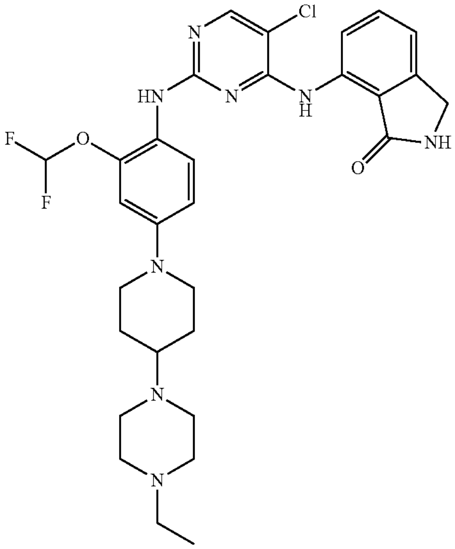 [SMILES: CCN1CCN(C2CCN(c3ccc(Nc4ncc(Cl)c(Nc5cccc6c5C(=O)NC6)n4)c(OC(F)F)c3)CC2)CC1] | 7-((5-chloro-2-((2-(difluoromethoxy)-4-(4-(4-ethylpiperazin-1-yl)piperidin-1-yl)phenyl)amino)pyrimidin-4-yl)amino)isoindolin-1-one |
| I-81 | 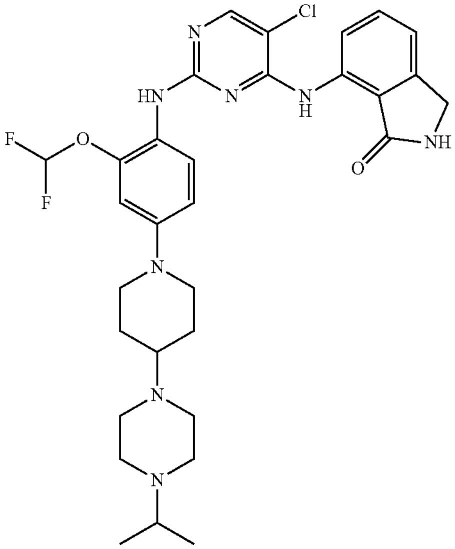 [SMILES: CC(C)N1CCN(C2CCN(c3ccc(Nc4ncc(Cl)c(Nc5cccc6c5C(=O)NC6)n4)c(OC(F)F)c3)CC2)CC1] | 7-((5-chloro-2-((2-(difluoromethoxy)-4-(4-(4-isopropylpiperazin-1-yl)piperidin-1-yl)phenyl)amino)pyrimidin-4-yl)amino)isoindolin-1-one |
| I-82 | 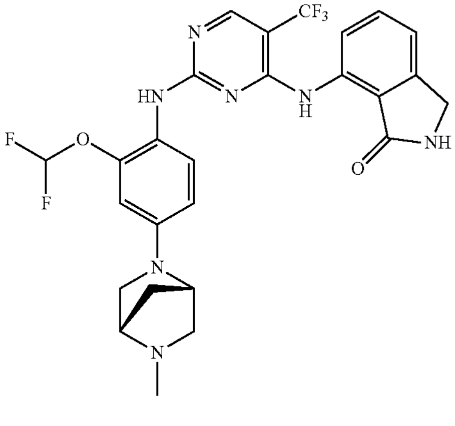 [SMILES: CN1C[C@@H]2C[C@H]1CN2c1ccc(Nc2ncc(C(F)(F)F)c(Nc3cccc4c3C(=O)NC4)n2)c(OC(F)F)c1] | 7-((2-((2-(difluoromethoxy)-4-((1S,4S)-5-methyl-2,5-diazabicyclo[2.2.1]heptan-2-yl)phenyl)amino)-5-(trifluoromethyl)pyrimidin-4-yl)amino)isoindolin-1-one |

-continued
| Compound I.D. | Structure | IUPAC Name |
| --- | --- | --- |
| I-83 | 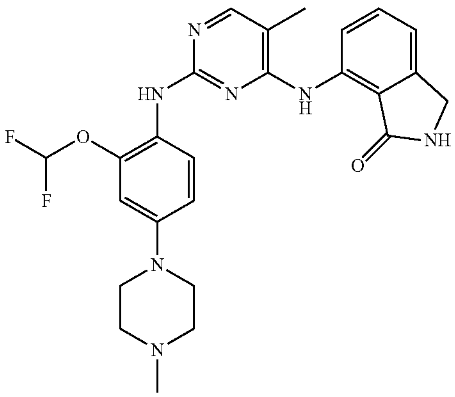 [SMILES: Cc1cnc(Nc2ccc(N3CCN(C)CC3)cc2OC(F)F)nc1Nc1cccc2c1C(=O)NC2] | 7-((2-((2-(difluoromethoxy)-4-(4-methylpiperazin-1-yl)phenyl)amino)-5-methylpyrimidin-4-yl)amino)isoindolin-1-one |
| I-84 | 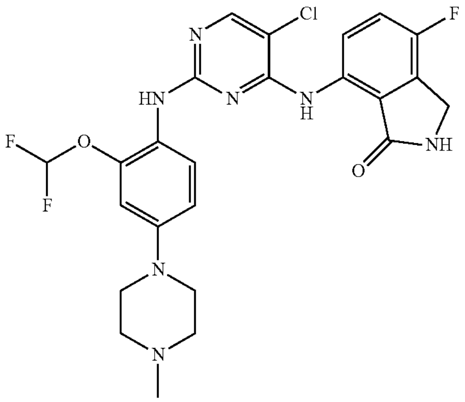 [SMILES: CN1CCN(c2ccc(Nc3ncc(Cl)c(Nc4ccc(F)c5c4C(=O)NC5)n3)c(OC(F)F)c2)CC1] | 7-((5-chloro-2-((2-(difluoromethoxy)-4-(4-methylpiperazin-1-yl)phenyl)amino)pyrimidin-4-yl)amino)-4-fluoroisoindolin-1-one |
| | | and |
| I-85 | 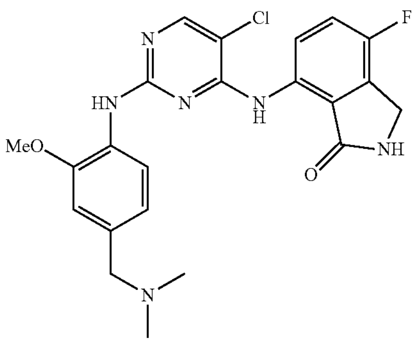 [SMILES: COc1cc(CN(C)C)ccc1Nc1ncc(Cl)c(Nc2ccc(F)c3c2C(=O)NC3)n1] | 7-((5-chloro-2-((4-((dimethylamino)methyl)-2-methoxyphenyl)amino)pyrimidin-4-yl)amino)-4-fluoroisoindolin-1-one | or a pharmaceutically acceptable salt, solvate and/or prodrug thereof.

In some embodiments, the compounds of Formula I are selected from:

| Compound I.D. | Structure | IUPAC Name |
|---|---|---|
| I-1 | 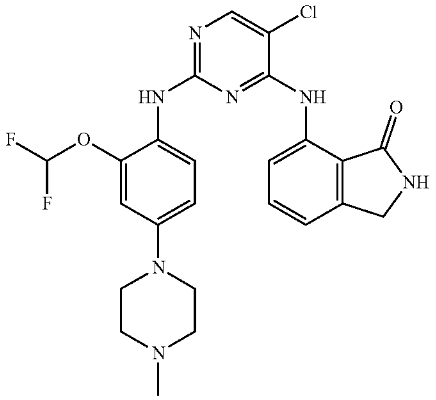 | 7-((5-chloro-2-((2-(difluoromethoxy)-4-(4-methylpiperazin-1-yl)phenyl)amino)pyrimidin-4-yl)amino)isoindolin-1-one |
| I-3 | 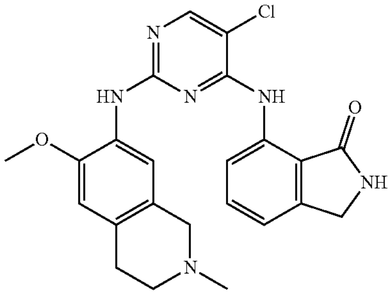 [SMILES: COc1cc2c(cc1Nc1ncc(Cl)c(Nc3cccc4c3C(=O)NC4)n1)CN(C)CC2] | 7-((5-chloro-2-((6-methoxy-2-methyl-1,2,3,4-tetrahydroisoquinolin-7-yl)amino)pyrimidin-4-yl)amino)isoindolin-1-one |
| I-9 | 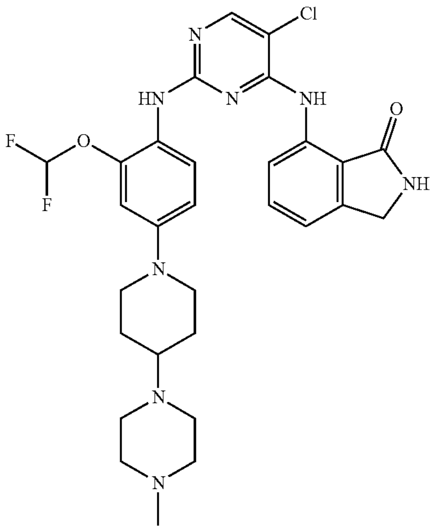 | 7-((5-chloro-2-((2-(difluoromethoxy)-4-(4-(4-methylpiperazin-1-yl)piperidin-1-yl)phenyl)amino)pyrimidin-4-yl)amino)isoindolin-1-one |

-continued

| Compound I.D. | Structure | IUPAC Name |
|---|---|---|
| I-12 | 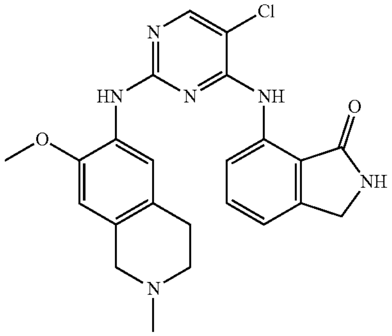 [SMILES: COc1cc2c(cc1Nc1ncc(Cl)c(Nc3cccc4c3C(=O)NC4)n1)CCN(C)C2] | 7-((5-chloro-2-((7-methoxy-2-methyl-1,2,3,4-tetrahydroisoquinolin-6-yl)amino)pyrimidin-4-yl)amino)isoindolin-1-one |
| I-16 | 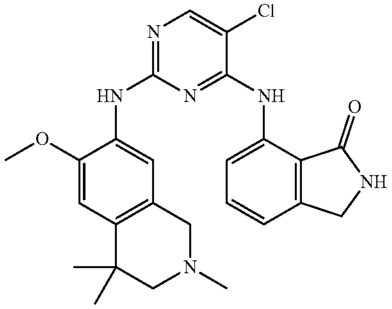 [SMILES: COc1cc2c(cc1Nc1ncc(Cl)c(Nc3cccc4c3C(=O)NC4)n1)CN(C)CC2(C)C] | 7-((5-chloro-2-((6-methoxy-2,4,4-trimethyl-1,2,3,4-tetrahydroisoquinolin-7-yl)amino)pyrimidin-4-yl)amino)isoindolin-1-one |
| I-17 | 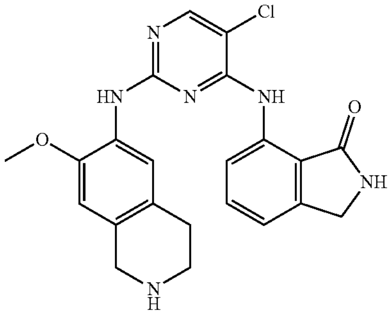 [SMILES: COc1cc2c(cc1Nc1ncc(Cl)c(Nc3cccc4c3C(=O)NC4)n1)CCNC2] | 7-((5-chloro-2-((7-methoxy-1,2,3,4-tetrahydroisoquinolin-6-yl)amino)pyrimidin-4-yl)amino)isoindolin-1-one |
| I-18 | 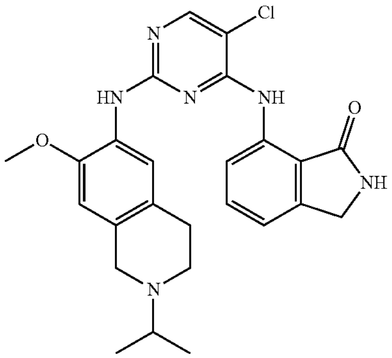 [SMILES: COc1cc2c(cc1Nc1ncc(Cl)c(Nc3cccc4c3C(=O)NC4)n1)CCN(C(C)C)C2] | 7-((5-chloro-2-((2-isopropyl-7-methoxy-1,2,3,4-tetrahydroisoquinolin-6-yl)amino)pyrimidin-4-yl)amino)isoindolin-1-one |

-continued

| Compound I.D. | Structure | IUPAC Name |
|---|---|---|
| I-19 | 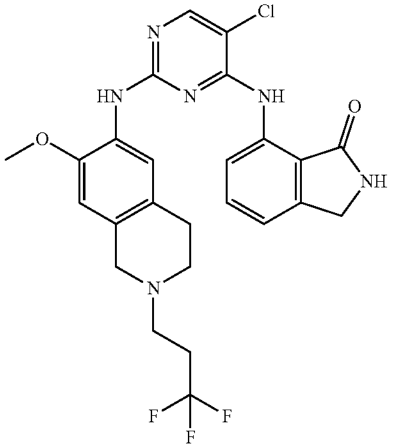 [SMILES: COc1cc2c(cc1Nc1ncc(Cl)c(Nc3cccc4c3C(=O)NC4)n1)CCN(CCC(F)(F)F)C2] | 7-((5-chloro-2-((7-methoxy-2-(3,3,3-trifluoropropyl)-1,2,3,4-tetrahydroisoquinolin-6-yl)amino)pyrimidin-4-yl)amino)isoindolin-1-one |
| I-20 | 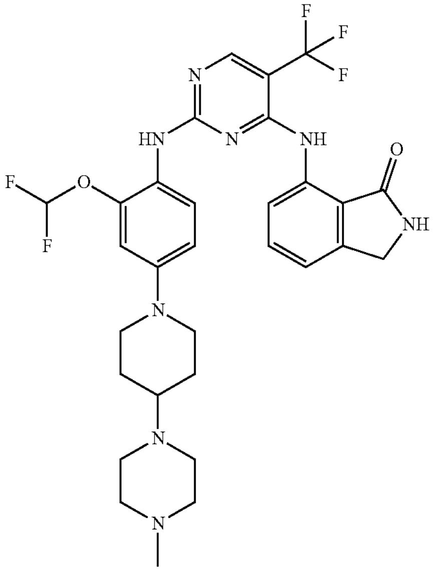 [SMILES: CN1CCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-methylpiperazin-1-yl)piperidin-1-yl)phenyl)amino)-5-(trifluoromethyl)pyrimidin-4-yl)amino)isoindolin-1-one |
| I-21 | 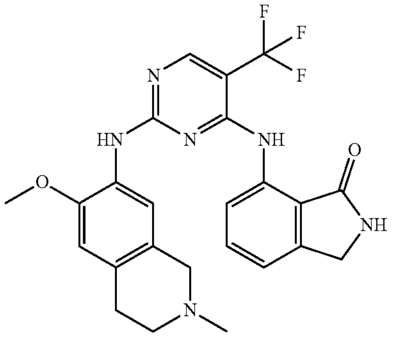 [SMILES: COc1cc2c(cc1Nc1ncc(C(F)(F)F)c(Nc3cccc4c3C(=O)NC4)n1)CN(C)CC2] | 7-((2-((6-methoxy-2-methyl-1,2,3,4-tetrahydroisoquinolin-7-yl)amino)-5-(trifluoromethyl)pyrimidin-4-yl)amino)isoindolin-1-one |

-continued

| Compound I.D. | Structure | IUPAC Name |
|---|---|---|
| I-22 | 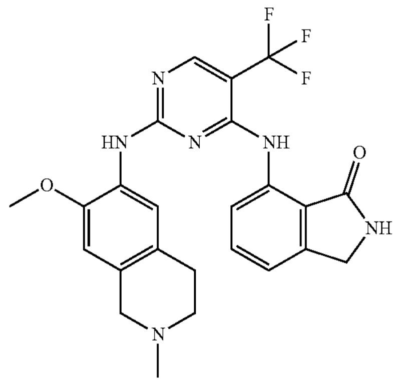 [SMILES: COc1cc2c(cc1Nc1ncc(C(F)(F)F)c(Nc3cccc4c3C(=O)NC4)n1)CCN(C)C2] | 7-((2-((7-methoxy-2-methyl-1,2,3,4-tetrahydroisoquinolin-6-yl)amino)-5-(trifluoromethyl)pyrimidin-4-yl)amino)isoindolin-1-one |
| I-23 | 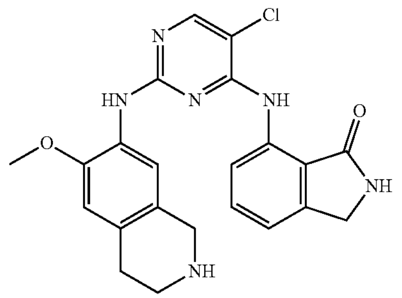 [SMILES: COc1cc2c(cc1Nc1ncc(Cl)c(Nc3cccc4c3C(=O)NC4)n1)CNCC2] | 7-((5-chloro-2-((6-methoxy-1,2,3,4-tetrahydroisoquinolin-7-yl)amino)pyrimidin-4-yl)amino)isoindolin-1-one |
| I-24 | 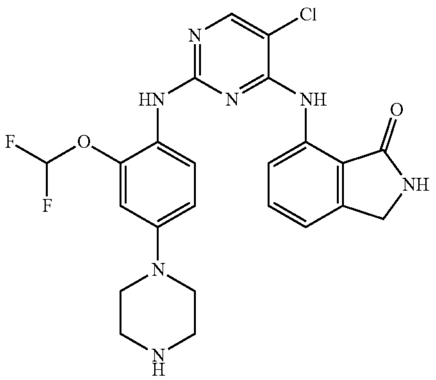 [SMILES: O=C1NCc2cccc(Nc3nc(Nc4ccc(N5CCNCC5)cc4OC(F)F)ncc3Cl)c21] | 7-((5-chloro-2-((2-(difluoromethoxy)-4-(piperazin-1-yl)phenyl)amino)pyrimidin-4-yl)amino)isoindolin-1-one |
| I-25 | 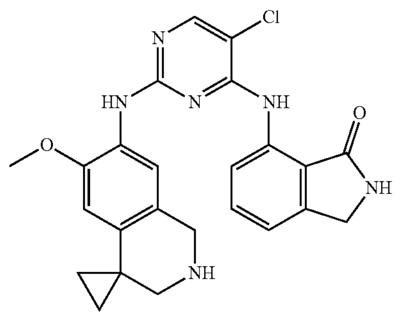 [SMILES: COc1cc2c(cc1Nc1ncc(Cl)c(Nc3cccc4c3C(=O)NC4)n1)CNCC21CC1] | 7-((5-chloro-2-((6'-methoxy-2',3'-dihydro-1'H-spiro[cyclopropane-1,4'-isoquinolin]-7'-yl)amino)pyrimidin-4-yl)amino)isoindolin-1-one |

-continued

| Compound I.D. | Structure | IUPAC Name |
|---|---|---|
| I-26 | 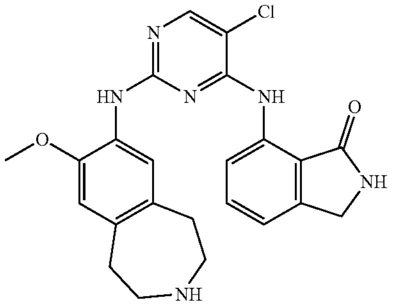 [SMILES: COc1cc2c(cc1Nc1ncc(Cl)c(Nc3cccc4c3C(=O)NC4)n1)CCNCC2] | 7-((5-chloro-2-((8-methoxy-2,3,4,5-tetrahydro-1H-benzo[d]azepin-7-yl)amino)pyrimidin-4-yl)amino)isoindolin-1-one |
| I-27 | 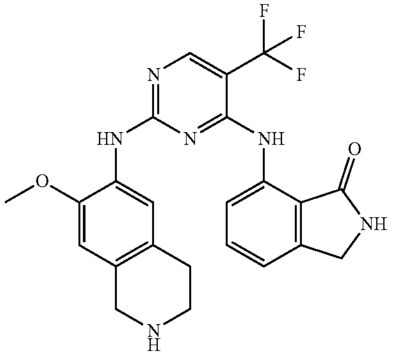 [SMILES: COc1cc2c(cc1Nc1ncc(C(F)(F)F)c(Nc3cccc4c3C(=O)NC4)n1)CCNC2] | 7-((5-chloro-2-((8-methoxy-2,3,4,5-tetrahydro-1H-benzo[d]azepin-7-yl)amino)pyrimidin-4-yl)amino)isoindolin-1-one |
| I-28 | 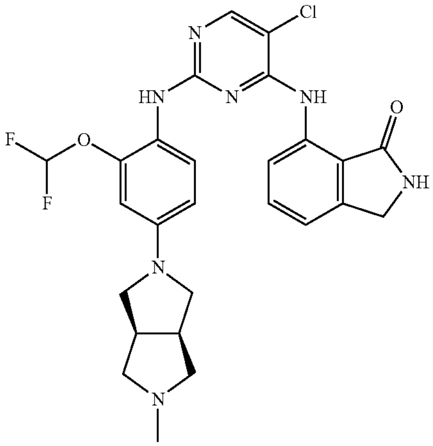 [SMILES: CN1C[C@@H]2CN(c3ccc(Nc4ncc(Cl)c(Nc5cccc6c5C(=O)NC6)n4)c(OC(F)F)c3)C[C@@H]2C1] | 7-((5-chloro-2-((2-(difluoromethoxy)-4-((3aR,6aS)-5-methylhexahydropyrrolo[3,4-c]pyrrol-2(1H)-yl)phenyl)amino)pyrimidin-4-yl)amino)isoindolin-1-one |
| I-29 | 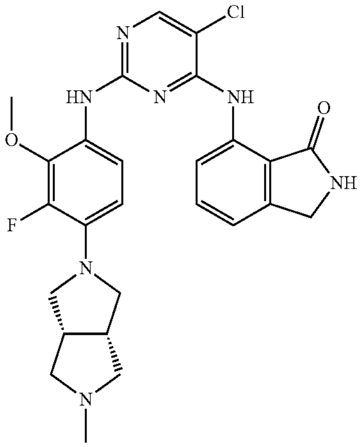 [SMILES: COc1c(Nc2ncc(Cl)c(Nc3cccc4c3C(=O)NC4)n2)ccc(N2C[C@H]3CN(C)C[C@H]3C2)c1F] | 7-((5-chloro-2-((3-fluoro-2-methoxy-4-((3aR,6aS)-5-methylhexahydropyrrolo[3,4-c]pyrrol-2(1H)-yl)phenyl)amino)pyrimidin-4-yl)amino)isoindolin-1-one |

-continued

| Compound I.D. | Structure | IUPAC Name |
| --- | --- | --- |
| I-30 | 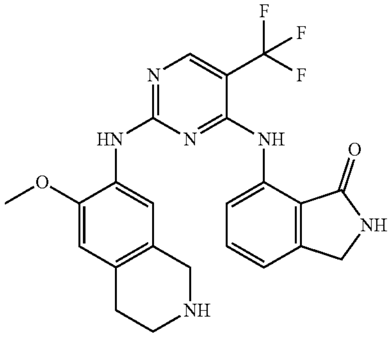 [SMILES: COc1cc2c(cc1Nc1ncc(C(F)(F)F)c(Nc3cccc4c3C(=O)NC4)n1)CNCC2] | 7-((2-((6-methoxy-1,2,3,4-tetrahydroisoquinolin-7-yl)amino)-5-(trifluoromethyl)pyrimidin-4-yl)amino)isoindolin-1-one |
| I-31 | 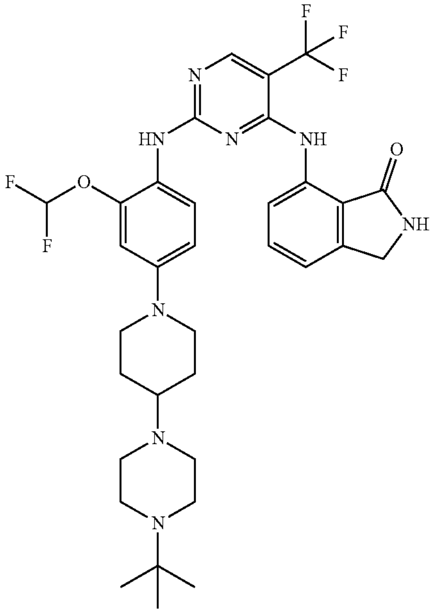 [SMILES: CC(C)(C)N1CCN(C2CCN(c3ccc(Nc4ncc(C(F)(F)F)c(Nc5cccc6c5C(=O)NC6)n4)c(OC(F)F)c3)CC2)CC1] | 7-((2-((4-(4-(4-(tert-butyl)piperazin-1-yl)piperidin-1-yl)-2-(difluoromethoxy)phenyl)amino)-5-(trifluoromethyl)pyrimidin-4-yl)amino)isoindolin-1-one |
| I-32 | 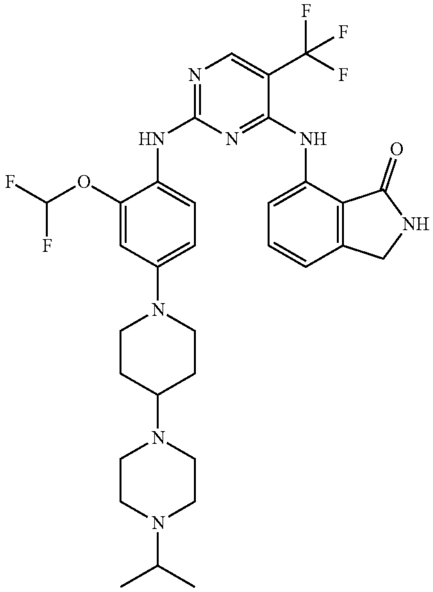 [SMILES: CC(C)N1CCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-isopropylpiperazin-1-yl)piperidin-1-yl)phenyl)amino)-5-(trifluoromethyl)pyrimidin-4-yl)amino)isoindolin-1-one |

-continued

| Compound I.D. | Structure | IUPAC Name |
|---|---|---|
| I-33 | 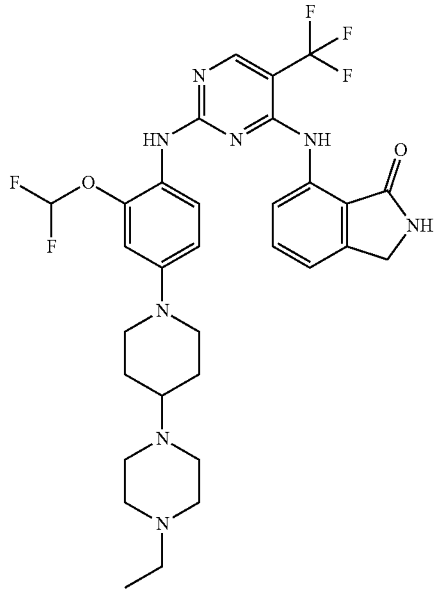 [SMILES: CCN1CCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-ethylpiperazin-1-yl)piperidin-1-yl)phenyl)amino)-5-(trifluoromethyl)pyrimidin-4-yl)amino)isoindolin-1-one |
| I-34 | 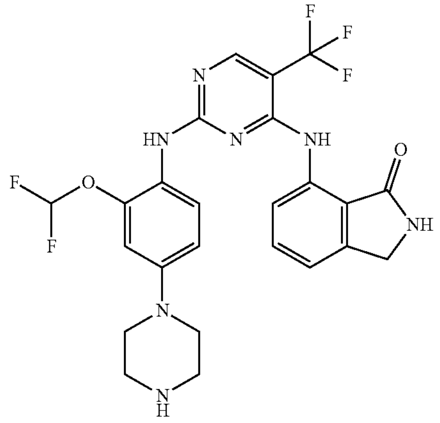 [SMILES: O=C1NCc2cccc(Nc3nc(Nc4ccc(N5CCNCC5)cc4OC(F)F)ncc3C(F)(F)F)c21] | 7-((2-((2-(difluoromethoxy)-4-(piperazin-1-yl)phenyl)amino)-5-(trifluoromethyl)pyrimidin-4-yl)amino)isoindolin-1-one |
| I-38 | 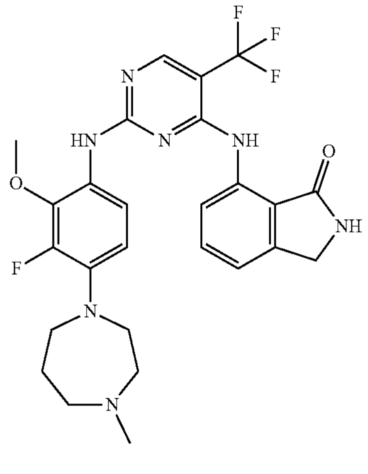 [SMILES: COc1c(Nc2ncc(C(F)(F)F)c(Nc3cccc4c3C(=O)NC4)n2)ccc(N2CCCN(C)CC2)c1F] | 7-((2-((3-fluoro-2-methoxy-4-(4-methyl-1,4-diazepan-1-yl)phenyl)amino)-5-(trifluoromethyl)pyrimidin-4-yl)amino)isoindolin-1-one |

-continued

| Compound I.D. | Structure | IUPAC Name |
|---|---|---|
| I-41 | 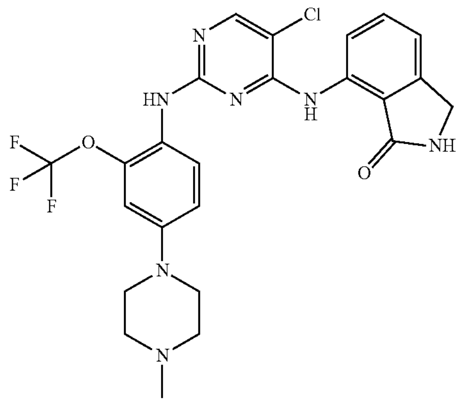 [SMILES: CN1CCN(c2ccc(Nc3ncc(Cl)c(Nc4cccc5c4C(=O)NC5)n3)c(OC(F)(F)F)c2)CC1] | 7-((5-chloro-2-((4-(4-methylpiperazin-1-yl)-2-(trifluoromethoxy)phenyl)amino) pyrimidin-4-yl)amino)isoindolin-1-one |
| I-44 | 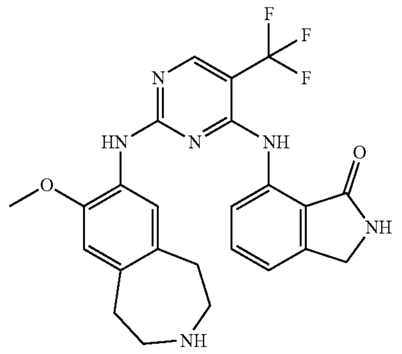 [SMILES: COc1cc2c(cc1Nc1ncc(C(F)(F)F)c(Nc3cccc4c3C(=O)NC4)n1)CCNCC2] | 7-((2-((8-methoxy-2,3,4,5-tetrahydro-1H-benzo[d]azepin-7-yl)amino)-5-(trifluoromethyl)pyrimidin-4-yl)amino)isoindolin-1-one |
| I-46 | 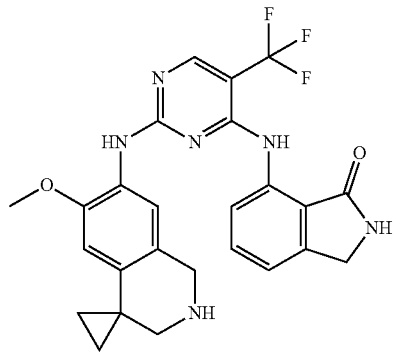 [SMILES: COc1cc2c(cc1Nc1ncc(C(F)(F)F)c(Nc3cccc4c3C(=O)NC4)n1)CNCC21CC1] | 7-((2-((6'-methoxy-2',3'-dihydro-1'H-spiro[cyclopropane-1,4'-isoquinolin]-7'-yl)amino)-5-(trifluoromethyl)pyrimidin-4-yl)amino)isoindolin-1-one |

-continued

| Compound I.D. | Structure | IUPAC Name |
| --- | --- | --- |
| I-48 | 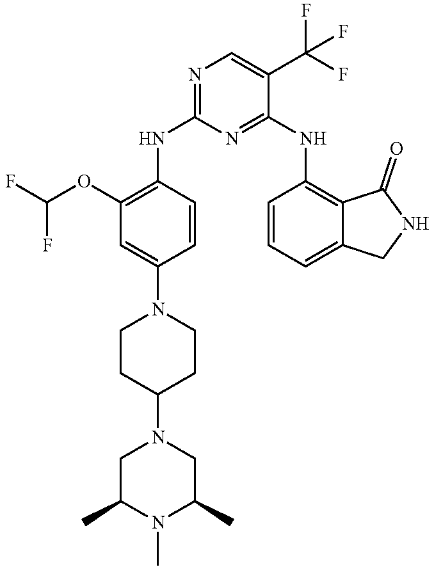 [SMILES: C[C@@H]1CN(C2CCN(c3ccc(Nc4ncc(C(F)(F)F)c(Nc5cccc6c5C(=O)NC6)n4)c(OC(F)F)c3)CC2)C[C@H](C)N1C] | 7-((2-((2-(difluoromethoxy)-4-(4-((3S,5R)-3,4,5-trimethylpiperazin-1-yl)piperidin-1-yl)phenyl)amino)-5-(trifluoromethyl)pyrimidin-4-yl)amino)isoindolin-1-one |
| I-49 | 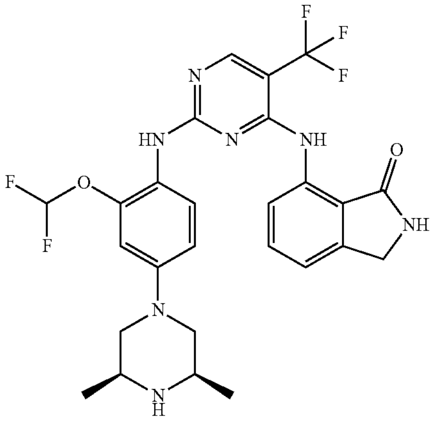 [SMILES: C[C@@H]1CN(c2ccc(Nc3ncc(C(F)(F)F)c(Nc4cccc5c4C(=O)NC5)n3)c(OC(F)F)c2)C[C@H](C)N1] | 7-((2-((2-(difluoromethoxy)-4-((3S,5R)-3,5-dimethylpiperazin-1-yl)phenyl)amino)-5-(trifluoromethyl)pyrimidin-4-yl)amino)isoindolin-1-one |
| I-50 | 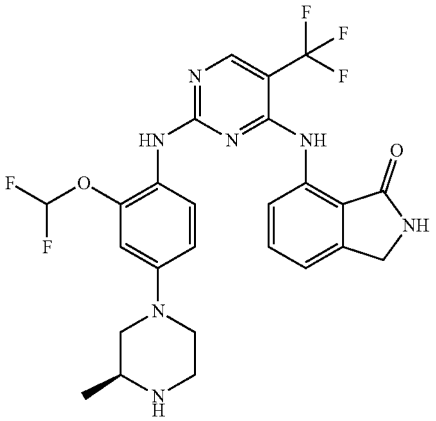 [SMILES: C[C@H]1CN(c2ccc(Nc3ncc(C(F)(F)F)c(Nc4cccc5c4C(=O)NC5)n3)c(OC(F)F)c2)CCN1] | (S)-7-((2-((2-(difluoromethoxy)-4-(3-methylpiperazin-1-yl)phenyl)amino)-5-(trifluoromethyl)pyrimidin-4-yl)amino)isoindolin-1-one |

-continued

| Compound I.D. | Structure | IUPAC Name |
|---|---|---|
| I-53 | 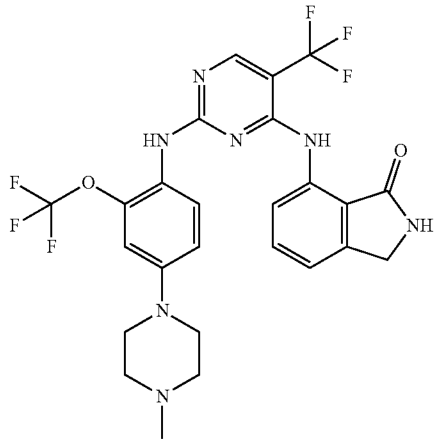 [SMILES: CN1CCN(c2ccc(Nc3ncc(C(F)(F)F)c(Nc4cccc5c4C(=O)NC5)n3)c(OC(F)(F)F)c2)CC1] | 7-((2-((4-(4-methylpiperazin-1-yl)-2-(trifluoromethoxy)phenyl)amino)-5-(trifluoromethyl)pyrimidin-4-yl)amino)isoindolin-1-one |
| I-54 | 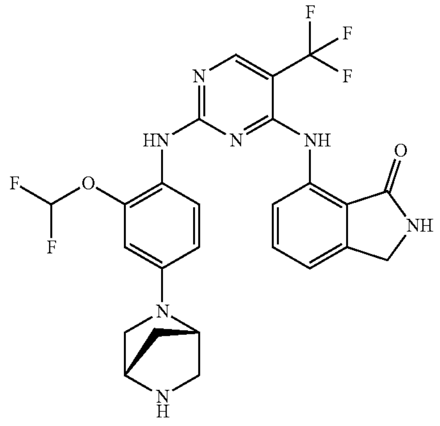 [SMILES: O=C1NCc2cccc(Nc3nc(Nc4ccc(N5C[C@@H]6C[C@H]5CN6)cc4OC(F)F)ncc3C(F)(F)F)c21] | 7-((2-((4-((1S,4S)-2,5-diazabicyclo[2.2.1]heptan-2-yl)-2-(difluoromethoxy)phenyl)amino)-5-(trifluoromethyl)pyrimidin-4-yl)amino)isoindolin-1-one |
| I-55 | 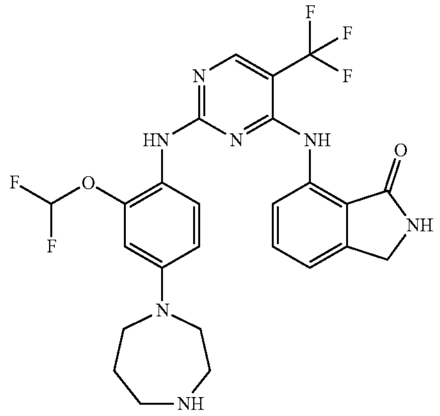 [SMILES: O=C1NCc2cccc(Nc3nc(Nc4ccc(N5CCCNCC5)cc4OC(F)F)ncc3C(F)(F)F)c21] | 7-((2-((4-(1,4-diazepan-1-yl)-2-(difluoromethoxy)phenyl)amino)-5-(trifluoromethyl)pyrimidin-4-yl)amino)isoindolin-1-one |

-continued

| Compound I.D. | Structure | IUPAC Name |
|---|---|---|
| I-57 | 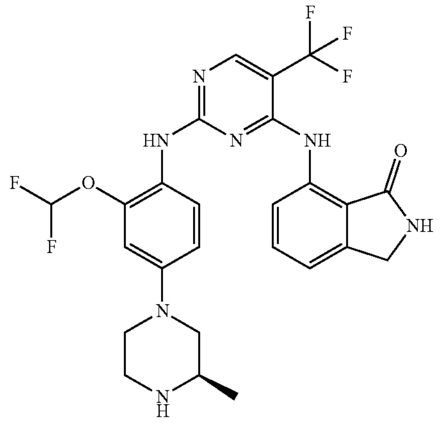 [SMILES: C[C@@H]1CN(c2ccc(Nc3ncc(C(F)(F)F)c(Nc4cccc5c4C(=O)NC5)n3)c(OC(F)F)c2)CCN1] | (R)-7-((2-((2-(difluoromethoxy)-4-(3-methylpiperazin-1-yl)phenyl)amino)-5-(trifluoromethyl)pyrimidin-4-yl)amino)isoindolin-1-one and |
| I-59 | 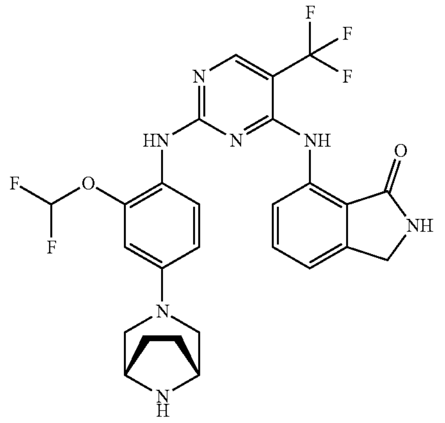 | 7-((2-((4-((1R,5S)-3,8-diazabicyclo[3.2.1]octan-3-yl)-2-(difluoromethoxy)phenyl)amino)-5-(trifluoromethyl)pyrimidin-4-yl)amino)isoindolin-1-one |
| I-64 | 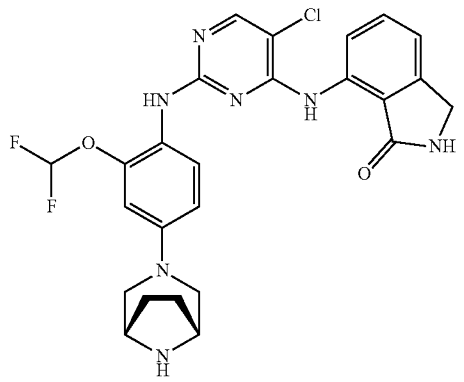 | 7-((2-((4-((1R,5S)-3,8-diazabicyclo[3.2.1]octan-3-yl)-2-(difluoromethoxy)phenyl)amino)-5-chloropyrimidin-4-yl)amino)isoindolin-1-one |

-continued

| Compound I.D. | Structure | IUPAC Name |
|---|---|---|
| I-67 | 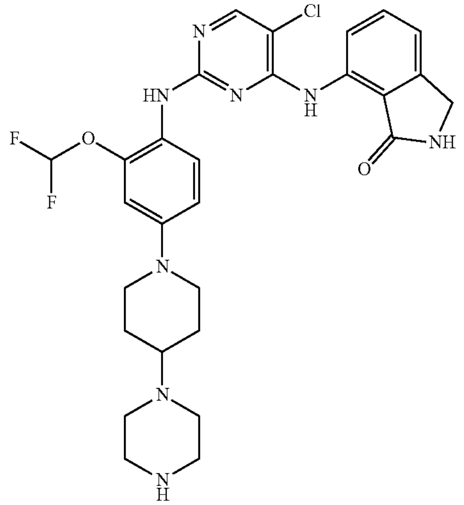 [SMILES: O=C1NCc2cccc(Nc3nc(Nc4ccc(N5CCC(N6CCNCC6)CC5)cc4OC(F)F)ncc3Cl)c21] | 7-((5-chloro-2-((2-(difluoromethoxy)-4-(4-(piperazin-1-yl)piperidin-1-yl)phenyl)amino)pyrimidin-4-yl)amino)isoindolin-1-one |
| I-68 | 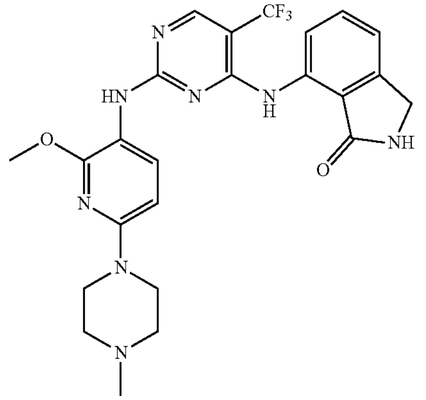 [SMILES: COc1nc(N2CCN(C)CC2)ccc1Nc1ncc(C(F)(F)F)c(Nc2cccc3c2C(=O)NC3)n1] | 7-((2-((2-methoxy-6-(4-methylpiperazin-1-yl)pyridin-3-yl)amino)-5-(trifluoromethyl)pyrimidin-4-yl)amino)isoindolin-1-one |
| I-69 | 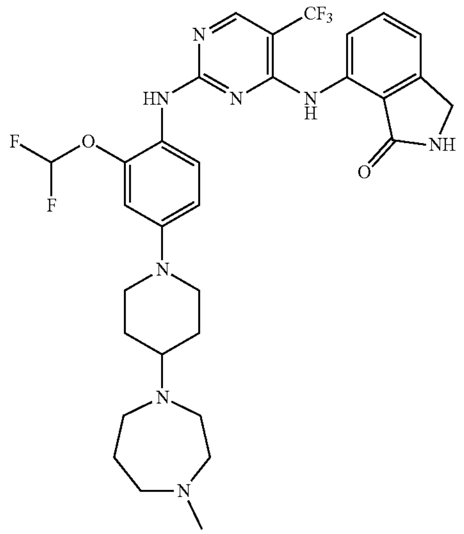 [SMILES: CN1CCCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-methyl-1,4-diazepan-1-yl)piperidin-1-yl)phenyl)amino)-5-(trifluoromethyl)pyrimidin-4-yl)amino)isoindolin-1-one |

-continued

| Compound I.D. | Structure | IUPAC Name |
|---|---|---|
| I-70 | 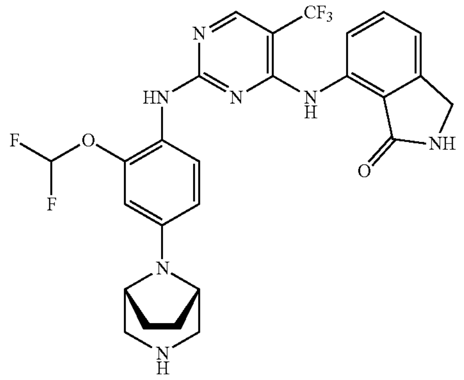 | 7-((2-((4-((1R,5S)-3,8-diazabicyclo[3.2.1]octan-8-yl)-2-(difluoromethoxy)phenyl)amino)-5-(trifluoromethyl)pyrimidin-4-yl)amino)isoindolin-1-one |
| I-73 | 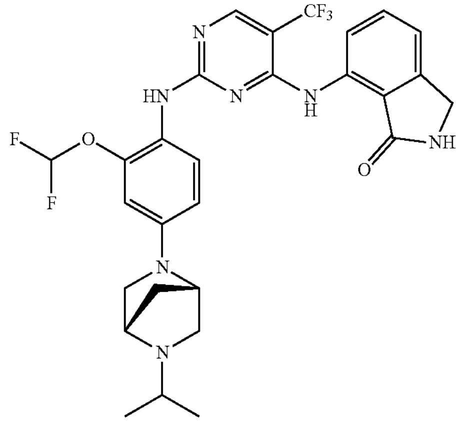 [SMILES: CC(C)N1C[C@@H]2C[C@H]1CN2c1ccc(Nc2ncc(C(F)(F)F)c(Nc3cccc4c3C(=O)NC4)n2)c(OC(F)F)c1] | 7-((2-((2-(difluoromethoxy)-4-((1S,4S)-5-isopropyl-2,5-diazabicyclo[2.2.1]heptan-2-yl)phenyl)amino)-5-(trifluoromethyl)pyrimidin-4-yl)amino)isoindolin-1-one |
| I-74 | 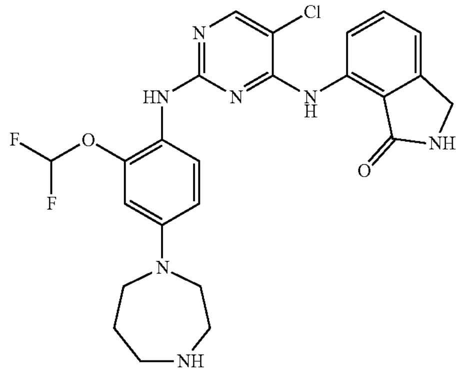 [SMILES: O=C1NCc2cccc(Nc3nc(Nc4ccc(N5CCCNCC5)cc4OC(F)F)ncc3Cl)c21] | 7-((2-((4-(1,4-diazepan-1-yl)-2-(difluoromethoxy)phenyl)amino)-5-chloropyrimidin-4-yl)amino)isoindolin-1-one |

-continued
| Compound I.D. | Structure | IUPAC Name |
|---|---|---|
| I-76 | 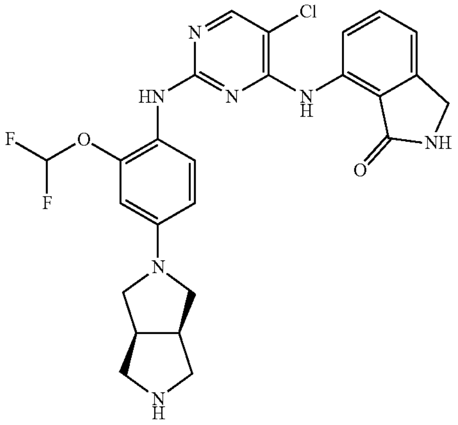 [SMILES: O=C1NCc2cccc(Nc3nc(Nc4ccc(N5C[C@H]6CNC[C@H]6C5)cc4OC(F)F)ncc3Cl)c21] | 7-((5-chloro-2-((2-(difluoromethoxy)-4-((3aR,6aS)-hexahydropyrrolo[3,4-c]pyrrol-2(1H)-yl)phenyl)amino)pyrimidin-4-yl)amino)isoindolin-1-one |
| I-78 | 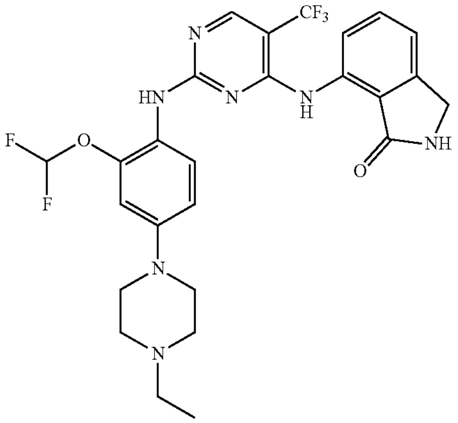 [SMILES: CCN1CCN(c2ccc(Nc3ncc(C(F)(F)F)c(Nc4cccc5c4C(=O)NC5)n3)c(OC(F)F)c2)CC1] | 7-((2-((2-(difluoromethoxy)-4-(4-ethylpiperazin-1-yl)phenyl)amino)-5-(trifluoromethyl)pyrimidin-4-yl)amino)isoindolin-1-one |
| I-83 | 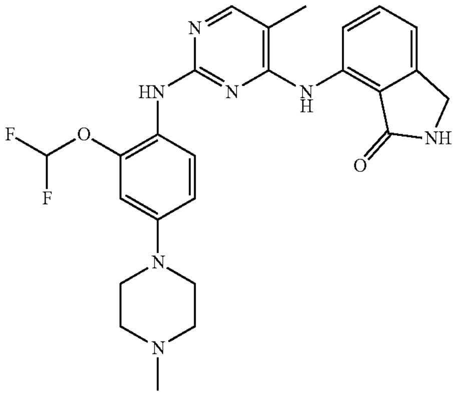 [SMILES: Cc1cnc(Nc2ccc(N3CCN(C)CC3)cc2OC(F)F)nc1Nc1cccc2c1C(=O)NC2] | 7-((2-((2-(difluoromethoxy)-4-(4-methylpiperazin-1-yl)phenyl)amino)-5-methylpyrimidin-4-yl)amino)isoindolin-1-one and |

-continued

| Compound I.D. | Structure | IUPAC Name |
|---|---|---|
| I-84 | 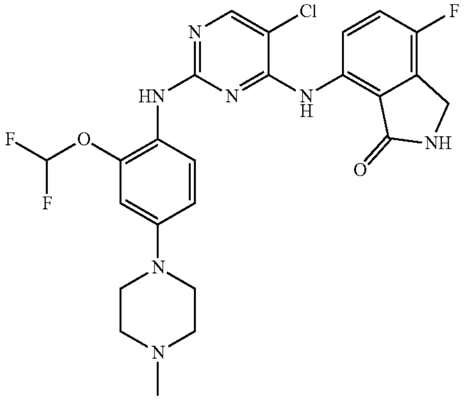 [SMILES: CN1CCN(c2ccc(Nc3ncc(Cl)c(Nc4ccc(F)c5c4C(=O)NC5)n3)c(OC(F)F)c2)CC1] | 7-((5-chloro-2-((2-(difluoromethoxy)-4-(4-methylpiperazin-1-yl)phenyl)amino)pyrimidin-4-yl)amino)-4-fluoroisoindolin-1-one |

or a pharmaceutically acceptable salt, solvate and/or prodrug thereof.

In some embodiments, the compounds of Formula I are selected from:

| Compound I.D. | Structure | IUPAC Name |
|---|---|---|
| I-12 | 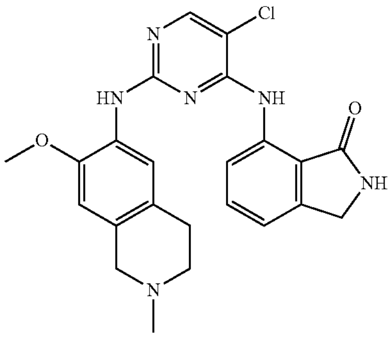 [SMILES: COc1cc2c(cc1Nc1ncc(Cl)c(Nc3cccc4c3C(=O)NC4)n1)CCN(C)C2] | 7-((5-chloro-2-((7-methoxy-2-methyl-1,2,3,4-tetrahydroisoquinolin-6-yl)amino)pyrimidin-4-yl)amino)isoindolin-1-one |
| I-17 | 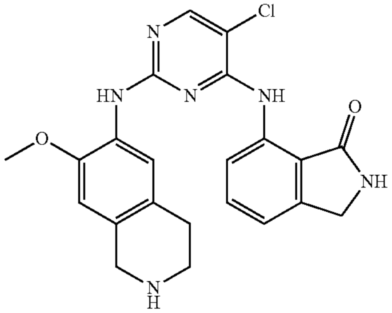 [SMILES: COc1cc2c(cc1Nc1ncc(Cl)c(Nc3cccc4c3C(=O)NC4)n1)CCNC2] | 7-((5-chloro-2-((7-methoxy-1,2,3,4-tetrahydroisoquinolin-6-yl)amino)pyrimidin-4-yl)amino)isoindolin-1-one |

-continued

| Compound I.D. | Structure | IUPAC Name |
| --- | --- | --- |
| I-18 | 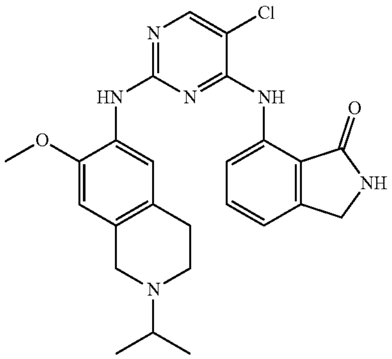 [SMILES: COc1cc2c(cc1Nc1ncc(Cl)c(Nc3cccc4c3C(=O)NC4)n1)CCN(C(C)C)C2] | 7-((5-chloro-2-((2-isopropyl-7-methoxy-1,2,3,4-tetrahydroisoquinolin-6-yl)amino)pyrimidin-4-yl)amino)isoindolin-1-one |
| I-24 | 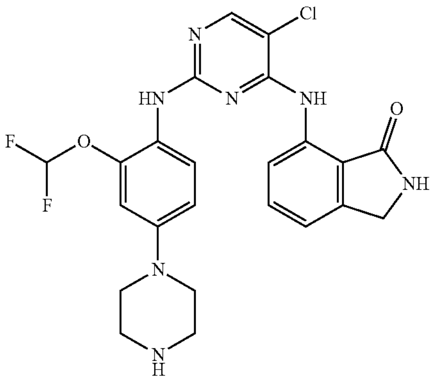 [SMILES: O=C1NCc2cccc(Nc3nc(Nc4ccc(N5CCNCC5)cc4OC(F)F)ncc3Cl)c21] | 7-((5-chloro-2-((2-(difluoromethoxy)-4-(piperazin-1-yl)phenyl)amino)pyrimidin-4-yl)amino)isoindolin-1-one |
| I-27 | 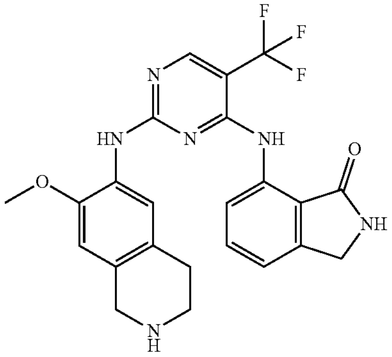 [SMILES: COc1cc2c(cc1Nc1ncc(C(F)(F)F)c(Nc3cccc4c3C(=O)NC4)n1)CCNC2] | 7-((5-chloro-2-((8-methoxy-2,3,4,5-tetrahydro-1H-benzo[d]azepin-7-yl)amino)pyrimidin-4-yl)amino)isoindolin-1-one |
| I-34 | 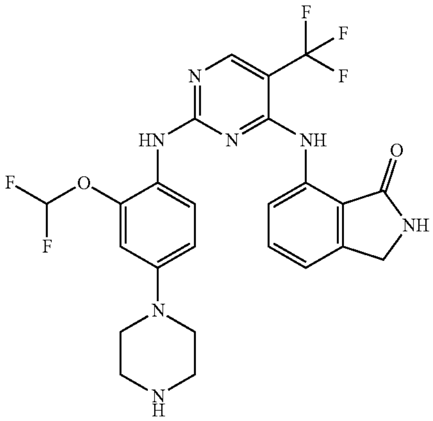 [SMILES: O=C1NCc2cccc(Nc3nc(Nc4ccc(N5CCNCC5)cc4OC(F)F)ncc3C(F)(F)F)c21] | 7-((2-((2-(difluoromethoxy)-4-(piperazin-1-yl)phenyl)amino)-5-(trifluoromethyl)pyrimidin-4-yl)amino)isoindolin-1-one |

-continued

| Compound I.D. | Structure | IUPAC Name |
|---|---|---|
| I-46 | 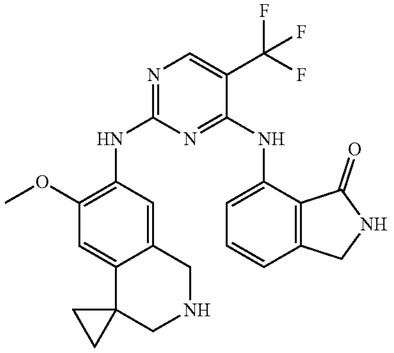 [SMILES: COc1cc2c(cc1Nc1ncc(C(F)(F)F)c(Nc3cccc4c3C(=O)NC4)n1)CNCC21CC1] | 7-((2-((6'-methoxy-2',3'-dihydro-1'H-spiro[cyclopropane-1,4'-isoquinolin]-7'-yl)amino)-5-(trifluoromethyl)pyrimidin-4-yl)amino)isoindolin-1-one |
| I-49 | 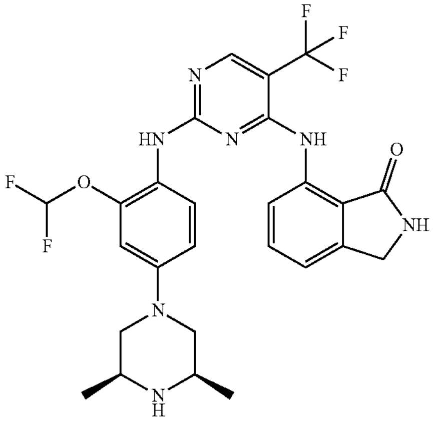 [SMILES: C[C@@H]1CN(c2ccc(Nc3ncc(C(F)(F)F)c(Nc4cccc5c4C(=O)NC5)n3)c(OC(F)F)c2)C[C@H](C)N1] | 7-((2-((2-(difluoromethoxy)-4-((3S,5R)-3,5-dimethylpiperazin-1-yl)phenyl)amino)-5-(trifluoromethyl)pyrimidin-4-yl)amino)isoindolin-1-one |
| I-50 | 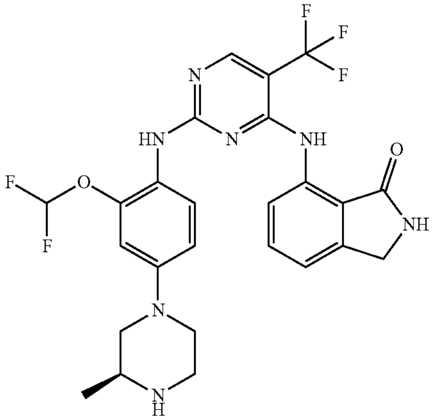 [SMILES: C[C@H]1CN(c2ccc(Nc3ncc(C(F)(F)F)c(Nc4cccc5c4C(=O)NC5)n3)c(OC(F)F)c2)CCN1] | (S)-7-((2-((2-(difluoromethoxy)-4-(3-methylpiperazin-1-yl)phenyl)amino)-5-(trifluoromethyl)pyrimidin-4-yl)amino)isoindolin-1-one |

-continued

| Compound I.D. | Structure | IUPAC Name |
| --- | --- | --- |
| I-54 | 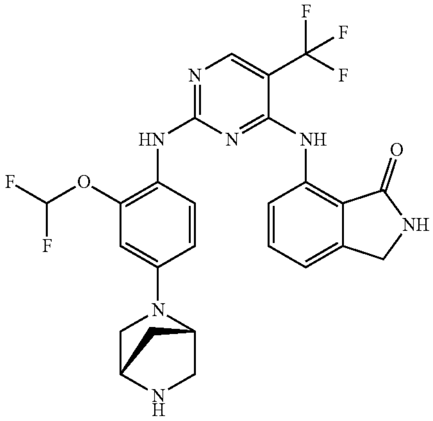 [SMILES: O=C1NCc2cccc(Nc3nc(Nc4ccc(N5C[C@@H]6C[C@H]5CN6)cc4OC(F)F)ncc3C(F)(F)F)c21] | 7-((2-((4-((1S,4S)-2,5-diazabicyclo[2.2.1]heptan-2-yl)-2-(difluoromethoxy)phenyl)amino)-5-(trifluoromethyl)pyrimidin-4-yl)amino)isoindolin-1-one |
| I-55 | 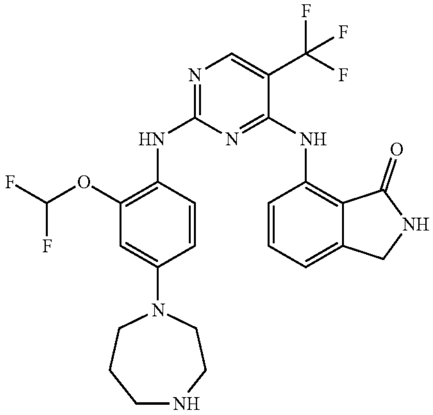 [SMILES: O=C1NCc2cccc(Nc3nc(Nc4ccc(N5CCCNCC5)cc4OC(F)F)ncc3C(F)(F)F)c21] | 7-((2-((4-(1,4-diazepan-1-yl)-2-(difluoromethoxy)phenyl)amino)-5-(trifluoromethyl)pyrimidin-4-yl)amino)isoindolin-1-one |
| I-57 | 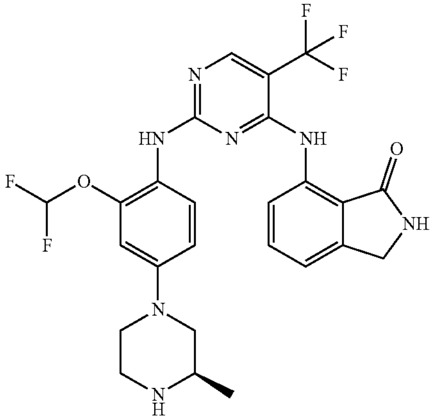 [SMILES: C[C@@H]1CN(c2ccc(Nc3ncc(C(F)(F)F)c(Nc4cccc5c4C(=O)NC5)n3)c(OC(F)F)c2)CCN1] | (R)-7-((2-((2-(difluoromethoxy)-4-(3-methylpiperazin-1-yl)phenyl)amino)-5-(trifluoromethyl)pyrimidin-4-yl)amino)isoindolin-1-one and |

-continued
| Compound I.D. | Structure | IUPAC Name |
|---|---|---|
| I-59 | 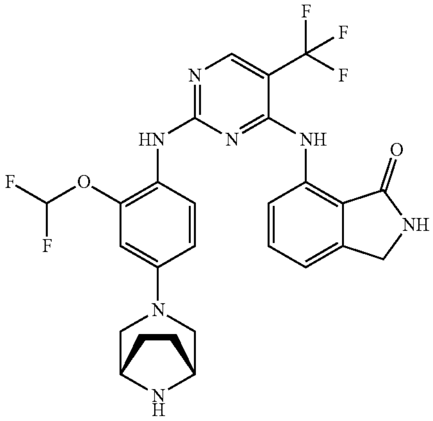 | 7-((2-((4-((1R,5S)-3,8-diazabicyclo[3.2.1]octan-3-yl)-2-(difluoromethoxy)phenyl)amino)-5-(trifluoromethyl)pyrimidin-4-yl)amino)isoindolin-1-one |
| I-64 | 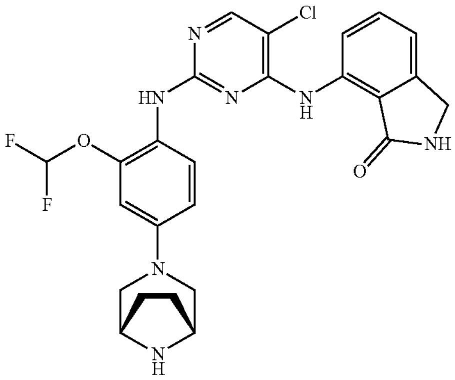 | 7-((2-((4-((1R,5S)-3,8-diazabicyclo[3.2.1]octan-3-yl)-2-(difluoromethoxy)phenyl)amino)-5-chloropyrimidin-4-yl)amino)isoindolin-1-one |
| I-67 | 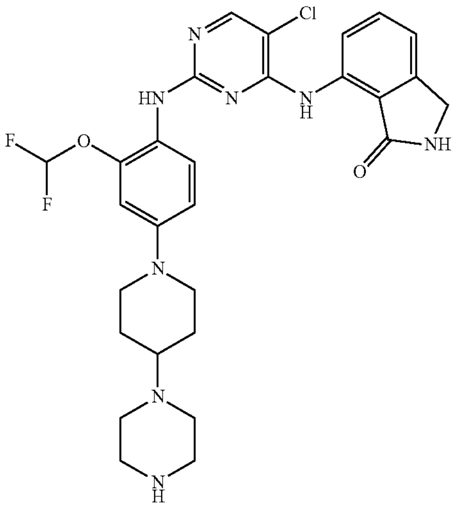 [SMILES: O=C1NCc2cccc(Nc3nc(Nc4ccc(N5CCC(N6CCNCC6)CC5)cc4OC(F)F)ncc3Cl)c21] | 7-((5-chloro-2-((2-(difluoromethoxy)-4-(4-(piperazin-1-yl)piperidin-1-yl)phenyl)amino)pyrimidin-4-yl)amino)isoindolin-1-one |

-continued

| Compound I.D. | Structure | IUPAC Name |
|---|---|---|
| I-68 | 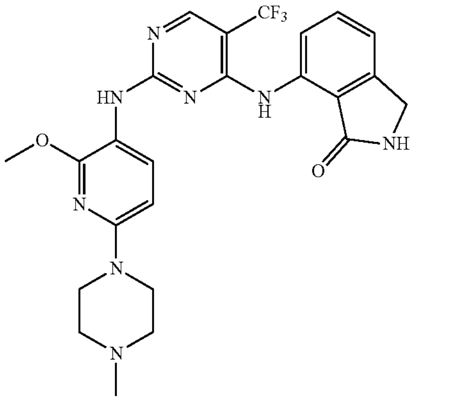 [SMILES: COc1nc(N2CCN(C)CC2)ccc1Nc1ncc(C(F)(F)F)c(Nc2cccc3c2C(=O)NC3)n1] | 7-((2-((2-methoxy-6-(4-methylpiperazin-1-yl)pyridin-3-yl)amino)-5-(trifluoromethyl)pyrimidin-4-yl)amino)isoindolin-1-one |
| I-69 | 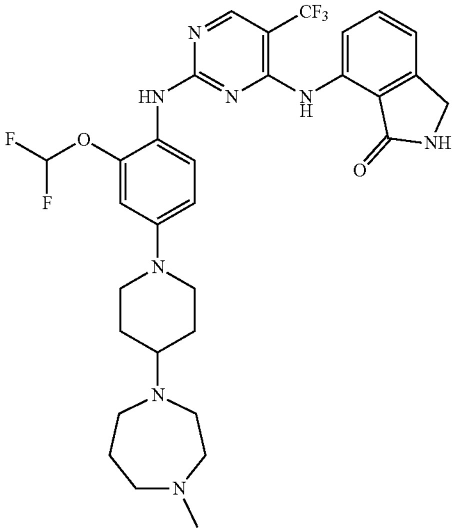 [SMILES: CN1CCCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-methyl-1,4-diazepan-1-yl)piperidin-1-yl)phenyl)amino)-5-(trifluoromethyl)pyrimidin-4-yl)amino)isoindolin-1-one |
| I-70 | 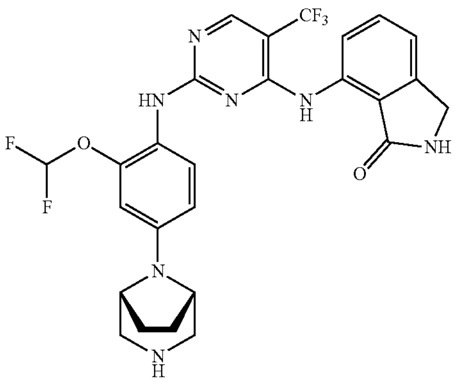 | 7-((2-((4-((1R,5S)-3,8-diazabicyclo[3.2.1]octan-8-yl)-2-(difluoromethoxy)phenyl)amino)-5-(trifluoromethyl)pyrimidin-4-yl)amino)isoindolin-1-one |

-continued

| Compound I.D. | Structure | IUPAC Name |
|---|---|---|
| I-73 | 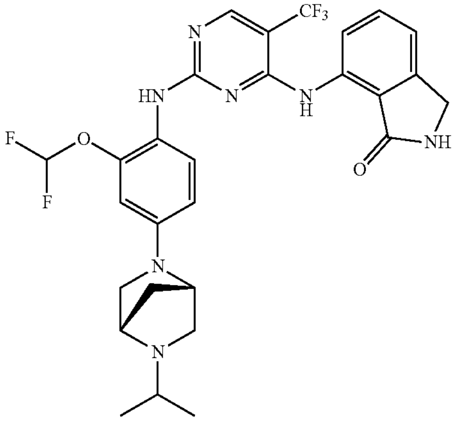 [SMILES: CC(C)N1C[C@@H]2C[C@H]1CN2c1ccc(Nc2ncc(C(F)(F)F)c(Nc3cccc4c3C(=O)NC4)n2)c(OC(F)F)c1] | 7-((2-((2-(difluoromethoxy)-4-((1S,4S)-5-isopropyl-2,5-diazabicyclo[2.2.1]heptan-2-yl)phenyl)amino)-5-(trifluoromethyl)pyrimidin-4-yl)amino)isoindolin-1-one |
| I-74 | 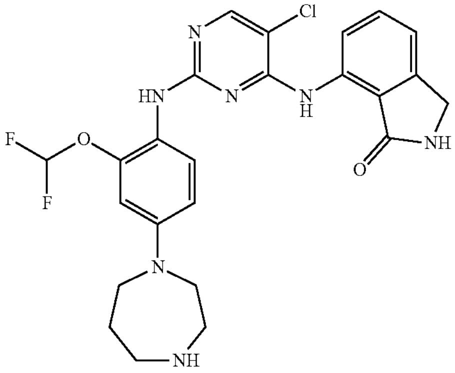 [SMILES: O=C1NCc2cccc(Nc3nc(Nc4ccc(N5CCCNCC5)cc4OC(F)F)ncc3Cl)c21] | 7-((2-((4-(1,4-diazepan-1-yl)-2-(difluoromethoxy)phenyl)amino)-5-chloropyrimidin-4-yl)amino)isoindolin-1-one |
| I-76 | 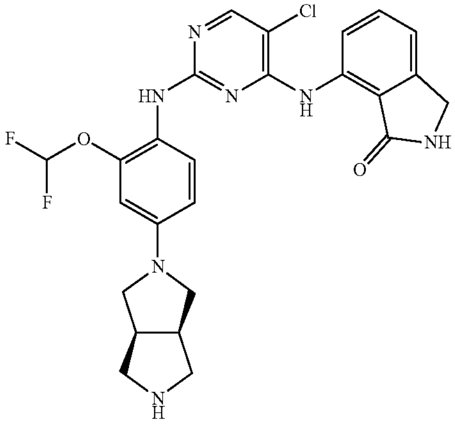 [SMILES: O=C1NCc2cccc(Nc3nc(Nc4ccc(N5C[C@H]6CNC[C@H]6C5)cc4OC(F)F)ncc3Cl)c21] | 7-((5-chloro-2-((2-(difluoromethoxy)-4-((3aR,6aS)-hexahydropyrrolo[3,4-c]pyrrol-2(1H)-yl)phenyl)amino)pyrimidin-4-yl)amino)isoindolin-1-one |

-continued
| Compound I.D. | Structure | IUPAC Name |
|---|---|---|
| I-78 | 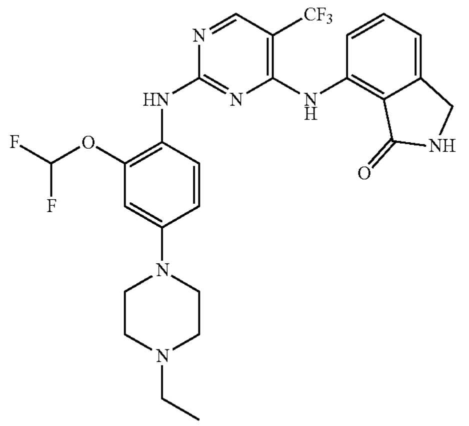 [SMILES: CCN1CCN(c2ccc(Nc3ncc(C(F)(F)F)c(Nc4cccc5c4C(=O)NC5)n3)c(OC(F)F)c2)CC1] | 7-((2-((2-(difluoromethoxy)-4-(4-ethylpiperazin-1-yl)phenyl)amino)-5-(trifluoromethyl)pyrimidin-4-yl)amino)isoindolin-1-one |
| I-83 | 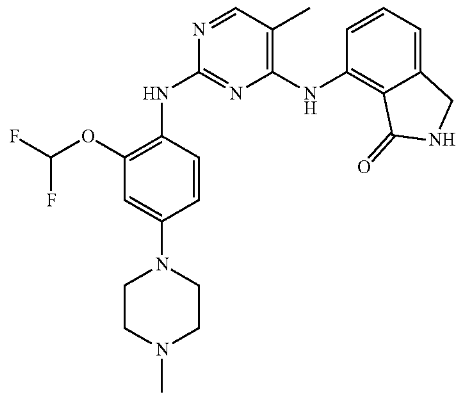 [SMILES: Cc1cnc(Nc2ccc(N3CCN(C)CC3)cc2OC(F)F)nc1Nc1cccc2c1C(=O)NC2] | 7-((2-((2-(difluoromethoxy)-4-(4-methylpiperazin-1-yl)phenyl)amino)-5-methylpyrimidin-4-yl)amino)isoindolin-1-one and |
| I-84 | 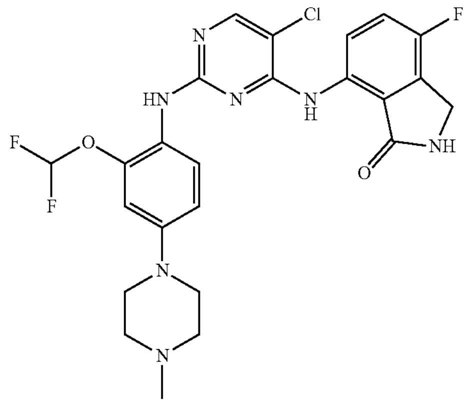 [SMILES: CN1CCN(c2ccc(Nc3ncc(Cl)c(Nc4ccc(F)c5c4C(=O)NC5)n3)c(OC(F)F)c2)CC1] | 7-((5-chloro-2-((2-(difluoromethoxy)-4-(4-methylpiperazin-1-yl)phenyl)amino)pyrimidin-4-yl)amino)-4-fluoroisoindolin-1-one | or a pharmaceutically acceptable salt, solvate and/or prodrug thereof.

The present application further includes compounds of Formula I-A, or a pharmaceutically acceptable salt, solvate and/or prodrug thereof:

(I-A)

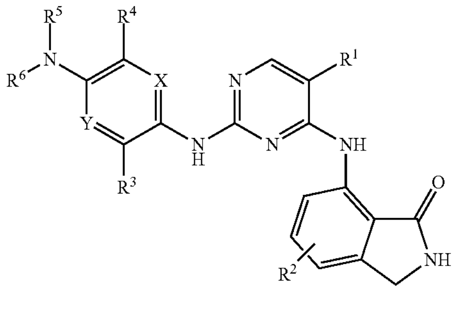

wherein $R^1$ is selected from H, halo, $C_{1-4}$alkyl, $OC_{1-4}$alkyl, $C_{1-4}$haloalkyl, $OC_{1-4}$haloalkyl, CN, $C_{1-4}$hydroxyalkyl and $OC_{1-4}$hydroxyalkyl;

$R^2$ is selected from H, halo, CN, $C_{1-4}$alkyl, $C_{1-4}$haloalkyl, $OC_{1-4}$alkyl and $OC_{1-4}$haloalkyl;

$R^3$ is selected from H, halo, $C_{1-4}$alkyl, $OC_{1-4}$alkyl, $C_{1-4}$haloalkyl, $OC_{1-4}$haloalkyl, X is selected from $CR^a$ and N;

Y is selected from $CR^b$ and N;

$R^a$ and $R^b$ are independently selected from H, halo, $C_{1-4}$alkyl and $C_{1-4}$haloalkyl;

$R^4$ is selected from H, halo, CN, $C_{1-4}$alkyl, $C_{1-4}$haloalkyl, $OC_{1-4}$alkyl and $OC_{1-4}$haloalkyl;

$R^5$ is selected from H, $C_{1-6}$alkyl, $C_{3-10}$cycloalkyl, $C_{3-10}$heterocycloalkyl, $C_{1-6}$alkylene$C_{3-10}$cycloalkyl, $C_{1-6}$alkylene$C_{3-10}$heterocycloalkyl, $C_{1-6}$alkylalkyleneOR$^8$, and $C_{1-6}$alkylalkyleneNR$^8$R$^9$, and all alkyl, alkylene, heterocycloalkyl and cycloalkyl groups of $R^5$ are optionally substituted with one or more of halo, $C_{1-6}$alkyl and $C_{1-6}$haloalkyl;

$R^6$ is selected from H, $C_{1-6}$alkyl and $C_{1-6}$haloalkyl; or $R^5$ and $R^6$ are joined to form, together with the atom therebetween, $C_3$-12heterocycloalkyl, optionally containing one additional heteromoiety selected from $NR^{10}$, O, S, S(O) and $SO_2$, and optionally substituted with one or more substituents selected from halo, OH, =O, $C_{1-6}$alkyl, $C_{3-6}$cycloalkyl, $C_{3-6}$heterocycloalkyl, $C_{1-6}$alkylene$C_{3-6}$cycloalkyl, $C_{1-6}$alkylene$C_{3-6}$heterocycloalkyl, NH($C_{1-6}$alkyl), N($C_{1-6}$alkyl)($C_{1-6}$alkyl), $SC_{1-6}$alkyl, S(O)$C_{1-6}$alkyl and $SO_2C_{1-6}$alkyl, wherein all alkyl, alkylene, cycloalkyl and heterocycloalkyl, groups of the optional substituents on the $C_{4-12}$heterocycloalkyl formed by $R^5$ and $R^6$ are also optionally substituted with one or more of halo, $C_{1-6}$alkyl, $OC_{1-6}$alkyl, $C_{1-6}$haloalkyl and $OC_{1-6}$haloalkyl; and $R^8$, $R^9$, and $R^{10}$ are independently selected from H, $C_{1-6}$alkyl and $C_{1-6}$haloalkyl.

The present application also includes compounds of Formula I-B, or a pharmaceutically acceptable salt, solvate and/or prodrug thereof:

(I-B)

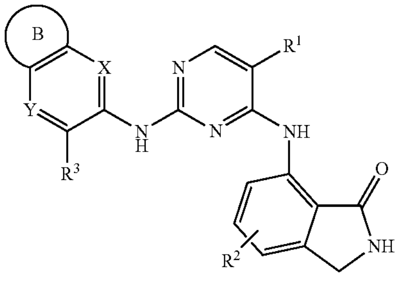

wherein $R^1$ is selected from H, halo, $C_{1-4}$alkyl, $OC_{1-4}$alkyl, $C_{1-4}$haloalkyl, $OC_{1-4}$haloalkyl, CN, $C_{1-4}$hydroxyalkyl and $OC_{1-4}$hydroxyalkyl;

$R^2$ is selected from H, halo, CN, $C_{1-4}$alkyl, $C_{1-4}$haloalkyl, $OC_{1-4}$alkyl and $OC_{1-4}$haloalkyl;

$R^3$ is selected from H, halo, $C_{1-4}$alkyl, $OC_{1-4}$alkyl, $C_{1-4}$haloalkyl, $OC_{1-4}$haloalkyl, X is selected from $CR^a$ and N;

Y is selected from $CR^b$ and N;

$R^a$ and $R^b$ are independently selected from H, halo, $C_{1-4}$alkyl and $C_{1-4}$haloalkyl; and ring B is selected from $C_{3-12}$cycloalkyl and $C_{3-12}$heterocycloalkyl, wherein the ring B is optionally substituted with one or more substituents selected from halo, =O, OH, $C_{1-6}$alkyl, $C_{3-6}$cycloalkyl, aryl, $C_{5-6}$heteroaryl, $C_{3-6}$heterocycloalkyl, $C_{1-6}$alkylene$C_{3-6}$cycloalkyl, $C_{1-6}$alkylenearyl, $C_{1-6}$alkylene$C_{5-6}$heteroaryl, $C_{1-6}$alkylene$C_{3-6}$heterocycloalkyl, $OC_{1-6}$alkyl, $OC_{1-6}$alkyleneOC$_{1-6}$alkyl, NH($C_{1-6}$alkyl), N($C_{1-6}$alkyl)($C_{1-6}$alkyl), $SC_{1-6}$alkyl, S(O)$C_{1-6}$alkyl and $SO_2C_{1-6}$alkyl, wherein all alkyl, alkylene, cycloalkyl, heterocycloalkyl, aryl and heteroaryl groups of the optional substituents on the ring B are also optionally substituted with one or more of halo, $C_{1-6}$alkyl, $OC_{1-6}$alkyl, $C_{1-6}$haloalkyl and $OC_{1-6}$haloalkyl.

The embodiments for $R^1$-$R^{10}$, $R^a$, $R^b$, X, Y and ring B described above for compounds of Formula I also apply to the compounds of Formula I-A and I-B.

The compounds of the present application are suitably formulated in a conventional manner into compositions using one or more carriers. Accordingly, the present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier.

The compounds of the application may be administered to a subject in a variety of forms depending on the selected route of administration, as will be understood by those skilled in the art. The compounds of the application may be administered, for example, by oral, parenteral, buccal, sublingual, nasal, rectal, patch, pump (for periodic or continuous delivery) or transdermal administration and the pharmaceutical compositions formulated accordingly. Conventional procedures and ingredients for the selection and preparation of suitable compositions are described, for example, in Remington's Pharmaceutical Sciences (2000-

20th edition) and in The United States Pharmacopeia: The National Formulary (USP 24 NF19) published in 1999.

Parenteral administration includes intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

Compounds of the application may be orally administered, for example, with an inert diluent or with an assimilable edible carrier, they may be enclosed in hard- or soft-shell gelatin capsules, they may be compressed into tablets, or they may be incorporated directly with the food of the diet. For oral therapeutic administration, the compounds may be incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the compounds of the application are protected with differentially degradable coatings, such as by microencapsulation, multiple coatings, etc. Liposome delivery systems include, for example, small unilamellar vesicles, large unilamellar vesicles and multilamellar vesicles. Liposomes can be formed from a variety of phospholipids, such as cholesterol, stearylamine or phosphatidylcholines. For oral administration in a capsule form, useful carriers or diluents include lactose and dried corn starch.

Liquid preparations for oral administration may take the form of, for example, solutions, syrups or suspensions, or they are suitably presented as a dry product for constitution with water or other suitable vehicle before use. When aqueous suspensions and/or emulsions are administered orally, the compounds of the application are suitably suspended or dissolved in an oily phase that is combined with emulsifying and/or suspending agents. If desired, certain sweetening and/or flavoring and/or coloring agents may be added. Such liquid preparations for oral administration may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

Compounds of the application may also be administered parenterally. Solutions of compounds of the application can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

The compounds of the application may be formulated for parenteral administration by injection, including using conventional catheterization techniques or infusion. Formulations for injection may be presented in unit dosage form, e.g., in ampules or in multi-dose containers, with an added preservative. The compositions may take such forms as sterile suspensions, solutions or emulsions in oily or aqueous vehicles, and may contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

Compositions for nasal administration may conveniently be formulated as aerosols, drops, gels and powders.

For intranasal administration or administration by inhalation, the compounds of the application are conveniently delivered in the form of a solution, dry powder formulation or suspension from a pump spray container that is squeezed or pumped by the subject patient or as an aerosol spray presentation from a pressurized container or a nebulizer. Aerosol formulations typically comprise a solution or fine suspension of the compounds of the application in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of compounds of the application and a suitable powder base such as lactose or starch. The aerosol dosage forms can also take the form of a pump-atomizer.

Compositions suitable for buccal or sublingual administration include tablets, lozenges, and pastilles, wherein the compounds of the application are formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: *Remington's Pharmaceutical Sciences,* 16th Ed., Mack Publishing, Easton, P A, 1980, pp. 1530-1533 for further discussion of suppository dosage forms.

Compounds of the application may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The compounds of the application including pharmaceutically acceptable salts, solvates and prodrugs thereof are suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient (one or more compounds of the application), and from about 1 wt % to about 99.95 wt % or about 30 wt % to about 99.90 wt % of a pharmaceutically acceptable carrier, all percentages by weight being based on the total composition.

Compounds of the application may be used alone or in combination with other known agents useful for treating diseases, disorders or conditions treatable by inhibiting NUAK2 and/or NUAK1. When used in combination with other agents useful in treating diseases, disorders or conditions that are treatable by inhibiting NUAK2 and/or NUAK1, it is an embodiment that the compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In some embodiments, compounds of the present application are administered with another therapeutic agent simultaneously or sequentially in separate unit dosage forms or together in a single unit dosage form. Accordingly, the present application provides a single unit dosage form comprising one or more compounds of the application (e.g. a compound of Formula I), an additional therapeutic agent, and a pharmaceutically acceptable carrier.

The dosage of compounds of the application can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compounds of the application may be administered initially in a suitable dosage that may be adjusted as required, depending on the clinical response. Dosages will generally be selected to maintain a serum level of compounds of the application from about 0.01 μg/cc to about 1000 μg/cc, or about 0.1 μg/cc to about 100 μg/cc. As a representative example, oral dosages of one or more compounds of the application will range between about 0.05 mg per day to about 1000 mg per day for an adult, suitably about 0.1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or about 0.1 mg/kg to about 1 mg/kg. Compounds of the application may be administered in a single daily, weekly or monthly dose or the total daily dose may be divided into two, three or four daily doses.

To be clear, in the above, the term "a compound" also includes embodiments wherein one or more compounds are referenced. Likewise, the term "compounds of the application" also includes embodiments wherein only one compound is referenced.

III. METHODS AND USES

The compounds of the application have been shown to be capable of inhibiting or blocking NUAK2 and/or NUAK1 in cells. The compounds have also been shown to inhibit tumor cell growth and to inhibit the localization of YAP/TAZ to the nucleus of a cell.

Accordingly, the present application includes a method of inhibiting NUAK2 and/or NUAK1, in a cell, either in a biological sample or in a subject, comprising administering an effective amount of one or more compounds of the application to the cell. The application also includes a use of one or more compounds of the application for inhibiting NUAK2 and/or NUAK1 in a cell as well as a use of one or more compounds of the application for the preparation of a medicament for inhibiting NUAK2 and/or NUAK1 in a cell. The application further includes one or more compounds of the application for use in inhibiting NUAK2 and/or NUAK1.

As the compounds of the application have been shown to inhibit NUAK2 and/or NUAK1, the compounds of the application are useful for treating diseases, disorders or conditions by inhibiting NUAK2 and/or NUAK1. Therefore, the compounds of the present application are useful as medicaments. Accordingly, the present application includes one or more compounds of the application for use as a medicament.

The present application also includes a method of treating a disease, disorder or condition that is treatable by inhibiting NUAK2 and/or NUAK1 comprising administering a therapeutically effective amount of one or more compounds of the application to a subject in need thereof.

The present application also includes a use of one or more compounds of the application for treatment of a disease, disorder or condition that is treatable by inhibiting NUAK2 and/or NUAK1 as well as a use of one or more compounds of the application for the preparation of a medicament for treatment of a disease, disorder or condition that is treatable by inhibiting NUAK2 and/or NUAK1. The application further includes one or more compounds of the application for use in treating a disease, disorder or condition that is treatable by inhibiting NUAK2 and/or NUAK1.

As noted above, "NUAK" is a protein kinase that belongs to the NUAK family SNF1-like kinase 1 and 2, also known as AMPK-related protein kinase 5 (ARK5) or SNARK respectively. In some embodiments, these serine/threonine-protein kinases are enzymes that in humans are encoded by the NUAK1 (Gene ID: 9891) and NUAK2 (Gene ID: 81788) gene comprising the amino acid sequence disclosed in *Journal of Biological Chemistry* 2003, 278 (1): 48-53.

In some embodiments, the disease, disorder or condition that is treatable by inhibiting NUAK2 and/or NUAK1 is a neoplastic disorder. Accordingly, the present application also includes a method of treating a neoplastic disorder comprising administering a therapeutically effective amount of one or more compounds of the application to a subject in need thereof. The present application also includes a use of one or more compounds of the application for treatment of a neoplastic disorder as well as a use of one or more compounds of the application for the preparation of a medicament for treatment of a neoplastic disorder. The application further includes one or more compounds of the application for use in treating a neoplastic disorder. In an embodiment, the treatment is in an amount effective to ameliorate at least one symptom of the neoplastic disorder, for example, reduced cell proliferation or reduced tumor mass, among others, in a subject in need of such treatment.

Compounds of the application have been demonstrated to inhibit the growth of cancer cells. Therefore, in another embodiment of the present application, the disease, disorder or condition that is treatable by inhibiting NUAK2 and/or NUAK1 is cancer. Accordingly, the present application also includes a method of treating cancer comprising administering a therapeutically effective amount of one or more compounds of the application to a subject in need thereof. The present application also includes a use of one or more compounds of the application for treatment of cancer as well as a use of one or more compounds of the application for the preparation of a medicament for treatment of cancer. The application further includes one or more compounds of the application for use in treating cancer. In an embodiment, the compound is administered or used for the prevention of cancer in a subject such as a mammal having a predisposition for cancer.

In some embodiments, the cancer is any cancer in which the cells show increased expression of the gene(s) encoding NUAK1 and/or NUAK2. By "increased expression" it is meant any increase in expression of the gene(s) encoding NUAK1 and/or NUAK2 in the cell compared to expression of the gene(s) encoding NUAK1 and/or NUAK2 in a corresponding normal or healthy cell.

In some embodiments, the cancer is selected from one or more of solid tumors, breast cancer, colon cancer, bladder cancer, skin cancer, head and neck cancer, liver cancer, lung cancer, pancreatic cancer, ovarian cancer, prostate cancer, bone cancer and glioblastoma. In some embodiments, the cancer is breast cancer. In some embodiments, the cancer is skin cancer. In some embodiments, the cancer is head and neck cancer. In some embodiments, the cancer is colorectal cancer (CRC). In some embodiments, the cancer is lung cancer. In some embodiments, the cancer is pancreatic cancer. In some embodiments, the cancer is ovarian cancer. In some embodiments, the cancer is prostate cancer. In some embodiments, the cancer is glioblastoma. In some embodiments, the cancer is osteosarcoma.

As noted above, MYC-driven tumors are addicted to NUAK activity and full function of the spliceosome is relevant for their survival [*Mol Cell.* 2020, 77(6):1322-1339]. MYC drives gene expression needed for cell growth and division and is deregulated in many tumors. Accordingly, in some embodiments, the cancer that is treated using one or more compounds of the application are cancers wherein the MYC family oncogene is amplified or otherwise deregulated (see for eg. *Signal Transduction and Targeted Therapy,* 2018, vol. 3, Article 5).

In some embodiments, the compounds of the application have been shown to inhibit the localization of YAP/TAZ to the nucleus of a cell. Accordingly, the present application also includes a method of inhibiting localization of YAP/TAZ to the nucleus of a cell comprising administering an effective amount of one of more compounds of the application to a cell in need thereof. Also included is a use of one or more compounds of the application to inhibit localization of YAP/TAZ to the nucleus of a cell, a use of one or more compounds of the application for the preparation of a medicament to inhibit localization of YAP/TAZ to the nucleus of a cell and one or more compounds of the application for use inhibit localization of YAP/TAZ to the nucleus of a cell.

The present application also includes a method of treating a disease, disorder or condition by inhibiting localization of YAP/TAZ to the nucleus of a cell comprising administering an effective amount of one of more compounds of the application to a subject in need thereof. Also included is a use of one or more compounds of the application to treat a disease, disorder or condition by inhibiting localization of YAP/TAZ to the nucleus of a cell, a use of one or more compounds of the application for the preparation of a medicament to treat a disease, disorder or condition by inhibiting localization of YAP/TAZ to the nucleus of a cell and one or more compounds of the application for use to treat a disease, disorder or condition by inhibiting localization of YAP/TAZ to the nucleus of a cell.

As noted above, accumulating evidence indicates that YAP/TAZ function in a cooperative manner with other established signaling pathways, in particular, crosstalking with TGFβ and Wnt signalling pathways (*Am. J. Physiol. Lung Cell. Mol. Physiol.* 2015, 309, L756-L767; Cell 2012, 151, 1443-1456). Accordingly, in some embodiments, the disease, disorder or condition treated by inhibiting localization of YAP/TAZ to the nucleus of a cell is one that benefits from inhibition, directly or indirectly, of the TGFβ and/or Wnt signalling pathways.

In some embodiments, the disease, disorder or condition that is treated by inhibiting localization of YAP/TAZ to the nucleus of a cell is any cancer or fibrosis in which the cells show increased activation of TAZ and/or YAP. By "increased activation" it is meant any increase in activation of TAZ and/or YAP in the cell compared to activation of TAZ and/or YAP in a corresponding normal or healthy cell. In some embodiments, the cancer is selected from one or more of breast cancer, bladder cancer, liver cancer, human melanoma, colorectal cancer, hepatocellular cancer, cholangiocarcinoma, mesothelioma, osteosarcoma and glioblastoma. In some embodiments, the fibrosis is liver fibrosis, lung fibrosis and/or kidney fibrosis.

Another indication that can potentially benefit from inhibiting the NUAK-YAP/TAZ-TGFβ signaling axis is fibrosis. Fibrosis is a response to tissue or organ injury such as chronic inflammation or chemical and mechanical insults. In pathologic circumstances, fibrosis evolves into an uncontrolled process characterized by the progressive accumulation of extracellular matrix (ECM), mainly collagen, that ultimately disrupts normal organ architecture and leads to organ function loss. A key step in fibrosis is the conversion of quiescent fibroblasts into active myofibroblasts that deposit extracellular matrix (ECM) and secrete TGFβ which is a principal factor driving this activation process (Science 2002, 296: 1646-1647). Fibrosis, which impacts several organs such as the liver, lung, and kidney, is responsible for up to 45% of deaths in the industrialized world (*J. Clin. Invest.* 2007, 117, 524-529; *Front. Pharmacol.* 2017, 8, 855). Current therapeutics are mostly supportive rather than curative and there is an urgent need to identify drugs with a therapeutic potential to address this disease. NUAK inhibition, which modulates YAP/TAZ and TGFβ signaling, is a novel approach to treat fibrosis.

In some embodiments, the disease, disorder or condition that is treatable by inhibiting NUAK2 and/or NUAK1 is a disease, disorder or condition associated with an uncontrolled and/or abnormal cellular activity affected directly or indirectly by inhibiting NUAK2 and/or NUAK1. In another embodiment, the uncontrolled and/or abnormal cellular activity that is affected directly or indirectly by inhibiting NUAK2 and/or NUAK1 is proliferative activity in a cell. Accordingly, the application also includes a method of inhibiting proliferative activity in a cell, comprising administering an effective amount of one or more compounds of the application to the cell. The present application also includes a use of one or more compounds of the application for inhibition of proliferative activity in a cell as well as a use of one or more compounds of the application for the preparation of a medicament for inhibition of proliferative activity in a cell. The application further includes one or more compounds of the application for use in inhibiting proliferative activity in a cell.

The present application also includes a method of inhibiting uncontrolled and/or abnormal cellular activities affected directly or indirectly by inhibiting NUAK2 and/or NUAK1 in a cell, either in a biological sample or in a subject, comprising administering an effective amount of one or more compounds of the application to the cell. The application also includes a use of one or more compounds of the application for inhibition of uncontrolled and/or abnormal cellular activities affected directly or indirectly by inhibiting NUAK2 and/or NUAK1 in a cell as well as a use of one or more compounds of the application for the preparation of a medicament for inhibition of uncontrolled and/or abnormal cellular activities affected directly or indirectly by inhibiting NUAK2 and/or NUAK1 in a cell. The application further includes one or more compounds of the application for use in inhibiting uncontrolled and/or abnormal cellular activities affected directly or indirectly by inhibiting NUAK2 and/or NUAK1 in a cell.

The present application also includes a method of treating a disease, disorder or condition that is treatable by inhibiting NUAK2 and/or NUAK1 comprising administering a therapeutically effective amount of one or more compounds of the application in combination with another agent useful for treatment of a disease, disorder or condition that is treatable by inhibiting NUAK2 and/or NUAK1 to a subject in need thereof. The present application also includes a use of one or more compounds of the application in combination with another known agent useful for treatment of a disease, disorder or condition that is treatable by inhibiting NUAK2 and/or NUAK1 for treatment of a disease, disorder or condition that is treatable by inhibiting NUAK2 and/or NUAK1, as well as a use of one or more compounds of the application in combination with another known agent useful for treatment of a disease, disorder or condition that is treatable by inhibiting NUAK2 and/or NUAK1 for the preparation of a medicament for treatment of a disease, disorder or condition that is treatable by inhibiting NUAK2 and/or NUAK1. The application further includes one or more compounds of the application in combination with another known agent useful for treatment of a disease, disorder or condition that is treatable by inhibiting NUAK2 and/or NUAK1 for use in treating a disease, disorder or condition that is treatable by inhibiting NUAK2 and/or NUAK1. In an embodiment, the disease, disorder or condition treatable by inhibiting NUAK2 and/or NUAK1 is cancer and/or fibrosis.

In a further embodiment, the disease, disorder or condition that is treatable by inhibiting NUAK2 and/or NUAK1 is cancer and the one or more compounds of the application are administered in combination with one or more additional cancer treatments. In another embodiment, the additional cancer treatment is selected from radiotherapy, chemotherapy, targeted therapy such as antibody therapy and small molecule therapy such as tyrosine-kinase inhibitors therapy, immunotherapy, hormonal therapy and anti-angiogenic therapy.

As noted above, accumulating evidence indicates that YAP/TAZ function in a cooperative manner with other established signaling pathways, in particular, crosstalking with TGFβ and Wnt signalling pathways (*Am. J. Physiol. Lung Cell. Mol. Physiol.* 2015, 309, L756-L767; Cell 2012, 151, 1443-1456). Importantly, in the context of immune-oncology, TGFβ has been demonstrated to have a key role in regulating antitumor immune response and contributes to resistance to anti-PD-1-PD-L1 treatment in cancer patients (*ACS Med. Chem. Lett.* 2018, 9, 1117). Therefore, targeting the TGFβ pathway (through NUAK-YAP/TAZ inhibition) in combination with anti-PD1 or anti-PD-L1 antibodies may help overcome resistance and produce a more effective antitumor response. Therefore, in some embodiments, the one or more compounds of the application are administered with are used in combination with treatment with, or use of, anti-PDI and/or anti-PD-L1 antibodies.

In some embodiments, both NUAK2 and NUAK1 are inhibited in the uses and methods of the application. In some embodiments, inhibition of NUAK2 is greater than inhibition of NUAK1 in the uses and methods of the application. In some embodiments, inhibition of NUAK2 and/or NUAK1 is selective over inhibition of one or more other kinases in a cell or subject. In some embodiments the other kinase is Aurora A kinase.

In some embodiments, the subject is a mammal. In some embodiments, the subject is human.

It will be appreciated by a person skilled in the art that the therapeutic methods and uses of the application would typically comprise administering or use an effective amount of the one or more compounds of the application in a pharmaceutical composition of the application. For example in the context of treating a disease, disorder or condition treatable by inhibition NUAK2 and/or NUAK1, an effective amount is an amount that, for example, inhibits NUAK2/NUAK1, compared to the inhibition without administration of the one or more compounds. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art. The effective amount is one that following treatment therewith manifests as an improvement in or reduction of any disease, disorder or condition symptom. In some embodiments, when the disease is cancer, amounts that are effective cause a reduction in the number, growth rate, size and/or distribution of tumours.

Treatment methods comprise administering to a subject a therapeutically effective amount of one or more of the compounds of the application and optionally consist of a single administration, or alternatively comprise a series of administrations, and optionally comprise concurrent administration or use of one or more other therapeutic agents. For example, in some embodiments, the compounds of the application may be administered at least once a week. In some embodiments, the compounds may be administered to the subject from about one time per two or three weeks, or about one time per week to about once daily for a given treatment. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required. For example, the compounds are administered to the subject in an amount and for duration sufficient to treat the subject. In some embodiments, treatment comprises prophylactic treatment. For example, a subject with early cancer can be treated to prevent progression, or alternatively a subject in remission can be treated with a compound or composition of the application to prevent recurrence.

IV. METHODS OF PREPARATION OF COMPOUNDS OF THE APPLICATION

Compounds of the present application can be prepared by various synthetic processes. The choice of particular structural features and/or substituents may influence the selection of one process over another. The selection of a particular process to prepare a given compound of Formula I is within the purview of the person of skill in the art. Some starting materials for preparing compounds of the present application are available from commercial chemical sources. Other starting materials, for example as described below, are readily prepared from available precursors using straightforward transformations that are well known in the art.

The compounds of Formula I generally can be prepared according to the processes illustrated in the Schemes below. In the structural formulae shown below the variables are as defined in Formula I unless otherwise stated. A person skilled in the art would appreciate that many of the reactions depicted in the Schemes below would be sensitive to oxygen and water and would know to perform the reaction under an anhydrous, inert atmosphere if needed. Reaction temperatures and times are presented for illustrative purposes only and may be varied to optimize yield as would be understood by a person skilled in the art.

Accordingly, in some embodiments, the compounds of Formula I, are prepared as shown in Scheme 1.

Scheme 1

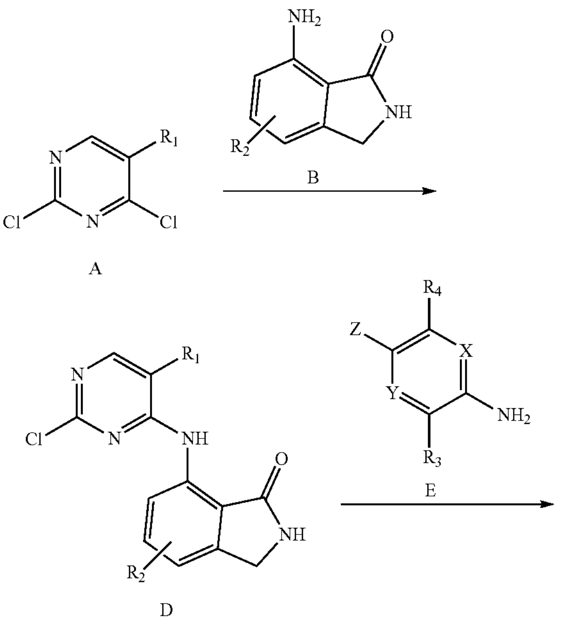

A

D

Formula I

Therefore in some embodiments, commercially available substituted dichloropyrimidines, A, wherein $R^1$ is as defined in Formula I or a protected version thereof, are coupled with 7-amino isoindolin-7-ones B, wherein $R^2$ is as defined in Formula I or a protected version thereof, under basic conditions to provide compounds D which are subsequently treated with various anilines of Formula E, wherein $R^3$, $R^4$, X, Y and Z are as defined in Formula I or protected versions thereof, under acidic or basic conditions to provide compounds of Formula I.

In an alternate embodiment, intermediate D, wherein $R^1$ and $R^2$ are as defined in Formula I or protected versions thereof, is coupled with a variety of amino-isoquinolines or amino-aza-isoquinolines of Formula F, wherein $R^3$ and ring B are as defined in Formula I or protected versions thereof, under acidic or basic conditions to provide compounds of Formula I as shown in Scheme 2.

Scheme 2

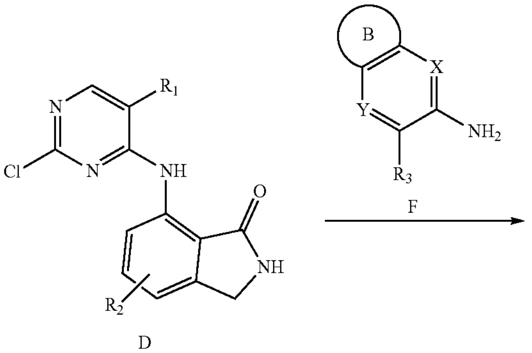

D F Formula I

In some embodiments, compounds of Formula I wherein X and Y are both carbon and $R_1$ is Cl, $R^2$=H and $R^3$=$OCF_2H$ are prepared as shown in Scheme 3.

Scheme 3

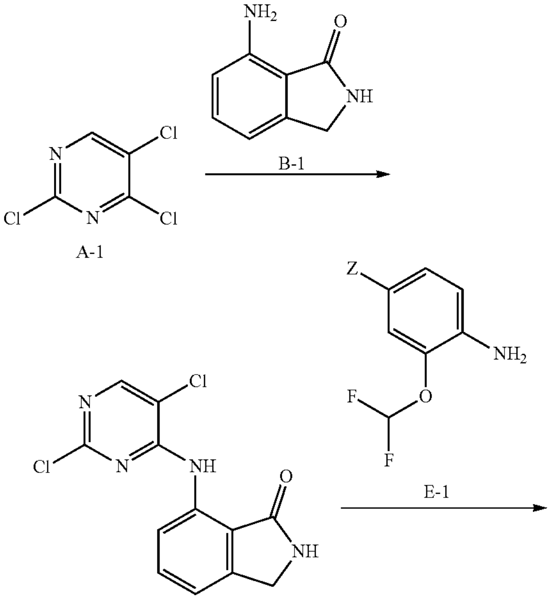

A-1 B-1 D-1 E-1 Formula I

Accordingly, treatment of commercially available 2,4,5-trichloropyrimidine A-1 with, for example, 7-aminoisoindolin-1-one B-1 provides intermediate D-1. Coupling of D-1 with anilines E-1 wherein Z is as defined in Formula I, or a protected version thereof, provides, after removal of any protecting groups if needed, compounds of Formula I.

Generally, the reactions described above are performed in a suitable inert organic solvent and at temperatures and for times that will optimize the yield of the desired compounds. Examples of suitable inert organic solvents include, but are not limited to, 2-propanol, dimethylformamide (DMF), dioxane, methylene chloride, chloroform, tetrahydrofuran (THF), toluene, and the like.

Salts of the compounds of the application are generally formed by dissolving the neutral compound in an inert organic solvent and adding either the desired acid or base and isolating the resulting salt by either filtration or other known means.

The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Prodrugs of the compounds of the present application may be, for example, conventional esters formed with available hydroxy, thiol, amino or carboxyl groups. For example, available hydroxy or amino groups may be acylated using an activated acid in the presence of a base, and optionally, in inert solvent (e.g. an acid chloride in pyridine).

EXAMPLES

The following non-limiting examples are illustrative of the present application:

Synthesis and Characterization of Compounds

General Method for Aniline Coupling Under Acidic Conditions

To a mixture of aniline (1.1-1.5 equiv.) and chloropyrimidine (1 equiv.) in a microwave vial was added IPA (0.05-1 M) and a few drops of conc. HCl (1-1.6 drops/mmol). The resulting mixture was irradiated in microwave at 130-140° C. for 2-4 h (most times 3 h at 140° C.). After evaporation of solvents, the residue was dissolved in DCM, basified with aq. $NaHCO_3$. After extracting with DCM, the combined extracts were concentrated and triturated with MeOH or EtOAc to give the desired product. Alternatively, the crude mixture was purified by prep-HPLC to give the desire product.

When the aniline has N-Boc moiety on the more basic amine, de-Boc happened simultaneously as a one-pot reaction.

Synthesis of 7-((5-chloro-2-((2-(difluoromethoxy)-4-(4-methylpiperazin-1-yl)phenyl)amino)pyrimidin-4-yl)amino)isoindolin-1-one (Compound I-1)

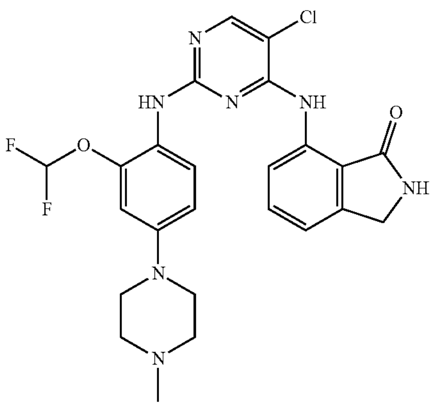 [SMILES: CN1CCN(c2ccc(Nc3ncc(Cl)c(Nc4cccc5c4C(=O)NC5)n3)c(OC(F)F)c2)CC1]

Step 1: Synthesis of 7-((2,5-dichloropyrimidin-4-yl)amino)isoindolin-1-one

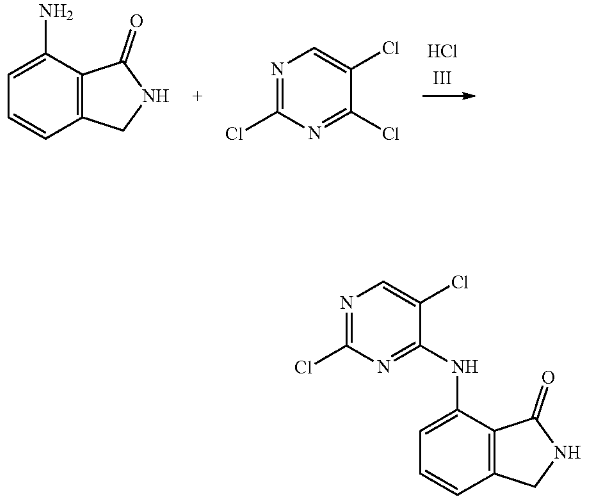

To a solution of 7-aminoisoindolin-1-one (1.00 g, 6.75 mmol) in hydrochloric acid (HCl) [0.1 M] (20 ml) at room temperature was added 2,4,5-trichloropyrimidine (0.774 ml, 6.75 mmol). The resulting mixture was heated to 120° C. for 3 hours prior to cooling back down to room temperature. The evident precipitate was collected by filtration and dried for 3 hours under vacuum to afford a white powder. This material was used in the subsequent reaction without further purification. (Yield=1.54 g, 77%); LCMS: [M+H] 295.22 (+ve)

Step 2: Synthesis of 3-((5-chloro-2-((2-(difluoromethoxy)-4-(4-methylpiperazin-1-yl)phenyl)amino)pyrimidin-4-yl)amino)thiophene-2-carboxamide

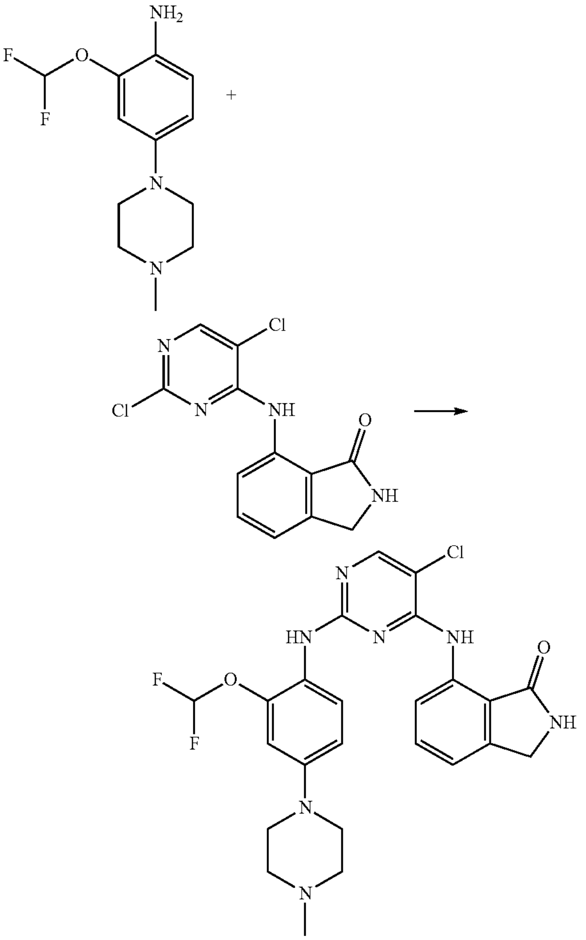

To a solution of 7-((2,5-dichloropyrimidin-4-yl)amino)isoindolin-1-one (0.100 g, 0.339 mmol) in 2-propanol (2 ml) at room temperature was added 2-(difluoromethoxy)-4-(4-methylpiperazin-1-yl)aniline (0.087 g, 0.339 mmol) and hydrochloric acid (0.028 ml, 0.339 mmol). The resulting solution was heated to 130° C. for 16 hours prior to cooling down to room temperature, and dilution with 1 N NaOH solution (50 mL). The aqueous layer was extracted with EtOAc (3×40 mL), and the combined organic extracts were dried with anhydrous sodium sulfate, filtered, and concentrated under reduced pressure to yield a light brown solid. This material was taken up in EtOAc and triturated with hexanes to afford a purple powder which was collected by filtration and dried under vacuum for 24 hours. Yield=0.103 g, 58%; $^{1}H$ NMR (500 MHz, MeOD-$d_4$) δ 8.38 (d, J=8.5 Hz, 1H), 8.06 (s, 1H), 7.58 (d, J=8.8 Hz, 1H), 7.33 (t, J=7.9 Hz, 1H), 7.14 (d, J=7.5 Hz, 1H), 6.94 (dd, J=8.8, 2.6 Hz, 1H), 6.89-6.84 (m, 1H), 6.73 (t, J=74.4 Hz, 1H), 4.44 (s, 2H), 3.31-3.24 (m, 4H), 2.72-2.63 (m, 4H), 2.40 (s, 3H); MS (ESI) m/z 516.4 $[M+H]^+$; LCMS: [M+H] 516.43 (+ve).

In a similar manner, the following compounds were synthesized:

| Compound I.D. | Structure | Yield (Overall) | NMR & MS |
|---|---|---|---|
| I-2 | 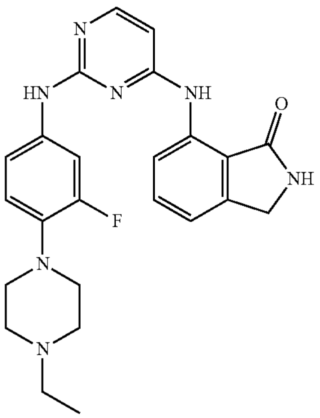 [SMILES: CCN1CCN(c2ccc(Nc3nccc(Nc4cccc5c4C(=O)NC5)n3)cc2F)CC1] | 22% | $^1$H NMR (500 MHz, DMSO-$d_6$) δ 10.01 (s, 1H), 9.38 (s, 1H), 8.79 (s, 1H), 8.57 (d, J = 7.5 Hz, 1H), 8.14 (d, J = 5.7 Hz, 1H), 7.74 (d, J = 15.3 Hz, 1H), 7.51 (t, J = 7.8 Hz, 1H), 7.34 (d, J = 8.5 Hz, 1H), 7.16 (d, J = 7.4 Hz, 1H), 6.98 (t, J = 9.4 Hz, 1H), 6.37 (d, J = 5.7 Hz, 1H), 4.39 (s, 2H), 2.97 (s, 4H), 2.43-2.35 (m, 2H), 1.04 (t, J = 7.1 Hz, 3H); MS (ESI) m/z 448.6 [M + H]$^+$ |
| I-3 | 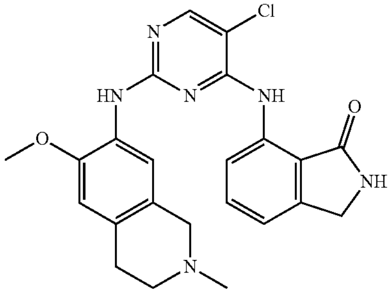 [SMILES: COc1cc2c(cc1Nc1ncc(Cl)c(Nc3cccc4c3C(=O)NC4)n1)CN(C)CC2] | 45% | $^1$H NMR (500 MHz, MeOD-$d_4$) δ 8.56 (d, J = 8.3 Hz, 1H), 8.10 (s, 1H), 7.76 (s, 1H), 7.52 (t, J = 7.9 Hz, 1H), 7.19 (d, J = 7.5 Hz, 1H), 6.81 (s, 1H), 4.45 (s, 2H), 3.89 (s, 3H), 3.55 (s, 2H), 2.97 (t, J = 5.9 Hz, 2H), 2.78 (t, J = 6.0 Hz, 2H), 2.46 (s, 3H); MS (ESI) m/z 451.4 [M + H]$^+$ |
| I-4 | 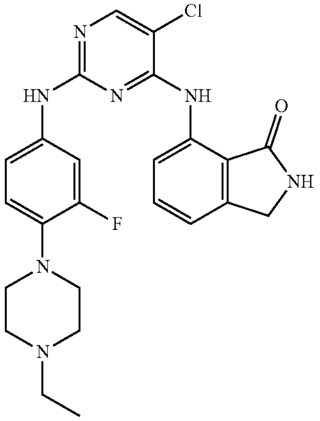 [SMILES: CCN1CCN(c2ccc(Nc3ncc(Cl)c(Nc4cccc5c4C(=O)NC5)n3)cc2F)CC1] | 46% | $^1$H NMR (500 MHz, DMSO-$d_6$) δ 10.73 (s, 1H), 9.57 (s, 1H), 8.83 (s, 1H), 8.75 (s, 1H), 8.28 (s, 1H), 7.67 (d, J = 16.0 Hz, 1H), 7.53 (t, J = 7.9 Hz, 1H), 7.31 (d, J = 8.4 Hz, 1H), 7.23 (d, J = 7.5 Hz, 1H), 7.01 (t, J = 9.4 Hz, 1H), 4.42 (s, 2H), 3.30 (s, 3H), 2.99 (s, 3H), 2.41-2.36 (m, 2H), 1.04 (t, J = 7.2 Hz, 3H); MS (ESI) m/z 482.1 [M + H]$^+$ |
| I-5 | 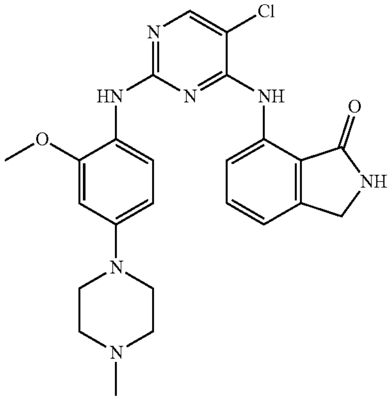 | 49% | $^1$H NMR (500 MHz, DMSO-$d_6$) δ 10.61 (s, 1H), 8.77 (s, 1H), 8.43 (dd, J = 19.5, 11.4 Hz, 1H), 8.35 (s, 1H), 8.13 (s, 1H), 7.34 (d, J = 8.4 Hz, 2H), 7.15 (d, J = 7.4 Hz, 1H), 6.66 (d, J = 2.3 Hz, 1H), 6.53 (dd, J = 8.7, 2.4 Hz, 1H), 4.38 (s, 2H), 3.75 (s, 3H), 3.23-3.15 (m, 4H), 2.48 (s, 4H), 2.25 (s, 3H); MS (ESI) m/z 480.4 [M + H]$^+$ |

-continued

| Compound I.D. | Structure | Yield (Overall) | NMR & MS |
|---|---|---|---|
| I-6 | 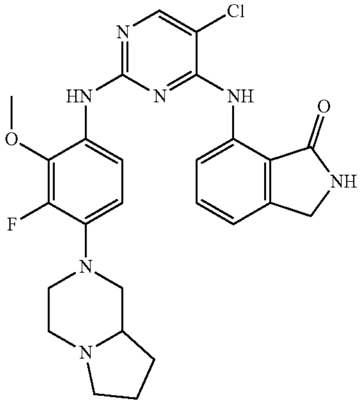 [SMILES: COc1c(Nc2ncc(Cl)c(Nc3cccc4c3C(=O)NC4)n2)ccc(N2CCN3CCCC3C2)c1F] | 35% | $^1$H NMR (500 MHz, DMSO-d$_6$) δ 10.67 (s, 1H), 8.80 (s, 1H), 8.76 (s, 1H), 8.44 (s, 1H), 8.19 (s, 1H), 7.37-7.26 (m, 2H), 7.17 (t, J = 7.3 Hz, 1H), 6.82 (t, J = 9.0 Hz, 1H), 4.39 (s, 2H), 3.78 (s, 3H), 3.43 (d, J = 10.4 Hz, 1H), 3.08-2.99 (m, 2H), 2.85 (td, J = 11.3, 2.7 Hz, 1H), 2.55 (d, J = 10.4 Hz, 2H), 2.33 (td, J = 10.9, 2.7 Hz, 1H), 2.15 (ddd, J = 26.2, 13.6, 5.6 Hz, 2H), 1.87-1.78 (m, 1H), 1.78-1.66 (m, 2H), 1.37 (ddd, J = 21.8, 11.2, 6.9 Hz, 1H); MS (ESI) m/z 524.4 [M + H]$^+$ |
| I-7 | 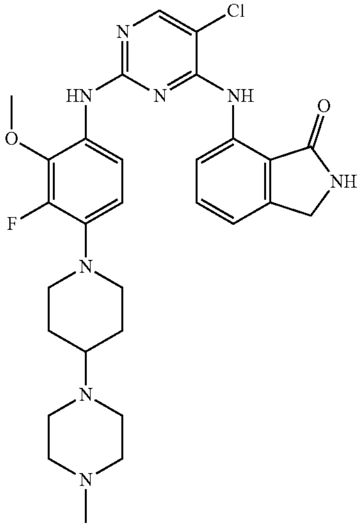 [SMILES: COc1c(Nc2ncc(Cl)c(Nc3cccc4c3C(=O)NC4)n2)ccc(N2CCC(N3CCN(C)CC3)CC2)c1F] | 37% | $^1$H NMR (500 MHz, DMSO-d$_6$) δ 10.67 (s, 1H), 8.79 (s, 1H), 8.75 (s, 1H), 8.44 (s, 1H), 8.18 (s, 1H), 7.32 (t, J = 7.7 Hz, 1H), 7.28 (d, J = 8.6 Hz, 1H), 7.16 (d, J = 7.5 Hz, 1H), 6.79 (t, J = 9.0 Hz, 1H), 4.39 (s, 2H), 3.78 (s, 3H), 3.39 (d, J = 11.8 Hz, 2H), 2.69 (t, J = 11.2 Hz, 2H), 2.52 (s, 4H), 2.39-2.27 (m, 4H), 2.15 (s, 3H), 1.88 (d, J = 11.4 Hz, 2H), 1.59 (qd, J = 12.2, 3.5 Hz, 2H); MS (ESI) m/z 581.4 [M + H]$^+$ |
| I-8 | 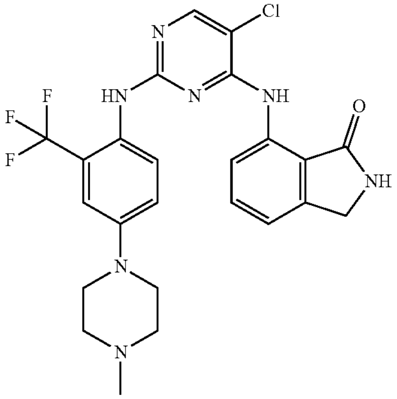 [SMILES: CN1CCN(c2ccc(Nc3ncc(Cl)c(Nc4cccc5c4C(=O)NC5)n3)c(C(F)(F)F)c2)CC1] | 21% | $^1$H NMR (500 MHz, DMSO-d$_6$) δ 10.62 (s, 1H), 8.85 (s, 1H), 8.78 (s, 1H), 8.24-8.04 (m, 2H), 7.35 (d, J = 8.8 Hz, 1H), 7.29 (dd, J = 8.8, 2.4 Hz, 1H), 7.22 (d, J = 2.5 Hz, 1H), 7.14 (dd, J = 17.1, 7.5 Hz, 2H), 4.36 (s, 2H), 3.30-3.22 (m, 4H), 2.26 (s, 3H); MS (ESI) m/z 518.4 [M + H]$^+$ |

-continued

| Compound I.D. | Structure | Yield (Overall) | NMR & MS |
|---|---|---|---|
| I-9 | 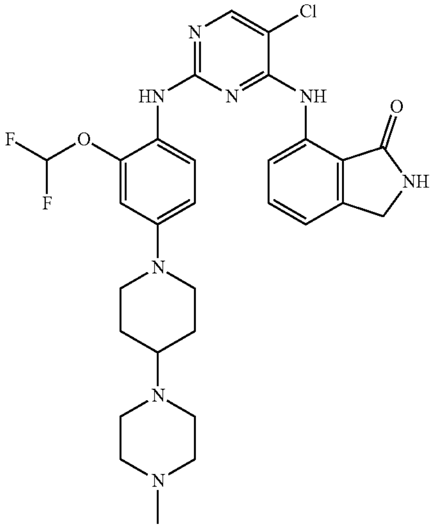 [SMILES: CN1CCN(C2CCN(c3ccc(Nc4ncc(Cl)c(Nc5cccc6c5C(=O)NC6)n4)c(OC(F)F)c3)CC2)CC1] | 10% | $^1$H NMR (500 MHz, DMSO-$d_6$) δ 10.64 (s, 1H), 8.80 (s, 1H), 8.70 (s, 1H), 8.36 (d, J = 11.0 Hz, 1H), 8.14 (s, 1H), 7.33 (d, J = 9.0 Hz, 1H), 7.30-7.25 (br s, 1H), 7.14 (d, J = 7.4 Hz, 1H), 7.05 (t, J = 74.3, 1H), 6.87 (dd, J = 11.7, 9.3 Hz, 1H), 6.78 (s, 1H), 4.38 (s, 2H), 3.76 (d, J = 12.3 Hz, 2H), 2.74 (t, J = 11.4 Hz, 2H), 2.42-2.24 (m, 4H), 2.15 (s, 3H), 1.87 (d, J = 11.7 Hz, 2H), 1.52 (ddd, J = 15.3, 12.4, 3.7 Hz, 2H); MS (ESI) m/z 599.3 [M + H]$^+$ |
| I-10 | 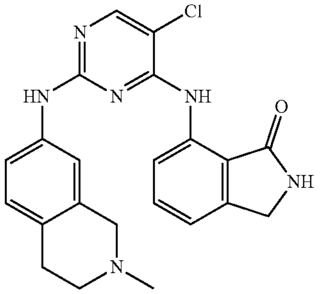 [SMILES: CN1CCc2ccc(Nc3ncc(Cl)c(Nc4cccc5c4C(=O)NC5)n3)cc2C1] | 72% | $^1$H NMR (500 MHz, DMSO-$d_6$) δ 10.72 (s, 1H), 9.45 (s, 1H), 8.82 (s, 1H), 8.71 (s, 1H), 8.25 (s, 1H), 7.50 (t, J = 7.9 Hz, 1H), 7.40 (s, 1H), 7.36 (d, J = 8.0 Hz, 1H), 7.22 (d, J = 7.5 Hz, 1H), 7.06 (d, J = 8.2 Hz, 1H), 4.42 (s, 2H), 3.45 (s, 2H), 2.79 (t, J = 5.7 Hz, 2H), 2.61 (t, J = 5.9 Hz, 2H), 2.34 (s, 3H); MS (ESI) m/z 421.5 [M + H]$^+$ |
| I-11 | 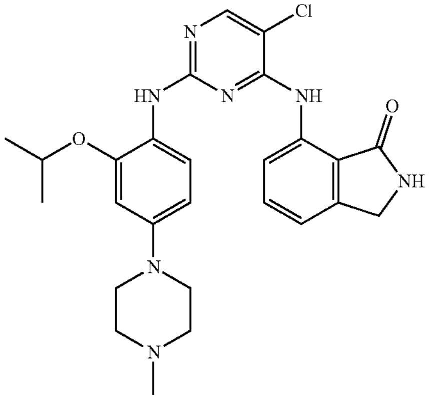 | 43% | $^1$H NMR (500 MHz, DMSO-$d_6$) δ 10.61 (s, 1H), 8.77 (s, 1H), 8.42 (d, J = 17.2 Hz, 1H), 8.17 (s, 1H), 8.15 (s, 1H), 7.41 (d, J = 8.6 Hz, 1H), 7.31 (t, J = 6.3 Hz, 1H), 7.14 (d, J = 7.5 Hz, 1H), 6.65 (d, J = 2.4 Hz, 1H), 6.55 (dd, J = 8.7, 2.4 Hz, 1H), 4.57 (dt, J = 12.1, 6.0 Hz, 1H), 4.38 (s, 2H), 3.20-3.12 (m, 4H), 2.50-2.46 (m, 4H), 2.25 (s, 3H), 1.18 (d, J = 6.0 Hz, 6H); MS (ESI) m/z 508.7 [M + H]$^+$ |
| I-12 | 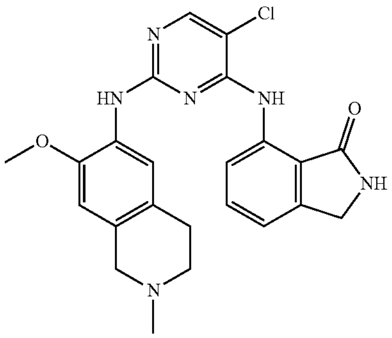 [SMILES: COc1cc2c(cc1Nc1ncc(Cl)c(Nc3cccc4c3C(=O)NC4)n1)CCN(C)C2] | 38% | $^1$H NMR (500 MHz, DMSO-$d_6$) δ 10.68 (s, 1H), 8.79 (s, 1H), 8.46 (d, J = 7.1 Hz, 1H), 8.35 (s, 1H), 8.20 (s, 1H), 7.46 (s, 1H), 7.37 (t, J = 7.8 Hz, 1H), 7.18 (d, J = 7.5 Hz, 1H), 6.77 (s, 1H), 4.39 (s, 2H), 3.76 (s, 3H), 3.50 (s, 2H), 2.74 (t, J = 5.6 Hz, 2H), 2.60 (t, J = 5.8 Hz, 2H), 2.36 (s, 3H); MS (ESI) m/z 451.6 [M + H]$^+$ |

-continued

| Compound I.D. | Structure | Yield (Overall) | NMR & MS |
|---|---|---|---|
| I-13 | 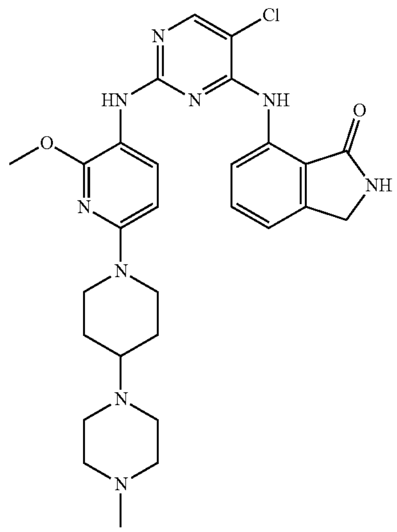 | 16% | $^1H$ NMR (500 MHz, DMSO-$d_6$) δ 10.61 (s, 1H), 8.77 (s, 1H), 8.45 (s, 1H), 8.12 (s, 1H), 7.54 (br d, J = 8.3 Hz, 1H), 7.40-7.23 (m, 1H), 7.13 (br d, J = 7.3 Hz, 1H), 6.39 (d, J = 8.4 Hz, 1H), 4.38 (s, 2H), 4.29 (br d, J = 12.7 Hz, 2H), 3.78 (s, 3H), 2.87-2.78 (m, 2H), 2.47-2.24 (m, 5H), 2.15 (s, 3H), 1.85 (br d, J = 11.4 Hz, 2H), 1.44 (dq, J = 3.4, 11.9 Hz, 2H); MS (ESI) m/z 564.6 $[M + H]^+$ |
| I-14 | 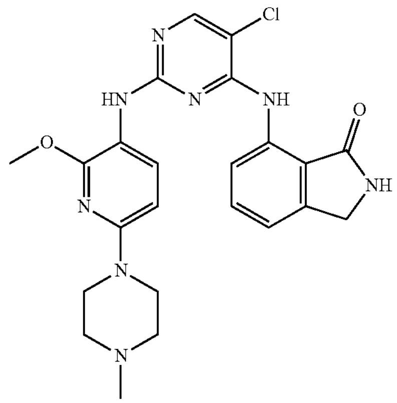 | 8% | $^1H$ NMR (500 MHz, DMSO-$d_6$) δ 10.62 (br s, 1H), 8.77 (s, 1H), 8.60-8.20 (m, 2H), 8.12 (s, 1H), 7.57 (br d, J = 8.2 Hz, 1H), 7.31 (br s, 1H), 7.15 (br d, J = 7.3 Hz, 1H), 6.39 (d, J = 8.4 Hz, 1H), 4.38 (s, 2H), 3.83-3.74 (m, 3H), 3.58-3.38 (m, 4H), 2.48-2.37 (m, 4H), 2.25 (s, 3H); MS (ESI) m/z 481.5 $[M + H]^+$ |
| I-15 | 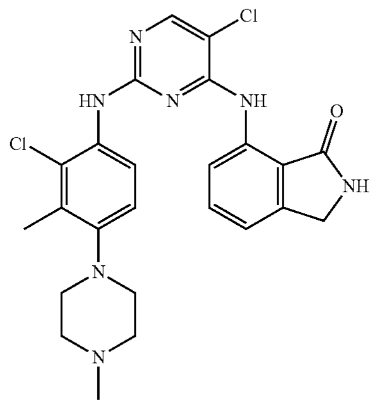 [SMILES: Cc1c(N2CCN(C)CC2)ccc(Nc2ncc(Cl)c(Nc3cccc4c3C(=O)NC4)n2)c1Cl] | 3% | $^1H$ NMR (500 MHz, DMSO-$d_6$) δ 10.67 (s, 1H), 8.99 (s, 1H), 8.78 (s, 1H), 8.28 (br s, 1H), 8.17 (s, 1H), 7.37 (d, J = 8.6 Hz, 1H), 7.22 (br t, J = 8.1 Hz, 1H), 7.14 (br d, J = 7.5 Hz, 1H), 7.11 (d, J = 8.6 Hz, 1H), 4.38 (s, 2H), 2.90 (br t, J = 4.4 Hz, 4H), 2.36-2.33 (m, 3H), 2.27 (s, 3H); MS (ESI) m/z 498.5 $[M + H]^+$ |

-continued

| Compound I.D. | Structure | Yield (Overall) | NMR & MS |
|---|---|---|---|
| I-16 | 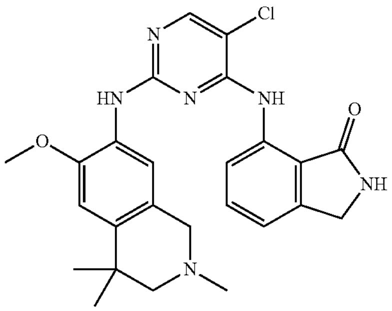 [SMILES: COc1cc2c(cc1Nc1ncc(Cl)c(Nc3cccc4c3C(=O)NC4)n1)CN(C)CC2(C)C] | 37% | $^{1}H$ NMR (500 MHz, DMSO-$d_6$) δ 10.67 (s, 1H), 8.79 (s, 1H), 8.47-8.41 (m, 1H), 8.38 (s, 1H), 8.19 (s, 1H), 7.38 (t, J = 7.9 Hz, 1H), 7.31 (s, 1H), 7.18 (d, J = 7.5 Hz, 1H), 7.00 (s, 1H), 4.39 (s, 2H), 3.78 (s, 3H), 3.38 (s, 2H), 2.36 (s, 2H), 2.32 (s, 3H), 1.32 (s, 5H); MS (ESI) m/z 479.6 $[M + H]^+$ |
| I-17 | 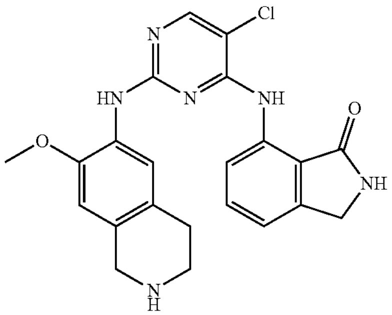 [SMILES: COc1cc2c(cc1Nc1ncc(Cl)c(Nc3cccc4c3C(=O)NC4)n1)CCNC2] | 56% | $^{1}H$ NMR (500 MHz, DMSO-$d_6$) δ 10.61 (s, 1H), 8.72 (s, 1H), 8.45-8.37 (m, 1H), 8.28 (s, 1H), 8.13 (s, 1H), 7.39 (s, 1H), 7.35 (t, J = 7.9 Hz, 1H), 7.10 (d, J = 7.4 Hz, 1H), 6.71 (s, 1H), 4.32 (s, 2H), 3.89 (s, 2H), 3.69 (s, 3H), 2.98 (t, J = 5.8 Hz, 2H), 2.61 (t, J = 5.7 Hz, 2H); MS (ESI) m/z 437.6 $[M + H]^+$ |
| I-18 | 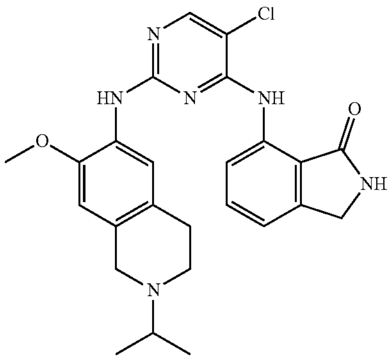 [SMILES: COc1cc2c(cc1Nc1ncc(Cl)c(Nc3cccc4c3C(=O)NC4)n1)CCN(C(C)C)C2] | 43% | $^{1}H$ NMR (500 MHz, DMSO-$d_6$) δ 10.60 (s, 1H), 8.72 (s, 1H), 8.38 (d, J = 6.1 Hz, 1H), 8.25 (s, 1H), 8.13 (s, 1H), 7.37 (s, 1H), 7.31 (t, J = 7.8 Hz, 1H), 7.10 (d, J = 7.5 Hz, 1H), 6.72 (s, 1H), 4.32 (s, 2H), 3.68 (s, 3H), 3.58 (s, 2H), 2.80 (dt, J = 13.0, 6.5 Hz, 1H), 2.63 (s, 4H), 1.01 (d, J = 6.5 Hz, 5H); MS (ESI) m/z 479.7 $[M + H]^+$ |
| I-20 | 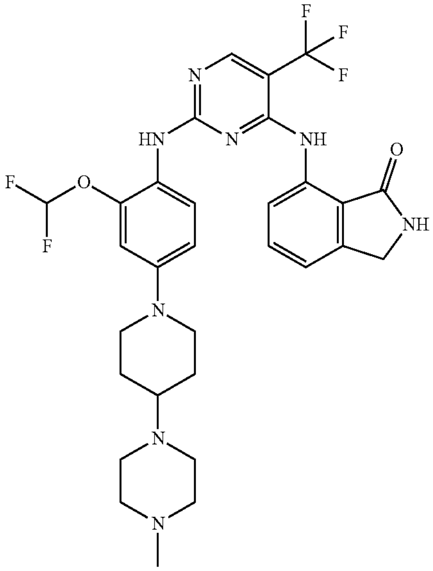 [SMILES: CN1CCN(C2CCN(c3ccc(Nc4ncc(C(F)(F)F)c(Nc5cccc6c5C(=O)NC6)n4)c(OC(F)F)c3)CC2)CC1] | 23% | $^{1}H$ NMR (500 MHz, DMSO-$d_6$) δ 10.64 (br s, 1H), 9.23 (s, 1H), 8.76 (s, 1H), 8.37 (br s, 1H), 7.99 (br s, 1H), 7.28 (d, J = 8.8 Hz, 1H), 7.21-6.86 (m, 4H), 6.80 (br s, 1H), 4.37 (br s, 2H), 3.79 (br d, J = 10.6 Hz, 2H), 2.77 (br t, J = 11.5 Hz, 2H), 2.44-2.27 (m, 4H), 2.18 (br s, 3H), 1.88 (br d, J = 12.5 Hz, 2H), 1.58-1.47 (m, 2H); MS (ESI) m/z 633.8 $[M + H]^+$ |

-continued

| Compound I.D. | Structure | Yield (Overall) | NMR & MS |
|---|---|---|---|
| I-21 | 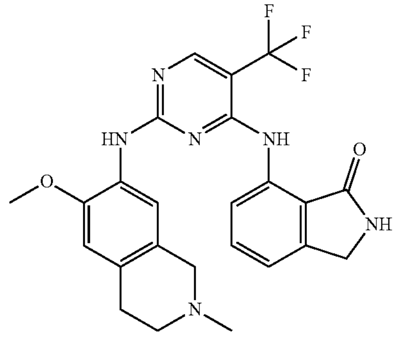 [SMILES: COc1cc2c(cc1Nc1ncc(C(F)(F)F)c(Nc3cccc4c3C(=O)NC4)n1)CN(C)CC2] | 36% | $^1$H NMR (500 MHz, DMSO-$d_6$) δ 10.63 (br s, 1H), 9.02 (s, 1H), 8.75 (s, 1H), 8.39 (s, 1H), 8.33-7.92 (m, 1H), 7.39-7.10 (m, 3H), 6.86 (s, 1H), 4.37 (s, 2H), 3.73 (s, 3H), 3.42-3.38 (m, 2H), 2.88 (br s, 2H), 2.66-2.59 (m, 2H), 2.34 (s, 3H); MS (ESI) m/z 485.5 $[M + H]^+$ |
| I-22 | 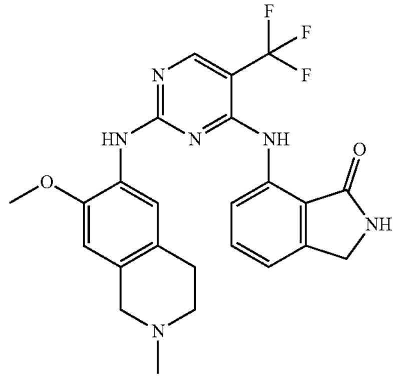 [SMILES: COc1cc2c(cc1Nc1ncc(C(F)(F)F)c(Nc3cccc4c3C(=O)NC4)n1)CCN(C)C2] | 26% | $^1$H NMR (500 MHz, DMSO-$d_6$) δ 10.64 (s, 1H), 9.00 (s, 1H), 8.76 (s, 1H), 8.65-7.96 (m, 2H), 7.27 (br s, 2H), 7.17 (br d, J = 7.2 Hz, 1H), 6.82 (s, 1H), 4.37 (s, 2H), 3.73 (s, 3H), 3.53 (s, 2H), 2.73 (br t, J = 5.6 Hz, 2H), 2.61 (br t, J = 5.7 Hz, 2H), 2.37 (s, 3H); MS (ESI) m/z 485.6 $[M + H]^+$ |
| I-23 | 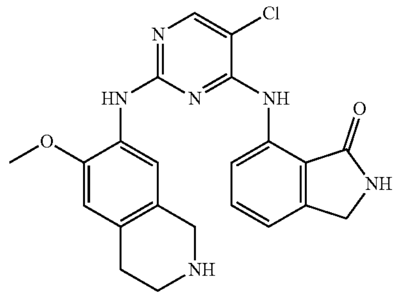 | 11% | $^1$H NMR (500 MHz, DMSO-$d_6$) δ 10.67 (s, 1H), 8.80 (s, 1H), 8.46 (d, J = 6.5 Hz, 1H), 8.33 (s, 1H), 8.20 (s, 1H), 7.41 (t, J = 7.9 Hz, 1H), 7.36 (s, 1H), 7.18 (d, J = 7.5 Hz, 1H), 6.77 (s, 1H), 4.40 (s, 2H), 3.77 (d, J = 4.9 Hz, 5H), 2.96 (t, J = 5.8 Hz, 2H), 2.71 (t, J = 5.6 Hz, 2H); MS (ESI) m/z 437.4 $[M + H]^+$ |
| I-24 | 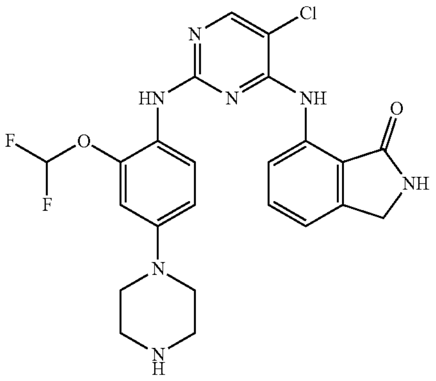 [SMILES: O=C1NCc2cccc(Nc3nc(Nc4ccc(N5CCNCC5)cc4OC(F)F)ncc3Cl)c21] | 23% | $^1$H NMR (500 MHz, DMSO-$d_6$) δ 10.65 (s, 1H), 8.79 (s, 1H), 8.72 (s, 1H), 8.34 (s, 1H), 8.14 (s, 1H), 7.34 (d, J = 8.8 Hz, 1H), 7.28 (s, 1H), 7.15 (d, J = 7.4 Hz, 1H), 7.05 (t, J = 74.3 Hz, 1H), 6.86 (dd, J = 8.8, 2.4 Hz, 1H), 6.77 (d, J = 1.8 Hz, 1H), 4.38 (s, 2H), 3.13-3.06 (m, 4H), 2.91-2.83 (m, 4H); MS (ESI) m/z 502.5 $[M + H]^+$ |

-continued

| Compound I.D. | Structure | Yield (Overall) | NMR & MS |
|---|---|---|---|
| I-25 | 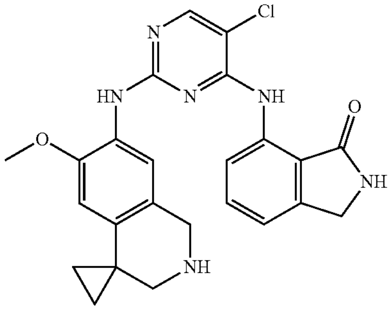 [SMILES: COc1cc2c(cc1Nc1ncc(Cl)c(Nc3cccc4c3C(=O)NC4)n1)CNCC21CC1] | 35% | $^1$H NMR (500 MHz, DMSO-$d_6$) δ 10.67 (s, 1H), 8.80 (s, 1H), 8.47 (d, J = 5.7 Hz, 1H), 8.33 (s, 1H), 8.19 (s, 1H), 7.43 (t, J = 7.9 Hz, 1H), 7.35 (s, 1H), 7.18 (d, J = 7.5 Hz, 1H), 6.35 (s, 1H), 4.40 (s, 2H), 3.87 (s, 2H), 3.74 (s, 3H), 2.77 (s, 2H), 1.01 (q, J = 4.5 Hz, 2H), 0.82 (q, J = 4.3 Hz, 2H); MS (ESI) m/z 463.5 $[M + H]^+$ |
| I-26 | 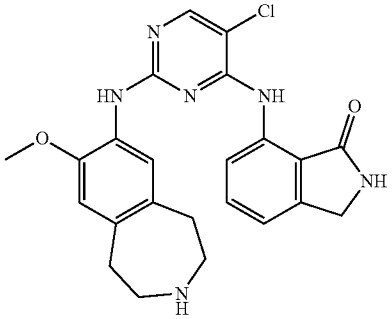 [SMILES: COc1cc2c(cc1Nc1ncc(Cl)c(Nc3cccc4c3C(=O)NC4)n1)CCNCC2] | 25% | $^1$H NMR (500 MHz, DMSO-$d_6$) δ 10.67 (s, 1H), 8.80 (s, 1H), 8.45 (d, J = 8.6 Hz, 1H), 8.31 (s, 1H), 8.19 (s, 1H), 7.42 (s, 1H), 7.35 (t, J = 7.8 Hz, 1H), 7.17 (d, J = 7.5 Hz, 1H), 6.86 (s, 1H), 4.39 (s, 2H), 3.76 (s, 3H), 2.86 (d, J = 6.7 Hz, 2H), 2.82 (d, J = 7.1 Hz, 2H), 2.77 (s, 4H); MS (ESI) m/z 451.4 $[M + H]^+$ |
| I-27 | 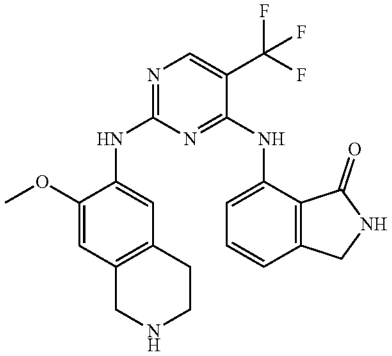 [SMILES: COc1cc2c(cc1Nc1ncc(C(F)(F)F)c(Nc3cccc4c3C(=O)NC4)n1)CCNC2] | 50% | $^1$H NMR (500 MHz, DMSO-$d_6$) δ 10.64 (s, 1H), 8.99 (s, 1H), 8.76 (s, 1H), 8.39 (s, 1H), 8.35-7.94 (m, 1H), 7.45-7.20 (m, 2H), 7.16 (br d, J = 7.2 Hz, 1H), 6.79 (s, 1H), 4.37 (s, 2H), 3.91 (s, 2H), 3.72 (s, 3H), 2.97 (t, J = 5.7 Hz, 2H), 2.65-2.57 (m, 2H); MS (ESI) m/z 471.5 $[M + H]^+$ |
| I-28 | 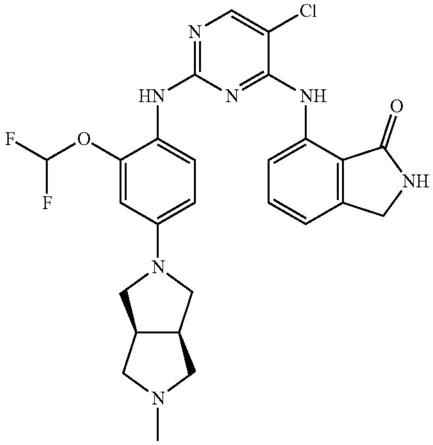 [SMILES: CN1C[C@@H]2CN(c3ccc(Nc4ncc(Cl)c(Nc5cccc6c5C(=O)NC6)n4)c(OC(F)F)c3)C[C@@H]2C1] | 46% | $^1$H NMR (500 MHz, DMSO-$d_6$) δ 10.62 (s, 1H), 8.78 (s, 1H), 8.67 (s, 1H), 8.48-8.17 (m, 1H), 8.12 (s, 1H), 7.32-7.20 (m, J = 8.7 Hz, 2H), 7.17-6.85 (m, 2H), 6.57 (dd, J = 2.3, 8.7 Hz, 1H), 6.51-6.43 (m, 1H), 4.38 (s, 2H), 3.44-3.40 (m, 2H), 3.13 (br dd, J = 2.6, 9.6 Hz, 2H), 2.98-2.88 (m, 2H), 2.61-2.55 (m, 2H), 2.47-2.41 (m, 2H), 2.25 (s, 3H); MS (ESI) m/z 542.4 $[M + H]^+$ |

-continued
| Compound I.D. | Structure | Yield (Overall) | NMR & MS |
|---|---|---|---|
| I-29 | 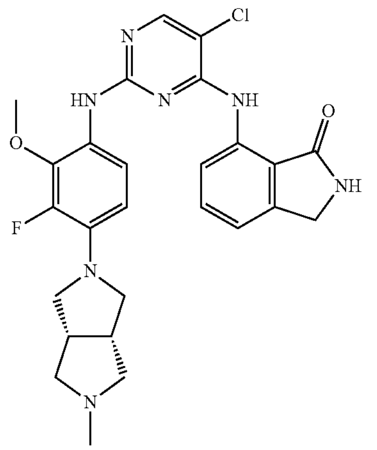 [SMILES: COc1c(Nc2ncc(Cl)c(Nc3cccc4c3C(=O)NC4)n2)ccc(N2C[C@H]3CN(C)C[C@H]3C2)c1F] | 57% | $^1$H NMR (500 MHz, DMSO-$d_6$) δ 10.64 (s, 1H), 8.79 (s, 1H), 8.72 (s, 1H), 8.47-8.30 (m, 1H), 8.16 (s, 1H), 7.30 (br t, J = 7.2 Hz, 1H), 7.19 (br d, J = 8.4 Hz, 1H), 7.14 (d, J = 7.5 Hz, 1H), 6.62 (t, J = 9.0 Hz, 1H), 4.38 (s, 2H), 3.76 (s, 3H), 3.11-3.03 (m, 2H), 2.87-2.79 (m, 2H), 2.66-2.59 (m, 2H), 2.39-2.32 (m, 2H), 2.25 (s, 3H); MS (ESI) m/z 524.5 $[M + H]^+$ |
| I-30 | 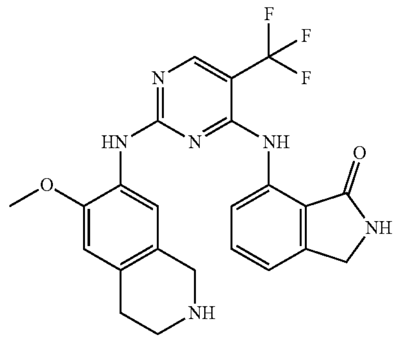 [SMILES: COc1cc2c(cc1Nc1ncc(C(F)(F)F)c(Nc3cccc4c3C(=O)NC4)n1)CNCC2] | 42% | $^1$H NMR (500 MHz, DMSO-$d_6$) δ 10.64 (s, 1H), 8.99 (s, 1H), 8.75 (s, 1H), 8.39 (s, 1H), 7.31 (br s, 1H), 7.22-7.15 (m, 2H), 6.82 (s, 1H), 4.37 (s, 2H), 3.77 (s, 2H), 3.73 (s, 3H), 2.99 (br t, J = 5.6 Hz, 2H), 2.79-2.71 (m, 2H); MS (ESI) m/z 471.5 $[M + H]^+$ |
| I-31 | 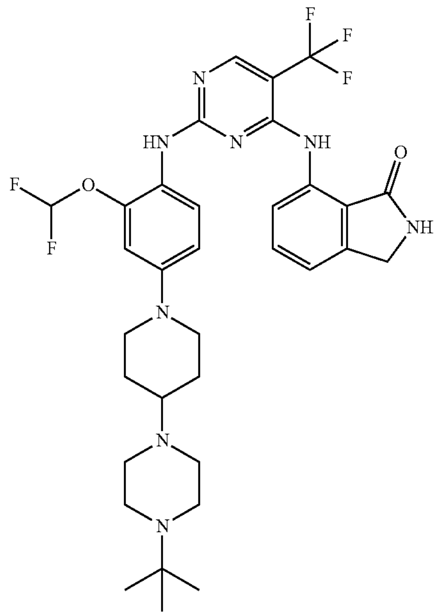 [SMILES: CC(C)(C)N1CCN(C2CCN(c3ccc(Nc4ncc(C(F)(F)F)c(Nc5cccc6c5C(=O)NC6)n4)c(OC(F)F)c3)CC2)CC1] | 22% | $^1$H NMR (500 MHz, DMSO-$d_6$) δ 10.63 (br s, 1H), 9.23 (s, 1H), 8.75 (s, 1H), 8.37 (br s, 1H), 7.94 (br s, 1H), 7.28 (d, J = 8.8 Hz, 1H), 7.23-6.85 (m, 4H), 6.80 (br s, 1H), 4.36 (br s, 2H), 3.78 (br d, J = 10.4 Hz, 2H), 2.84-2.72 (m, 2H), 2.40-2.28 (m, 1H), 1.89 (br d, J = 11.4 Hz, 2H), 1.52 (q, J = 10.7 Hz, 2H), 1.03 (br s, 9H); MS (ESI) m/z 675.7 $[M + H]^+$ |

-continued
| Compound I.D. | Structure | Yield (Overall) | NMR & MS |
|---|---|---|---|
| I-32 | 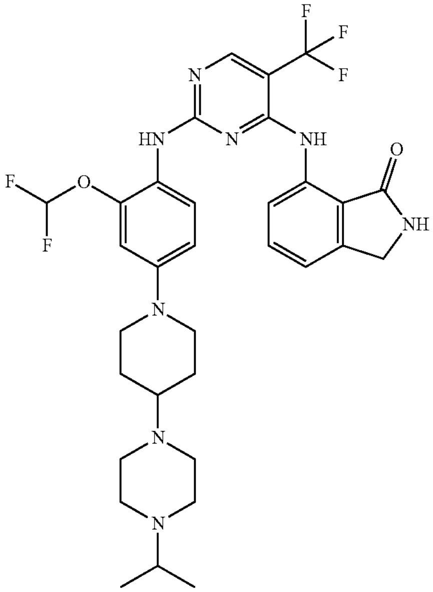 [SMILES: CC(C)N1CCN(C2CCN(c3ccc(Nc4ncc(C(F)(F)F)c(Nc5cccc6c5C(=O)NC6)n4)c(OC(F)F)c3)CC2)CC1] | 27% | $^1$H NMR (500 MHz, DMSO-$d_6$) δ 10.63 (br s, 1H), 9.24 (s, 1H), 8.76 (s, 1H), 8.37 (br s, 1H), 7.28 (d, J = 8.8 Hz, 1H), 7.23-6.93 (m, 3H), 6.92-6.86 (m, 1H), 6.80 (br s, 1H), 4.36 (br s, 2H), 3.78 (br d, J = 10.4 Hz, 2H), 2.76 (br t, J = 11.1 Hz, 2H), 2.65-2.55 (m, 2H), 2.48-2.28 (m, 6H), 1.88 (br d, J = 11.2 Hz, 2H), 1.58-1.47 (m, 2H), 0.97 (d, J = 6.5 Hz, 6H); MS (ESI) m/z 661.6 $[M + H]^+$ |
| I-33 | 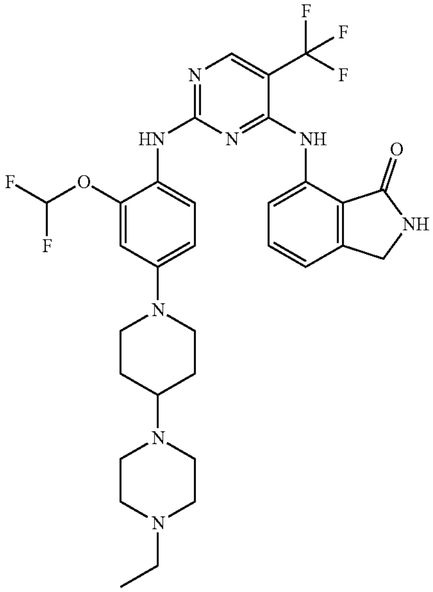 [SMILES: CCN1CCN(C2CCN(c3ccc(Nc4ncc(C(F)(F)F)c(Nc5cccc6c5C(=O)NC6)n4)c(OC(F)F)c3)CC2)CC1] | 29% | $^1$H NMR (500 MHz, DMSO-$d_6$) δ 10.63 (br s, 1H), 9.24 (s, 1H), 8.76 (br s, 1H), 8.37 (br s, 1H), 8.12-7.78 (m, 1H), 7.28 (d, J = 8.8 Hz, 1H), 7.22-6.86 (m, 3H), 6.80 (br s, 1H), 4.36 (br s, 2H), 3.78 (br d, J = 10.1 Hz, 2H), 3.42-3.35 (m, 1H), 2.77 (brt, J = 11.2 Hz, 2H), 2.45-2.16 (m, 7H), 1.88 (br d, J = 11.4 Hz, 2H), 1.58-1.47 (m, 2H), 0.99 (t, J = 7.1 Hz, 3H); MS (ESI) m/z 647.6 $[M + H]^+$ |

-continued
| Compound I.D. | Structure | Yield (Overall) | NMR & MS |
|---|---|---|---|
| I-34 | 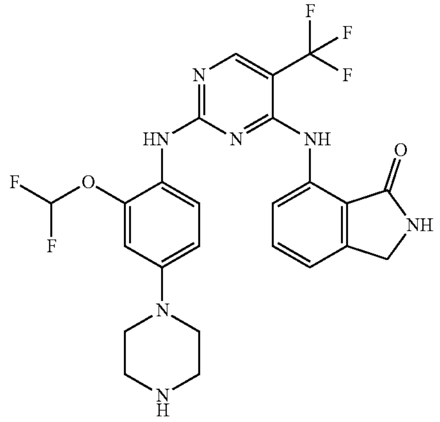 [SMILES: O=C1NCc2cccc(Nc3nc(Nc4ccc(N5CCNCC5)cc4OC(F)F)ncc3C(F)(F)F)c21] | 54% | $^1$H NMR (500 MHz, DMSO-$d_6$) δ 10.64 (br s, 1H), 9.25 (s, 1H), 8.76 (s, 1H), 8.37 (br s, 1H), 7.96 (br s, 1H), 7.30 (d, J = 8.8 Hz, 1H), 7.22-6.83 (m, 4H), 6.79 (br s, 1H), 4.36 (br s, 2H), 3.16-3.08 (m, 4H), 2.92-2.83 (m, 4H); MS (ESI) m/z 536.5 [M + H]$^+$ |
| I-35 | 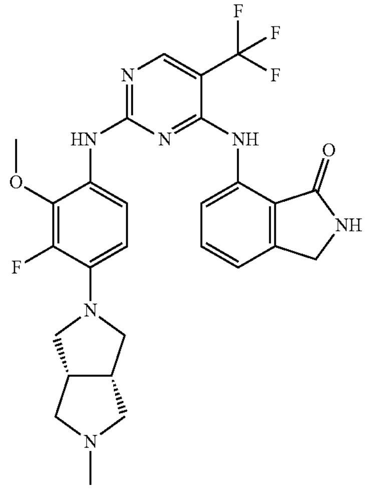 [SMILES: COc1c(Nc2ncc(C(F)(F)F)c(Nc3cccc4c3C(=O)NC4)n2)ccc(N2C[C@H]3CN(C)C[C@H]3C2)c1F] | 49% | $^1$H NMR (500 MHz, DMSO-$d_6$) δ 10.63 (br s, 1H), 9.28 (s, 1H), 8.76 (s, 1H), 8.39 (s, 1H), 8.03 (br s, 1H), 7.44-6.93 (m, 3H), 6.63 (br t, J = 8.9 Hz, 1H), 4.36 (s, 2H), 3.75 (s, 3H), 3.41-3.35 (m, 2H), 3.10 (br d, J = 8.6 Hz, 2H), 2.84 (br s, 2H), 2.67-2.58 (m, 2H), 2.39-2.31 (m, 2H), 2.26 (s, 3H); MS (ESI) m/z 558.5 [M + H]$^+$ |
| I-36 | 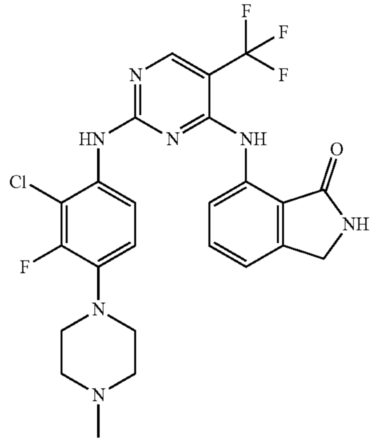 [SMILES: CN1CCN(c2ccc(Nc3ncc(C(F)(F)F)c(Nc4cccc5c4C(=O)NC5)n3)c(Cl)c2F)CC1] | 15% | $^1$H NMR (500 MHz, DMSO-$d_6$) δ 10.69 (br s, 1H), 9.68 (s, 1H), 8.77 (s, 1H), 8.42 (s, 1H), 8.33-7.83 (m, 1H), 7.28 (d, J = 8.7 Hz, 1H), 7.24-7.03 (m, 3H), 4.37 (s, 2H), 3.11 (br s, 4H), 2.64-2.52 (m, 4H), 2.27 (s, 3H); MS (ESI) m/z 536.4 [M + H]$^+$ |

-continued

| Compound I.D. | Structure | Yield (Overall) | NMR & MS |
|---|---|---|---|
| I-37 | 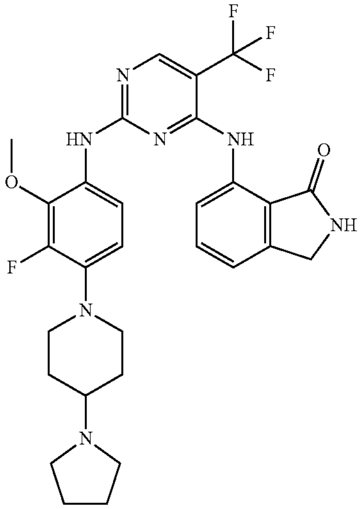 [SMILES: COc1c(Nc2ncc(C(F)(F)F)c(Nc3cccc4c3C(=O)NC4)n2)ccc(N2CCC(N3CCCC3)CC2)c1F] | 31% | $^1H$ NMR (500 MHz, DMSO-$d_6$) δ 10.65 (br s, 1H), 9.32 (s, 1H), 8.76 (s, 1H), 8.40 (s, 1H), 8.36-7.77 (m, 1H), 7.43-7.10 (m, 3H), 6.82 (br t, J = 8.6 Hz, 1H), 4.37 (s, 2H), 3.76 (s, 3H), 3.40-3.35 (m, 2H), 2.76 (br t, J = 11.0 Hz, 2H), 2.58-2.53 (m, 4H), 2.14 (br s, 1H), 1.98 (br d, J = 12.6 Hz, 2H), 1.70 (br s, 4H), 1.59 (q, J = 10.3 Hz, 2H); MS (ESI) m/z 586.7 $[M + H]^+$ |
| I-38 | 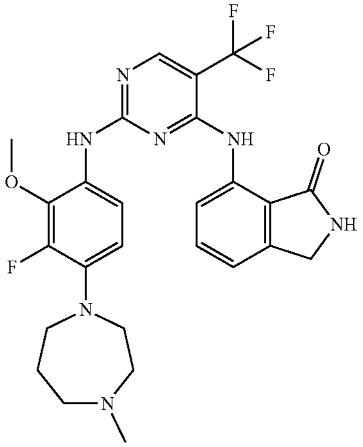 [SMILES: COc1c(Nc2ncc(C(F)(F)F)c(Nc3cccc4c3C(=O)NC4)n2)ccc(N2CCCN(C)CC2)c1F] | 32% | $^1H$ NMR (500 MHz, DMSO-$d_6$) δ 10.63 (br s, 1H), 9.25 (s, 1H), 8.75 (s, 1H), 8.38 (s, 1H), 8.28-7.75 (m, 1H), 7.35-7.10 (m, J = 6.0 Hz, 2H), 7.06 (br d, J = 8.6 Hz, 1H), 6.71 (br t, J = 9.1 Hz, 1H), 4.36 (s, 2H), 3.74 (s, 3H), 3.47-3.37 (m, 4H), 2.75-2.68 (m, 2H), 2.63-2.57 (m, 2H), 2.32 (s, 3H), 1.95 (quin, J = 5.5 Hz, 2H); MS (ESI) m/z 546.5 $[M + H]^+$ |
| I-39 | 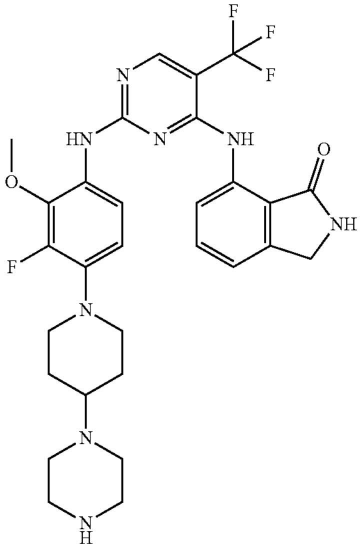 [SMILES: COc1c(Nc2ncc(C(F)(F)F)c(Nc3cccc4c3C(=O)NC4)n2)ccc(N2CCC(N3CCNCC3)CC2)c1F] | 15% | $^1H$ NMR (500 MHz, DMSO-$d_6$) δ 10.65 (br s, 1H), 9.31 (s, 1H), 8.76 (s, 1H), 8.40 (s, 1H), 8.35-7.89 (m, 1H), 7.37-7.13 (m, 3H), 6.82 (br t, J = 8.9 Hz, 1H), 4.37 (s, 2H), 3.76 (s, 3H), 3.46-3.39 (m, 2H), 2.77-2.67 (m, 6H), 2.49-2.43 (m, 4H), 2.35-2.28 (m, 1H), 1.88 (br d, J = 12.0 Hz, 2H), 1.61 (dq, J = 3.1, 11.7 Hz, 2H); MS (ESI) m/z 601.4 $[M + H]^+$ |

-continued

| Compound I.D. | Structure | Yield (Overall) | NMR & MS |
|---|---|---|---|
| I-40 | 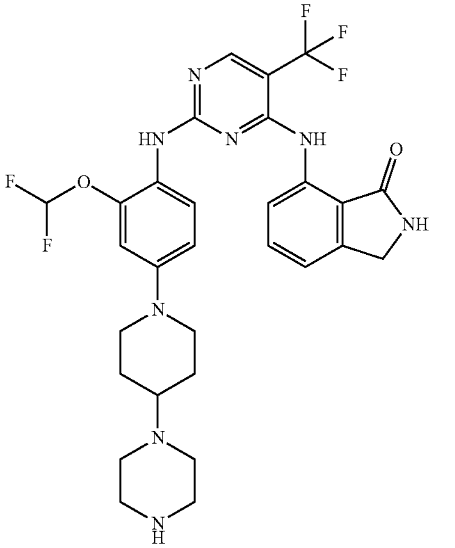 [SMILES: O=C1NCc2cccc(Nc3nc(Nc4ccc(N5CCC(N6CCNCC6)CC5)cc4OC(F)F)ncc3C(F)(F)F)c21] | 14% | $^1H$ NMR (500 MHz, DMSO-$d_6$) δ 10.63 (br s, 1H), 9.23 (s, 1H), 8.75 (s, 1H), 8.37 (br s, 1H), 8.13-7.78 (m, 1H), 7.28 (d, J = 8.8 Hz, 1H), 7.22-6.85 (m, 4H), 6.80 (br s, 1H), 4.36 (br s, 2H), 3.79 (br d, J = 11.0 Hz, 2H), 2.80-2.67 (m, 6H), 2.48-2.40 (m, 4H), 2.39-2.30 (m, 1H), 1.86 (br d, J = 11.4 Hz, 2H), 1.59-1.48 (m, 2H); MS (ESI) m/z 619.4 $[M + H]^+$ |
| I-41 | 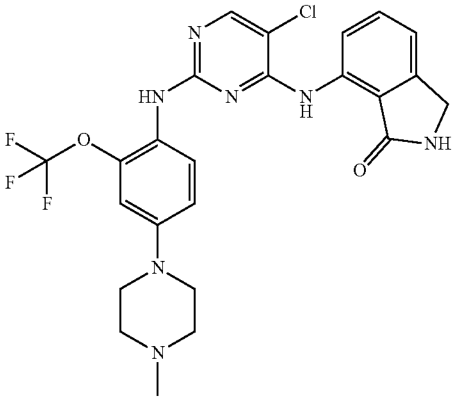 [SMILES: CN1CCN(c2ccc(Nc3ncc(Cl)c(Nc4cccc5c4C(=O)NC5)n3)c(OC(F)(F)F)c2)CC1] | 16% | $^1H$ NMR (500 MHz, DMSO-$d_6$) δ 10.65 (s, 1H), 8.95 (s, 1H), 8.78 (s, 1H), 8.31 (s, 1H), 8.15 (s, 1H), 7.39 (d, J = 8.9 Hz, 1H), 7.27 (d, J = 7.4 Hz, 1H), 7.14 (d, J = 7.4 Hz, 1H), 7.02 (dd, J = 8.9, 2.6 Hz, 1H), 6.93 (s, 1H), 4.38 (s, 2H), 3.27-3.16 (m, 4H), 2.48 (d, J = 5.0 Hz, 4H), 2.25 (s, 3H); MS (ESI) m/z 534.4 $[M + H]^+$ |
| I-42 | 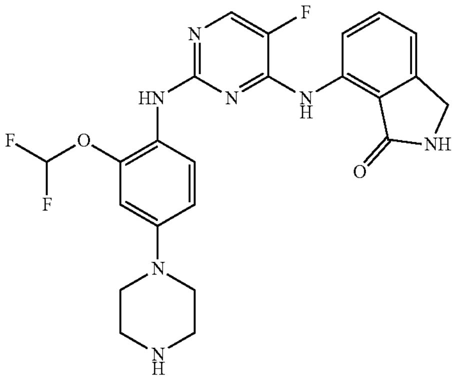 | 4% | $^1H$ NMR (500 MHz, DMSO-$d_6$) δ 10.44 (s, 1H), 8.84 (s, 1H), 8.47 (s, 1H), 8.38 (d, J = 6.0 Hz, 1H), 8.10 (d, J = 3.1 Hz, 1H), 7.38 (s, 1H), 7.34 (t, J = 7.8 Hz, 1H), 7.16 (d, J = 7.5 Hz, 1H), 7.05 (t, J = 74.6 Hz, 1H), 6.85 (dd, J = 8.8, 2.4 Hz, 1H), 6.76 (s, 1H), 4.39 (s, 2H), 3.11-3.05 (m, 4H), 2.90-2.83 (m, 4H); MS (ESI) m/z 486.1 $[M + H]^+$ |

-continued
| Compound I.D. | Structure | Yield (Overall) | NMR & MS |
|---|---|---|---|
| I-43 | 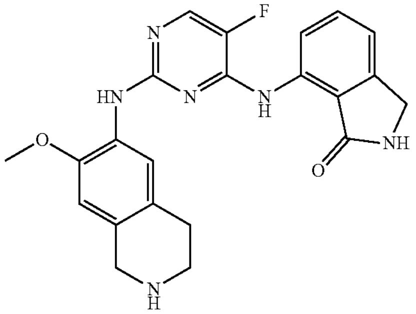 | 4% | $^1$H NMR (500 MHz, DMSO-$d_6$) δ 10.49 (s, 1H), 8.86 (s, 1H), 8.48 (d, J = 8.2 Hz, 1H), 8.19 (d, J = 3.1 Hz, 1H), 8.05 (s, 1H), 7.56 (s, 1H), 7.46 (t, J = 7.9 Hz, 1H), 7.19 (d, J = 7.5 Hz, 1H), 6.71 (s, 1H), 6.36 (d, J = 49.1 Hz, 1H), 4.41 (s, 2H), 3.85 (s, 2H), 3.78 (s, 3H), 3.69 (d, J = 4.7 Hz, 1H), 2.95 (t, J = 5.6 Hz, 2H), 2.64-2.59 (m, 2H); MS (ESI) m/z 421.2 [M + H]$^+$ |
| I-44 | 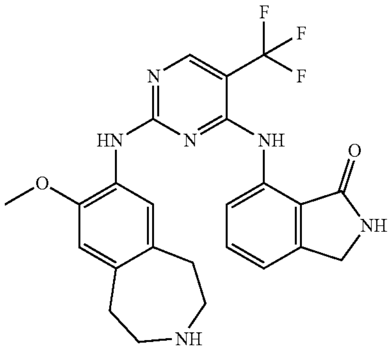 [SMILES: COc1cc2c(cc1Nc1ncc(C(F)(F)F)c(Nc3cccc4c3C(=O)NC4)n1)CCNCC2] | 6% | $^1$H NMR (500 MHz, DMSO-$d_6$) δ 10.63 (s, 1H), 8.96 (s, 1H), 8.76 (s, 1H), 8.39 (s, 1H), 7.24 (s, 2H), 7.16 (d, J = 7.0 Hz, 1H), 6.91 (s, 1H), 4.37 (s, 2H), 3.73 (s, 3H), 2.97-2.72 (m, 8H), 1.24 (d, J = 5.6 Hz, 1H); MS (ESI) m/z 485.1 [M + H]$^+$ |
| I-45 | 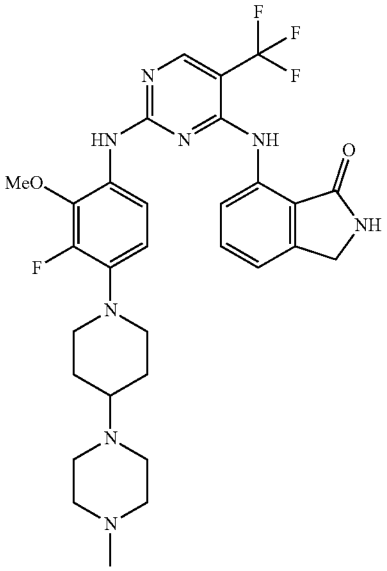 [SMILES: COc1c(Nc2ncc(C(F)(F)F)c(Nc3cccc4c3C(=O)NC4)n2)ccc(N2CCC(N3CCN(C)CC3)CC2)c1F] | 13% | $^1$H NMR (500 MHz, DMSO-$d_6$) δ 10.65 (br s, 1H), 9.31 (s, 1H), 8.76 (s, 1H), 8.40 (s, 1H), 8.35-7.92 (m, 1H), 7.39-7.08 (m, 3H), 6.82 (br t, J = 8.7 Hz, 1H), 4.37 (s, 2H), 3.76 (s, 3H), 3.45-3.40 (m, 2H), 2.78-2.68 (m, 2H), 2.43-2.23 (m, 5H), 2.16 (s, 3H), 1.89 (br d, J = 11.2 Hz, 2H), 1.65-1.55 (m, 2H); MS (ESI) m/z 615.6 [M + H]$^+$ |

-continued

| Compound I.D. | Structure | Yield (Overall) | NMR & MS |
|---|---|---|---|
| I-46 | 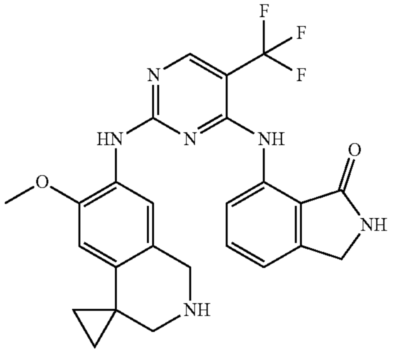 [SMILES: COc1cc2c(cc1Nc1ncc(C(F)(F)F)c(Nc3cccc4c3C(=O)NC4)n1)CNCC21CC1] | 25% | $^{1}H$ NMR (500 MHz, DMSO-$d_6$) δ 10.63 (s, 1H), 8.96 (s, 1H), 8.75 (s, 1H), 8.39 (s, 1H), 7.33 (s, 1H), 7.18 (d, J = 6.8 Hz, 2H), 6.38 (s, 1H), 4.37 (s, 2H), 3.86 (s, 2H), 3.71 (s, 3H), 2.78 (s, 2H), 1.04 (s, 2H), 0.85 (d, J = 5.0 Hz, 2H); MS (ESI) m/z 497.2 $[M + H]^+$ |
| I-47 | 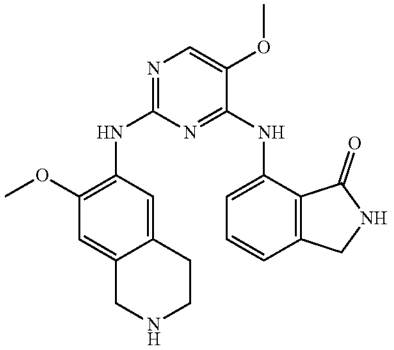 [SMILES: COc1cc2c(cc1Nc1ncc(OC)c(Nc3cccc4c3C(=O)NC4)n1)CCNC2] | 8% | $^{1}H$ NMR (500 MHz, DMSO-$d_6$) δ 10.51 (s, 1H), 8.70 (s, 1H), 8.63 (d, J = 8.3 Hz, 1H), 7.95 (s, 1H), 7.79 (s, 1H), 7.59 (s, 1H), 7.49 (t, J = 7.9 Hz, 1H), 7.15 (d, J = 7.5 Hz, 1H), 6.68 (s, 1H), 4.39 (s, 2H), 3.89 (s, 3H), 3.82 (s, 2H), 3.81 (s, 3H), 2.95 (t, J = 5.7 Hz, 2H), 2.62 (t, J = 5.5 Hz, 2H); MS (ESI) m/z 433.2 $[M + H]^+$ |
| I-48 | 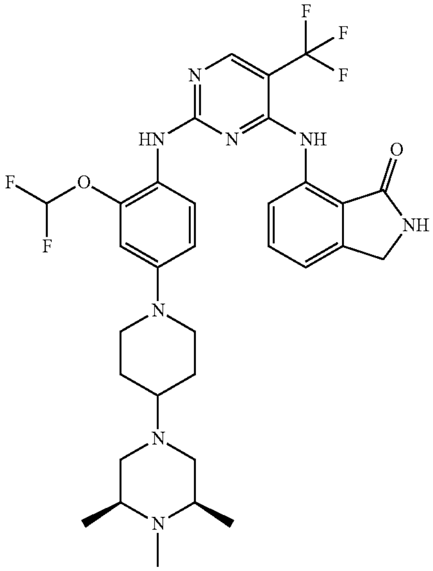 [SMILES: C[C@@H]1CN(C2CCN(c3ccc(Nc4ncc(C(F)(F)F)c(Nc5cccc6c5C(=O)NC6)n4)c(OC(F)F)c3)CC2)C[C@H](C)N1C] | 26% | $^{1}H$ NMR (500 MHz, DMSO-$d_6$) δ 10.63 (br s, 1H), 9.23 (s, 1H), 8.75 (s, 1H), 8.37 (br s, 1H), 8.18-7.74 (m, 1H), 7.28 (d, J = 8.9 Hz, 1H), 7.22-6.85 (m, 4H), 6.79 (br s, 1H), 4.36 (br s, 2H), 3.78 (br d, J = 10.8 Hz, 2H), 2.77 (br d, J = 9.4 Hz, 4H), 2.30 (br t, J = 10.5 Hz, 1H), 2.19-2.06 (m, 5H), 1.97-1.82 (m, 4H), 1.58-1.45 (m, 2H), 0.99 (d, J = 6.1 Hz, 6H); MS (ESI) m/z 661.5 $[M + H]^+$ |

-continued

| Compound I.D. | Structure | Yield (Overall) | NMR & MS |
|---|---|---|---|
| I-49 | 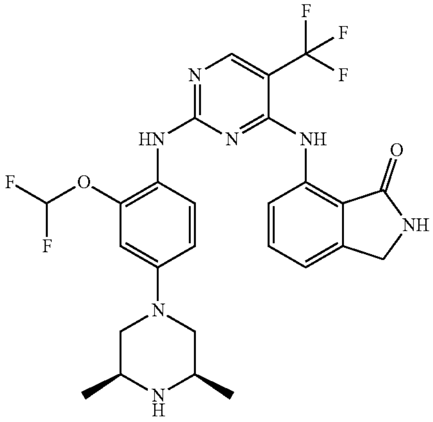 [SMILES: C[C@@H]1CN(c2ccc(Nc3ncc(C(F)(F)F)c(Nc4cccc5c4C(=O)NC5)n3)c(OC(F)F)c2)C[C@H](C)N1] | 17% | $^1$H NMR (500 MHz, DMSO-$d_6$) δ 10.63 (br s, 1H), 9.23 (s, 1H), 8.75 (s, 1H), 8.37 (br s, 1H), 8.06-7.77 (m, 1H), 7.28 (d, J = 8.8 Hz, 1H), 7.22-6.85 (m, 4H), 6.80 (br s, 1H), 4.36 (br s, 2H), 3.61 (br d, J = 10.0 Hz, 2H), 2.94-2.81 (m, 2H), 2.20 (br t, J = 10.8 Hz, 2H), 1.06 (d, J = 6.2 Hz, 6H); MS (ESI) m/z 564.3 [M + H]$^+$ |
| I-50 | 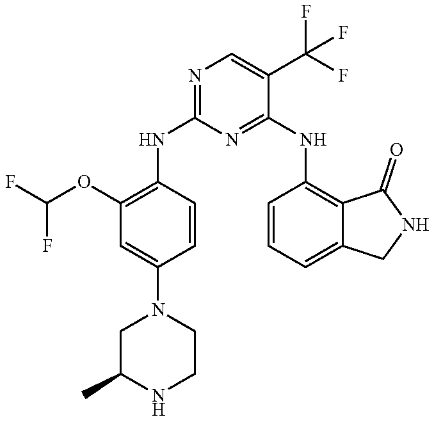 [SMILES: C[C@H]1CN(c2ccc(Nc3ncc(C(F)(F)F)c(Nc4cccc5c4C(=O)NC5)n3)c(OC(F)F)c2)CCN1] | 46% | $^1$H NMR (500 MHz, DMSO-$d_6$) δ 10.64 (br s, 1H), 9.23 (s, 1H), 8.75 (s, 1H), 8.37 (br s, 1H), 8.16-7.78 (m, 1H), 7.29 (d, J = 8.8 Hz, 1H), 7.23-6.84 (m, 4H), 6.79 (br s, 1H), 4.36 (br s, 2H), 3.58 (br t, J = 8.9 Hz, 2H), 3.00 (br d, J = 11.9 Hz, 1H), 2.87-2.74 (m, 2H), 2.70-2.58 (m, 1H), 2.27 (br t, J = 10.7 Hz, 1H), 1.06 (d, J = 6.2 Hz, 3H); MS (ESI) m/z 550.4 [M + H]$^+$ |
| I-51 | 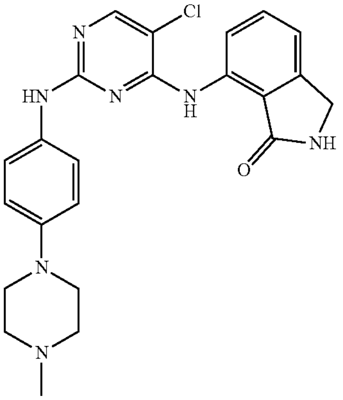 [SMILES: CN1CCN(c2ccc(Nc3ncc(Cl)c(Nc4cccc5c4C(=O)NC5)n3)cc2)CC1] | 16% | $^1$H NMR (500 MHz, DMSO-$d_6$) δ 10.68 (s, 1H), 9.30 (s, 1H), 8.80 (s, 1H), 8.73 (s, 1H), 8.20 (s, 1H), 7.48 (d, J = 8.4 Hz, 3H), 7.20 (d, J = 7.5 Hz, 1H), 6.93 (d, J = 9.0 Hz, 2H), 4.41 (s, 2H), 3.14-3.06 (m, 4H), 2.49-2.45 (m, 4H), 2.23 (s, 3H); MS (ESI) m/z 450.5 [M + H]$^+$ |

-continued
| Compound I.D. | Structure | Yield (Overall) | NMR & MS |
|---|---|---|---|
| I-52 | 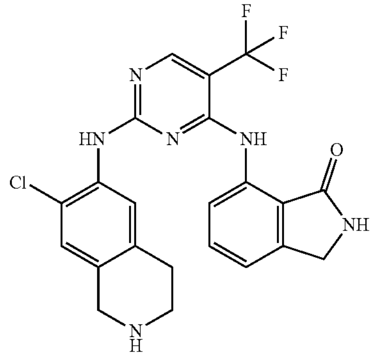 [SMILES: O=C1NCc2cccc(Nc3nc(Nc4cc5c(cc4Cl)CNCC5)ncc3C(F)(F)F)c21] | 20% | $^1$H NMR (500 MHz, DMSO-$d_6$) δ 10.69 (s, 1H), 9.56 (s, 1H), 8.77 (s, 1H), 8.41 (s, 1H), 7.26 (d, J = 5.5 Hz, 2H), 7.15 (d, J = 7.2 Hz, 1H), 4.36 (s, 2H), 3.90 (s, 2H), 2.95 (t, J = 5.7 Hz, 2H), 2.65 (t, J = 5.6 Hz, 2H), 1.73 (s, 1H); MS (ESI) m/z 475.3 [M + H]$^+$ |
| I-53 | 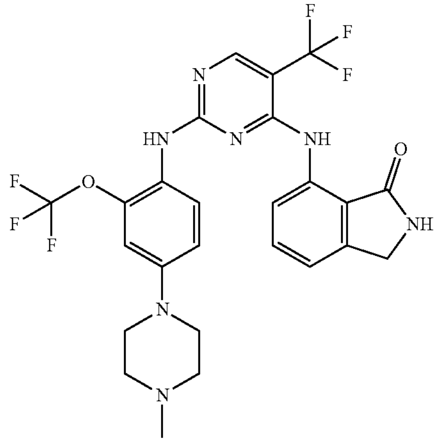 [SMILES: CN1CCN(c2ccc(Nc3ncc(C(F)(F)F)c(Nc4cccc5c4C(=O)NC5)n3)c(OC(F)(F)F)c2)CC1] | 20% | $^1$H NMR (500 MHz, DMSO-$d_6$) δ 10.65 (s, 1H), 9.46 (s, 1H), 8.76 (s, 1H), 8.38 (s, 1H), 7.36 (t, J = 9.5 Hz, 1H), 7.15 (s, 1H), 7.04 (d, J = 7.9 Hz, 1H), 6.96 (s, 1H), 4.35 (d, J = 10.8 Hz, 2H), 3.21 (d, J = 27.8 Hz, 4H), 2.26 (s, 3H); MS (ESI) m/z 568.2 [M + H]$^+$ |
| I-54 | 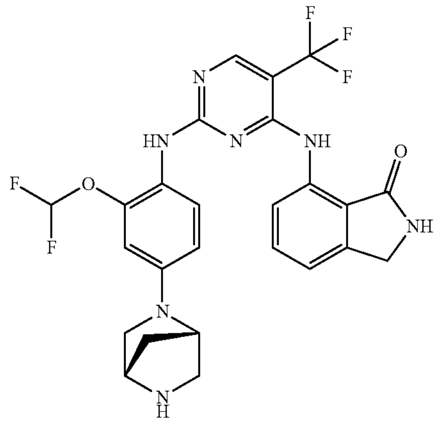 [SMILES: O=C1NCc2cccc(Nc3nc(Nc4ccc(N5C[C@@H]6C[C@H]5CN6)cc4OC(F)F)ncc3C(F)(F)F)c21] | 42% | $^1$H NMR (500 MHz, DMSO-$d_6$) δ 10.71-10.53 (m, 1H), 9.15 (br s, 1H), 8.74 (br s, 1H), 8.36 (br s, 1H), 8.11-7.89 (m, 1H), 7.69-7.42 (m, 1H), 7.21 (d, J = 8.6 Hz, 1H), 7.19-6.81 (m, 3H), 6.52 (br s, 1H), 6.42 (br s, 1H), 4.45-4.29 (m, 3H), 3.68 (br s, 1H), 3.58-3.49 (m, 1H), 3.00-2.84 (m, 3H), 1.83 (br d, J = 8.2 Hz, 1H), 1.69 (br d, J = 9.2 Hz, 1H); MS (ESI) m/z 548.4 [M + H]$^+$ |

-continued

| Compound I.D. | Structure | Yield (Overall) | NMR & MS |
|---|---|---|---|
| I-55 | 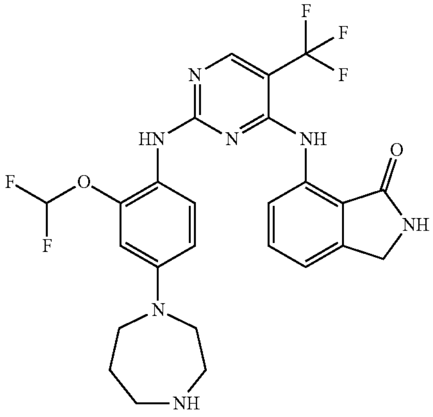 [SMILES: O=C1NCc2cccc(Nc3nc(Nc4ccc(N5CCCNCC5)cc4OC(F)F)ncc3C(F)(F)F)c21] | 38% | $^1$H NMR (500 MHz, DMSO-$d_6$) δ 10.61 (br s, 1H), 9.14 (br s, 1H), 8.75 (br s, 1H), 8.36 (br s, 1H), 8.02 (br s, 1H), 7.70-7.40 (m, 1H), 7.20 (d, J = 8.9 Hz, 1H), 7.18-6.84 (m, 3H), 6.65 (br s, 1H), 6.53 (br s, 1H), 4.36 (br s, 2H), 3.64-3.54 (m, 2H), 3.54-3.42 (m, 2H), 3.00-2.81 (m, 2H), 2.71 (br t, J = 5.4 Hz, 2H), 1.91-1.74 (m, 2H); MS (ESI) m/z 550.3 $[M + H]^+$ |
| I-56 | 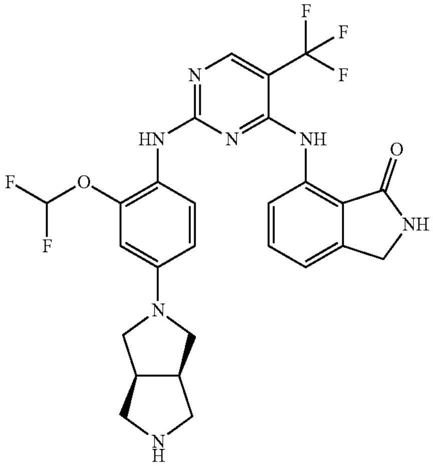 [SMILES: O=C1NCc2cccc(Nc3nc(Nc4ccc(N5C[C@H]6CNC[C@H]6C5)cc4OC(F)F)ncc3C(F)(F)F)c21] | 30% | $^1$H NMR (500 MHz, DMSO-$d_6$) δ 10.62 (br s, 1H), 9.19 (br s, 1H), 8.75 (br s, 1H), 8.36 (br s, 1H), 8.07-7.80 (m, 1H), 7.24 (d, J = 8.7 Hz, 1H), 7.20-6.83 (m, 3H), 6.56 (br s, 1H), 6.47 (br s, 1H), 4.36 (br s, 2H), 3.50-3.41 (m, 2H), 3.17-3.06 (m, 2H), 3.05-2.94 (m, 2H), 2.87 (br s, 2H), 2.73-2.60 (m, 2H); MS (ESI) m/z 562.4 $[M + H]^+$ |
| I-57 | 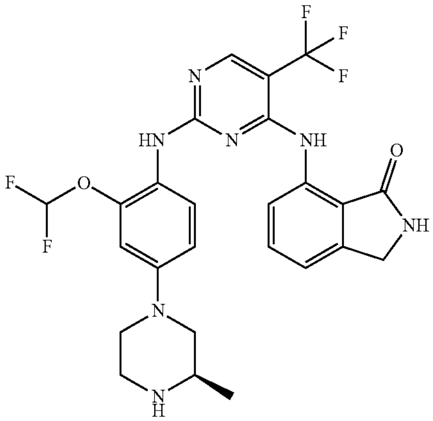 [SMILES: C[C@@H]1CN(c2ccc(Nc3ncc(C(F)(F)F)c(Nc4cccc5c4C(=O)NC5)n3)c(OC(F)F)c2)CCN1] | 28% | $^1$H NMR (500 MHz, DMSO-$d_6$) δ 10.64 (br s, 1H), 9.24 (s, 1H), 8.76 (br s, 1H), 8.37 (br s, 1H), 8.10-7.79 (m, 1H), 7.29 (d, J = 8.8 Hz, 1H), 7.22-6.84 (m, 4H), 6.79 (br s, 1H), 4.36 (br s, 2H), 3.65-3.52 (m, 2H), 3.00 (br d, J = 11.7 Hz, 1H), 2.88-2.75 (m, 2H), 2.67-2.59 (m, 1H), 2.27 (br t, J = 10.7 Hz, 1H), 1.06 (d, J = 6.2 Hz, 3H); MS (ESI) m/z 550.3 $[M + H]^+$ |

-continued
| Compound I.D. | Structure | Yield (Overall) | NMR & MS |
|---|---|---|---|
| I-58 | 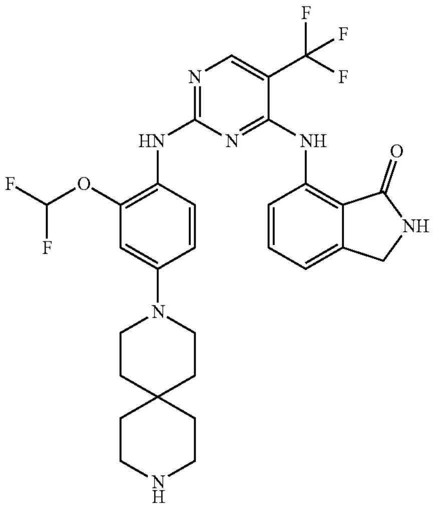 [SMILES: O=C1NCc2cccc(Nc3nc(Nc4ccc(N5CCC6(CCNCC6)CC5)cc4OC(F)F)ncc3C(F)(F)F)c21] | 7% | $^1H$ NMR (500 MHz, DMSO-$d_6$) δ 10.63 (br s, 1H), 9.22 (br s, 1H), 8.75 (br s, 1H), 8.36 (br s, 1H), 8.12-7.84 (m, 1H), 7.28 (d, J = 8.8 Hz, 1H), 7.22-6.85 (m, 4H), 6.78 (br s, 1H), 4.36 (br s, 2H), 3.27-3.20 (m, 4H), 2.80-2.69 (m, 4H), 1.64-1.55 (m, 4H), 1.48-1.40 (m, 4H); MS (ESI) m/z 604.4 $[M + H]^+$ |
| I-59 | 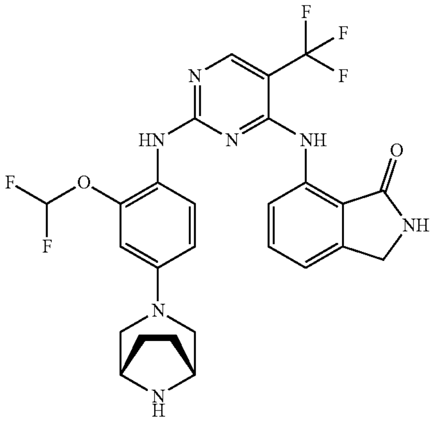 | 37% | $^1H$ NMR (500 MHz, DMSO-$d_6$) δ 10.62 (br s, 1H), 9.23 (s, 1H), 8.75 (br s, 1H), 8.36 (br s, 1H), 7.98-7.76 (m, 1H), 7.25 (d, J = 8.8 Hz, 1H), 7.20-6.84 (m, 3H), 6.80-6.70 (m, 1H), 6.65 (br s, 1H), 4.36 (br s, 2H), 3.55 (br s, 2H), 3.49-3.41 (m, 2H), 2.82 (br d, J = 9.9 Hz, 2H), 1.72 (s, 4H); MS (ESI) m/z 562.4 $[M + H]^+$ |
| I-60 | 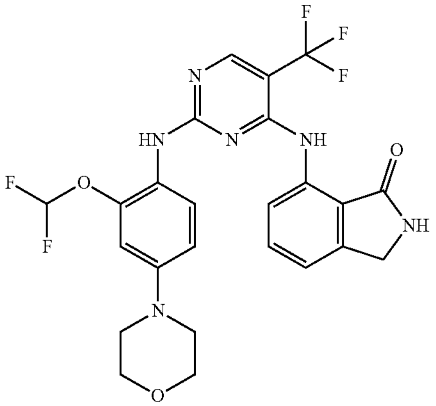 [SMILES: O=C1NCc2cccc(Nc3nc(Nc4ccc(N5CCOCC5)cc4OC(F)F)ncc3C(F)(F)F)c21] | 5% | $^1H$ NMR (500 MHz, DMSO-$d_6$) δ 10.64 (s, 1H), 9.27 (s, 1H), 8.75 (s, 1H), 8.37 (s, 1H), 7.34 (d, J = 8.8 Hz, 1H), 7.16 (s, 1H), 7.06 (t, J = 73.4 Hz, 1H), 6.91 (s, 1H), 6.83 (s, 1H), 4.37 (s, 2H), 3.84-3.74 (m, 4H), 3.19 (s, 4H); MS (ESI) m/z 537.0 $[M + H]^+$ |

-continued

| Compound I.D. | Structure | Yield (Overall) | NMR & MS |
|---|---|---|---|
| I-61 | 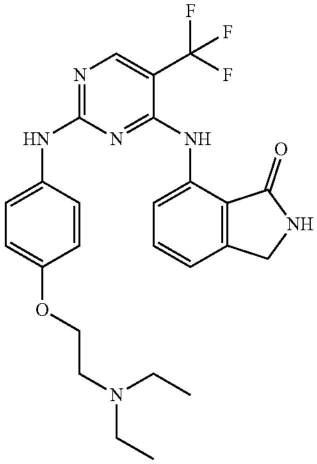 [SMILES: CCN(CC)CCOc1ccc(Nc2ncc(C(F)(F)F)c(Nc3cccc4c3C(=O)NC4)n2)cc1] | 7% | $^1$H NMR (500 MHz, DMSO-d$_6$) δ 10.26 (s, 1H), 8.95 (s, 1H), 8.73 (s, 1H), 8.38 (s, 1H), 7.91 (s, 1H), 7.31 (d, J = 8.8 Hz, 2H), 7.11 (s, 1H), 7.04 (dd, J = 8.0, 3.7 Hz, 3H), 4.33 (s, 2H), 4.10 (t, J = 6.0 Hz, 2H), 2.84 (t, J = 6.0 Hz, 2H), 2.60 (dd, J = 14.2, 7.1 Hz, 4H), 1.01 (dd, J = 11.9, 4.7 Hz, 6H); MS (ESI) m/z 501.2 [M + H]$^+$ |
| I-62 | 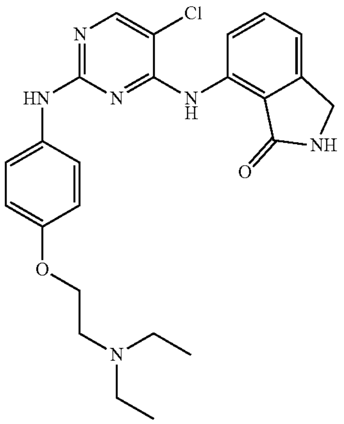 [SMILES: CCN(CC)CCOc1ccc(Nc2ncc(Cl)c(Nc3cccc4c3C(=O)NC4)n2)cc1] | 9% | $^1$H NMR (500 MHz, DMSO-d$_6$) δ 10.69 (s, 1H), 9.37 (s, 1H), 8.82 (s, 1H), 8.71 (s, 1H), 8.22 (s, 1H), 7.59-7.46 (m, 3H), 7.20 (d, J = 7.5 Hz, 1H), 6.92 (d, J = 8.9 Hz, 2H), 4.41 (s, 3H), 4.41 (s, 2H), 4.01 (t, J = 6.2 Hz, 2H), 4.01 (t, J = 6.2 Hz, 2H), 2.78 (t, J = 6.2 Hz, 2H), 2.78 (t, J = 6.2 Hz, 2H), 2.56 (q, J = 7.1 Hz, 4H), 0.99 (t, J = 7.1 Hz, 6H), 0.99 (t, J = 7.1 Hz, 6H); MS (ESI) m/z 467.2 [M + H]$^+$ |
| I-63 | 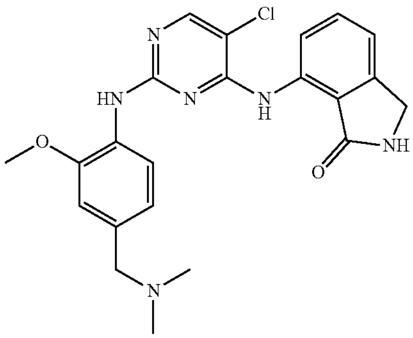 [SMILES: COc1cc(CN(C)C)ccc1Nc1ncc(Cl)c(Nc2cccc3c2C(=O)NC3)n1] | 25% | H NMR (500 MHz, DMSO) δ 10.66 (s, 1H), 8.80 (s, 1H), 8.47 (d, J = 9.2 Hz, 2H), 8.20 (s, 1H), 7.62 (d, J = 7.9 Hz, 1H), 7.36 (t, J = 7.8 Hz, 1H), 7.16 (d, J = 7.5 Hz, 1H), 7.02 (d, J = 1.1 Hz, 1H), 6.89 (d, J = 8.0 Hz, 1H), 4.39 (s, 2H), 3.79 (s, 3H), 3.41 (s, 2H), 2.19 (s, 6H) MS (ESI) m/z 439.3 [M + H]$^+$ |

-continued

| Compound I.D. | Structure | Yield (Overall) | NMR & MS |
|---|---|---|---|
| I-64 | 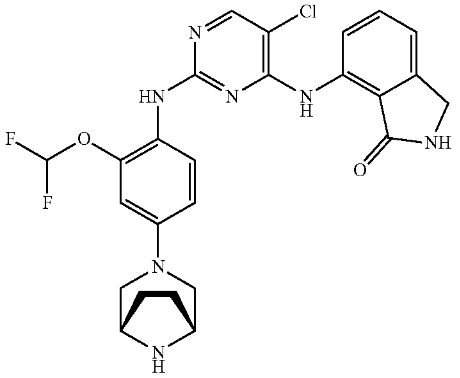 | 34% | $^{1}H$ NMR (500 MHz, DMSO-d6) δ 10.62 (s, 1H), 8.78 (s, 1H), 8.69 (s, 1H), 8.43-8.18 (m, 1H), 8.12 (s, 1H), 7.31-7.20 (m, J = 8.9 Hz, 2H), 7.17-6.85 (m, 2H), 6.74 (dd, J = 2.4, 8.9 Hz, 1H), 6.66-6.60 (m, 1H), 4.38 (s, 2H), 3.55 (br s, 2H), 3.43 (br d, J = 9.4 Hz, 2H), 2.81 (br d, J = 9.2 Hz, 2H), 1.72 (s, 4H); MS (ESI) m/z 528.3 $[M + H]^{+}$ |
| I-65 | 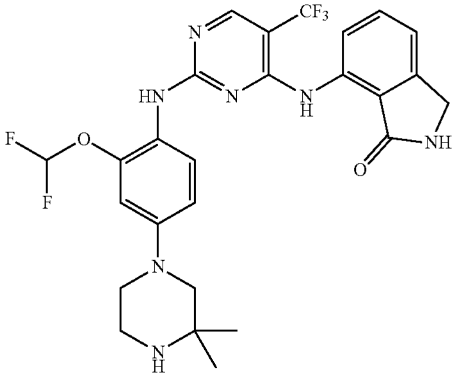 [SMILES: CC1(C)CN(c2ccc(Nc3ncc(C(F)(F)F)c(Nc4cccc5c4C(=O)NC5)n3)c(OC(F)F)c2)CCN1] | 40% | $^{1}H$ NMR (500 MHz, DMSO-d6) δ 10.62 (br. s., 1 H), 9.24 (s, 1 H), 8.75 (br. s., 1 H,) 8.36 (br. s., 1 H), 7.90 (br. s., 1 H), 7.26 (d, J = 8.80 Hz, 1 H,) 6.88-7.22 (m, 3 H), 6.86 (d, J = 7.09 Hz, 1 H), 6.76 (br. s., 1 H), 4.35 (br. s., 2 H), 3.09 (br. s., 2 H), 2.92 (br. s., 4 H), 1.14 (s, 6 H); MS (ESI) m/z 564.5 $[M + H]^{+}$ |
| I-66 | 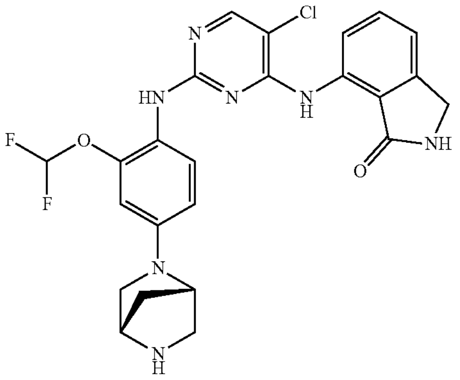 [SMILES: O=C1NCc2cccc(Nc3nc(Nc4ccc(N5C[C@@H]6C[C@H]5CN6)cc4OC(F)F)ncc3Cl)c21] | 11% | $^{1}H$ NMR (500 MHz, DMSO-d6) δ 10.62 (br s, 1H), 8.77 (br s, 1H), 8.61 (s, 1H), 8.51-8.19 (m, 1H), 8.11 (s, 1H), 7.37-7.21 (m, 2H), 7.17-6.82 (m, 2H), 6.50 (br d, J = 7.8 Hz, 1H), 6.40 (br s, 1H), 4.37 (br s, 3H), 3.70 (br s, 1H), 3.56-3.49 (m, 1H), 2.99-2.84 (m, 3H), 1.83 (br d, J = 9.0 Hz, 1H), 1.69 (br d, J = 8.9 Hz, 1H); MS (ESI) m/z 514.6 $[M + H]^{+}$ |

-continued
| Compound I.D. | Structure | Yield (Overall) | NMR & MS |
|---|---|---|---|
| I-67 | 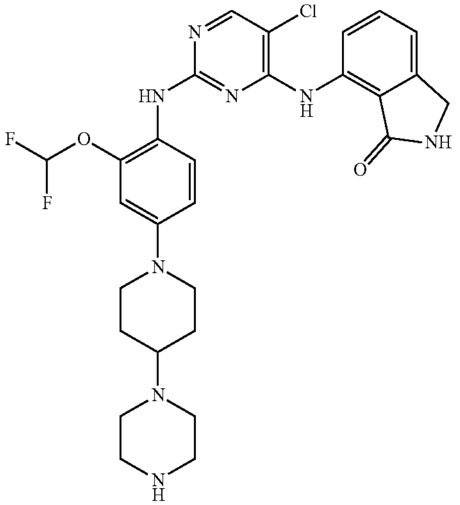 [SMILES: O=C1NCc2cccc(Nc3nc(Nc4ccc(N5CCC(N6CCNCC6)CC5)cc4OC(F)F)ncc3Cl)c21] | 15% | $^1$H NMR (500 MHz, DMSO-d6) δ 10.64 (s, 1H), 8.79 (s, 1H), 8.70 (s, 1H), 8.44-8.29 (m, 1H), 8.14 (s, 1H), 7.35-7.04 (m, 4H), 6.92-6.85 (m, 1H), 6.78 (br s, 1H), 4.38 (s, 2H), 3.77 (br d, J = 12.2 Hz, 2H), 2.83-2.67 (m, 6H), 2.48-2.42 (m, 2H), 2.39-2.28 (m, 1H), 1.94-1.80 (m, 2H), 1.62-1.47 (m, 2H); MS (ESI) m/z 585.4 $[M + H]^+$ |
| I-68 | 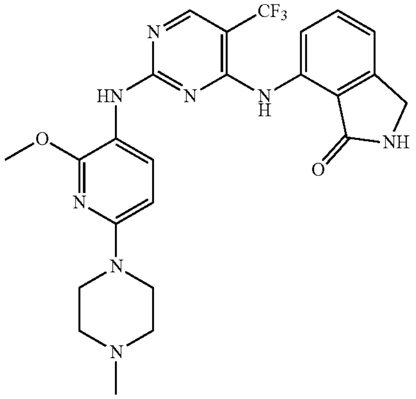 [SMILES: COc1nc(N2CCN(C)CC2)ccc1Nc1ncc(C(F)(F)F)c(Nc2cccc3c2C(=O)NC3)n1] | 52% | $^1$H NMR (500 MHz, DMSO-d6) δ 10.58 (br. s., 1 H), 9.05 (s, 1 H), 8.75 (br. s., 1 H), 8.35 (br. s., 1 H), 8.00 (br. s., 1 H), 7.49 (br. s., 1 H), 7.13 (br. s., 2 H), 6.41 (br. s., 1 H), 4.39-4.46 (m, 1 H), 4.36 (t, J = 5.01 Hz, 2 H), 3.69-3.87 (m, 3 H), 3.47-3.60 (m, 4 H), 2.38-2.47 (m, 4 H), 2.25 (s, 3 H); MS (ESI) m/z 515.5 $[M + H]^+$ |
| I-69 | 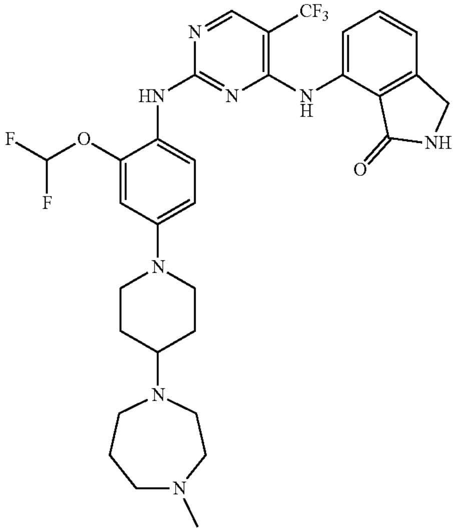 [SMILES: CN1CCCN(C2CCN(c3ccc(Nc4ncc(C(F)(F)F)c(Nc5cccc6c5C(=O)NC6)n4)c(OC(F)F)c3)CC2)CC1] | 16% | $^1$H NMR (500 MHz, DMSO-d6) δ 10.63 (br. s., 1 H), 9.23 (s, 1 H), 8.75 (s, 1 H), 8.36 (br. s., 1 H), 7.97 (br. s., 1 H), 7.27 (d, J = 8.80 Hz, 1 H), 6.83-7.21 (m, 4 H), 6.78 (br. s., 1 H), 4.36 (br. s., 2 H), 3.79 (d, J = 10.15 Hz, 2 H), 3.44 (m, J = 6.90, 3.60 Hz, 1 H), 2.68-2.80 (m, 6 H), 2.61-2.67 (m, 1 H), 2.55-2.60 (m, 2 H), 2.28 (s, 3 H), 1.79 (d, J = 11.86 Hz, 2 H), 1.67-1.75 (m, 2 H), 1.49-1.60 (m, 2 H); MS (ESI) m/z 647.6 $[M + H]^+$ |

-continued

| Compound I.D. | Structure | Yield (Overall) | NMR & MS |
|---|---|---|---|
| I-70 | 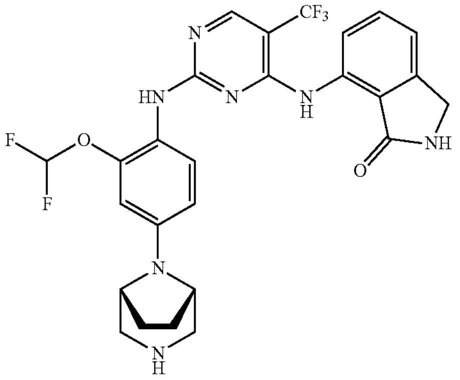 | 31% | $^1H$ NMR (500 MHz, DMSO-d6) δ 10.63 (br. s., 1 H), 9.17 (br. s., 1 H), 8.76 (br. s., 1 H), 8.37 (br. s., 1 H), 8.06 (br. s., 1 H), 7.24 (d, J = 8.80 Hz, 1 H), 6.86-7.22 (m, 3 H), 6.75 (br. s., 1 H), 6.66 (br. s., 1 H), 4.29-4.45 (m, 2 H), 4.09-4.24 (m, 2 H), 3.03 (m, J = 12.00 Hz, 2 H), 1.88-2.02 (m, 4 H); MS (ESI) m/z 562.5 $[M + H]^+$ |
| I-71 | 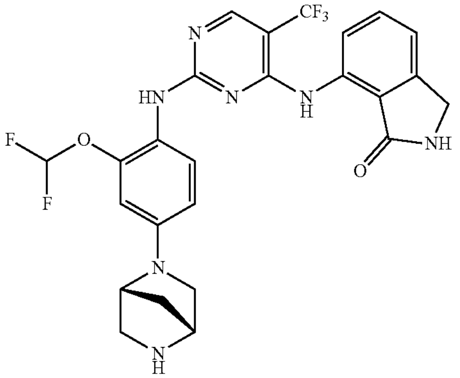 | 34% | $^1H$ NMR (500 MHz, DMSO-d6) δ 10.61 (br. s., 1 H), 9.16 (br. s., 1 H), 8.75 (br. s., 1 H), 8.36 (br. s., 1 H), 8.00 (br. s., 1 H), 7.56 (br. s., 1 H), 7.21 (d, J = 8.49 Hz, 1 H), 6.85-7.19 (m, 3 H), 6.52 (br. s., 1 H), 6.43 (br. s., 1 H), 4.29-4.49 (m, 3 H), 3.72 (br. s., 1 H), 3.53 (d, J = 7.70 Hz, 1 H), 2.96 (dd, J = 16.44, 9.23 Hz, 2 H), 2.84-2.90 (m, 1 H), 1.85 (m, J = 8.40 Hz, 1 H), 1.71 (m, J = 9.20 Hz, 1 H); MS (ESI) m/z 548.5 $[M + H]^+$ |
| I-72 | 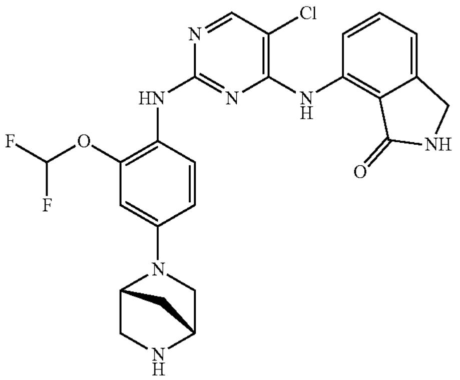 [SMILES: O=C1NCc2cccc(Nc3nc(Nc4ccc(N5C[C@H]6C[C@@H]5CN6)cc4OC(F)F)ncc3Cl)c21] | 24% | $^1H$ NMR (500 MHz, DMSO-d6) δ = 10.62 (br s, 1H), 8.77 (br s, 1H), 8.61 (s, 1H), 8.54-8.17 (m, 1H), 8.11 (s, 1H), 7.36-7.20 (m, 2H), 7.16-6.83 (m, 2H), 6.50 (br d, J = 8.7 Hz, 1H), 6.39 (br s, 1H), 4.37 (br s, 3H), 3.67 (br s, 1H), 3.55-3.49 (m, 1H), 2.98-2.83 (m, 3H), 1.82 (br d, J = 8.9 Hz, 1H), 1.68 (br d, J = 8.6 Hz, 1H); MS (ESI) m/z 514.5 $[M + H]^+$ |
| I-73 | 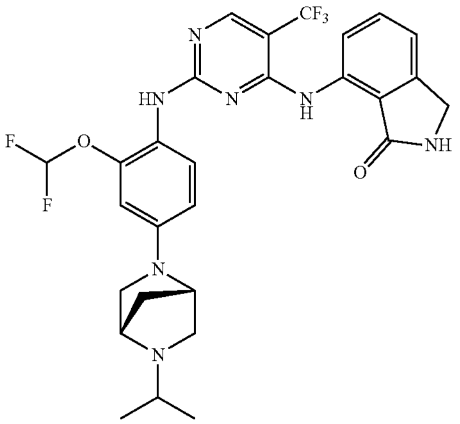 [SMILES: CC(C)N1C[C@@H]2C[C@H]1CN2c1ccc(Nc2ncc(C(F)(F)F)c(Nc3cccc4c3C(=O)NC4)n2)c(OC(F)F)c1] | 21% | $^1H$ NMR (500 MHz, DMSO-d6) δ 10.61 (br s, 1H), 9.15 (br s, 1H), 8.74 (br s, 1H), 8.36 (br s, 1H), 8.00 (br s, 1H), 7.23-6.84 (m, 4H), 6.53 (br s, 1H), 6.44 (br s, 1H), 4.35 (br s, 3H), 3.77 (br s, 1H), 3.26-3.18 (m, 1H), 3.05 (br d, J = 8.1 Hz, 1H), 2.48-2.41 (m, 1H), 1.85 (br s, 2H), 1.08-0.94 (m, 6H); MS (ESI) m/z 590.6 $[M + H]^+$ |

-continued

| Compound I.D. | Structure | Yield (Overall) | NMR & MS |
|---|---|---|---|
| I-74 | 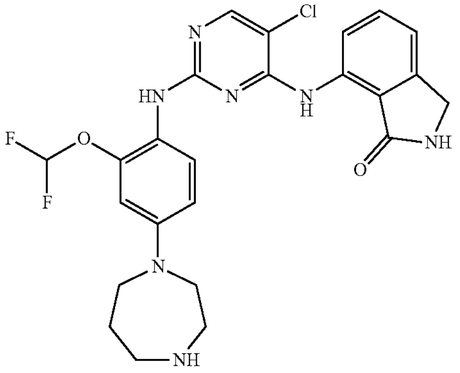 | 37% | $^1$H NMR (500 MHz, DMSO-d6) δ 10.62 (br s, 1H), 8.77 (br s, 1H), 8.59 (br s, 1H), 8.36 (br s, 1H), 8.11 (br s, 1H), 7.40-7.19 (m, 2H), 7.17-6.83 (m, 2H), 6.63 (br d, J = 8.7 Hz, 1H), 6.50 (br s, 1H), 4.37 (br s, 2H), 3.61-3.54 (m, 2H), 3.52-3.46 (m, 2H), 2.94-2.85 (m, 2H), 2.73-2.65 (m, 2H), 1.87-1.76 (m, 2H); MS (ESI) m/z 516.4 $[M + H]^+$ |
| I-75 | 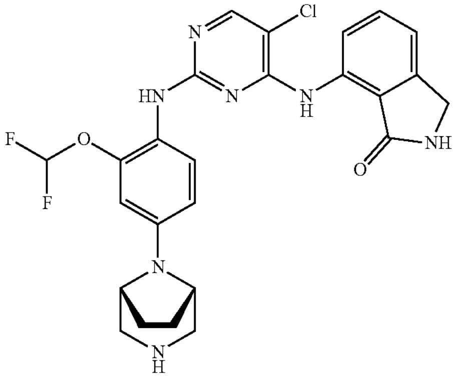 | 31% | $^1$H NMR (500 MHz, DMSO-d6) δ 10.64 (br s, 1H), 8.77 (br s, 1H), 8.62 (s, 1H), 8.40 (br s, 1H), 8.13 (s, 1H), 7.37-7.23 (m, 2H), 7.19-6.84 (m, 2H), 6.72 (br d, J = 8.7 Hz, 1H), 6.63 (br s, 1H), 4.37 (br s, 2H), 4.13 (br s, 2H), 3.02 (br d, J = 12.2 Hz, 2H), 2.49-2.44 (m, 2H), 2.01-1.87 (m, 4H); MS (ESI) m/z 528.5 $[M + H]^+$ |
| I-76 | 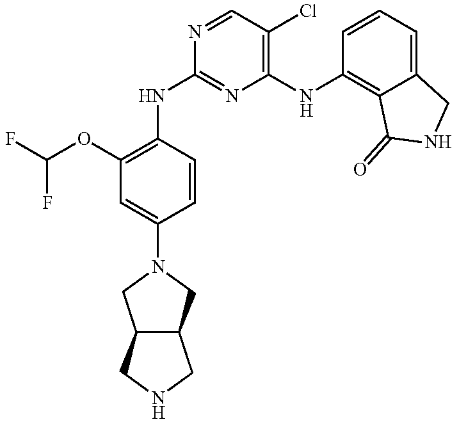 [SMILES: O=C1NCc2cccc(Nc3nc(Nc4ccc(N5C[C@H]6CNC[C@H]6C5)cc4OC(F)F)ncc3Cl)c21] | 34% | $^1$H NMR (500 MHz, DMSO-d6) δ 10.62 (br s, 1H), 8.77 (br s, 1H), 8.65 (br s, 1H), 8.36 (br s, 1H), 8.11 (br s, 1H), 7.27 (br d, J = 7.8 Hz, 2H), 7.16-6.84 (m, 2H), 6.55 (br d, J = 8.7 Hz, 1H), 6.46 (br s, 1H), 4.37 (br s, 2H), 3.10 (br d, J = 9.4 Hz, 2H), 3.05-2.96 (m, 2H), 2.87 (br s, 2H), 2.73-2.62 (m, 2H); MS (ESI) m/z 528.5 $[M + H]^+$ |

-continued
| Compound I.D. | Structure | Yield (Overall) | NMR & MS |
|---|---|---|---|
| I-77 | 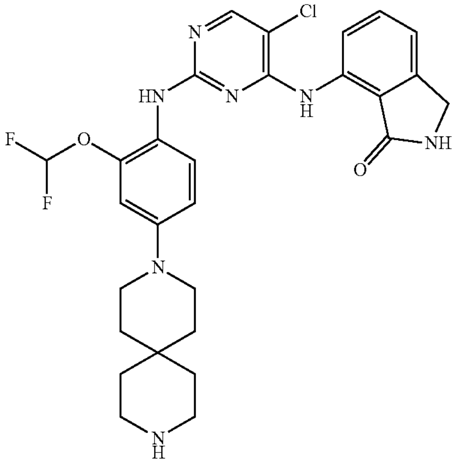 [SMILES: O=C1NCc2cccc(Nc3nc(Nc4ccc(N5CCC6(CCNCC6)CC5)cc4OC(F)F)ncc3Cl)c21] | 16% | $^1$H NMR (500 MHz, DMSO-d6) δ 10.63 (br s, 1H), 8.78 (br s, 1H), 8.68 (br s, 1H), 8.38 (br s, 1H), 8.13 (s, 1H), 7.35-7.23 (m, 2H), 7.19-6.84 (m, 3H), 6.76 (br s, 1H), 4.38 (br s, 2H), 3.22-3.15 (m, 4H), 2.77-2.68 (m, 4H), 1.63-1.55 (m, 4H), 1.46-1.38 (m, 4H); MS (ESI) m/z 570.6 $[M + H]^+$ |
| I-78 | 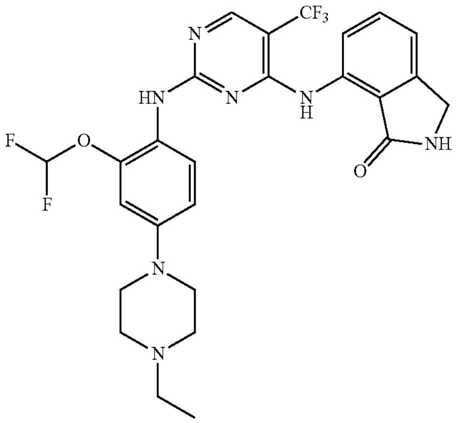 [SMILES: CCN1CCN(c2ccc(Nc3ncc(C(F)(F)F)c(Nc4cccc5c4C(=O)NC5)n3)c(OC(F)F)c2)CC1] | 37% | $^1$H NMR (500 MHz, DMSO-d6) δ 10.64 (br s, 1H), 9.26 (s, 1H), 8.76 (s, 1H), 8.37 (br s, 1H), 8.12-7.79 (m, 1H), 7.30 (d, J = 8.7 Hz, 1H), 7.22-6.86 (m, 4H), 6.81 (br s, 1H), 4.36 (br s, 2H), 3.22 (br s, 4H), 2.56-2.52 (m, 4H), 2.44-2.35 (m, 2H), 1.06 (t, J = 7.2 Hz, 3H); MS (ESI) m/z 564.5 $[M + H]^+$ |
| I-79 | 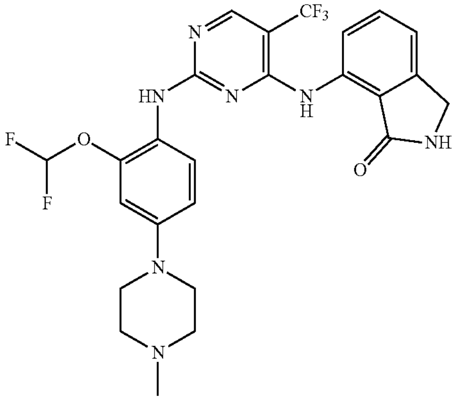 [SMILES: CN1CCN(c2ccc(Nc3ncc(C(F)(F)F)c(Nc4cccc5c4C(=O)NC5)n3)c(OC(F)F)c2)CC1] | 29% | $^1$H NMR (500 MHz, DMSO-d6) δ 10.64 (br s, 1H), 9.26 (s, 1H), 8.76 (s, 1H), 8.37 (br s, 1H), 8.10-7.76 (m, 1H), 7.30 (d, J = 8.8 Hz, 1H), 7.22-6.86 (m, 4H), 6.81 (br s, 1H), 4.36 (br s, 2H), 3.27-3.20 (m, 4H), 2.26 (s, 3H); MS (ESI) m/z 550.6 $[M + H]^+$ |

-continued

| Compound I.D. | Structure | Yield (Overall) | NMR & MS |
|---|---|---|---|
| I-80 | 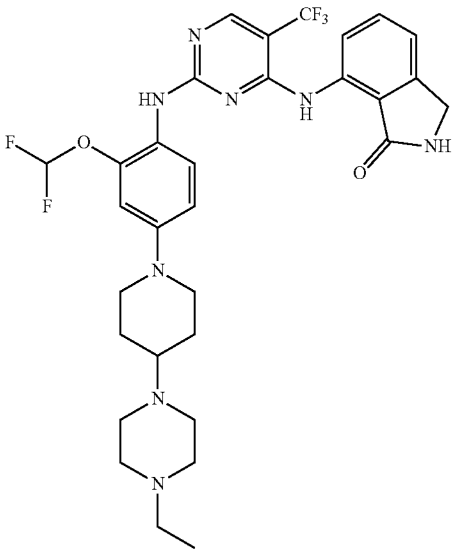 | 36% | $^1$H NMR (500 MHz, DMSO-d6) δ 10.64 (s, 1H), 8.79 (s, 1H), 8.70 (s, 1H), 8.47-8.28 (m, 1H), 8.14 (s, 1H), 7.34-7.24 (m, 2H), 7.20-6.89 (m, 2H), 6.87 (dd, J = 2.5, 8.9 Hz, 1H), 6.79-6.75 (m, 1H), 4.38 (s, 2H), 3.81-3.72 (m, 2H), 2.74 (br t, J = 11.4 Hz, 2H), 2.43-2.27 (m, 6H), 1.88 (br d, J = 12.0 Hz, 2H), 1.57-1.47 (m, 2H), 0.99 (t, J = 7.2 Hz, 3H); MS (ESI) m/z 613.6 [M + H]$^+$ |
| I-81 | 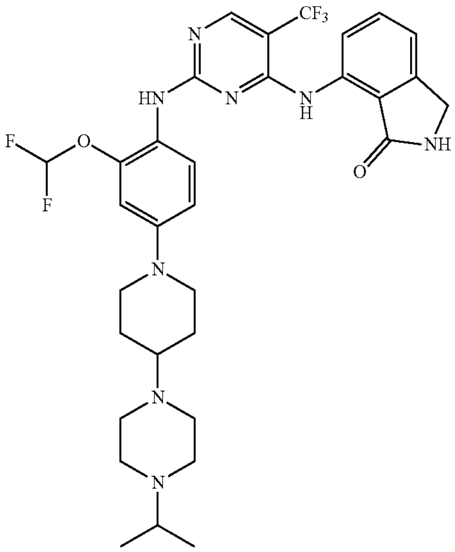 | 30% | $^1$H NMR (500 MHz, DMSO-d6) δ 10.64 (s, 1H), 8.79 (s, 1H), 8.70 (s, 1H), 8.50-8.26 (m, 1H), 8.14 (s, 1H), 7.36-7.23 (m, 2H), 7.20-6.89 (m, 2H), 6.86 (dd, J = 2.4, 8.9 Hz, 1H), 6.80-6.75 (m, 1H), 4.38 (s, 2H), 3.75 (br d, J = 12.3 Hz, 2H), 2.73 (br t, J = 11.3 Hz, 2H), 2.59 (br d, J = 6.2 Hz, 2H), 2.48-2.38 (m, 4H), 2.33 (br s, 1H), 1.87 (br d, J = 11.7 Hz, 2H), 1.57-1.46 (m, 2H), 0.97 (d, J = 6.5 Hz, 6H); MS (ESI) m/z 627.7 [M + H]$^+$ |
| I-82 | 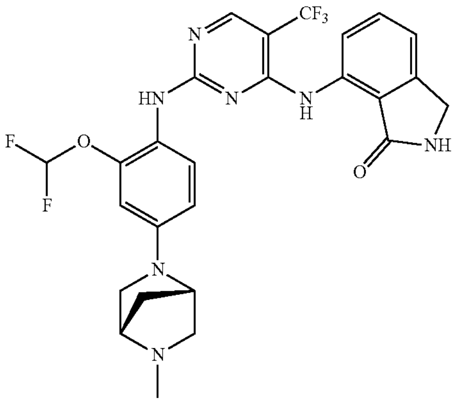 [SMILES: CN1C[C@@H]2C[C@H]1CN2c1ccc(Nc2ncc(C(F)(F)F)c(Nc3cccc4c3C(=O)NC4)n2)c(OC(F)F)c1] | 39% | $^1$H NMR (500 MHz, DMSO-d6) δ 10.61 (br s, 1H), 9.16 (br s, 1H), 8.75 (br s, 1H), 8.37 (br s, 1H), 7.97 (br s, 1H), 7.29-6.83 (m, 4H), 6.54 (br s, 1H), 6.45 (br s, 1H), 4.35 (br s, 3H), 3.47 (s, 1H), 3.24-3.17 (m, 1H), 2.80 (br d, J = 8.1 Hz, 1H), 2.63-2.55 (m, 1H), 2.33 (br s, 3H), 1.91 (br d, J = 8.9 Hz, 1H), 1.80 (br d, J = 8.4 Hz, 1H); MS (ESI) m/z 562.5 [M + H]$^+$ |

-continued
| Compound I.D. | Structure | Yield (Overall) | NMR & MS |
|---|---|---|---|
| I-83 | 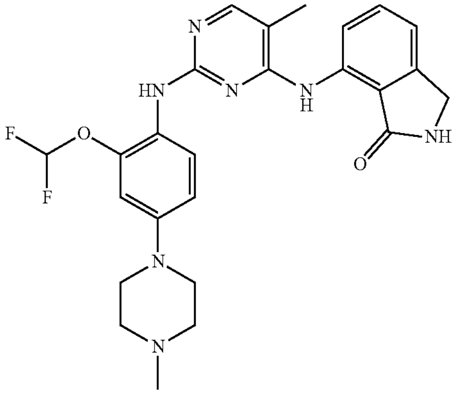 [SMILES: Cc1cnc(Nc2ccc(N3CCN(C)CC3)cc2OC(F)F)nc1Nc1cccc2c1C(=O)NC2] | 28% | $^1$H NMR (500 MHz, DMSO-d6) δ 10.15 (s, 1H), 8.75 (s, 1H), 8.44 (br d, J = 7.7 Hz, 1H), 8.16 (s, 1H), 7.90 (s, 1H), 7.46 (d, J = 8.8 Hz, 1H), 7.31 (t, J = 7.8 Hz, 1H), 7.21-6.90 (m, 2H), 6.87 (dd, J = 2.6, 8.9 Hz, 1H), 6.80-6.76 (m, 1H), 4.37 (s, 2H), 3.20-3.14 (m, 4H), 2.49-2.46 (m, 3H), 2.25 (s, 3H), 2.10 (s, 3H); MS (ESI) m/z 496.6 $[M + H]^+$ |
| I-84 | 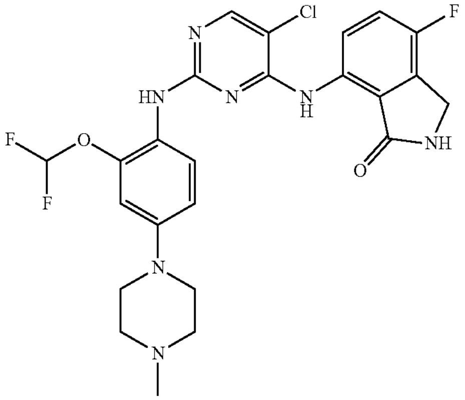 [SMILES: CN1CCN(c2ccc(Nc3ncc(Cl)c(Nc4ccc(F)c5c4C(=O)NC5)n3)c(OC(F)F)c2)CC1] | 38% | $^1$H NMR (500 MHz, DMSO-$d_6$) δ 10.48 (s, 1H), 9.02 (s, 1H), 8.73 (s, 1H), 8.38 (s, 1H), 8.14 (s, 1H), 7.34 (d, J = 8.8 Hz, 1H), 7.06 (s, 1H), 7.05 (t, J = 74.5 Hz, 1H), 6.88 (dd, J = 8.8, 2.1 Hz, 1H), 6.79 (s, 1H), 4.47 (s, 2H), 3.25-3.17 (m, 4H), 2.50-2.46 (m, 4H), 2.25 (s, 3H); MS (ESI) m/z 534.6 $[M + H]^+$ |
| I-85 | 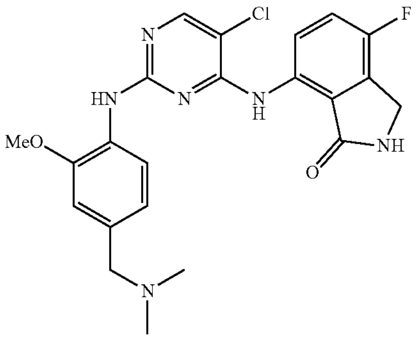 [SMILES: COc1cc(CN(C)C)ccc1Nc1ncc(Cl)c(Nc2ccc(F)c3c2C(=O)NC3)n1] | 17% | $^1$H NMR (500 MHz, DMSO-$d_6$) δ 10.50 (s, 1H), 9.03 (s, 1H), 8.54-8.48 (m, 2H), 8.19 (s, 1H), 7.60 (d, J = 7.9 Hz, 1H), 7.17 (t, J = 8.6 Hz, 1H), 7.02 (s, 1H), 6.89 (d, J = 8.0 Hz, 1H), 4.51-4.47 (m, 3H), 3.78 (s, 3H), 2.19 (s, 6H); MS (ESI) m/z 457.6 $[M + H]^+$ |

Synthesis of 7-((5-chloro-2-((7-methoxy-2-(3,3,3-trifluoropropyl)-1,2,3,4-tetrahydroisoquinolin-6-yl)amino)pyrimidin-4-yl)amino)isoindolin-1-one (Compound 1-19)

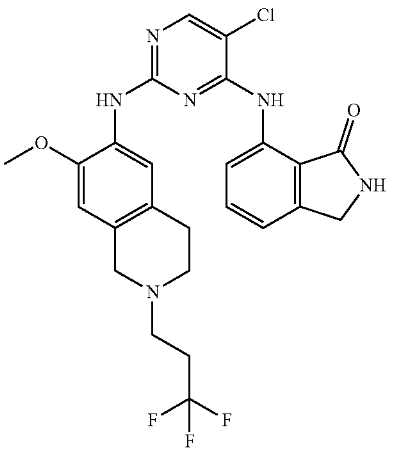 [SMILES: COc1cc2c(cc1Nc1ncc(Cl)c(Nc3cccc4c3C(=O)NC4)n1)CCN(CCC(F)(F)F)C2]

To a suspension of 7-((5-chloro-2-((7-methoxy-1,2,3,4-tetrahydroisoquinolin-6-yl)amino)pyrimidin-4-yl)amino)isoindolin-1-one (0.045 g, 0.103 mmol, Compound 1-17) in methanol (MeOH) (2 ml) was added 3,3,3-trifluoropropanal (0.231 g, 2.060 mmol) and acetic acid, glacial, 99.8% (0.012 ml, 0.206 mmol) in an ice bath. The resulting mixture was stirred for 5 minutes prior to the portionwise addition of sodium triacetoxyborohydride (0.437 g, 2.060 mmol). After warming to 21° C. and stirring for 2 hours, the reaction was diluted with water (20 ml), and the aqueous layer was extracted with EtOAc (3×20 mL). The combined organic extracts were dried with anhydrous sodium sulfate, filtered, and concentrated under reduced pressure to yield a yellow solid. This material was taken up in EtOAc and triturated with hexanes to afford the title compound Example 19 as a light-yellow powder (0.011 g, 18%) which was collected by filtration and dried under vacuum for 24 hours. $^1H$ NMR (500 MHz, DMSO-$d_6$) δ 10.67 (s, 1H), 8.80 (s, 1H), 8.44 (s, 1H), 8.37 (s, 1H), 8.20 (s, 1H), 7.46 (s, 1H), 7.37 (t, J=7.8 Hz, 1H), 7.17 (d, J=7.5 Hz, 1H), 6.77 (s, 1H), 4.39 (s, 2H), 3.76 (s, 3H), 3.64 (s, 2H), 2.73 (s, 4H), 2.66-2.53 (m, 4H); MS (ESI) m/z 533.7 [M+H]+

Preparation of Intermediates

In a manner similar to Step 1 above the following intermediate compounds were synthesized:

| Intermediate | Name | Yield & Mass |
|---|---|---|
| 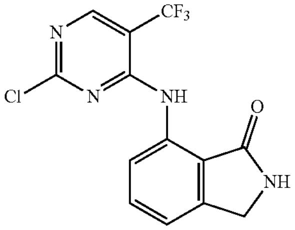 [SMILES: O=C1NCc2cccc(Nc3nc(Cl)ncc3C(F)(F)F)c21] | 7-((2-chloro-5-(trifluoromethyl)pyrimidin-4-yl)amino)isoindolin-1-one<br>Exact Mass: 328.03 | 33% yield<br>LCMS<br>$[M]^+$ 329 |

-continued

| Intermediate | Name | Yield & Mass |
|---|---|---|
| 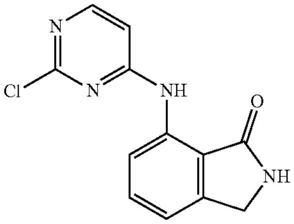 [SMILES: O=C1NCc2cccc(Nc3ccnc(Cl)n3)c21] | 7-((2-chloropyrimidin-4-yl)amino)isoindolin-1-one<br>Exact Mass: 260.05 | 76% yield<br>LCMS<br>$[M]^+$ 261 |
| 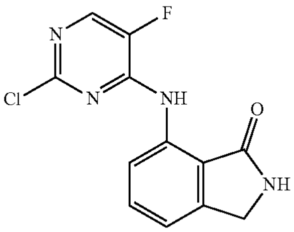 [SMILES: O=C1NCc2cccc(Nc3nc(Cl)ncc3F)c21] | 7-((2-chloro-5-fluoropyrimidin-4-yl)amino)isoindolin-1-one<br>Exact Mass: 278.04 | 93% yield<br>LCMS<br>$[M]^+$ 279 |
| 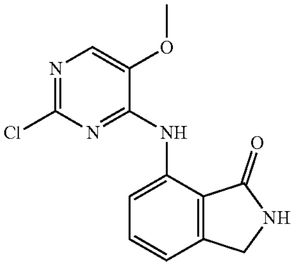 [SMILES: COc1cnc(Cl)nc1Nc1cccc2c1C(=O)NC2] | 7-((2-chloro-5-methoxypyrimidin-4-yl)amino)isoindolin-1-one<br>Exact Mass: 290.06 | 52% yield<br>LCMS<br>$[M]^+$ 291 |
| 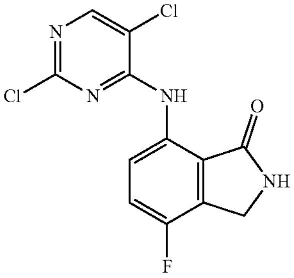 [SMILES: O=C1NCc2c(F)ccc(Nc3nc(Cl)ncc3Cl)c21] | 7-((2,5-Dichloropyrimidin-4-yl)amino)-4-fluoroisoindolin-1-one (2)<br>Exact Mass: 313.3 | >80% yield<br>$[M]^+$ 315 |

Commercially Available Anilines as Reagents in the Synthesis of Compounds

Below is a list of commercially available anilines that were coupled to the pyrimidine core in the methods described above.

| Aniline | Name |
|---|---|
| 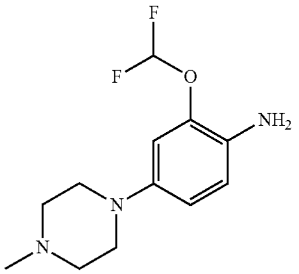 [SMILES: CN1CCN(c2ccc(N)c(OC(F)F)c2)CC1] | 2-(difluoromethoxy)-4-(4-methylpiperazin-1-yl)aniline |
| 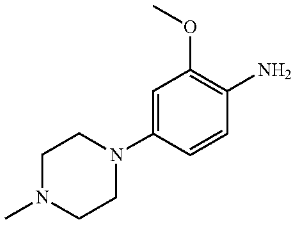 [SMILES: COc1cc(N2CCN(C)CC2)ccc1N] | 2-methoxy-4-(4-methylpiperazin-1-yl)aniline |
| 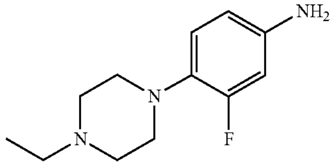 [SMILES: CCN1CCN(c2ccc(N)cc2F)CC1] | 4-(4-ethylpiperazin-1-yl)-3-fluoroaniline |
| 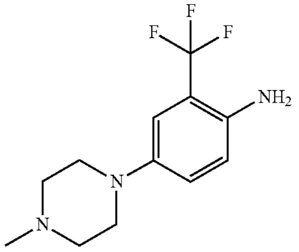 [SMILES: CN1CCN(c2ccc(N)c(C(F)(F)F)c2)CC1] | 4-(4-methylpiperazin-1-yl)-2-(trifluoromethyl)aniline |
| 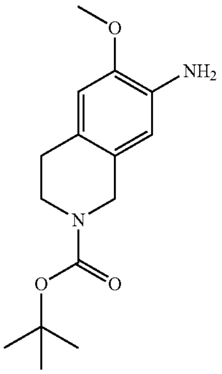 [SMILES: COc1cc2c(cc1N)CN(C(=O)OC(C)(C)C)CC2] | tert-butyl 7-amino-6-methoxy-3,4-dihydroisoquinoline-2(1H)-carboxylate |
| 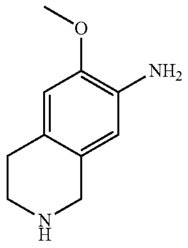 | 6-methoxy-1,2,3,4-tetrahydroisoquinolin-7-amine |

-continued
| Aniline | Name |
|---|---|
| 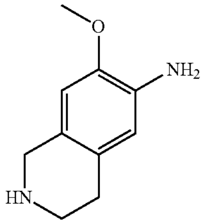 | 7-methoxy-1,2,3,4-tetrahydroisoquinolin-6-amine |
| 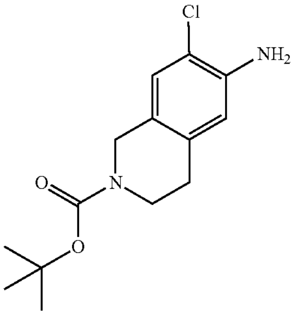 [SMILES: CC(C)(C)OC(=O)N1CCc2cc(N)c(Cl)cc2C1] | tert-butyl 6-amino-7-chloro-3,4-dihydroisoquinoline-2(1H)-carboxylate |
| 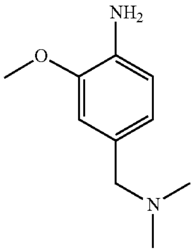 | 4-((dimethylamino)methyl)-2-methoxyaniline |
| 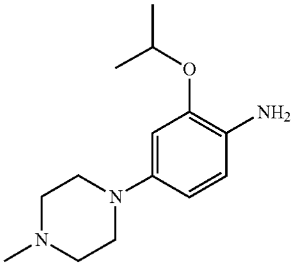 [SMILES: CC(C)Oc1cc(N2CCN(C)CC2)ccc1N] | 2-isopropoxy-4-(4-methylpiperazin-1-yl)aniline |
| 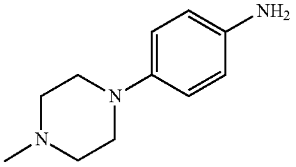 | 4-(4-methylpiperazin-1-yl)aniline |

-continued

| Aniline | Name |
| --- | --- |
| 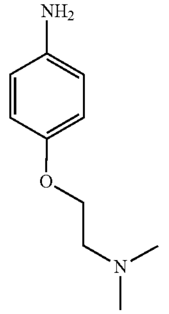 | 4-(2-(dimethylamino)ethoxy)aniline |

Preparation of Anilines as Reagents in the Synthesis of Compounds

Method A:

Scheme 4

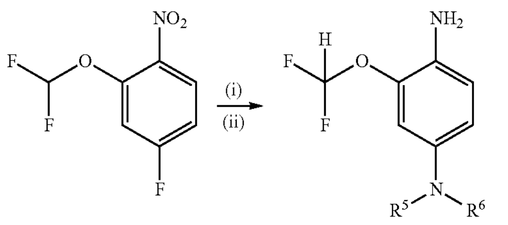

i) $HNR^5R^6$, $K_2CO_3$, DMF, 60° C.; ii) Hydrazine (aq), Raney-nickel, methanol, 50° C.

To a 30 mL vial charged with of 2-(difluoromethoxy)-4-fluoro-1-nitrobenzene (414 mg, 2 mmol, 1 eqv)) and cis-1,2,6-trimethylpiperazine (282 mg, 2.2 mmol, 1.1 eqv) was added DMF (5 mL) and $K_2CO_3$ (415 mg, 3 mmol, 1.5 eqv). The resulting mixture was stirred at 60° C. for 30 min. $H_2O$ (25 mL) was added slowly to the reaction mixture and the resulting yellow precipitate was collected by suction filtration, washed with $H_2O$ and air-dried to give a yellow solid. LC-MS calcd. $[C_{14}H_{19}F_2N_3O_3+H]^+$ 316.1, found 316.4.

The above yellow solid was redissolved in MeOH (40 mL). Hydrazine monohydrate (0.39 mL, 8 mmol, 4 eqv) was added, followed by Raney-nickel, 2800 (137 mg, 1.6 mmol, 0.7 eqv). The resulting mixture was heated at 50° C. for 20 min. Additional hydrazine monohydrate (0.19 mL, 4 mmol, 2 eqv) was added, followed by Raney-nickel, 2800 (69 mg, 0.8 mmol). The resulting mixture was heated at 50° C. for 15 min. The mixture was filtered, rinsed with MeOH (10 mL) and the filtrate was concentrated and dried to give a dark purple oil (14.762-14.223 g=539 mg, yield 94% over 2 steps). LC-MS calcd. for $[C_{14}H_{21}F_2N_3O+H]^+$ 286.17; found 286.36.

Method B (Reductive Amination Method Followed by Reduction):

Scheme 5

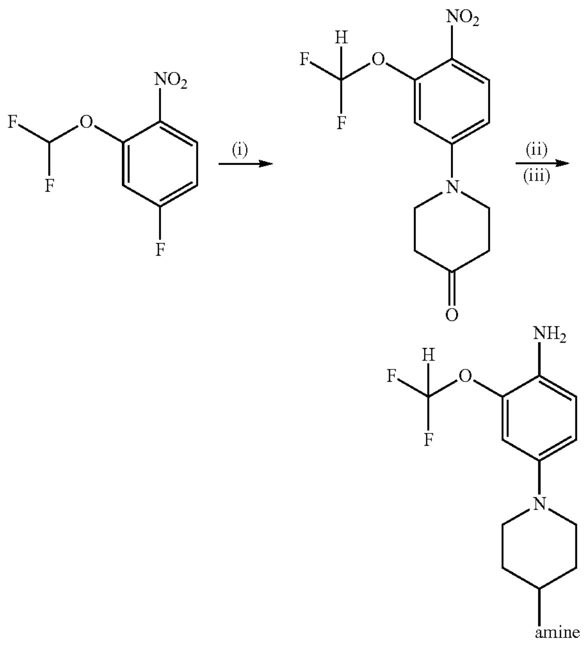

i) Piperidine•HCl, $K_2CO_3$, DMF, 60° C.;

ii) amine, sodium triacetoxyborohydride, DCE, 50° C.;

(iii) Hydrazine (aq), Raney-nickel, methanol, 50° C.

To a 50 mL vial charged with 2-(difluoromethoxy)-4-fluoro-1-nitrobenzene (1.41 mL, 10 mmol) and piperidin-4-one HCl (1.424 g, 10.5 mmol) was added DMF (20 mL) and $K_2CO_3$ (2.90 g, 21 mmol). The resulting mixture was stirred at 60° C. for 1 h. It was quenched with $H_2O$ (100 mL) with stirring and the resulting precipitates were collected by filtration, rinsed with $H_2O$ (20 mL), air-dried and dried to give 1-(3-(difluoromethoxy)-4-nitrophenyl)piperidin-4-one (yellow solid, 2.784 g, 95%). MS (ESI) m/z 287.2 $[M+H]^+$.

To a 50 mL vial charged with 1-(3-(difluoromethoxy)-4-nitrophenyl)piperidin-4-one (859 mg, 3 mmol) and amine (e.g. 1-ethylpiperazine; 360 mg, 3.15 mmol) was added DCE (10 mL) and sodium triacetoxyborohydride (954 mg, 4.5 mmol), followed by 2 drops of HOAc. The resulting mixture was stirred at room temperature for 2 h. Aqueous workup with DCM afforded a yellow oil.

The above yellow oil was redissolved in MeOH (20 mL). Hydrazine monohydrate (0.58 mL, 12 mmol) was added, followed by Raney-nickel, 2800 (129 mg, 1.5 mmol). The resulting mixture was stirred at rt for 1 h. Additional Raney-nickel, 2800 (129 mg, 1.5 mmol) was added and the resulting mixture was stirred at room temperature for 30 min, filtered, rinsed with MeOH (20 m. The filtrate was concentrated and dried to 2-(difluoromethoxy)-4-(4-(4-ethylpiperazin-1-yl)piperidin-1-yl)aniline (brown crystalline solid, 934 mg, 80% over 2 steps, 91.32% purity). MS (ESI) m/z 355.5 $[M+H]^+$.

In a similar manner, the following intermediate compounds were prepared:

| Method | Aniline | Name | Yield & Mass |
|---|---|---|---|
| A | 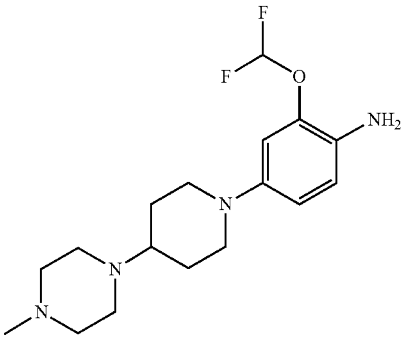 [SMILES: CN1CCN(C2CCN(c3ccc(N)c(OC(F)F)c3)CC2)CC1] | 2-(difluoromethoxy)-4-(4-(4-methylpiperazin-1-yl)piperidin-1-yl)aniline Exact Mass: 340.21 | 94% yield, LCMS $[M]^+$ 341 |
| A | 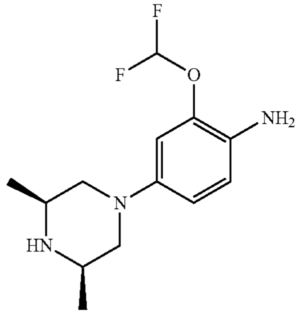 [SMILES: C[C@@H]1CN(c2ccc(N)c(OC(F)F)c2)C[C@H](C)N1] | 2-(difluoromethoxy)-4-((3S,5R)-3,5-dimethylpiperazin-1-yl)aniline Exact Mass: 271.15 | 86% yield, LCMS $[M]^+$ 272 |
| A | 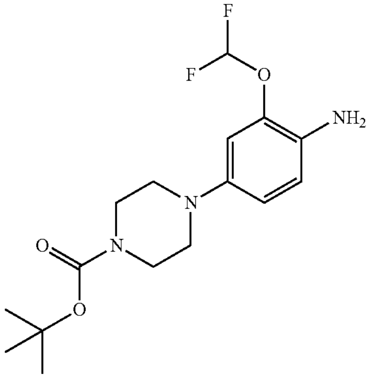 [SMILES: CC(C)(C)OC(=O)N1CCN(c2ccc(N)c(OC(F)F)c2)CC1] | tert-butyl 4-(4-amino-3-(difluoromethoxy)phenyl) piperazine-1-carboxylate Exact Mass: 343.17 | 99% yield, LCMS $[M]^+$ 344 |

-continued

| Method | Aniline | Name | Yield & Mass |
|---|---|---|---|
| A | 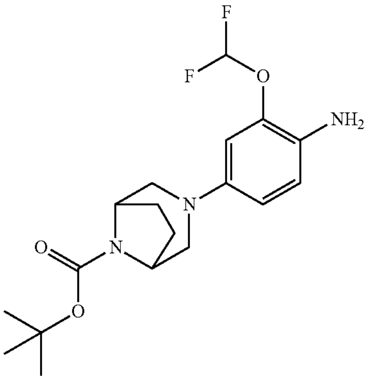 [SMILES: CC(C)(C)OC(=O)N1C2CCC1CN(c1ccc(N)c(OC(F)F)c1)C2] | tert-butyl 3-(4-amino-3-(difluoromethoxy)phenyl)-3,8-diazabicyclo[3.2.1]octane-8-carboxylate<br>Exact Mass: 369.19 | 90% yield, LCMS $[M]^+$ 370 |
| A | 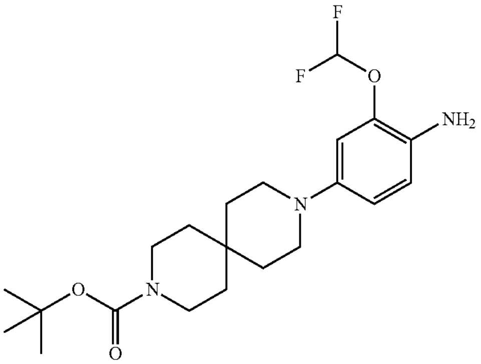 [SMILES: CC(C)(C)OC(=O)N1CCC2(CC1)CCN(c1ccc(N)c(OC(F)F)c1)CC2] | tert-butyl 9-(4-amino-3-(difluoromethoxy)phenyl)-3,9-diazaspiro[5.5]undecane-3-carboxylate<br>Exact Mass: 411.23 | 99% yield, LCMS $[M]^+$ 412 |
| A | 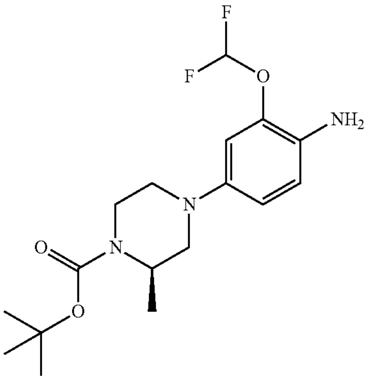 [SMILES: C[C@@H]1CN(c2ccc(N)c(OC(F)F)c2)CCN1C(=O)OC(C)(C)C] | tert-butyl (R)-4-(4-amino-3-(difluoromethoxy)phenyl)-2-methylpiperazine-1-carboxylate<br>Exact Mass: 357.19 | 92% yield, LCMS $[M]^+$ 358 |
| A | 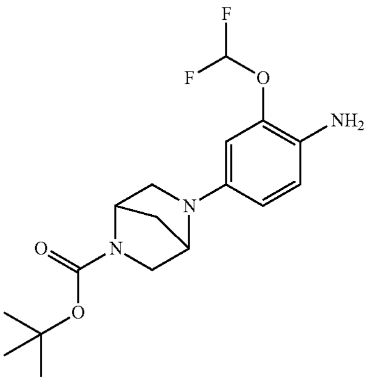 [SMILES: CC(C)(C)OC(=O)N1CC2CC1CN2c1ccc(N)c(OC(F)F)c1] | tert-butyl 5-(4-amino-3-(difluoromethoxy)phenyl)-2,5-diazabicyclo[2.2.1]heptane-2-carboxylate<br>Exact Mass: 355.17 | 96% yield, LCMS $[M]^+$ 356 |

-continued

| Method | Aniline | Name | Yield & Mass |
| --- | --- | --- | --- |
| A | 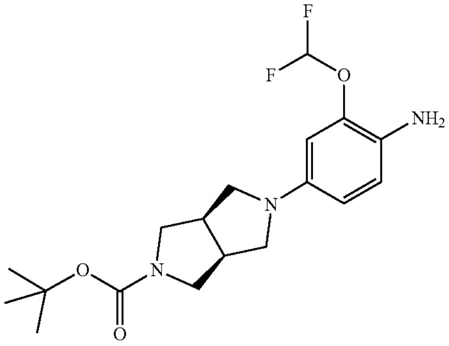 [SMILES: CC(C)(C)OC(=O)N1C[C@@H]2CN(c3ccc(N)c(OC(F)F)c3)C[C@@H]2C1] | tert-butyl (3aR,6aS)-5-(4-amino-3-(difluoromethoxy)phenyl) hexahydropyrrolo[3,4-c]pyrrole-2(1H)-carboxylate Exact Mass: 369.19 | 94% yield, LCMS $[M]^+$ 370 |
| A | 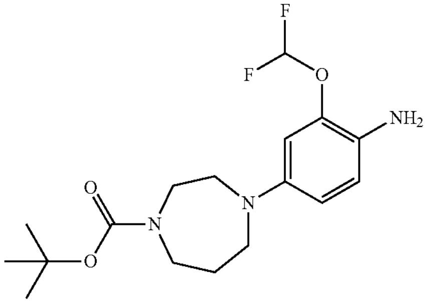 [SMILES: CC(C)(C)OC(=O)N1CCCN(c2ccc(N)c(OC(F)F)c2)CC1] | tert-butyl 4-(4-amino-3-(difluoromethoxy)phenyl)-1,4-diazepane-1-carboxylate Exact Mass: 357.19 | 96% yield, LCMS $[M]^+$ 358 |
| B | 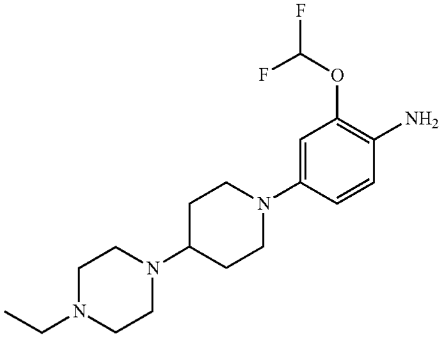 [SMILES: CCN1CCN(C2CCN(c3ccc(N)c(OC(F)F)c3)CC2)CC1] | 2-(difluoromethoxy)-4-(4-(4-ethylpiperazin-1-yl)piperidin-1-yl)aniline Exact Mass: 354.22 | 80% yield, LCMS $[M]^+$ 355 |
| B | 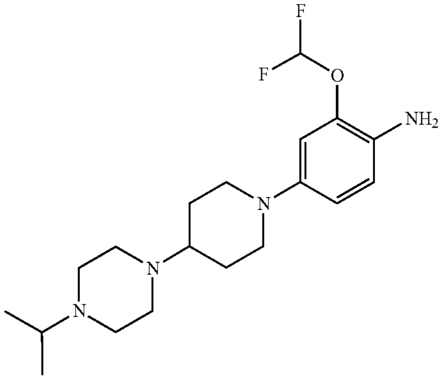 [SMILES: CC(C)N1CCN(C2CCN(c3ccc(N)c(OC(F)F)c3)CC2)CC1] | 2-(difluoromethoxy)-4-(4-(4-isopropylpiperazin-1-yl)piperidin-1-yl)aniline Exact Mass: 368.24 | 79% yield, LCMS $[M]^+$ 369 |

-continued

| Method | Aniline | Name | Yield & Mass |
|---|---|---|---|
| B | 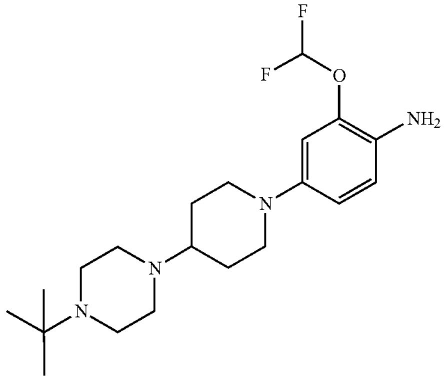 [SMILES: CC(C)(C)N1CCN(C2CCN(c3ccc(N)c(OC(F)F)c3)CC2)CC1] | 4-(4-(4-(tert-butyl)piperazin-1-yl)piperidin-1-yl)-2-(difluoromethoxy)aniline Exact Mass: 382.25 | 96% yield, LCMS $[M]^+$ 383 |
| B | 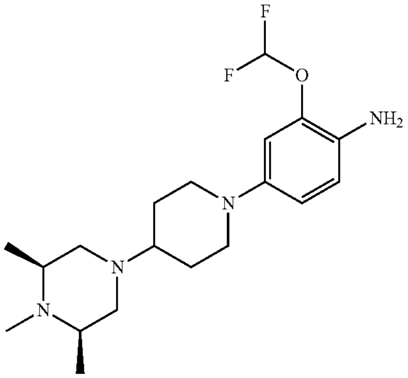 [SMILES: C[C@@H]1CN(C2CCN(c3ccc(N)c(OC(F)F)c3)CC2)C[C@H](C)N1C] | 2-(difluoromethoxy)-4-(4-((3S,5R)-3,4,5-trimethylpiperazin-1-yl)piperidin-1-yl)aniline Exact Mass: 368.24 | 79% yield, LCMS $[M]^+$ 369 |
| B | 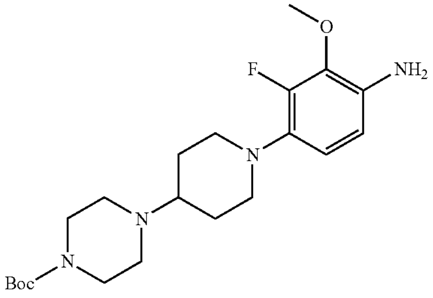 [SMILES: COc1c(N)ccc(N2CCC(N3CCN(C(=O)OC(C)(C)C)CC3)CC2)c1F] | tert-butyl 4-(1-(4-amino-2-fluoro-3-methoxyphenyl)piperidin-4-yl)piperazine-1-carboxylate Exact Mass: 408.25 | 89% yield over 2 steps, LCMS $[M + H]^+$ |
| B | 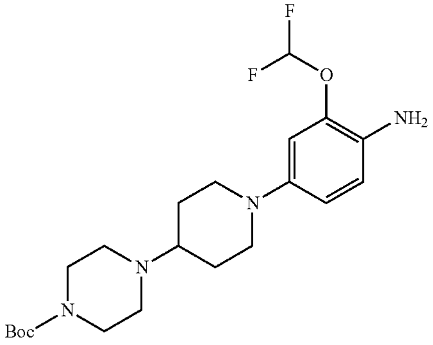 [SMILES: CC(C)(C)OC(=O)N1CCN(C2CCN(c3ccc(N)c(OC(F)F)c3)CC2)CC1] | tert-butyl 4-(1-(4-amino-3-(difluoromethoxy)phenyl) piperidin-4-yl)piperazine-1-carboxylate Exact Mass: 426.24 | 91% yield, LCMS $[M]^+$ 427 |

Method C: Synthesis of Aniline (Amine Substitution Followed by Nitro Reduction)

Scheme 6

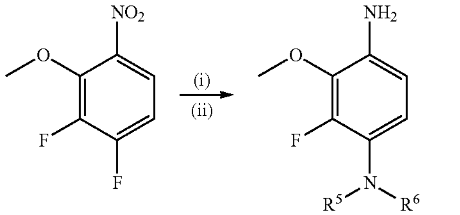

i) $HNR^5R^6$, $K_2CO_3$, DMF, 60° C.; ii) Hydrazine (aq), Raney-nickel, methanol, 50° C.

To a mixture of fluoro-nitrobenzene/pyridine (1 equiv.) and substituted piperazine or its HCl salt or di-HCl salt (1-1.1 equiv.) in DMF (0.4 M) was added $K_2CO_3$ (3 equiv. for free base, 3.5-4 equiv. for HCl, di-HCl salt). The resulting mixture was stirred at 60-70° C. for 30 min to 1 h. After cooling to room temperature, $H_2O$ (25 mL) was added slowly to the reaction mixture and the resulting precipitates were collected by suction filtration, washed with $H_2O$ and air-dried to give the nitro intermediate as a solid. If no precipitate formed, regular aqueous workup by EtOAc extraction was taken to obtain the nitro intermediate as an oil or solid.

A solution or suspension of the above nitro intermediate in MeOH (0.2-0.5 M) was treated with hydrazine monohydrate (4 equiv.) and Raney-nickel, 2800 (0.5-0.8 equiv.). The resulting mixture was stirred at room temperature or heated at 50° C. for 15 min to 1 h. If not completed, additional hydrazine monohydrate (1-2 equiv.) and Raney-nickel, 2800 (0.1-0.4 equiv.) were added and the resulting mixture was heated at 50° C. for 15-30 min. After filtration and rinsing with MeOH, the filtrate was concentrated and dried to give the desired aniline as a solid or oil.

The following anilines were prepared using method C:

| Method | Aniline | Name | Yield & Mass |
| --- | --- | --- | --- |
| C | 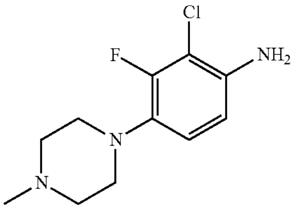 | 2-chloro-3-fluoro-4-(4-methylpiperazin-1-yl)aniline Exact Mass: 243.09 | 98% yield over 2 steps, LCMS $[M + H]^+$ 244 |
| C | 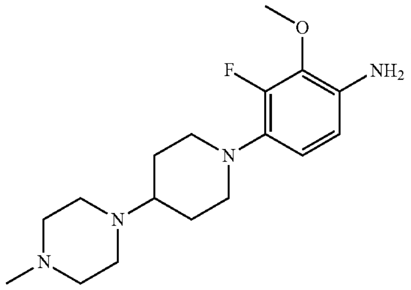 [SMILES: COc1c(N)ccc(N2CCC(N3CCN(C)CC3)CC2)c1F] | 3-fluoro-2-methoxy-4-(4-(4-methylpiperazin-1-yl)piperidin-1-yl)aniline Exact Mass: 322.22 | 90% yield over 2 steps, LCMS $[M + H]^+$ 323 |
| C | 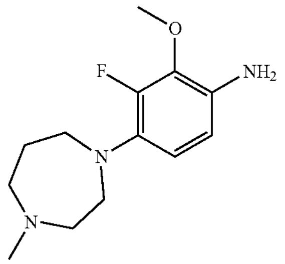 [SMILES: COc1c(N)ccc(N2CCCN(C)CC2)c1F] | 3-fluoro-2-methoxy-4-(4-methyl-1,4-diazepan-1-yl)aniline Exact Mass: 253.16 | 93% yield over 2 steps, LCMS $[M + H]^+$ 254 |
| C | 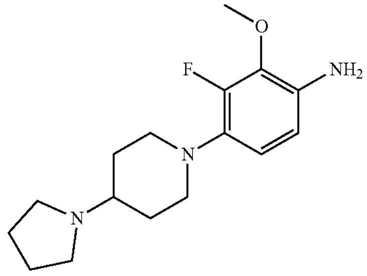 [SMILES: COc1c(N)ccc(N2CCC(N3CCCC3)CC2)c1F] | 3-fluoro-2-methoxy-4-(4-(pyrrolidin-1-yl)piperidin-1-yl)aniline Exact Mass: 293.19 | 80% yield over 2 steps, LCMS $[M + H]^+$ 294 |

-continued

| Method | Aniline | Name | Yield & Mass |
|---|---|---|---|
| C | 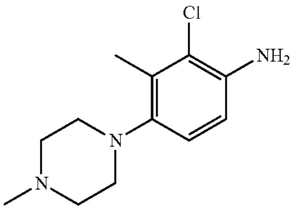 [SMILES: Cc1c(N2CCN(C)CC2)ccc(N)c1Cl] | 2-chloro-3-methyl-4-(4-methylpiperazin-1-yl)aniline Exact Mass: 239.12 | 100% yield over 2 steps, LCMS $[M + H]^+$ 240 |
| C | 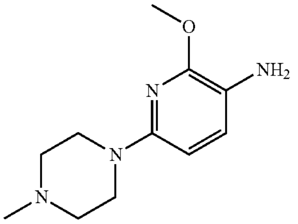 [SMILES: COc1nc(N2CCN(C)CC2)ccc1N] | 2-methoxy-6-(4-methylpiperazin-1-yl)pyridin-3-amine Exact Mass: 222.15 | 76% yield over 2 steps, LCMS $[M + H]^+$ 223 |
| C | 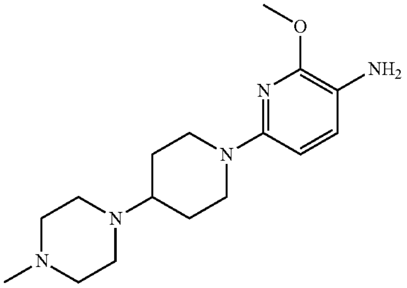 [SMILES: COc1nc(N2CCC(N3CCN(C)CC3)CC2)ccc1N] | methylpiperazin-1- 2-methoxy-6-(4-(4- yl) piperidin-1-yl)pyridin-3-amine Exact Mass: 305.22 | 54% yield over 2 steps, LCMS $[M + H]^+$ 306 |
| C | 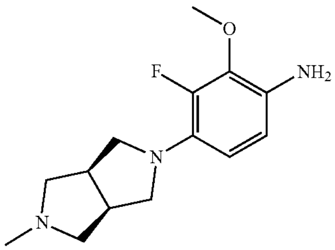 [SMILES: COc1c(N)ccc(N2C[C@H]3CN(C)C[C@H]3C2)c1F] | 3-fluoro-2-methoxy-4-((3aR,6aS)-5-methylhexahydropyrrolo[3,4-c]pyrrol-2(1H)-yl)aniline Exact Mass: 265.16 | 99% yield over 2 steps, LCMS $[M + H]^+$ 266 |
| C | 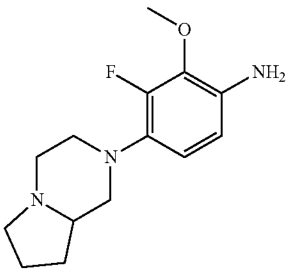 [SMILES: COc1c(N)ccc(N2CCN3CCCC3C2)c1F] | 3-fluoro-4-(hexahydropyrrolo[1,2-a]pyrazin-2(1H)-yl)-2-methoxyaniline Exact Mass: 265.16 | 99% yield over 2 steps, LCMS $[M + H]^+$ 266 |

Synthesis of tert-butyl 7-amino-8-methoxy-1,2,4,5-tetrahydro-3H-benzo[d]azepine-3-carboxylate

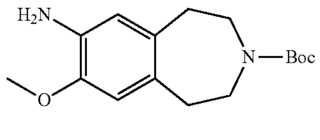 [SMILES: COc1cc2c(cc1N)CCN(C(=O)OC(C)(C)C)CC2]

Step 1: To a stirred mixture of 7-methoxy-2,3,4,5-tetrahydro-1H-3-benzazepine hydrochloride (1.00 g, 4.68 mmol, Enamine) and sulphuric acid (10 ml) at 0° C. was added guanidine nitrate (0.571 g, 4.68 mmol). The resulting mixture was stirred from 0° C. to room temperature over 1 hour prior to being quenched with ice, and basified with a 4N aqueous sodium hydroxide solution. The aqueous layer was extracted with EtOAc (2×100 ml), and the combined organic extracts were dried with anhydrous sodium sulfate, filtered, and concentrated under reduced pressure to yield a yellow oil/semi-solid (0.829 g, 80% yield). This material was used in the subsequent reaction without further purification.

Step 2: To a solution of 7-methoxy-8-nitro-2,3,4,5-tetrahydro-1H-benzo[d]azepine (0.829 g, 3.73 mmol) in dichloromethane (DCM) (50 ml) was added triethylamine (1.300 ml, 9.33 mmol) and di-tert-butyl dicarbonate (0.977 g, 4.48 mmol). The resulting mixture was stirred for 16 hours at 21° C. prior to dilution with water (100 ml). The aqueous layer was extracted with EtOAc (3×40 mL), and the combined organic extracts were dried with anhydrous sodium sulfate, filtered, and concentrated under reduced pressure to yield a light brown oil (1.1 g, 92% yield). This material was used in the subsequent reaction without further purification.

Step 3: To a solution of tert-butyl 7-methoxy-8-nitro-1,2,4,5-tetrahydro-3H-benzo[d]azepine-3-carboxylate (1.11 g, 3.44 mmol) in methanol (MeOH) (50 ml) at room temperature was added Hydrazine monohydrate (1.028 ml, 13.77 mmol) and Raney-nickel, 2800 (0.236 g, 2.75 mmol). The resulting mixture was stirred at room temperature for 1 hour (exothermic). After the reaction was deemed complete by LCMS, the reaction mixture was filtered through a pad of Celite™, and the filtrate concentrated under reduced pressure. The light red residual oil/semi-solid was then dried further under vacuum prior to use in the subsequent reaction without any further purification. Isolated (720 mg, 72% yield, LCMS $[M+H]^+$ 293)

Synthesis of tert-butyl 7'-amino-6'-methoxy-1'H-spiro[cyclopropane-1,4'-isoquinoline]-2'(3'H)-carboxylate

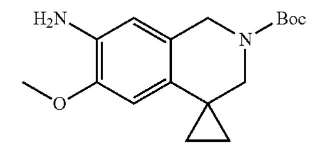 [SMILES: COc1cc2c(cc1N)CN(C(=O)OC(C)(C)C)CC21CC1]

Step 1: To a stirred mixture of 6'-methoxy-2',3'-dihydro-1'H-spiro[cyclopropane-1,4'-isoquinoline] hydrochloride (1.00 g, 4.43 mmol) and Sulphuric acid (10 ml) at 0° C. was added guanidine nitrate (0.541 g, 4.43 mmol, Enamine). The resulting mixture was stirred from 0° C. to room temperature over 1 hour prior to being quenched with ice, and basified with a 4N aqueous sodium hydroxide solution. The aqueous layer was extracted with EtOAc (2×100 ml), and the combined organic extracts were dried with anhydrous sodium sulfate, filtered, and concentrated under reduced pressure to yield a yellow oil/semi-solid (1.04 g, 90% yield). This material was used in the subsequent reaction without further purification.

Step 2: To a solution of 6'-methoxy-7'-nitro-2',3'-dihydro-1'H-spiro[cyclopropane-1,4'-isoquinoline] (1.04 g, 4.44 mmol) in dichloromethane (DCM) (75 ml) was added triethylamine (1.547 ml, 11.10 mmol) and di-tert-butyl dicarbonate (1.163 g, 5.33 mmol). The resulting mixture was stirred for 16 hours at 21° C. prior to dilution with water (100 ml). The aqueous layer was extracted with EtOAc (3×40 mL), and the combined organic extracts were dried with anhydrous sodium sulfate, filtered, and concentrated under reduced pressure to yield a light brown oil (1.33 g, 90% yield). This material was used in the subsequent reaction without further purification.

Step 3: To a solution of tert-butyl 6'-methoxy-7'-nitro-1'H-spiro[cyclopropane-1,4'-isoquinoline]-2'(3'H)-carboxylate (1.33 g, 3.98 mmol) in methanol (MeOH) (50 ml) at room temperature was added hydrazine monohydrate (1.187 ml, 15.91 mmol) and Raney-nickel, 2800 (0.273 g, 3.18 mmol). The resulting mixture was stirred at room temperature for 1 hour (exothermic). After the reaction was deemed complete by LCMS, the reaction mixture was filtered through a pad of Celite, and the filtrate concentrated under reduced pressure. The light-yellow residual oil/semi-solid was then dried further under vacuum prior to use in the subsequent reaction without any further purification. Isolated (1.02 g, 84% yield, LCMS $[M+H]^+$ 305)

Synthesis of 4-(4-methylpiperazin-1-yl)-2-(trifluoromethoxy)aniline (7-5)

Scheme 7

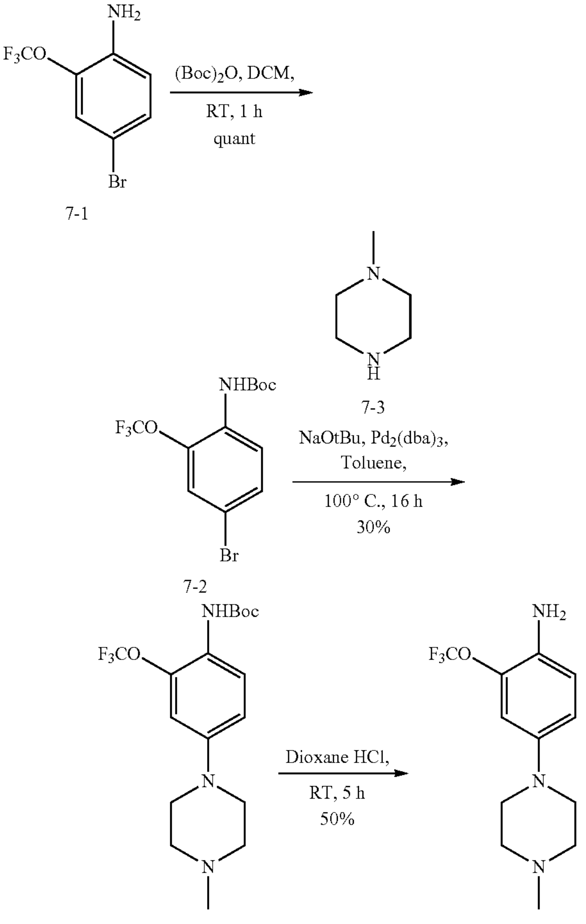

7-1 7-3 7-2 7-4 7-5

Step 1: Synthesis of tert-butyl (4-bromo-2-(trifluoromethoxy) phenyl) carbamate (7-2)

To a stirred solution of compound 7-1 (6 g, 23.4 mmol) in DCM (60 mL), TEA (4.8 mL, 35.1 mmol) was treated with di-tert-butyl dicarbonate (7.6 mL, 35.1 mmol) followed by DMAP (0.572 g, 35.1 mmol) at 0° C. to room temperature for 1 h. The reaction mixture was poured into ice water (1×200 mL), and extracted with DCM (1×200 mL), Separated organic layer was dried over $Na_2SO_4$ and concentrated under reduced pressure to afford crude Compound 7-2 (7 g, quant) as an off white solid. LCMS $[M+H]^+$ 356.2. Step 2: Synthesis of tert-butyl (4-(4-methylpiperazin-1-yl)-2-(trifluoromethoxy) phenyl) carbamate (7-4):

To a stirred solution of compound 7-2 (7 g, 19.7 mmol) in toluene (70 mL), was treated with compound 7-3 (3.5 mL, 31.6 mmol), NaO-t-Bu (2.3 g, 23.6 mmol) followed by Davephos (0.75 g, 2.0 mmol) degassed for 15 min then added $Pd_2(dba)_3$ (0.365 g. 2.0 mmol). The reaction mixture was heated to 120° C. for 16 h before cooling to room temperature. Then, the reaction mixture was filtered through a Celite bed, which was washed with 5% methanol in DCM (300 mL). Then, the combined filtrate was concentrated under reduced pressure to give crude residue: which was purified by column chromatography (neutral alumina) using an eluent 100% petroleum ether to afford compound 7-4 (4 g (33% pure by LMCS), 30%) as a brown liquid; LCMS $[M+H]^+$ 376.4. Step 3: Synthesis of 4-(4-methylpiperazin-1-yl)-2-(trifluoromethoxy)aniline (7-5)

To a solution of compound 7-4 (4 g (33% pure by LCMS), 4.8 mmol) in 4M dioxane·HCl (20 mL) allowed to room temperature for 5 h. The solvent was concentrated under reduced pressure and the reaction mixture was poured into ice water (1×100 mL), basified using saturated sodium bicarbonate and extracted with DCM (1×200 mL). Separated organic layer was dried over $Na_2SO_4$ and concentrated under reduced pressure to give crude residue: Which was purified by prep-HPLC to afford 4-(4-methylpiperazin-1-yl)-2-(trifluoromethoxy)aniline (0.5 g, 50%) as a brown gummy liquid. LCMS $[M+H]^+$ 276.1

Synthesis of 2-(difluoromethoxy)-4-morpholinoaniline (8-8)

Scheme 8

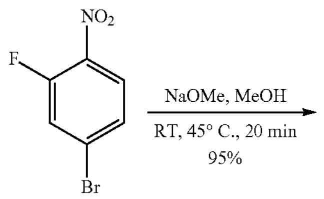

8-1

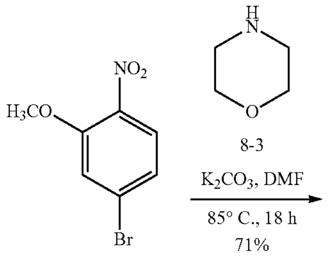

8-3

8-2

-continued

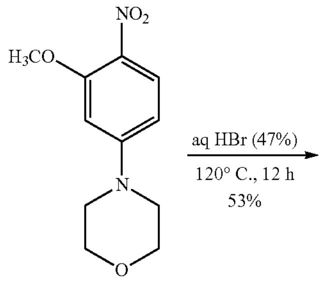

8-4

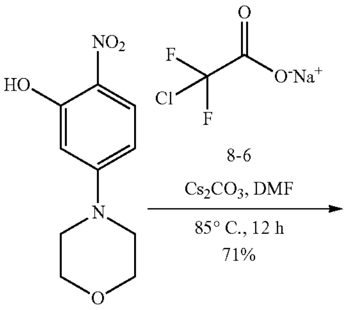

8-6

8-5

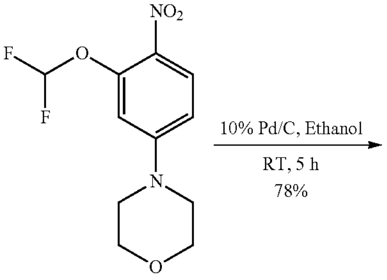

8-7

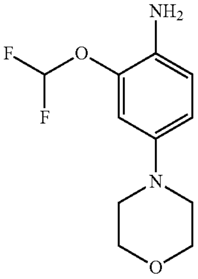

8-8

Step 1: Synthesis of 4-bromo-2-methoxy-1-nitrobenzene (8-2)

To a stirred solution of compound 8-1 (15 g, 68.5 mmol) in methanol (150 mL) was added 30% NaOMe in MeOH (18.5 mL) at room temperature and stirred for 20 min at 40° C. Then, the reaction mixture was diluted with ice water (500 mL); obtained precipitate was filtered, washed with water (100 mL) and dried under vacuum to afford crude compound 8-2 (15 g, 95%) as a pale-yellow solid. Crude compound taken for next step without further purification; LCMS $[M+H]^+$ 232.1.

Step 2: Synthesis of 4-(3-methoxy-4-nitrophenyl) morphine (8-4)

To a stirred solution of compound 8-3 (15 g, 65 mmol) in DMF (150 mL) was added potassium carbonate (35.84 g, 260 mmol) followed by compound 3 (16.8 mL, 195 mmol) and the reaction mixture was stirred at 85° C. for 18 h before cooling to room temperature. The reaction mixture was diluted with ice water (300 mL); obtained precipitate was filtered, washed with water (200 mL) and dried under vacuum to afford compound 8-4 (11 g, 71%) as a pale yellow solid. Crude compound taken for next step without further purification; LCMS $[M+H]^+$ 239.

Step 3: Synthesis of 5-morpholino-2-nitrophenol (8-5)

To a stirred solution of compound 8-4 (3 g, 12.6 mmol) in 47% aq. HBr (30 mL) and the reaction mixture was heated at 120° C. for 12 h before cooling to room temperature. The reaction mixture was poured into ice water and basified with $NaHCO_3$ and extracted with EtOAc (3×300 mL). The combined organic layer was dried over $Na_2SO_4$ and concentrated under reduced pressure to afford crude compound 8-5 (1.5 g, 53%) as a green solid. Crude compound taken for next step without further purification. LCMS $[M+H]^+$ 225.

Step 4: Synthesis of 4-(3-(difluoromethoxy)-4-nitrophenyl) morpholine (8-7)

To a stirred solution of compound 8-5 (1.5 g, 6.7 mmol) in DMF (25 mL) was added cesium carbonate (6.52 g, 20.1 mmol) followed by compound 8-6 (1.11 g, 7.35 mmol) and resulted reaction mixture was stirred at 90° C. for 3 h before cooling to room temperature. The reaction mixture was poured into ice water and extracted with EtOAc (2×200 mL). The combined organic layer was washed with chilled water (200 mL), dried over $Na_2SO_4$ and concentrated under reduced pressure to give crude compound. The crude product was triturated with 10% diethyl ether in n-pentane (50 mL) obtained precipitate was filtered and dried under vacuum to afford compound 8-7 (1.3 g, 71%) as a green solid. LCMS $[M+H]^+$ 275.

Step 5: Synthesis of 2-(difluoromethoxy)-4-morpholinoaniline (8-8)

To a solution of compound 8-7 (1.3 g, 4.7 mmol) in ethanol (30 mL) was added 10% Pd/C (0.7 g) at room temperature under hydrogen balloon pressure for 5 h. The reaction mixture was filtered through Celite pad and washed with methanol (100 mL). The filtrate was concentrated under vacuum to afford crude compound, which was purified by column chromatography (neutral alumina) using 10-20% EtOAc in petroleum ether as an eluent to afford 2-(difluoromethoxy)-4-morpholinoaniline (0.9 g, 78% yield) as a brown solid. LCMS $[M+H]^+$ 245.

Synthesis of 6-methoxy-2-methyl-1, 2, 3, 4-tetrahydroisoquinolin-7-amine (9-7)

Scheme 9

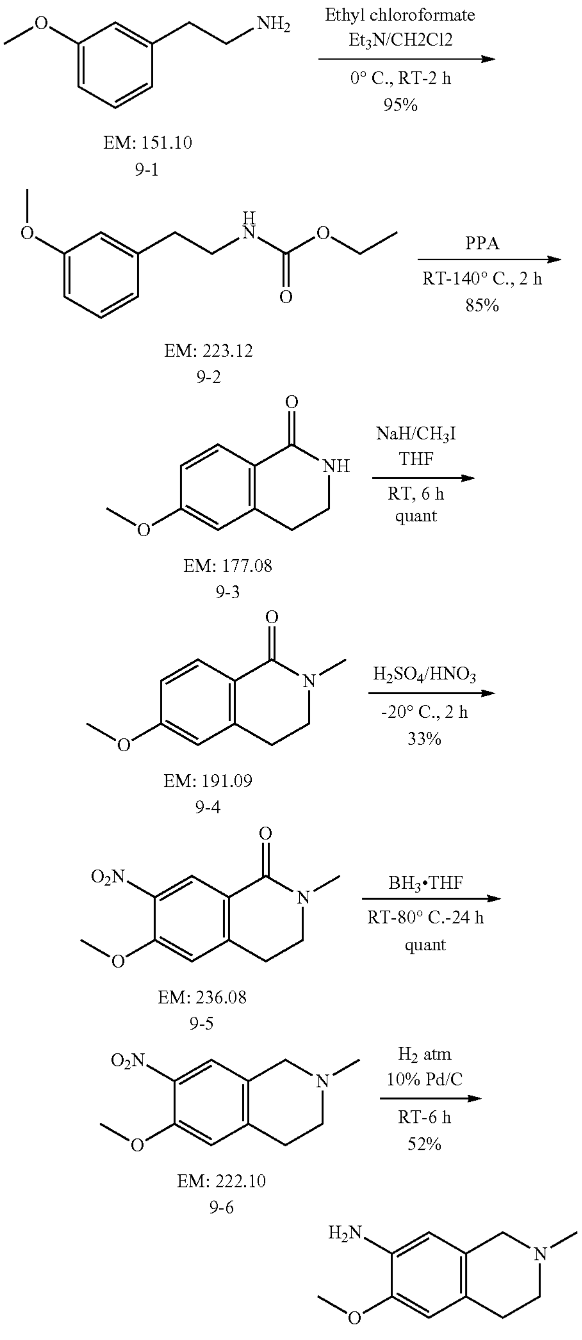

EM: 151.10
9-1

EM: 223.12
9-2

EM: 177.08
9-3

EM: 191.09
9-4

EM: 236.08
9-5

EM: 222.10
9-6

Exact Mass: 192.13
9-7

Step 1: Synthesis of ethyl (3-methoxyphenethyl) carbamate (9-2)

To a stirred solution of compound 9-1 (5 g, 33.1 mmol) in DCM (50 mL) was added triethylamine (6.91 mL, 49.6 mmol), followed by ethyl chloroformate (3.78 mL, 39.7 mmol) at 0° C. for 5 min and maintained at the same temperature for 2 h. Then, the mixture was quenched with ice cold water (200 mL) extracted with ethyl acetate (2×300 mL), combined organic layer was washed with water and brine solution, dried over $Na_2SO_4$ and concentrated under reduced pressure to afford crude compound 9-2 (7 g (Crude) 95%) as a brown liquid. LC-MS: m/z 224.3 (M+H); Step 2: Synthesis of 6-methoxy-3,4-dihydroisoquinolin-1(2H)-one (9-3)

A solution of compound 9-2 (6 g, 26.9 mmol) in polyphosphoric acid (30 g) was stirred at room temperature. Then, the reaction mixture was heated to 140° C. for 1 h before cooling to room temperature. Then, the mixture was quenched with ice water (100 mL), basified with 6N NaOH solution up to pH 9-10 and then extracted with EtOAc (2×300 mL). Combined organic layer was washed with water and brine solution, separated organic layer was dried over $Na_2SO_4$ and concentrated under reduced pressure to give a crude residue, which was purified by column chromatography (silica gel 100-200 mesh) using an eluent 1-5% MeOH in DCM to afford compound 9-3 (4 g, 85%) as a brown solid. LC-MS: m/z 178.2 Step 3: Synthesis of 6-methoxy-2-methyl-3,4-dihydroisoquinolin-1(2H)-one (9-4):

To a stirred solution of compound 9-3 (4 g, 22.6 mmol) in THE (80 mL) was added NaH (1.08 g, 27.1 mmol) portion wise at room temperature and stirred for 30 min. $CH_3I$ (1.68 mL, 27.1 mmol) was added to the above reaction mixture for 5 min and reaction mixture was stirred at room temperature for 6 h. Then, the reaction mixture was quenched with ice cold water (200 mL) extracted with EtOAc (2×200 mL), combined organic layer was washed with water and brine solution, dried over $Na_2SO_4$ and concentrated under reduced pressure to afford crude compound 9-4 (5 g, quant) as a brown liquid. LC-MS: m/z 192.1 (M+H); Step 4: Synthesis of 6-methoxy-2-methyl-7-nitro-3,4-dihydroisoquinolin-1 (2H)-one (9-5)

To a stirred solution of compound 9-4 (5 g, 26.1 mmol) in conc. $H_2SO_4$ (25 mL) was added $HNO_3$ (1.31 mL, 31.4 mmol) at −20° C. for 5 min and maintaining same temperature for 2 h. The reaction mixture was quenched with ice water (200 mL) solid was formed filtered washed with chilled water (200 mL) dried under vacuum to obtained crude residue, which was purified by column chromatography (silica gel 100-200 mesh) using an eluent 70-80% EtOAc in petroleum ether to afford compound 9-5 (2.1 g, 33%) as a pale-yellow solid; LCMS: m/z 237.3 ($[M+H]^+$):

Step 5: Synthesis of 6-methoxy-2-methyl-7-nitro-1, 2, 3, 4-tetrahydroisoquinoline (9-6)

To a solution of compound 9-5 (2 g, 8.5 mmol) in THE (100 mL) was added 1M borane in THE (42 mL, 42.3 mmol) at room temperature and reaction mixture was slowly heated to 80° C. for 20 h before cooling to room temperature. The reaction mixture was quenched with addition of methanol (20 mL) the resulting reaction mixture was concentrated under reduced pressure and crude residue was heated at 80° C. with 2N HCl (30 mL) for 3 h before cooling to room temperature. Then, the reaction mixture was basified with aq. $NH_3$ solution up to pH 8 to 9 and extracted with DCM (2×100 mL), dried over $Na_2SO_4$ and concentrated under reduced pressure to afford crude compound 6 (1.8 g, quant) as a brown liquid. LC-MS: m/z 223.4 (M+H). Step 6: Synthesis of 2-(difluoromethoxy)-5-fluoro-4-(4-methylpiperazin-1-yl) aniline (9-7)

To a solution of compound 9-6 (1.8 g, 8.1 mmol) in methanol (40 mL) was added 10% Pd/C (1.5 g, 10% w/w) under argon atmosphere and then stirred under $H_2$ atmosphere (balloon pressure) at room temperature for 6 h. Then, the reaction mixture was filtered through a Celite bed, which was washed with MeOH (100 mL) and the filtrate was concentrated under reduced pressure to obtained crude residue which was triturated with 20% diethyl ether in n-pentane (50 mL) and filtered washed with n-pentane dried under vacuum to afford 6-methoxy-2-methyl-1, 2, 3, 4-tetrahydroisoquinolin-7-amine (0.81 g, 52%) as a pale yellow solid. 1H NMR (400 MHz, $CDCl_3$) δ 6.51 (s, 1H), δ 6.37 (s, 1H), δ 3.81 (s, 3H), δ 3.63 (s, 2H), δ 3.44 (s, 2H), δ 2.81 (t, J=6.0 Hz, 2H), b 2.64 (t, J=6.0 Hz, 2H s), b 2.43 (s, 3H); LC-MS: m/z 193.3 (M+H).

Synthesis of 2-isopropyl-7-methoxy-1,2,3,4-tetrahydroisoquinolin-6-amine

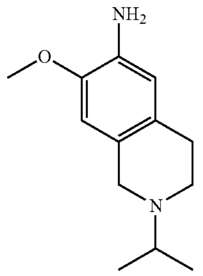 [SMILES: COc1cc2c(cc1N)CCN(C(C)C)C2]

To a vial charged with 7-methoxy-1,2,3,4-tetrahydroisoquinoline (163 mg, 1 mmol) and acetonitrile (10 mL) was added trifluoroacetic anhydride (0.71 mL, 5 mmol). The resulting pale-yellow solution (a bit exothermic) was stirred at room temperature for 10 min, then cooled to 0° C. Potassium nitrate (106 mg, 1.05 mmol) was added, and the resulting mixture was stirred at 0° C. for 1 h. Solvents were removed and the residue was treated with 1 M aq. NaOH (3 mL, 3 mmol), MeOH (10 mL). The resulting mixture was heated at 65° C. for 30 min.

After removal of solvents and aqueous workup, the residue was redissolved in DCE (15 mL) and sodium triacetoxyborohydride (318 mg, 1.5 mmol) was added, followed by acetone (0.15 mL, 2 mmol) and 2 drops of HOAc. The resulting mixture was stirred at room temperature overnight. After aqueous workup, it was purified by chromatography (KP SNAP 25 g column, gradient: EtOAc/hex 0-100% then MeOH/DCM 0-20%) to give 2-isopropyl-7-methoxy-6-nitro-1,2,3,4-tetrahydroisoquinoline (yellow oil, 64 mg). MS (ESI) m/z 251.2 $[M+H]^+$.

The above oil was redissolved in MeOH (8 mL) and treated with hydrazine monohydrate (0.1 mL, 2 mmol). After adding Raney-nickel, 2800 (34 mg, 0.4 mmol), the resulting mixture was stirred at rt for 45 min, filtered, rinsed with MeOH (10 mL) and the filtrate was concentrated and dried to give 2-isopropyl-7-methoxy-1,2,3,4-tetrahydroisoquinolin-6-amine (yellow crystalline solid, 60 mg). MS (ESI) m/z 221.3 $[M+H]^+$.

Synthesis of 6-methoxy-2,4,4-trimethyl-1,2,3,4-tetrahydroisoquinolin-7-amine

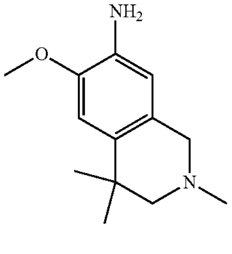

To a stirred mixture of 6-methoxy-2,4,4-trimethyl-1,2,3,4-tetrahydroisoquinoline (0.955 g, 4.65 mmol) and sulphuric acid (14 ml) at 0° C. was added guanidine nitrate (0.568 g, 4.65 mmol). The resulting mixture was stirred at 0° C. for 45 minutes prior to being quenched with ice and basified with a 4N aqueous sodium hydroxide solution. The aqueous layer was extracted with EtOAc (2×100 ml), and the combined organic extracts were dried with anhydrous sodium sulfate, filtered, and concentrated under reduced pressure to yield 6-methoxy-2,4,4-trimethyl-7-nitro-1,2,3,4-tetrahydroisoquinoline as a yellow oil (660 mg, 51.6% yield). This material was used in the subsequent reaction without further purification. LRMS: 251.08 (+ve)

To a solution of 6-methoxy-2,4,4-trimethyl-7-nitro-1,2,3,4-tetrahydroisoquinoline (0.420 g, 1.678 mmol) in methanol (MeOH) (9 ml) at room temperature was added hydrazine monohydrate (0.501 ml, 6.71 mmol) and Raney-nickel, 2800 (0.115 g, 1.342 mmol). The resulting mixture was stirred at room temperature for 1 hour (exothermic). After the reaction was deemed complete by LCMS, the reaction mixture was filtered through a pad of Celite, and the filtrate concentrated under reduced pressure. The light-yellow residue was then dried further under vacuum to give the 6-methoxy-2,4,4-trimethyl-1,2,3,4-tetrahydroisoquinolin-7-amine (185 mg, 47% yield) which was use in the subsequent reaction without any further purification. LRMS: 221.29 (+ve)

Synthesis of 6-methoxy-2,4,4-trimethyl-1,2,3,4-tetrahydroisoquinolin-7-amine (10-7)

Scheme 10

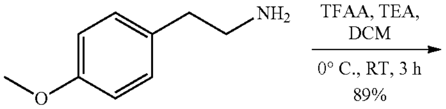

10-1

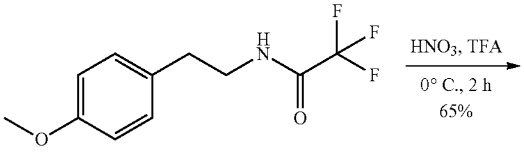

10-2

-continued

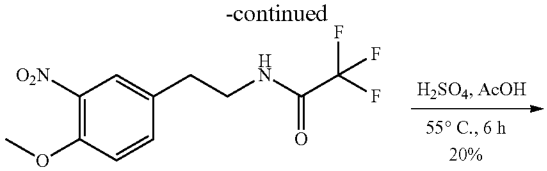

10-3

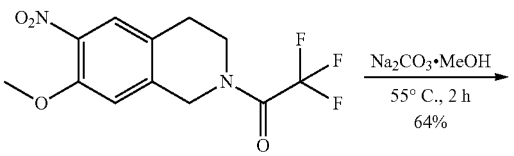

10-4

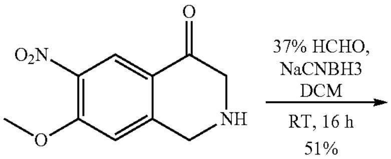

10-5

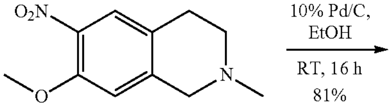

10-6

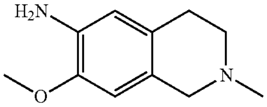

10-7

Step 1: Synthesis of 2,2,2-trifluoro-N-(4-methoxyphenethyl) acetamide (10-2)

To a stirred solution of compound 10-1 (24 g, 158.9 mmol) in dry DCM (240 mL) was added triethylamine (52 mL, 381.3 mmol) and TFAA (26.5 mL, 190.6 mmol) at 0° C. The reaction mixture was allowed to stir at room temperature for 3 h. Then, the reaction mixture was quenched with water (300 mL) and extracted with DCM (2×250 mL). The combined organic layer was dried over $Na_2SO_4$ and concentrated under reduced pressure to give crude residue. The crude compound was purified by column chromatography (silica gel, 100-200 mesh) using an eluent 0-30% EtOAc in petroleum ether to afford compound 10-2 (35 g, 89%) as an off white solid.

Step 2: Synthesis of 2,2,2-trifluoro-N-(4-methoxy-3-nitrophenethyl)acetamide (10-3)

To a stirred solution of compound 10-2 (38.5 g, 155.8 mmol) in TFA (390 mL) was added 65% $HNO_3$ (12.5 mL) at 0° C. for 2 h. Then, the solvent was concentrated under reduced pressure to give crude residue. The residue was diluted with water (400 mL) and extracted with diluted with EtOAc (2×400 mL). The combined organic layers were dried over with sodium sulfate and concentrated under reduced pressure to give crude compound. The crude compound was purified by column chromatography (silica gel, 100-200 mesh) using an eluent 0-40% EtOAc in petroleum ether to afford compound 10-3 (30 g, 65%) as a pale-yellow solid.

Step 3: Synthesis of 2,2,2-trifluoro-1-(7-methoxy-6-nitro-3,4-dihydroisoquinolin-2(1H)-yl)ethan-1-one (10-4)

To a mixture of 40% $H_2SO_4$ in AcOH (260 mL) was added compound 10-3 (26 g, 89 mmol) followed by paraformaldehyde (14.6 g, 489.5 mmol) at room temperature. Then, the reaction mixture was heated to 55° C. for 6 h before cooling to room temperature. The reaction mixture was poured into ice cold water and extracted with EtOAc (2×500 mL). The combined organic layers were dried over sodium sulfate and concentrated under reduced pressure to give crude residue. The crude compound was purified by column chromatography (silica gel, 100-200 mesh) using an eluent 0-40% EtOAc in petroleum ether to afford compound 10-4 (5.5 g, 20%) as a pale-yellow solid.

Step 4: Synthesis of 7-methoxy-6-nitro-1,2,3,4-tetrahydroisoquinoline (10-5)

To a stirred solution of compound 10-4 (6.2 g, 20.4 mmol) in MeOH (60 mL) was added saturated $Na_2CO_3$ solution (60 mL) at room temperature under argon atm. Then, the reaction mixture was heated to 55° C. for 2 h before cooling to room temperature. The reaction mixture was concentrated under reduced pressure to give crude residue. The residue was diluted with water (500 mL) and extracted with DCM (2×200 mL). The combined organic layers were dried over $Na_2SO_4$ and concentrated under reduced pressure to give crude residue. The crude compound was purified by column chromatography (neutral alumina) using an eluent 0-5% MeOH in DCM to afford compound 10-5 (2.7 g, 64%) as a pale-yellow solid.

Step 5: Synthesis of 7-methoxy-2-methyl-6-nitro-1,2,3,4-tetrahydroisoquinoline (10-6)

To a stirred solution of compound 10-5 (2.7 g, 13 mmol) in DCM:AcOH (27 mL: 10 mL) was added 37% formaldehyde (4.2 mL, 52 mmol) and $NaCNBH_3$ (1.6 g, 26 mmol) at room temperature under argon atmosphere. Then, the reaction mixture was stirred at room temperature for 16 h. The reaction mixture was concentrated under reduced pressure to give residue. The residue was diluted with water (500 mL) and extracted with DCM (2×200 mL). The combined organic layers were dried over $Na_2SO_4$ and concentrated under reduced pressure to give crude residue. The crude compound was purified by column chromatography (silica gel, 230-400 mesh) using an eluent 0-5% MeOH in DCM to afford compound 10-6 (1.5 g, 51%) as a pale-yellow solid.

Step 6: Synthesis of 7-methoxy-2-methyl-1,2,3,4-tetrahydroisoquinolin-6-amine (10-7)

To a stirred suspension of compound 10-6 (1.5 g, 6.7 mmol) in EtOH (20 mL) was added 10% Pd/C (400 mg) and stirred under $H_2$ balloon atmosphere at room temperature for 16 h. The reaction mixture was filtered through Celite bed and washed with EtOH (200 mL). The combined solvent was concentrated under reduced pressure to give crude compound. The crude compound was triturated with diethyl ether to afford 7-methoxy-2-methyl-1,2,3,4-tetrahydroisoquinolin-6-amine (1.05 g, 81% yield) as a pale-yellow solid.

$^1H$ NMR (400 MHz, DMSO-$d_6$): δ 6.43 (s, 1H), δ 6.33 (s, 1H), δ 4.45 (s, 2H) δ 3.69 (s, 3H), δ 3.32 (s, 2H), δ 2.60 (t, J=5.6 Hz, 2H), δ 2.54-2.47 (m, 2H), b 2.29 (s, 3H). LCMS m/z 193.21 ($[M+H]^+$)

Synthesis of 7-((2-((2-(difluoromethoxy)-4-(3,3-dimethylpiperazin-1-yl)phenyl)amino)-5-(trifluoromethyl)pyrimidin-4-yl)amino)isoindolin-1-one (11-3)

Scheme 11

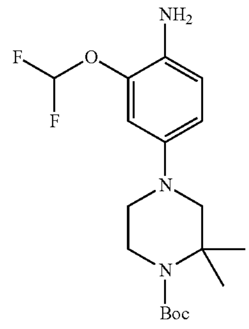

11-1

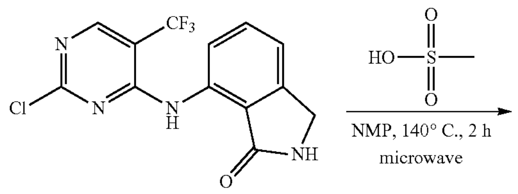

11-2

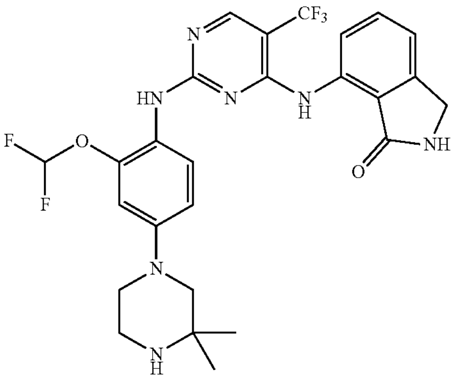

11-3

To a vial charged with tert-butyl-4-(4-amino-3-(difluoromethoxy)phenyl)-2,2-dimethylpiperazine-1-carboxylate 11-1 (156 mg, 0.42 mmol) and 7-((2-chloro-5-(trifluoromethyl)pyrimidin-4-yl)amino)isoindolin-1-one 11-2 (204 mg, 0.3 mmol based on 48.42% purity) was added NMP (2 mL) and methanesulfonic acid (58 uL, 0.9 mmol). The resulting mixture was heated in microwave at 140° C. for 2 h, and was then diluted with DMSO (1 mL)/TFA (0.2 mL), filtered and purified by PREP-HPLC to give a light brown solid 11-3 (4.9691-4.9005 g=68.6 mg, yield 40%). $^1H$ NMR (500 MHz, DMSO-$d_6$) δ 10.62 (br. s., 1H), 9.24 (s, 1H), 8.75 (br. s., 1H) 8.36 (br. s., 1H), 7.90 (br. s., 1H), 7.26 (d, J=8.80 Hz, 1H) 6.88-7.22 (m, 3H), 6.86 (d, J=7.09 Hz, 1H), 6.76 (br. s., 1H), 4.35 (br. s., 2H), 3.09 (br. s., 2H), 2.92 (br. s., 4H), 1.14 (s, 6H); MS (ESI) m/z 564.5 $[M+H]^+$.

In a similar manner, the following intermediates were used:

| Aniline | Name |
|---|---|
| 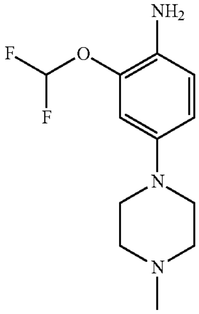 [SMILES: CN1CCN(c2ccc(N)c(OC(F)F)c2)CC1] | 2-(Difluoromethoxy)-4-(4-methylpiperazin-1-yl)aniline |
| 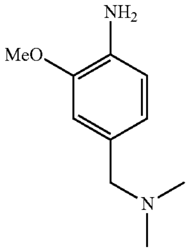 | 4-((Dimethylamino)methyl)-2-methoxyaniline |
| 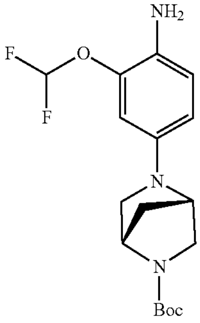 [SMILES: CC(C)(C)OC(=O)N1C[C@@H]2C[C@H]1CN2c1ccc(N)c(OC(F)F)c1] | tert-butyl-(1S,4S)-5-(4-amino-3-(difluoromethoxy)phenyl)-2,5-diazabicyclo[2.2.1]heptane-2-carboxylate |
| 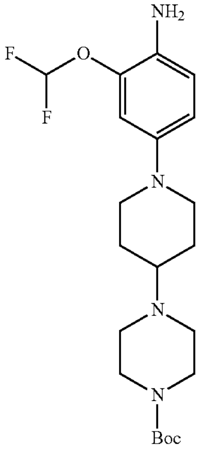 [SMILES: CC(C)(C)OC(=O)N1CCN(C2CCN(c3ccc(N)c(OC(F)F)c3)CC2)CC1] | tert-butyl-4-(1-(4-amino-3-(difluoromethoxy)phenyl)piperidin-4-yl)piperazine-1-carboxylate |

-continued

| Aniline | Name |
|---|---|
| 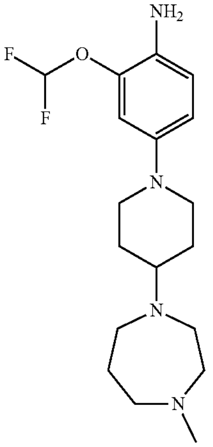 [SMILES: CN1CCCN(C2CCN(c3ccc(N)c(OC(F)F)c3)CC2)CC1] | 2-(difluoromethoxy)-4-(4-(4-methyl-1,4-diazepan-1-yl)piperidin-1-yl)aniline |
| 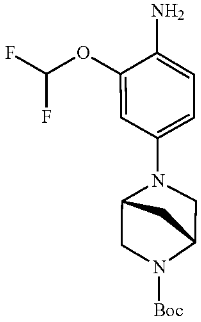 [SMILES: CC(C)(C)OC(=O)N1C[C@H]2C[C@@H]1CN2c1ccc(N)c(OC(F)F)c1] | tert-butyl-(1R,4R)-5-(4-amino-3-(difluoromethoxy)phenyl)-2,5-diazabicyclo[2.2.1]heptane-2-carboxylate |
| 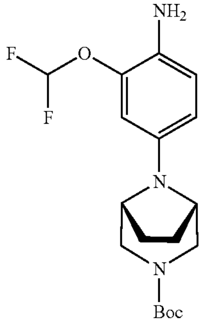 | tert-butyl (1R,5S)-8-(4-amino-3-(difluoromethoxy)phenyl)-3,8-diazabicyclo[3.2.1]octane-3-carboxylate |

Biological Assays

NUAK2 Enzymatic Assay

To identify small molecule NUAK inhibitors, a biochemical NUAK2 enzymatic assay were outsourced to Eurofins. This assay was done radiometrically using full-length, recombinant enzyme. NUAK2 (h) was incubated with 8 mM MOPS pH 7.0, 0.2 mM EDTA, 300 μM KKKVSRSGLYR-SPSMPENLNRPR, 10 mM magnesium acetate and [9-33P]-ATP (specific activity and concentration as required). The reaction was initiated by the addition of the Mg/ATP mix. After incubation for 40 minutes at room temperature, the reaction was stopped by the addition of phosphoric acid to a concentration of 0.5%. 10 μL of the reaction was then spotted onto a P30 filtermat and washed four times for 4 minutes in 0.425% phosphoric acid and once in methanol prior to drying and scintillation counting. Compounds were routinely counter-screened against Aurora A and NUAK1. The results are shown in Table 1 where $IC_{50}$'s are reported in the following ranges: A: 0.1-10 nM; B: 11-100 nM; C: 101-1000 nM; D: >1000 nM for the compounds of Formula (I)

TABLE 1

$IC_{50}$'s(nM) for representative compounds of the application for inhibition of NUAK2, NUAK1 and Aurora-A

| Compound I.D. | NUAK2 ($IC_{50}$, nM) | NUAK1 ($IC_{50}$, nM) | AUR-A ($IC_{50}$, nM) |
|---|---|---|---|
| I-1 | A | B | C |
| I-2 | B | A | A |
| I-3 | B | C | C |
| I-4 | A | B | A |
| I-5 | A | B | B |
| I-6 | B | B | C |
| I-7 | B | B | C |
| I-8 | B | C | C |
| I-9 | A | B | C |
| I-10 | A | A | A |
| I-11 | C | D | D |
| I-12 | A | B | D |
| I-13 | A | B | B |
| I-14 | B | A | B |
| I-15 | B | B | C |
| I-16 | B | B | D |
| I-17 | B | B | D |
| I-18 | A | B | D |
| I-19 | B | C | D |
| I-20 | A | B | C |
| I-21 | B | B | C |
| I-22 | A | B | C |
| I-23 | B | B | C |
| I-24 | A | B | D |
| I-25 | B | B | D |
| I-26 | B | B | D |
| I-27 | B | B | D |
| I-28 | A | B | D |
| I-29 | B | B | C |
| I-30 | A | A | C |
| I-31 | A | B | C |
| I-32 | B | B | C |
| I-33 | B | B | C |
| I-34 | B | B | D |
| I-35 | B | B | C |
| I-36 | B | A | B |
| I-37 | A | B | B |
| I-38 | A | B | C |
| I-39 | B | B | B |
| I-40 | A | B | C |
| I-41 | B | C | C |
| I-42 | B | C | C |
| I-43 | B | C | C |
| I-44 | A | C | C |
| I-45 | B | B | B |
| I-46 | A | B | D |
| I-47 | B | C | D |
| I-48 | A | B | C |
| I-49 | A | B | D |
| I-50 | A | B | D |
| I-51 | A | A | A |
| I-52 | B | B | B |
| I-53 | B | C | D |
| I-54 | A | B | D |
| I-55 | A | B | D |
| I-56 | B | B | C |
| I-57 | A | B | D |
| I-58 | B | B | C |
| I-59 | A | B | C |
| I-60 | B | B | C |
| I-61 | B | B | C |
| I-62 | A | A | B |
| I-63 | A | B | C |
| I-64 | A | B | D |
| I-65 | A | C | C |
| I-66 | A | B | C |
| I-67 | A | B | C |
| I-68 | A | B | C |
| I-69 | A | B | C |
| I-70 | A | B | C |
| I-71 | A | B | C |
| I-72 | A | B | C |
| I-73 | A | A | C |
| I-74 | A | B | C |
| I-75 | A | A | A |
| I-76 | A | B | C |
| I-77 | B | B | C |
| I-78 | A | B | C |
| I-79 | A | B | C |
| I-80 | B | B | C |
| I-81 | B | B | C |
| I-82 | A | B | C |
| I-83 | A | B | D |
| I-84 | A | N/A | D |
| I-85 | B | N/A | D |

Cell-Based YAP/TAZ Localization Assay

Compounds of the application were tested for their ability to inhibit localization of YAP/TAZ to the nucleus of cells using an assay generally described in Nature Communications, 2018, 9:3510. Live cell imaging of Clover-YAP expressing MDA-MB-231 cells was carried out using a custom WAVE-FX-X1 spinning disc confocal system (Quorum Technologies) with a modified Yokogawa CSU-X1 scanhead on an AxioObserver Z1 inverted microscope (Carl Zeiss) with a ×40 NA 1.2 Plan Apochromat (Carl Zeiss) objective. Cells were plated in a 35 mm glass-bottom dish (Mat-Tek, P35G-1.5-14-C) and were maintained in a stage-top incubator at 37° C. and 5% $CO_2$ during imaging. Cells were cultured in phenol-red free RPMI medium (Thermo Fisher Scientific, 11835030) with 5% FBS and 200 nM SiR-DNA (Spirochrom, SC007) was added 1 h prior to imaging to visualize the nuclei. Localization of Clover-YAP was monitored every 10 min for 2 h. Volocity software was used for image acquisition and processing. Representative NUAK inhibitors (e.g. compound I-34 and compound 1-56) potently inhibit nuclear localization of YAP/TAZ in the MDA-MB-231 breast cancer cell line (FIG. 1).

Cell-Based Phosho-MYPT1 Assay:

Compounds with sufficient activity in the biochemical NUAK assay can be evaluated in a cell-based assay to confirm their targeted activity. To allow direct assessment of target engagement by NUAK inhibitors in cells, an antibody to MYPT1, a NUAK substrate, which specifically recognizes the phosphorylated Ser445 epitope in endogenous MYPT1 protein will be utilized (*Biochem J.* 2014 457 (Pt 1): 215-225*; Biochem J.* 201 461 (Pt 2): 233-245).

MDA-MB-231 cells are incubated in the absence (DMSO) or presence of represented compound (at selected concentrations) for 1 hour. Cells are then lysed at 4° C. for 30 mins in RIPA buffer (50 mM tris-HCL, 150 mM NaCl, 1 mM EDTA, 0.1% SDS, 1% NP-40, 0.5% Sodium deoxycholate) containing protease and phosphatase inhibitors. Samples were separated by sodium dodecyl sulfate-polyacrylamide gel electrophoresis (SDS-PAGE), transferred to nitrocellulose and immunoblotted for the detection of $pSer^{445}$MYPT1 or ACTIN.

Tumor Cell Growth Inhibition Assay:

MDA-MB-231 cells were seeded into a 384-well plate at 1,000 cells/well in 50 μl medium (Alpha-MEM containing 10% FBS, 100 mg/ml Normocin, Invivogen and 50 mg/ml Gentamycin, Invitrogen). Plates were then incubated overnight for the cells to attach. An HP D300 digital dispenser was used to dose cells with DMSO or test compounds across a 16-point range of concentrations (high dose of 10 uM to low dose of 5 nM). Plates were incubated in a humidified 5% $CO_2$ incubator at 37° C. After 5 days, plates were removed from the incubator and equilibrated to room temperature. An equal volume of ATPlite assay reagent was then added to each well, and samples processed according to manufacturer's instructions (Perkin Elmer). Luminescent signals were then measured using an Envision plate reader equipped with a US-Luminescence detector. Results for representative compounds of the application are presented in Table 2.

TABLE 2

Antiproliferation for representative NUAK inhibitors for compounds of the application in the breast tumor cell line MDA-MB-231

| Example # | Tumor Growth Inhibition ($IC_{50}$, uM) |
|---|---|
| I-27 | 0.036 |
| I-33 | 0.038 |
| I-34 | 0.032 |
| I-54 | 0.048 |
| I-56 | 0.043 |
| I-59 | 0.054 |
| I-63 | 0.398 |

While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

The invention claimed is:

1. A compound of Formula I, or a pharmaceutically acceptable salt and/or solvate thereof:

(I)

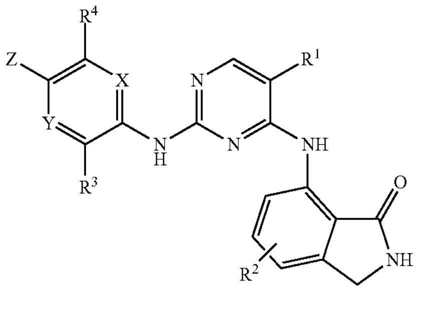

wherein $R^1$ is selected from H, halo, $C_{1-4}$alkyl, $OC_{1-4}$alkyl, $C_{1-4}$haloalkyl, $OC_{1-4}$haloalkyl, CN, $C_{1-4}$hydroxyalkyl and $OC_{1-4}$hydroxyalkyl;

$R^2$ is selected from H, halo, CN, $C_{1-4}$alkyl, $C_{1-4}$haloalkyl, $OC_{1-4}$alkyl and $OC_{1-4}$haloalkyl;

$R^3$ is selected from H, halo, $C_{1-4}$alkyl, $OC_{1-4}$alkyl, $C_{1-4}$haloalkyl, $OC_{1-4}$haloalkyl, X is selected from $CR^a$ and N;

Y is selected from $CR^b$ and N;

$R^a$ and $R^b$ are independently selected from H, halo, $C_{1-4}$alkyl and $C_{1-4}$haloalkyl;

Z is selected from $C_{1-6}$alkyleneNR$^5$R$^6$, $OC_{1-6}$alkyleneNR$^5$R$^6$, NR$^7$C$_{1-6}$alkyleneNR$^5$R$^6$, NR$^7$C$_{1-6}$alkyleneOR$^5$ and NR$^5$R$^6$;

$R^4$ is selected from H, halo, CN, $C_{1-4}$alkyl, $C_{1-4}$haloalkyl, $OC_{1-4}$alkyl and $OC_{1-4}$haloalkyl; or Z and $R^4$ are joined to form, together with the atoms therebetween a ring B which is selected from $C_{3-12}$cycloalkyl and $C_{3-12}$heterocycloalkyl, wherein the ring B is optionally substituted with one or more substituents selected from halo, =O, OH, $C_{1-6}$alkyl, $C_{3-6}$cycloalkyl, aryl, $C_{5-6}$heteroaryl, $C_{3-6}$heterocycloalkyl, $C_{1-6}$alkyleneC$_{3-6}$cycloalkyl, $C_{1-6}$alkylenearyl, $C_{1-6}$alkyleneC$_{5-6}$heteroaryl, $C_{1-6}$alkyleneC$_{3-6}$heterocycloalkyl, C(O)C$_{1-6}$alkyl, $OC_{1-6}$alkyl, $OC_{1-6}$alkyleneOC$_{1-6}$alkyl, C(O)NH$_2$, C(O)NH(C$_{1-6}$alkyl), C(O)N(C$_{1-6}$alkyl)(C$_{1-6}$alkyl), NHC(O)C$_{1-6}$alkyl, N(C$_{1-6}$alkyl)C(O)C$_{1-6}$alkyl, NH$_2$, NH(C$_{1-6}$alkyl), N(C$_{1-6}$alkyl)(C$_{1-6}$alkyl), SC$_{1-6}$alkyl, S(O)C$_{1-6}$alkyl and SO$_2$C$_{1-6}$alkyl, wherein all alkyl, alkylene, cycloalkyl, heterocycloalkyl, aryl and heteroaryl groups of the optional substituents on the ring B are also optionally substituted with one or more of halo, $C_{1-6}$alkyl, $OC_{1-6}$alkyl, $C_{1-6}$haloalkyl and $OC_{1-6}$haloalkyl;

$R^5$ is selected from H, $C_{1-6}$alkyl, $C_{3-10}$cycloalkyl, $C_{3-10}$heterocycloalkyl, $C_{2-6}$alkenyl, $C_{2-6}$alkynyl, $C_{1-6}$alkyleneC$_{3-10}$cycloalkyl, $C_{1-6}$alkyleneC$_{3-10}$heterocycloalkyl, $C_{1-6}$alkylalkyleneOR$^8$ and $C_{1-6}$alkylalkyleneNR$^8$R$^9$, and all alkyl, alkenyl, alkynyl, alkylene, heterocycloalkyl and cycloalkyl groups of $R^5$ are optionally substituted with one or more of halo, $C_{1-6}$alkyl and $C_{1-6}$haloalkyl;

$R^6$ is selected from H, $C_{1-6}$alkyl and $C_{1-6}$haloalkyl; or $R^5$ and $R^6$ are joined to form, together with the atom therebetween, $C_{3-12}$heterocycloalkyl, optionally containing one additional heteromoiety selected from NR$^{10}$, O, S, S(O) and SO$_2$, and optionally substituted with one or more substituents selected from halo, =O, OH, $C_{1-6}$alkyl, $C_{3-6}$cycloalkyl, aryl, $C_{5-6}$heteroaryl, $C_{3-6}$heterocycloalkyl, $C_{1-6}$alkyleneC$_{3-6}$cycloalkyl, $C_{1-6}$alkylenearyl, $C_{1-6}$alkyleneC$_{5-6}$heteroaryl, $C_{1-6}$alkyleneC$_{3-6}$heterocycloalkyl, C(O)C$_{1-6}$alkyl, $OC_{1-6}$alkyl, $OC_{1-6}$alkyleneOC$_{1-6}$alkyl, C(O)NH$_2$, C(O)NH(C$_{1-6}$alkyl), C(O)N(C$_{1-6}$alkyl)(C$_{1-6}$alkyl), NHC(O)C$_{1-6}$alkyl, N(C$_{1-6}$alkyl)C(O)C$_{1-6}$alkyl, NH$_2$, NH(C$_{1-6}$alkyl), N(C$_{1-6}$alkyl)(C$_{1-6}$alkyl), SC$_{1-6}$alkyl, S(O)C$_{1-6}$alkyl and SO$_2$C$_{1-6}$alkyl, wherein all alkyl, alkylene, cycloalkyl, heterocycloalkyl, aryl and heteroaryl groups of the optional substituents on the $C_{4-12}$heterocycloalkyl formed by $R^5$ and $R^6$ are also optionally substituted with one or more of halo, $C_{1-6}$alkyl, $OC_{1-6}$alkyl, $C_{1-6}$haloalkyl and $OC_{1-6}$haloalkyl; and $R^7$, $R^8$, $R^9$ and $R^{10}$ are independently selected from H, $C_{1-6}$alkyl and $C_{1-6}$haloalkyl.

2. The compound of claim 1, wherein $R^1$ is selected from Cl, F, Br, I, $CH_3$, $CH_2OH$, $OCH_3$, $OCF_3$, $OCF_2H$, $OCH_2F$, $CF_3$, $CF_2H$ and $CH_2F$.

3. The compound of claim 1, wherein $R^2$ is selected from H, F, $CH_3$, $CF_3$, $OCH_3$ and $OCF_3$.

4. The compound of claim 1, wherein $R^3$ is selected from $OCH_3$, $CF_3$, $OCF_2$, $OCHF_2$ and $OCH_2F$.

5. The compound of claim 1, wherein X is selected from N, CH, CF and $CCH_3$.

6. The compound of claim 1, wherein Y is selected from N, CH, CF and $CCH_3$.

7. The compound of claim 1, wherein Z is selected from $C_{1-4}$alkyleneNR$^5$R$^6$, OC$_{1-4}$alkyleneNR$^5$R$^6$, NR$^7$C$_{1-4}$alkyleneNR$^5$R$^6$, NR$^7$C$_{1-4}$alkyleneOR$^5$ and NR$^5$R$^6$, and R$^5$ and R$^6$ are independently selected from H and C$_{1-6}$alkyl.

8. The compound of claim 1, wherein Z is NR$^5$R$^6$, and R$^5$ and R$^6$ are joined to form, together with the atom therebetween, C$_{4-12}$heterocycloalkyl, optionally containing one additional heteromoiety selected from NR$^{10}$, O and S, and optionally substituted with one or two substituents selected from halo, =O, C$_{1-6}$alkyl, C$_{3-6}$cycloalkyl, C$_{3-6}$heterocycloalkyl, NH(C$_{1-6}$alkyl), N(C$_{1-6}$alkyl)(C$_{1-6}$alkyl), SC$_{1-6}$alkyl, S(O)C$_{1-6}$alkyl and SO$_2$C$_{1-6}$alkyl, wherein all alkyl, cycloalkyl, and heterocycloalkyl, groups of the optional substituents on the C$_{4-12}$heterocycloalkyl formed by R$^5$ and R$^6$ are also optionally substituted with one or more of halo, C$_{1-6}$alkyl, OC$_{1-6}$alkyl, C$_{1-6}$haloalkyl and OC$_{1-6}$haloalkyl.

9. The compound of claim 1, wherein Z is selected from:

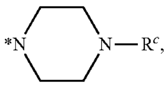, 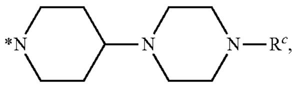,

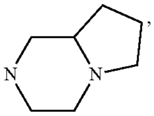, 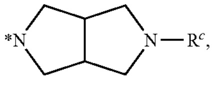,

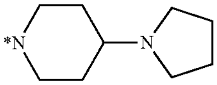, 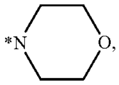, 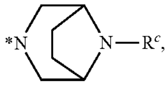,

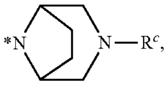, 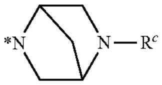

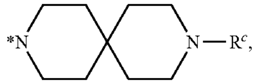, 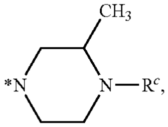,

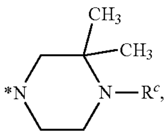, 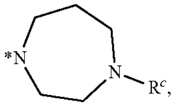,

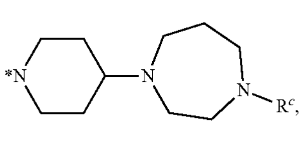, 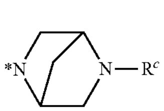 and

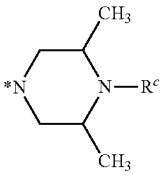

wherein R$^c$ is selected from H and C$_{1-6}$alkyl and * represents the point of attachment for Z in the compound of Formula I.

10. The compound of claim 1, wherein R$^5$ is selected from H, $CH_3$, $CH_2CH_3$, $CH(CH_3)_2$, $C(CH_3)_3$, $CF_3$, $CH_2CF_3$, and $(CH_2)_2OCH_3$.

11. The compound of claim 1, wherein R$^6$, R$^7$, R$^8$, R$^9$ and R$^{10}$ are independently selected from H and $CH_3$.

12. The compound of claim 1, wherein Z and R$^4$ are joined to form, together with the atoms therebetween a ring B which is selected from C$_{5-10}$cycloalkyl and C$_{5-10}$heterocycloalkyl, wherein the ring B is optionally substituted with one or more substituents selected from halo, =O, OH, C$_{1-4}$alkyl, C$_{3-6}$cycloalkyl, aryl, C$_{5-6}$heteroaryl, C$_{3-6}$heterocycloalkyl, C$_{1-5}$alkyleneC$_{3-6}$cycloalkyl, C$_{1-4}$alkylenearyl, C$_{1-4}$alkyleneC$_{5-6}$heteroaryl, C$_{1-4}$alkyleneC$_{3-6}$heterocycloalkyl, C(O)C$_{1-4}$alkyl, OC$_{1-4}$alkyl, OC$_{1-4}$alkyleneOC$_{1-4}$alkyl, C(O)NH$_2$, C(O)NH(C$_{1-4}$alkyl), C(O)N(C$_{1-4}$alkyl)(C$_{1-4}$alkyl), NHC(O)C$_{1-4}$alkyl, N(C$_{1-4}$alkyl)C(O)C$_{1-4}$alkyl, NH$_2$, NH(C$_{1-4}$alkyl), N(C$_{1-4}$alkyl)(C$_{1-4}$alkyl), SC$_{1-4}$alkyl, S(O)C$_{1-4}$alkyl and SO$_2$C$_{1-4}$alkyl, wherein all alkyl, alkylene, cycloalkyl, heterocycloalkyl, aryl and heteroaryl groups of the optional substituents on the ring B are also optionally substituted with one or more of halo, C$_{1-4}$alkyl, OC$_{1-4}$alkyl, C$_{1-4}$fluoroalkyl and OC$_{1-4}$fluoroalkyl.

13. The compound of claim 12, wherein ring B is selected from

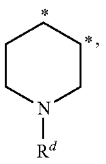, 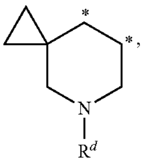, 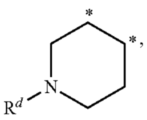,

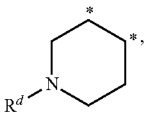, 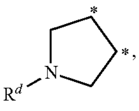, 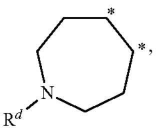,

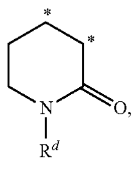, 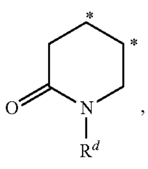, 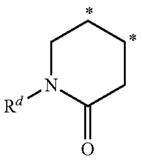 and

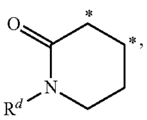, wherein R$^d$ is selected from H and C$_{1-6}$alkyl and * represents the points of attachment for ring B in the compound of Formula I.

14. The compound of claim 1, selected from

| Compound I.D. | Structure | Compound Name |
| --- | --- | --- |
| I-1 | 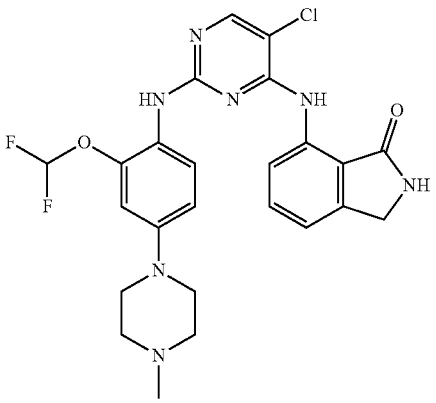 [SMILES: CN1CCN(c2ccc(Nc3ncc(Cl)c(Nc4cccc5c4C(=O)NC5)n3)c(OC(F)F)c2)CC1] | 7-((5-chloro-2-((2-(difluoromethoxy)-4-(4-methylpiperazin-1-yl)phenyl)amino)pyrimidin-4-yl)amino)isoindolin-1-one |
| I-2 | 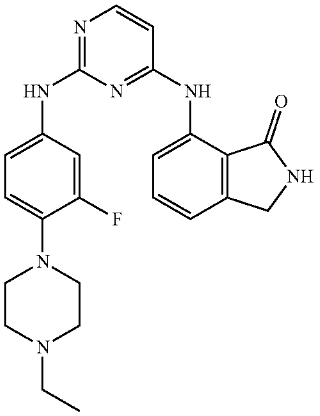 [SMILES: CCN1CCN(c2ccc(Nc3nccc(Nc4cccc5c4C(=O)NC5)n3)cc2F)CC1] | 7-((2-((4-(4-ethylpiperazin-1-yl)-3-fluorophenyl)amino)pyrimidin-4-yl)amino)isoindolin-1-one |
| I-3 | 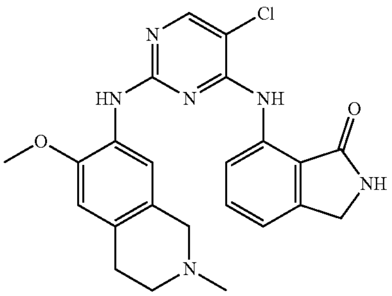 [SMILES: COc1cc2c(cc1Nc1ncc(Cl)c(Nc3cccc4c3C(=O)NC4)n1)CN(C)CC2] | 7-((5-chloro-2-((6-methoxy-2-methyl-1,2,3,4-tetrahydroisoquinolin-7-yl)amino)pyrimidin-4-yl)amino)isoindolin-1-one |
| I-4 | 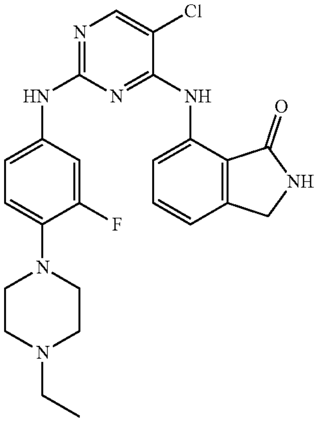 [SMILES: CCN1CCN(c2ccc(Nc3ncc(Cl)c(Nc4cccc5c4C(=O)NC5)n3)cc2F)CC1] | 7-((5-chloro-2-((4-(4-ethylpiperazin-1-yl)-3-fluorophenyl)amino)pyrimidin-4-yl)amino)isoindolin-1-one |

-continued
| Compound I.D. | Structure | Compound Name |
|---|---|---|
| I-5 | 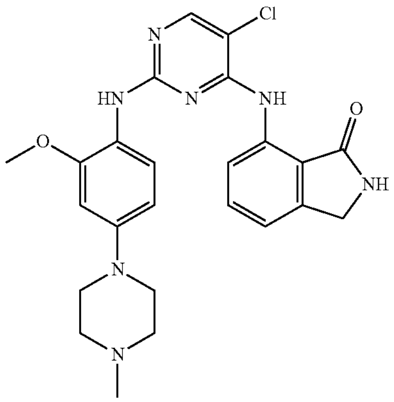 [SMILES: COc1cc(N2CCN(C)CC2)ccc1Nc1ncc(Cl)c(Nc2cccc3c2C(=O)NC3)n1] | 7-((5-chloro-2-((2-methoxy-4-(4-methylpiperazin-1-yl)phenyl)amino)pyrimidin-4-yl)amino)isoindolin-1-one |
| I-6 | 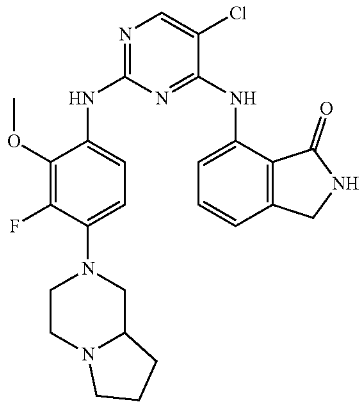 [SMILES: COc1c(Nc2ncc(Cl)c(Nc3cccc4c3C(=O)NC4)n2)ccc(N2CCN3CCCC3C2)c1F] | 7-((5-chloro-2-((3-fluoro-4-(hexahydropyrrolo[1,2-a]pyrazin-2(1H)-yl)-2-methoxyphenyl)amino)pyrimidin-4-yl)amino)isoindolin-1-one |
| I-7 | 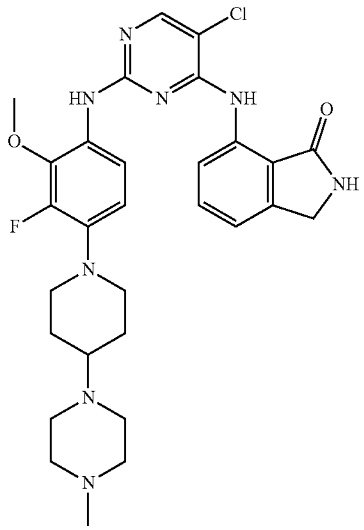 [SMILES: COc1c(Nc2ncc(Cl)c(Nc3cccc4c3C(=O)NC4)n2)ccc(N2CCC(N3CCN(C)CC3)CC2)c1F] | 7-((5-chloro-2-((3-fluoro-2-methoxy-4-(4-(4-methylpiperazin-1-yl)piperidin-1-yl)phenyl)amino)pyrimidin-4-yl)amino)isoindolin-1-one |

-continued
| Compound I.D. | Structure | Compound Name |
|---|---|---|
| I-8 | 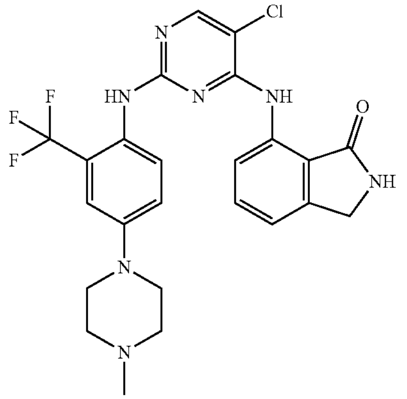 [SMILES: CN1CCN(c2ccc(Nc3ncc(Cl)c(Nc4cccc5c4C(=O)NC5)n3)c(C(F)(F)F)c2)CC1] | 7-((5-chloro-2-((4-(4-methylpiperazin-1-yl)-2-(trifluoromethyl)phenyl)amino)pyrimidin-4-yl)amino)isoindolin-1-one |
| I-9 | 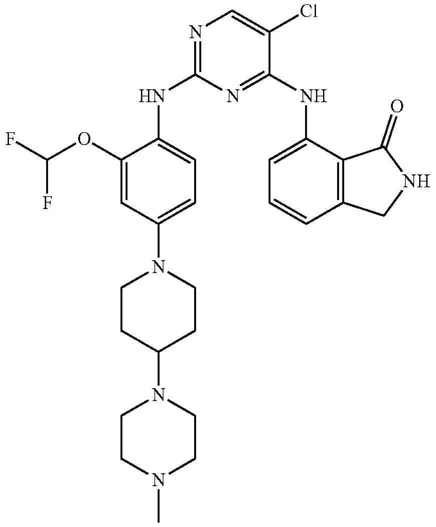 [SMILES: CN1CCN(C2CCN(c3ccc(Nc4ncc(Cl)c(Nc5cccc6c5C(=O)NC6)n4)c(OC(F)F)c3)CC2)CC1] | 7-((5-chloro-2-((2-(difluoromethoxy)-4-(4-(4-methylpiperazin-1-yl)piperidin-1-yl)phenyl)amino)pyrimidin-4-yl)amino)isoindolin-1-one |
| I-10 | 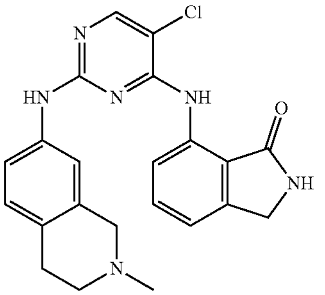 [SMILES: CN1CCc2ccc(Nc3ncc(Cl)c(Nc4cccc5c4C(=O)NC5)n3)cc2C1] | 7-((5-chloro-2-((2-methyl-1,2,3,4-tetrahydroisoquinolin-7-yl)amino)pyrimidin-4-yl)amino)isoindolin-1-one |

-continued
| Compound I.D. | Structure | Compound Name |
| --- | --- | --- |
| I-11 | 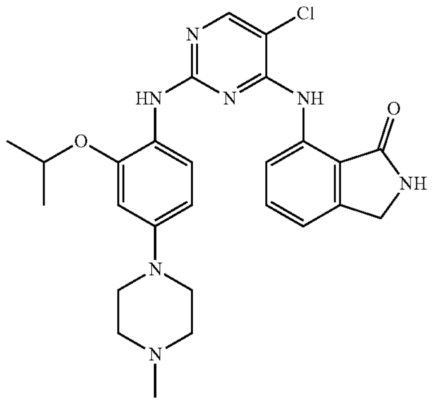 [SMILES: CC(C)Oc1cc(N2CCN(C)CC2)ccc1Nc1ncc(Cl)c(Nc2cccc3c2C(=O)NC3)n1] | 7-((5-chloro-2-((2-isopropoxy-4-(4-methylpiperazin-1-yl)phenyl)amino)pyrimidin-4-yl)amino)isoindolin-1-one |
| I-12 | 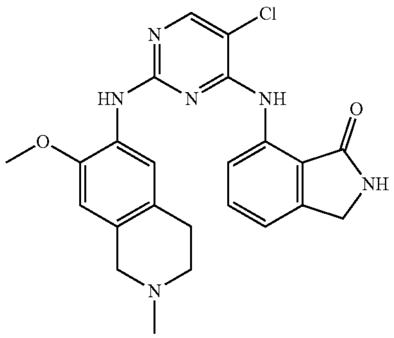 [SMILES: COc1cc2c(cc1Nc1ncc(Cl)c(Nc3cccc4c3C(=O)NC4)n1)CCN(C)C2] | 7-((5-chloro-2-((7-methoxy-2-methyl-1,2,3,4-tetrahydroisoquinolin-6-yl)amino)pyrimidin-4-yl)amino)isoindolin-1-one |
| I-13 | 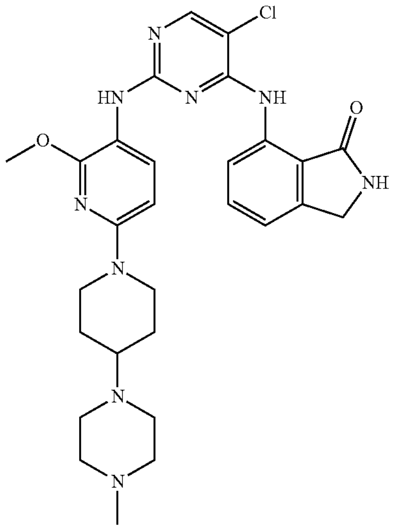 | 7-((5-chloro-2-((2-methoxy-6-(4-(4-methylpiperazin-1-yl)piperidin-1-yl)pyridin-3-yl)amino)pyrimidin-4-yl)amino)isoindolin-1-one |

-continued

| Compound I.D. | Structure | Compound Name |
| --- | --- | --- |
| I-14 | 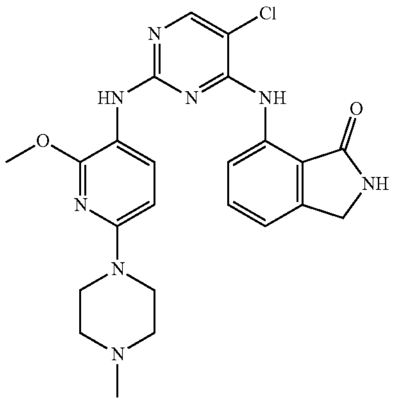 | 7-((5-chloro-2-((2-methoxy-6-(4-methylpiperazin-1-yl)pyridin-3-yl)amino)pyrimidin-4-yl)amino)isoindolin-1-one |
| I-15 | 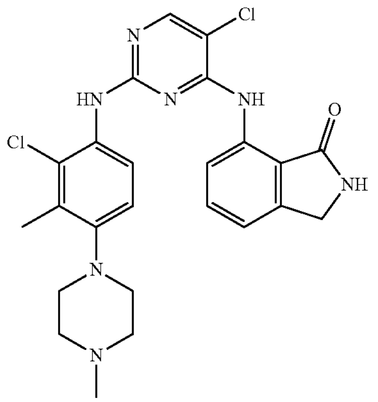 [SMILES: Cc1c(N2CCN(C)CC2)ccc(Nc2ncc(Cl)c(Nc3cccc4c3C(=O)NC4)n2)c1Cl] | 7-((5-chloro-2-((2-chloro-3-methyl-4-(4-methylpiperazin-1-yl)phenyl)amino)pyrimidin-4-yl)amino)isoindolin-1-one |
| I-16 | 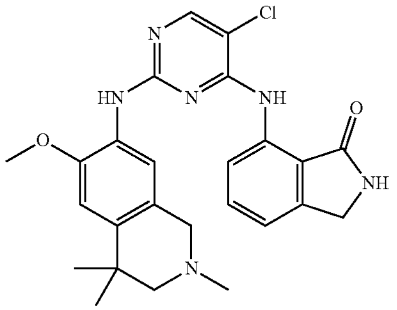 [SMILES: COc1cc2c(cc1Nc1ncc(Cl)c(Nc3cccc4c3C(=O)NC4)n1)CN(C)CC2(C)C] | 7-((5-chloro-2-((6-methoxy-2,4,4-trimethyl-1,2,3,4-tetrahydroisoquinolin-7-yl)amino)pyrimidin-4-yl)amino)isoindolin-1-one |
| I-17 | 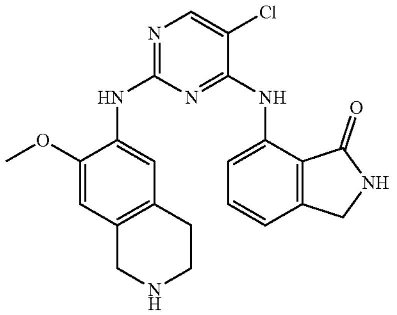 [SMILES: COc1cc2c(cc1Nc1ncc(Cl)c(Nc3cccc4c3C(=O)NC4)n1)CCNC2] | 7-((5-chloro-2-((7-methoxy-1,2,3,4-tetrahydroisoquinolin-6-yl)amino)pyrimidin-4-yl)amino)isoindolin-1-one |

-continued

| Compound I.D. | Structure | Compound Name |
|---|---|---|
| I-18 | 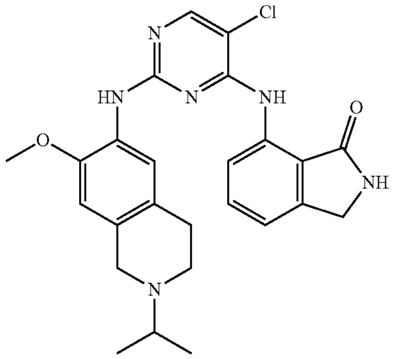 [SMILES: COc1cc2c(cc1Nc1ncc(Cl)c(Nc3cccc4c3C(=O)NC4)n1)CCN(C(C)C)C2] | 7-((5-chloro-2-((2-isopropyl-7-methoxy-1,2,3,4-tetrahydroisoquinolin-6-yl)amino)pyrimidin-4-yl)amino)isoindolin-1-one |
| I-19 | 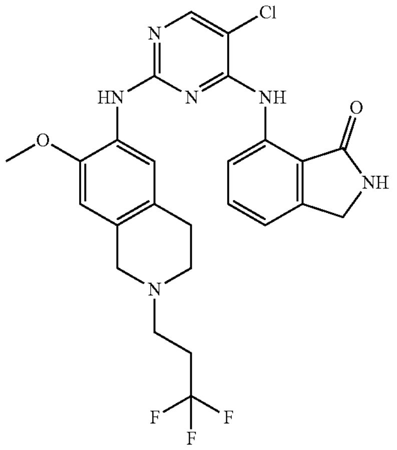 [SMILES: COc1cc2c(cc1Nc1ncc(Cl)c(Nc3cccc4c3C(=O)NC4)n1)CCN(CCC(F)(F)F)C2] | 7-((5-chloro-2-((7-methoxy-2-(3,3,3-trifluoropropyl)-1,2,3,4-tetrahydroisoquinolin-6-yl)amino)pyrimidin-4-yl)amino)isoindolin-1-one |
| I-20 | 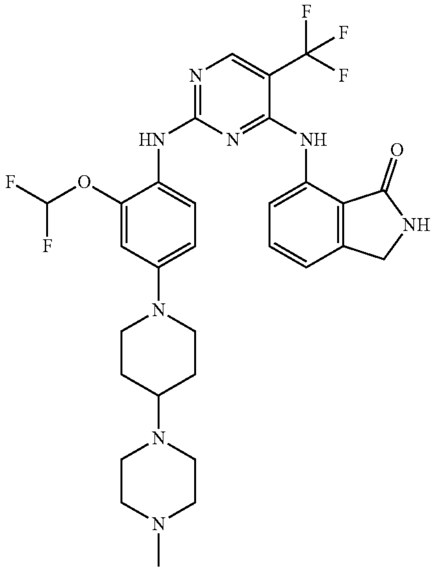 [SMILES: CN1CCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-methylpiperazin-1-yl)piperidin-1-yl)phenyl)amino)-5-(trifluoromethyl)pyrimidin-4-yl)amino)isoindolin-1-one |

-continued

| Compound I.D. | Structure | Compound Name |
| --- | --- | --- |
| I-21 | 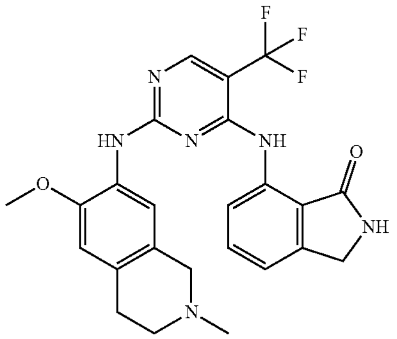 [SMILES: COc1cc2c(cc1Nc1ncc(C(F)(F)F)c(Nc3cccc4c3C(=O)NC4)n1)CN(C)CC2] | 7-((2-((6-methoxy-2-methyl-1,2,3,4-tetrahydroisoquinolin-7-yl)amino)-5-(trifluoromethyl)pyrimidin-4-yl)amino)isoindolin-1-one |
| I-22 | 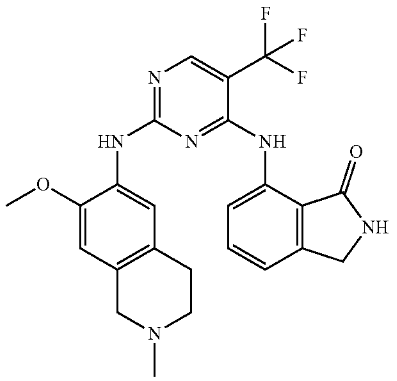 [SMILES: COc1cc2c(cc1Nc1ncc(C(F)(F)F)c(Nc3cccc4c3C(=O)NC4)n1)CCN(C)C2] | 7-((2-((7-methoxy-2-methyl-1,2,3,4-tetrahydroisoquinolin-6-yl)amino)-5-(trifluoromethyl)pyrimidin-4-yl)amino)isoindolin-1-one |
| I-23 | 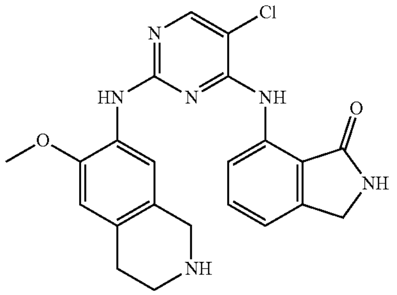 | 7-((5-chloro-2-((6-methoxy-1,2,3,4-tetrahydroisoquinolin-7-yl)amino)pyrimidin-4-yl)amino)isoindolin-1-one |
| I-24 | 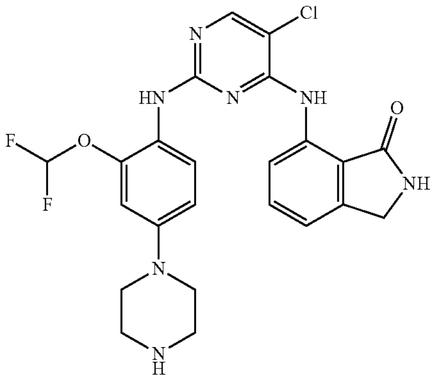 [SMILES: O=C1NCc2cccc(Nc3nc(Nc4ccc(N5CCNCC5)cc4OC(F)F)ncc3Cl)c21] | 7-((5-chloro-2-((2-(difluoromethoxy)-4-(piperazin-1-yl)phenyl)amino)pyrimidin-4-yl)amino)isoindolin-1-one |

-continued

| Compound I.D. | Structure | Compound Name |
|---|---|---|
| I-25 | 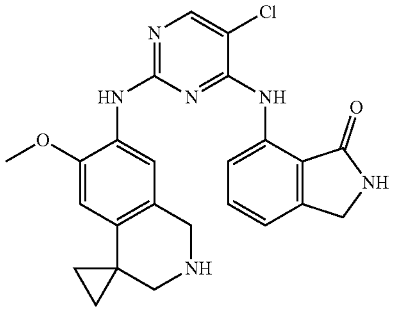 [SMILES: COc1cc2c(cc1Nc1ncc(Cl)c(Nc3cccc4c3C(=O)NC4)n1)CNCC21CC1] | 7-((5-chloro-2-((6'-methoxy-2',3'-dihydro-1'H-spiro[cyclopropane-1,4'-isoquinolin]-7'-yl)amino)pyrimidin-4-yl)amino)isoindolin-1-one |
| I-26 | 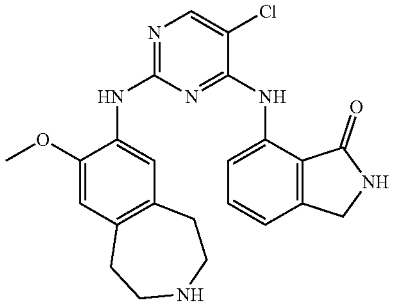 [SMILES: COc1cc2c(cc1Nc1ncc(Cl)c(Nc3cccc4c3C(=O)NC4)n1)CCNCC2] | 7-((5-chloro-2-((8-methoxy-2,3,4,5-tetrahydro-1H-benzo[d]azepin-7-yl)amino)pyrimidin-4-yl)amino)isoindolin-1-one |
| I-27 | 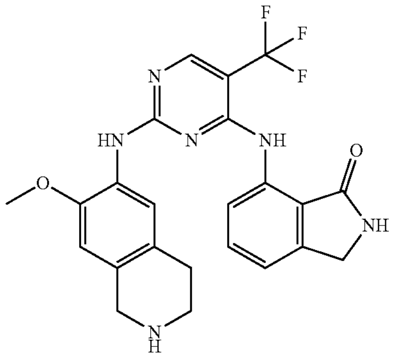 [SMILES: COc1cc2c(cc1Nc1ncc(C(F)(F)F)c(Nc3cccc4c3C(=O)NC4)n1)CCNC2] | 7-((5-chloro-2-((8-methoxy-2,3,4,5-tetrahydro-1H-benzo[d]azepin-7-yl)amino)pyrimidin-4-yl)amino)isoindolin-1-one |
| I-28 | 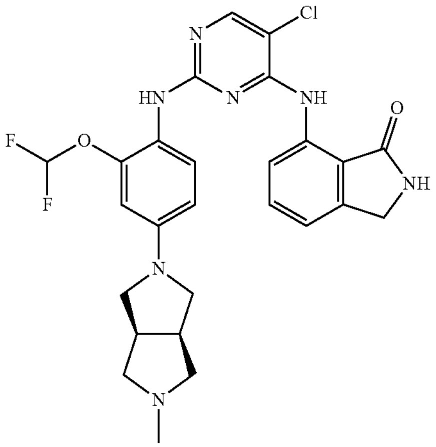 [SMILES: CN1C[C@@H]2CN(c3ccc(Nc4ncc(Cl)c(Nc5cccc6c5C(=O)NC6)n4)c(OC(F)F)c3)C[C@@H]2C1] | 7-((5-chloro-2-((2-(difluoromethoxy)-4-((3aR,6aS)-5-methylhexahydropyrrolo[3,4-c]pyrrol-2(1H)-yl)phenyl)amino)pyrimidin-4-yl)amino)isoindolin-1-one |

-continued

| Compound I.D. | Structure | Compound Name |
|---|---|---|
| I-29 | 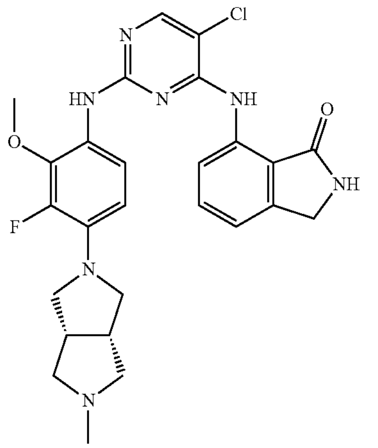 [SMILES: COc1c(Nc2ncc(Cl)c(Nc3cccc4c3C(=O)NC4)n2)ccc(N2C[C@H]3CN(C)C[C@H]3C2)c1F] | 7-((5-chloro-2-((3-fluoro-2-methoxy-4-((3aR,6aS)-5-methylhexahydropyrrolo[3,4-c]pyrrol-2(1H)-yl)phenyl)amino)pyrimidin-4-yl)amino)isoindolin-1-one |
| I-30 | 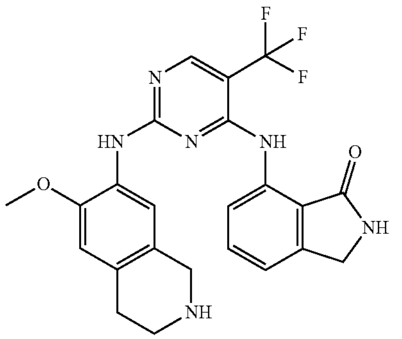 [SMILES: COc1cc2c(cc1Nc1ncc(C(F)(F)F)c(Nc3cccc4c3C(=O)NC4)n1)CNCC2] | 7-((2-((6-methoxy-1,2,3,4-tetrahydroisoquinolin-7-yl)amino)-5-(trifluoromethyl)pyrimidin-4-yl)amino)isoindolin-1-one |
| I-31 | 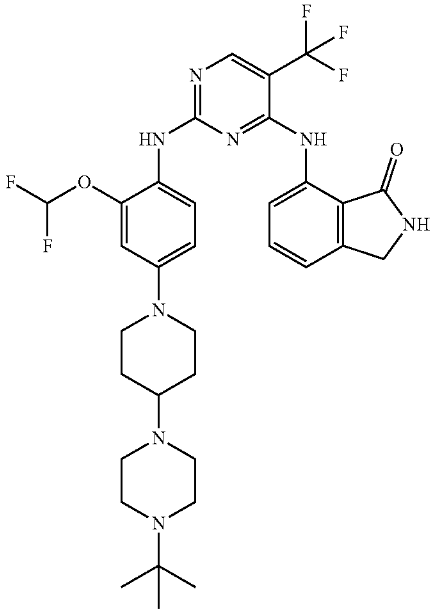 [SMILES: CC(C)(C)N1CCN(C2CCN(c3ccc(Nc4ncc(C(F)(F)F)c(Nc5cccc6c5C(=O)NC6)n4)c(OC(F)F)c3)CC2)CC1] | 7-((2-((4-(4-(4-(tert-butyl)piperazin-1-yl)piperidin-1-yl)-2-(difluoromethoxy)phenyl)amino)-5-(trifluoromethyl)pyrimidin-4-yl)amino)isoindolin-1-one |

-continued

| Compound I.D. | Structure | Compound Name |
| --- | --- | --- |
| I-32 | 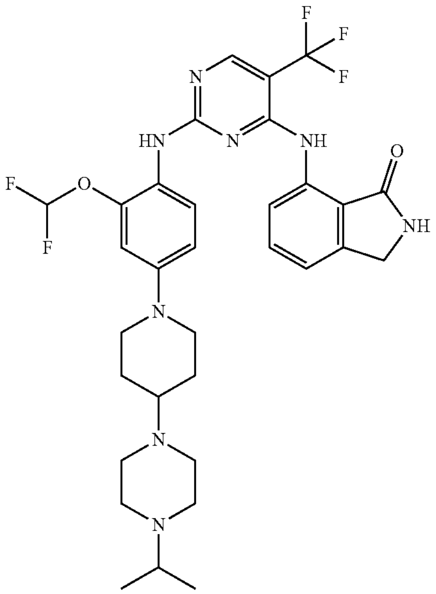 [SMILES: CC(C)N1CCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-isopropylpiperazin-1-yl)piperidin-1-yl)phenyl)amino)-5-(trifluoromethyl)pyrimidin-4-yl)amino)isoindolin-1-one |
| I-33 | 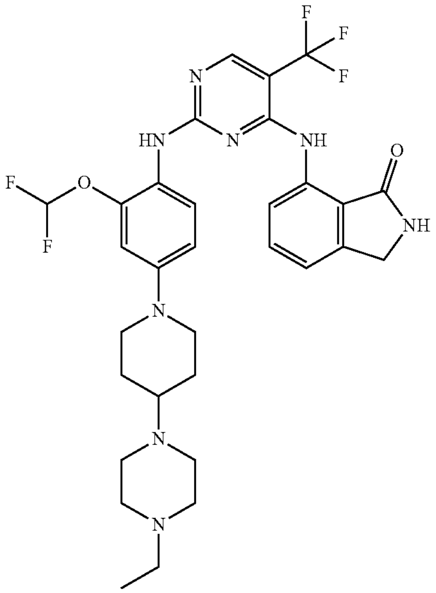 [SMILES: CCN1CCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-ethylpiperazin-1-yl)piperidin-1-yl)phenyl)amino)-5-(trifluoromethyl)pyrimidin-4-yl)amino)isoindolin-1-one |
| I-34 | 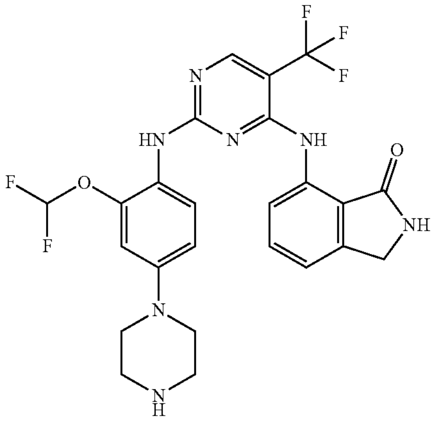 [SMILES: O=C1NCc2cccc(Nc3nc(Nc4ccc(N5CCNCC5)cc4OC(F)F)ncc3C(F)(F)F)c21] | 7-((2-((2-(difluoromethoxy)-4-(piperazin-1-yl)phenyl)amino)-5-(trifluoromethyl)pyrimidin-4-yl)amino)isoindolin-1-one |

-continued

| Compound I.D. | Structure | Compound Name |
|---|---|---|
| I-35 | 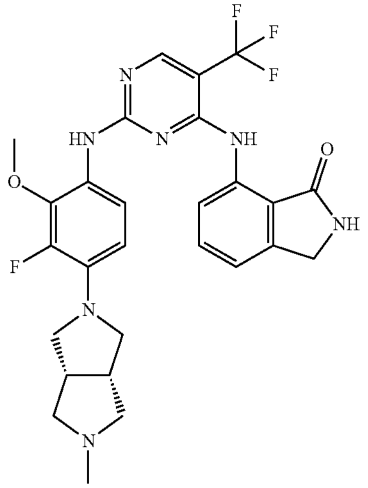 [SMILES: COc1c(Nc2ncc(C(F)(F)F)c(Nc3cccc4c3C(=O)NC4)n2)ccc(N2C[C@H]3CN(C)C[C@H]3C2)c1F] | 7-((2-((3-fluoro-2-methoxy-4-((3aR,6aS)-5-methylhexahydropyrrolo[3,4-c]pyrrol-2(1H)-yl)phenyl)amino)-5-(trifluoromethyl)pyrimidin-4-yl)amino)isoindolin-1-one |
| I-36 | 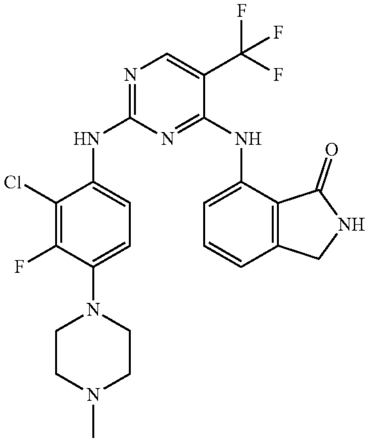 [SMILES: CN1CCN(c2ccc(Nc3ncc(C(F)(F)F)c(Nc4cccc5c4C(=O)NC5)n3)c(Cl)c2F)CC1] | 7-((2-((2-chloro-3-fluoro-4-(4-methylpiperazin-1-yl)phenyl)amino)-5-(trifluoromethyl)pyrimidin-4-yl)amino)isoindolin-1-one |
| I-37 | 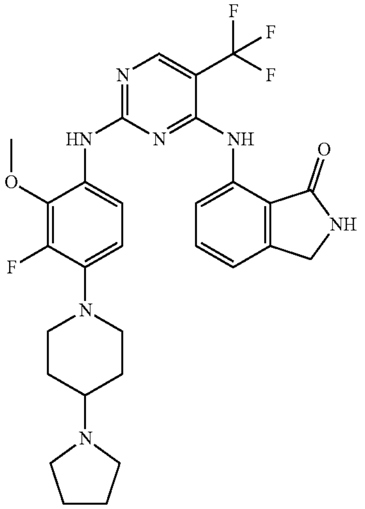 [SMILES: COc1c(Nc2ncc(C(F)(F)F)c(Nc3cccc4c3C(=O)NC4)n2)ccc(N2CCC(N3CCCC3)CC2)c1F] | 7-((2-((3-fluoro-2-methoxy-4-(4-(pyrrolidin-1-yl)piperidin-1-yl)phenyl)amino)-5-(trifluoromethyl)pyrimidin-4-yl)amino)isoindolin-1-one |

-continued

| Compound I.D. | Structure | Compound Name |
| --- | --- | --- |
| I-38 | 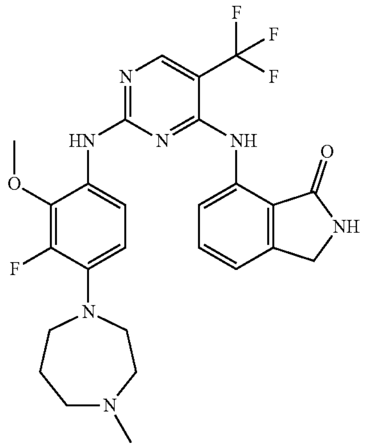 [SMILES: COc1c(Nc2ncc(C(F)(F)F)c(Nc3cccc4c3C(=O)NC4)n2)ccc(N2CCCN(C)CC2)c1F] | 7-((2-((3-fluoro-2-methoxy-4-(4-methyl-1,4-diazepan-1-yl)phenyl)amino)-5-(trifluoromethyl)pyrimidin-4-yl)amino)isoindolin-1-one |
| I-39 | 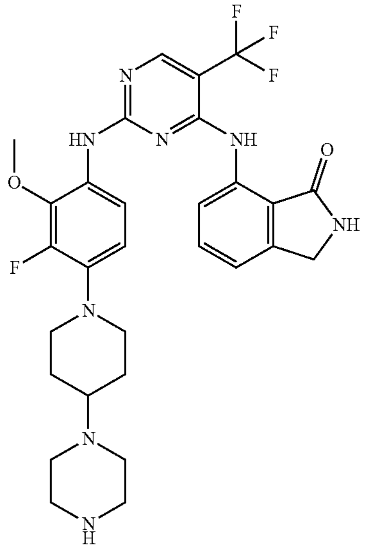 [SMILES: COc1c(Nc2ncc(C(F)(F)F)c(Nc3cccc4c3C(=O)NC4)n2)ccc(N2CCC(N3CCNCC3)CC2)c1F] | 7-((2-((3-fluoro-2-methoxy-4-(4-(piperazin-1-yl)piperidin-1-yl)phenyl)amino)-5-(trifluoromethyl)pyrimidin-4-yl)amino)isoindolin-1-one |
| I-40 | 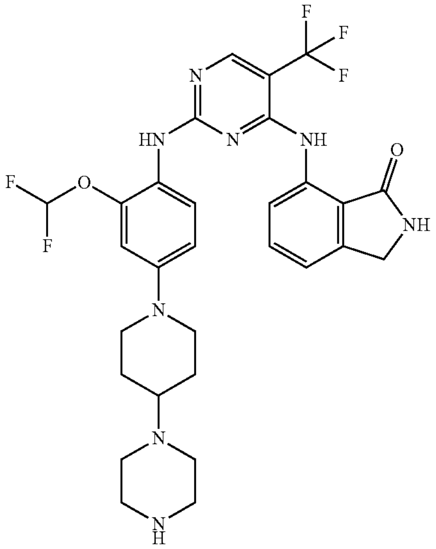 [SMILES: O=C1NCc2cccc(Nc3nc(Nc4ccc(N5CCC(N6CCNCC6)CC5)cc4OC(F)F)ncc3C(F)(F)F)c21] | 7-((2-((2-(difluoromethoxy)-4-(4-(piperazin-1-yl)piperidin-1-yl)phenyl)amino)-5-(trifluoromethyl)pyrimidin-4-yl)amino)isoindolin-1-one |

-continued

| Compound I.D. | Structure | Compound Name |
| --- | --- | --- |
| I-41 | 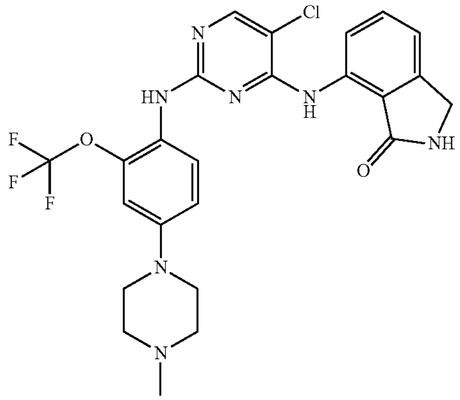 [SMILES: CN1CCN(c2ccc(Nc3ncc(Cl)c(Nc4cccc5c4C(=O)NC5)n3)c(OC(F)(F)F)c2)CC1] | 7-((5-chloro-2-((4-(4-methylpiperazin-1-yl)-2-(trifluoromethoxy)phenyl)amino) pyrimidin-4-yl)amino)isoindolin-1-one |
| I-42 | 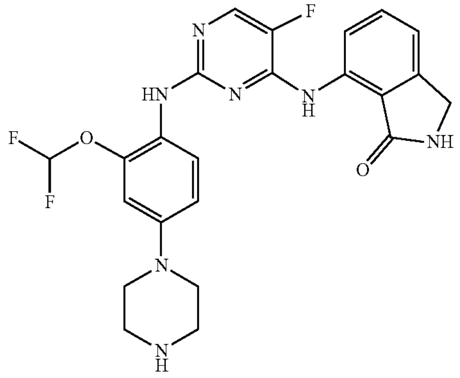 | 7-((2-((2-(difluoromethoxy)-4-(piperazin-1-yl)phenyl)amino)-5-fluoropyrimidin-4-yl) amino)isoindolin-1-one |
| I-43 | 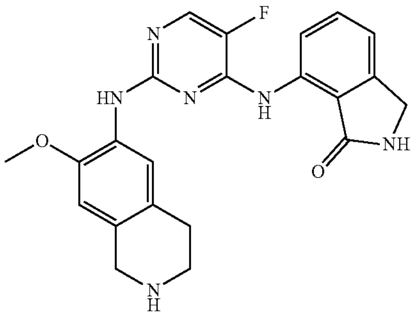 [SMILES: COc1cc2c(cc1Nc1ncc(F)c(Nc3cccc4c3C(=O)NC4)n1)CCNC2] | 7-((5-fluoro-2-((7-methoxy-1,2,3,4-tetrahydroisoquinolin-6-yl)amino)pyrimidin-4-yl)amino)isoindolin-1-one |
| I-44 | 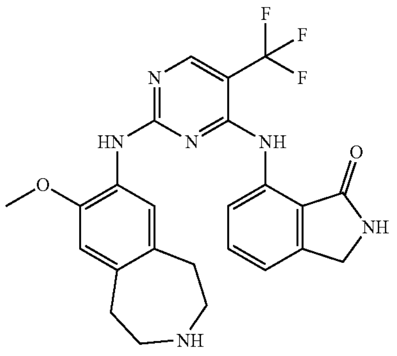 [SMILES: COc1cc2c(cc1Nc1ncc(C(F)(F)F)c(Nc3cccc4c3C(=O)NC4)n1)CCNCC2] | 7-((2-((8-methoxy-2,3,4,5-tetrahydro-1H-benzo[d]azepin-7-yl)amino)-5-(trifluoromethyl)pyrimidin-4-yl)amino)isoindolin-1-one |

-continued

| Compound I.D. | Structure | Compound Name |
| --- | --- | --- |
| I-45 | 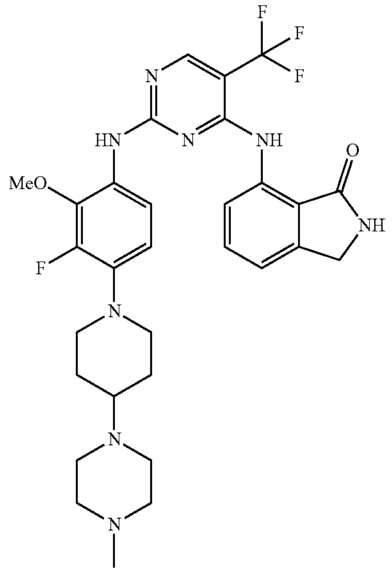 [SMILES: COc1c(Nc2ncc(C(F)(F)F)c(Nc3cccc4c3C(=O)NC4)n2)ccc(N2CCC(N3CCN(C)CC3)CC2)c1F] | 7-((2-((3-fluoro-2-methoxy-4-(4-(4-methylpiperazin-1-yl)piperidin-1-yl)phenyl)amino)-5-(trifluoromethyl)pyrimidin-4-yl)amino)isoindolin-1-one |
| I-46 | 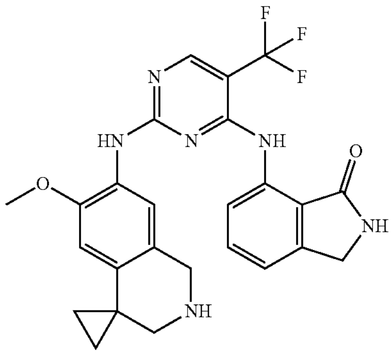 [SMILES: COc1cc2c(cc1Nc1ncc(C(F)(F)F)c(Nc3cccc4c3C(=O)NC4)n1)CNCC21CC1] | 7-((2-((6'-methoxy-2',3'-dihydro-1'H-spiro[cyclopropane-1,4'-isoquinolin]-7'-yl)amino)-5-(trifluoromethyl)pyrimidin-4-yl)amino)isoindolin-1-one |
| I-47 | 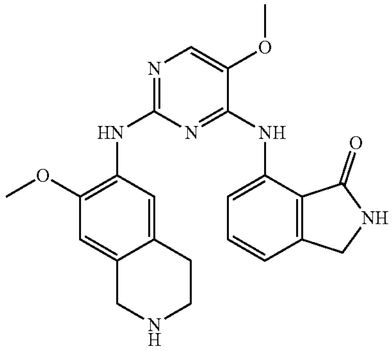 [SMILES: COc1cc2c(cc1Nc1ncc(OC)c(Nc3cccc4c3C(=O)NC4)n1)CCNC2] | 7-((5-methoxy-2-((7-methoxy-1,2,3,4-tetrahydroisoquinolin-6-yl)amino)pyrimidin-4-yl)amino)isoindolin-1-one |

-continued

| Compound I.D. | Structure | Compound Name |
|---|---|---|
| I-48 | 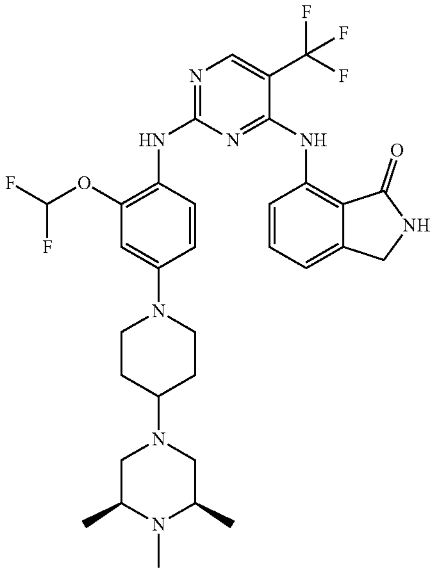 [SMILES: C[C@@H]1CN(C2CCN(c3ccc(Nc4ncc(C(F)(F)F)c(Nc5cccc6c5C(=O)NC6)n4)c(OC(F)F)c3)CC2)C[C@H](C)N1C] | 7-((2-((2-(difluoromethoxy)-4-(4-((3S,5R)-3,4,5-trimethylpiperazin-1-yl)piperidin-1-yl)phenyl)amino)-5-(trifluoromethyl)pyrimidin-4-yl)amino)isoindolin-1-one |
| I-49 | 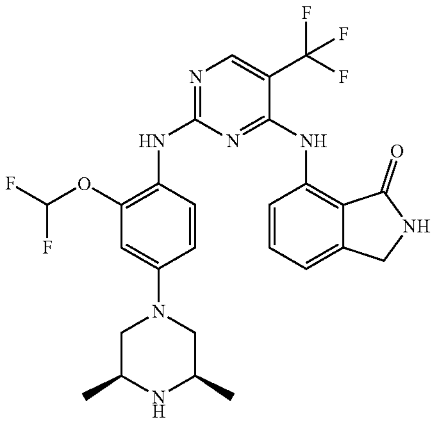 [SMILES: C[C@@H]1CN(c2ccc(Nc3ncc(C(F)(F)F)c(Nc4cccc5c4C(=O)NC5)n3)c(OC(F)F)c2)C[C@H](C)N1] | 7-((2-((2-(difluoromethoxy)-4-((3S,5R)-3,5-dimethylpiperazin-1-yl)phenyl)amino)-5-(trifluoromethyl)pyrimidin-4-yl)amino)isoindolin-1-one |
| I-50 | 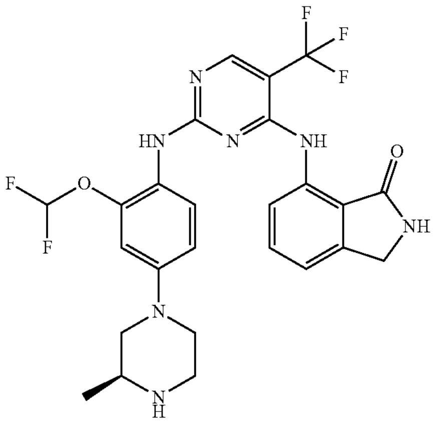 [SMILES: C[C@H]1CN(c2ccc(Nc3ncc(C(F)(F)F)c(Nc4cccc5c4C(=O)NC5)n3)c(OC(F)F)c2)CCN1] | (S)-7-((2-((2-(difluoromethoxy)-4-(3-methylpiperazin-1-yl)phenyl)amino)-5-(trifluoromethyl)pyrimidin-4-yl)amino)isoindolin-1-one |

-continued
| Compound I.D. | Structure | Compound Name |
| --- | --- | --- |
| I-51 | 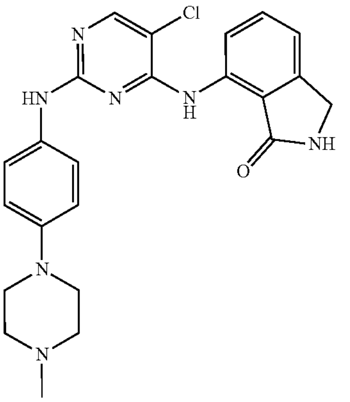 [SMILES: CN1CCN(c2ccc(Nc3ncc(Cl)c(Nc4cccc5c4C(=O)NC5)n3)cc2)CC1] | 7-((5-chloro-2-((4-(4-methylpiperazin-1-yl)phenyl)amino)pyrimidin-4-yl)amino)isoindolin-1-one |
| I-52 | 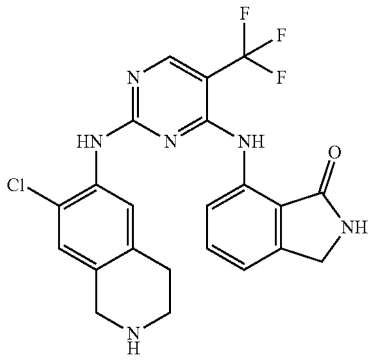 [SMILES: O=C1NCc2cccc(Nc3nc(Nc4cc5c(cc4Cl)CNCC5)ncc3C(F)(F)F)c21] | 7-((2-((7-chloro-1,2,3,4-tetrahydroisoquinolin-6-yl)amino)-5-(trifluoromethyl)pyrimidin-4-yl)amino)isoindolin-1-one |
| I-53 | 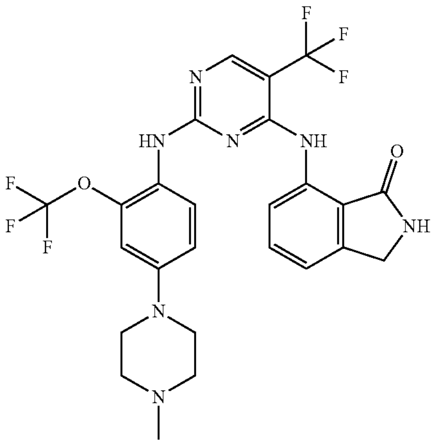 [SMILES: CN1CCN(c2ccc(Nc3ncc(C(F)(F)F)c(Nc4cccc5c4C(=O)NC5)n3)c(OC(F)(F)F)c2)CC1] | 7-((2-((4-(4-methylpiperazin-1-yl)-2-(trifluoromethoxy)phenyl)amino)-5-(trifluoromethyl)pyrimidin-4-yl)amino)isoindolin-1-one |

-continued

| Compound I.D. | Structure | Compound Name |
| --- | --- | --- |
| I-54 | 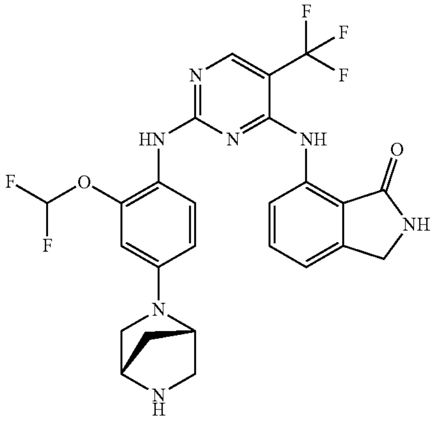 [SMILES: O=C1NCc2cccc(Nc3nc(Nc4ccc(N5C[C@@H]6C[C@H]5CN6)cc4OC(F)F)ncc3C(F)(F)F)c21] | 7-((2-((4-((1S,4S)-2,5-diazabicyclo[2.2.1]heptan-2-yl)-2-(difluoromethoxy)phenyl)amino)-5-(trifluoromethyl)pyrimidin-4-yl)amino)isoindolin-1-one |
| I-55 | 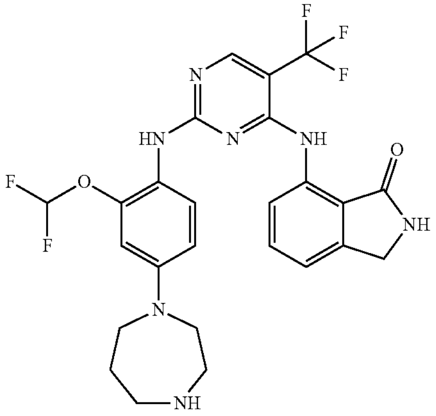 [SMILES: O=C1NCc2cccc(Nc3nc(Nc4ccc(N5CCCNCC5)cc4OC(F)F)ncc3C(F)(F)F)c21] | 7-((2-((4-(1,4-diazepan-1-yl)-2-(difluoromethoxy)phenyl)amino)-5-(trifluoromethyl)pyrimidin-4-yl)amino)isoindolin-1-one |
| I-56 | 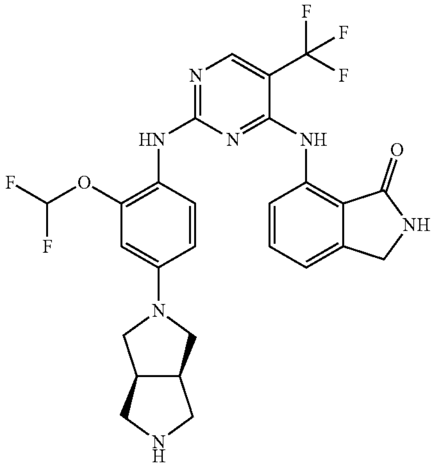 [SMILES: O=C1NCc2cccc(Nc3nc(Nc4ccc(N5C[C@H]6CNC[C@H]6C5)cc4OC(F)F)ncc3C(F)(F)F)c21] | 7-((2-((2-(difluoromethoxy)-4-((3aR,6aS)-hexahydropyrrolo[3,4-c]pyrrol-2(1H)-yl)phenyl)amino)-5-(trifluoromethyl)pyrimidin-4-yl)amino)isoindolin-1-one |

-continued

| Compound I.D. | Structure | Compound Name |
| --- | --- | --- |
| I-57 | 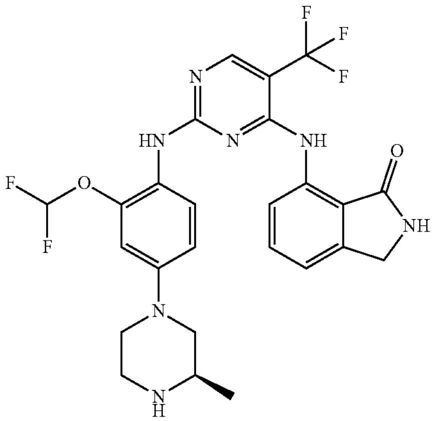 [SMILES: C[C@@H]1CN(c2ccc(Nc3ncc(C(F)(F)F)c(Nc4cccc5c4C(=O)NC5)n3)c(OC(F)F)c2)CCN1] | (R)-7-((2-((2-(difluoromethoxy)-4-(3-methylpiperazin-1-yl)phenyl)amino)-5-(trifluoromethyl)pyrimidin-4-yl)amino)isoindolin-1-one |
| I-58 | 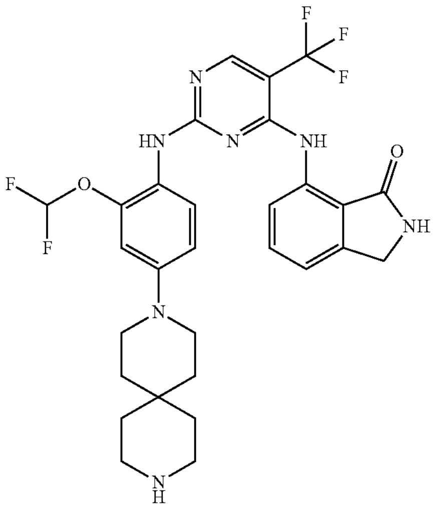 [SMILES: O=C1NCc2cccc(Nc3nc(Nc4ccc(N5CCC6(CCNCC6)CC5)cc4OC(F)F)ncc3C(F)(F)F)c21] | 7-((2-((2-(difluoromethoxy)-4-(3,9-diazaspiro[5.5]undecan-3-yl)phenyl)amino)-5-(trifluoromethyl)pyrimidin-4-yl)amino)isoindolin-1-one |
| I-59 | 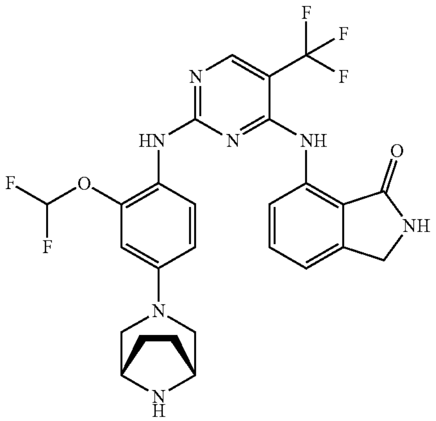 | 7-((2-((4-((1R,5S)-3,8-diazabicyclo[3.2.1]octan-3-yl)-2-(difluoromethoxy)phenyl)amino)-5-(trifluoromethyl)pyrimidin-4-yl)amino)isoindolin-1-one |

-continued
| Compound I.D. | Structure | Compound Name |
|---|---|---|
| I-60 | 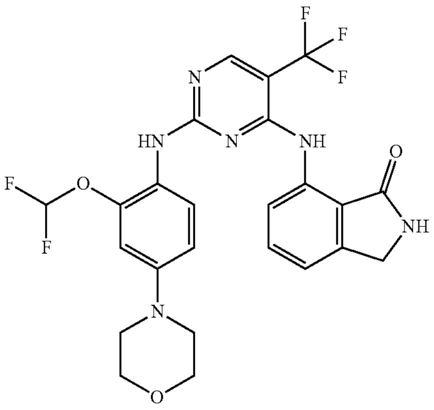 | 7-((2-((2-(difluoromethoxy)-4-morpholinophenyl)amino)-5-(trifluoromethyl)pyrimidin-4-yl)amino)isoindolin-1-one |
| I-61 | 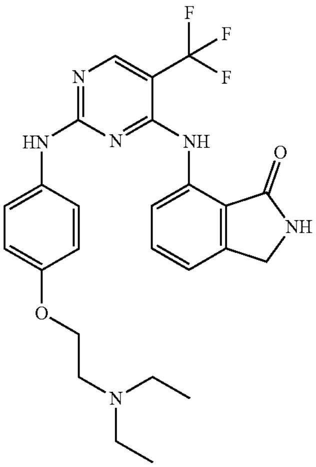 [SMILES: CCN(CC)CCOc1ccc(Nc2ncc(C(F)(F)F)c(Nc3cccc4c3C(=O)NC4)n2)cc1] | 7-((2-((4-(2-(diethylamino)ethoxy)phenyl)amino)-5-(trifluoromethyl)pyrimidin-4-yl)amino)isoindolin-1-one |
| I-62 | 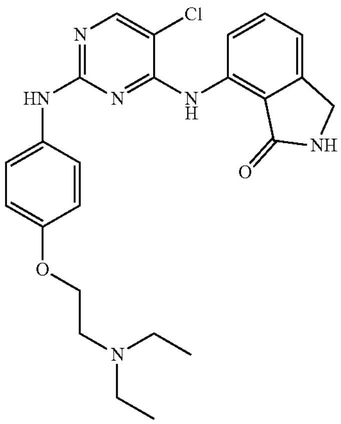 [SMILES: CCN(CC)CCOc1ccc(Nc2ncc(Cl)c(Nc3cccc4c3C(=O)NC4)n2)cc1] | 7-((5-chloro-2-((4-(2-(diethylamino)ethoxy)phenyl)amino)pyrimidin-4-yl)amino)isoindolin-1-one |

-continued

| Compound I.D. | Structure | Compound Name |
| --- | --- | --- |
| I-64 | 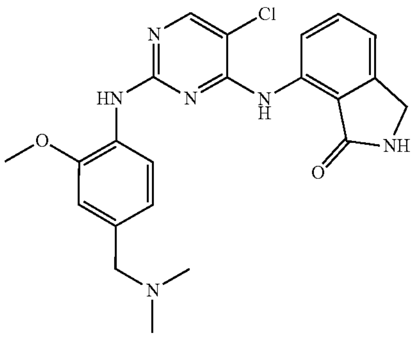 [SMILES: COc1cc(CN(C)C)ccc1Nc1ncc(Cl)c(Nc2cccc3c2C(=O)NC3)n1] | 7-((5-chloro-2-((4-((dimethylamino)methyl)-2-methoxyphenyl)amino)pyrimidin-4-yl)amino)isoindolin-1-one |
| I-64 | 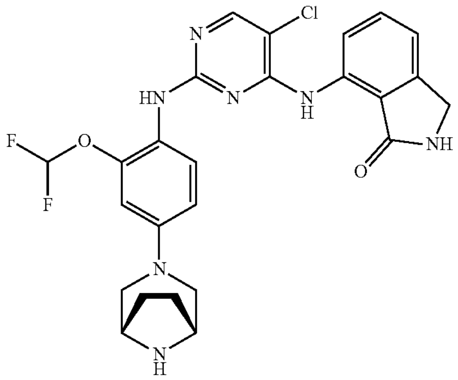 | 7-((2-((4-((1R,5S)-3,8-diazabicyclo[3.2.1]octan-3-yl)-2-(difluoromethoxy)phenyl)amino)-5-chloropyrimidin-4-yl)amino)isoindolin-1-one |
| I-65 | 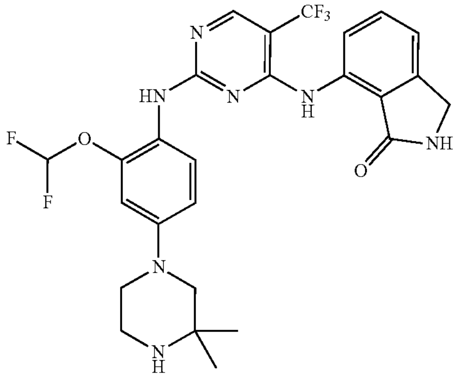 [SMILES: CC1(C)CN(c2ccc(Nc3ncc(C(F)(F)F)c(Nc4cccc5c4C(=O)NC5)n3)c(OC(F)F)c2)CCN1] | 7-((2-((2-(difluoromethoxy)-4-(3,3-dimethylpiperazin-1-yl)phenyl)amino)-5-(trifluoromethyl)pyrimidin-4-yl)amino)isoindolin-1-one |
| I-66 | 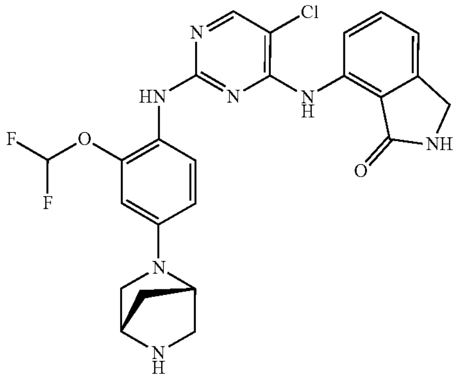 [SMILES: O=C1NCc2cccc(Nc3nc(Nc4ccc(N5C[C@@H]6C[C@H]5CN6)cc4OC(F)F)ncc3Cl)c21] | 7-((2-((4-((1S,4S)-2,5-diazabicyclo[2.2.1]heptan-2-yl)-2-(difluoromethoxy)phenyl)amino)-5-chloropyrimidin-4-yl) amino)isoindolin-1-one |

-continued

| Compound I.D. | Structure | Compound Name |
|---|---|---|
| I-67 | 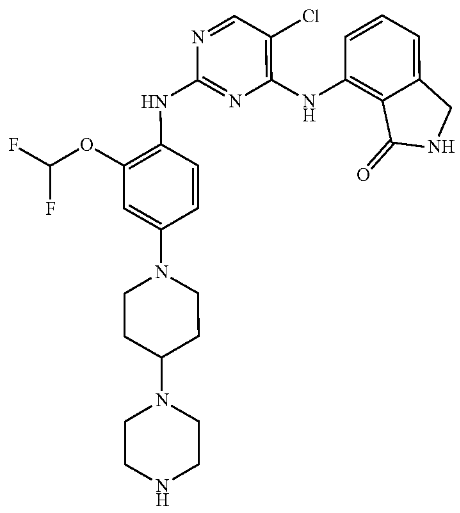 [SMILES: O=C1NCc2cccc(Nc3nc(Nc4ccc(N5CCC(N6CCNCC6)CC5)cc4OC(F)F)ncc3Cl)c21] | 7-((5-chloro-2-((2-(difluoromethoxy)-4-(4-(piperazin-1-yl)piperidin-1-yl)phenyl)amino)pyrimidin-4-yl)amino)isoindolin-1-one |
| I-68 | 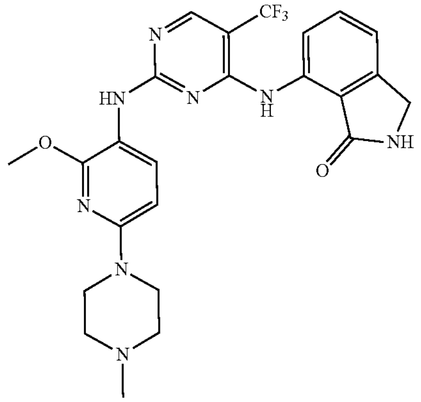 [SMILES: COc1nc(N2CCN(C)CC2)ccc1Nc1ncc(C(F)(F)F)c(Nc2cccc3c2C(=O)NC3)n1] | 7-((2-((2-methoxy-6-(4-methylpiperazin-1-yl)pyridin-3-yl)amino)-5-(trifluoromethyl)pyrimidin-4-yl)amino)isoindolin-1-one |
| I-69 | 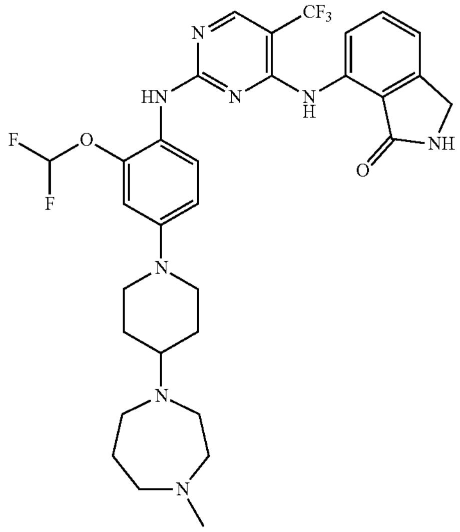 [SMILES: CN1CCCN(C2CCN(c3ccc(Nc4ncc(C(F)(F)F)c(Nc5cccc6c5C(=O)NC6)n4)c(OC(F)F)c3)CC2)CC1] | 7-((2-((2-(difluoromethoxy)-4-(4-(4-methyl-1,4-diazepan-1-yl)piperidin-1-yl)phenyl)amino)-5-(trifluoromethyl)pyrimidin-4-yl)amino)isoindolin-1-one |

-continued

| Compound I.D. | Structure | Compound Name |
|---|---|---|
| I-70 | 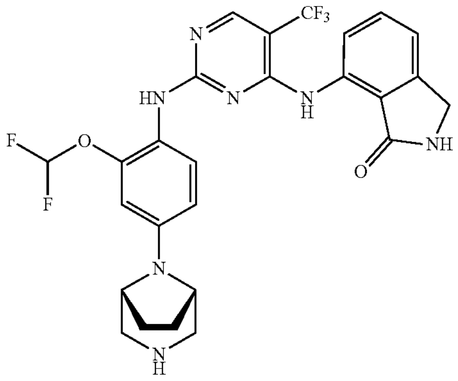 | 7-((2-((4-((1R,5S)-3,8-diazabicyclo[3.2.1]octan-8-yl)-2-(difluoromethoxy)phenyl)amino)-5-(trifluoromethyl)pyrimidin-4-yl)amino)isoindolin-1-one |
| I-71 | 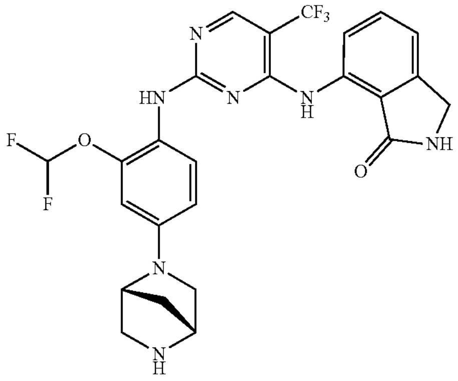 | 7-((2-((4-((1R,4R)-2,5-diazabicyclo[2.2.1]heptan-2-yl)-2-(difluoromethoxy)phenyl)amino)-5-(trifluoromethyl)pyrimidin-4-yl)amino)isoindolin-1-one |
| I-72 | 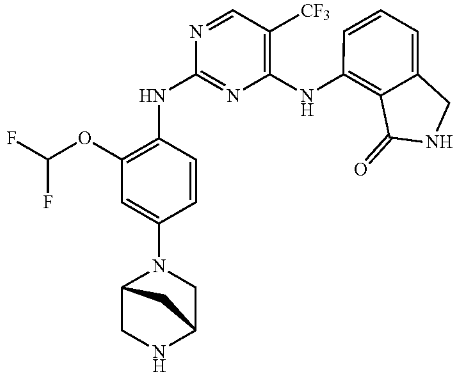 | 7-((2-((4-((1R,4R)-2,5-diazabicyclo[2.2.1]heptan-2-yl)-2-(difluoromethoxy)phenyl)amino)-5-(chloropyrimidin-4-yl)amino)isoindolin-1-one |
| I-73 | 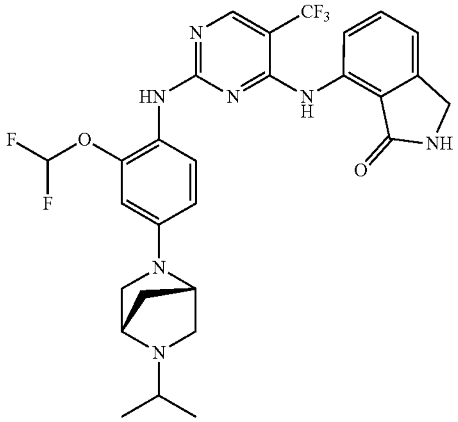 | 7-((2-((2-(difluoromethoxy)-4-((1S,4S)-5-isopropyl-2,5-diazabicyclo[2.2.1]heptan-2-yl)phenyl)amino)-5-(trifluoromethyl)pyrimidin-4-yl)amino)isoindolin-1-one |

-continued
| Compound I.D. | Structure | Compound Name |
|---|---|---|
| I-74 | 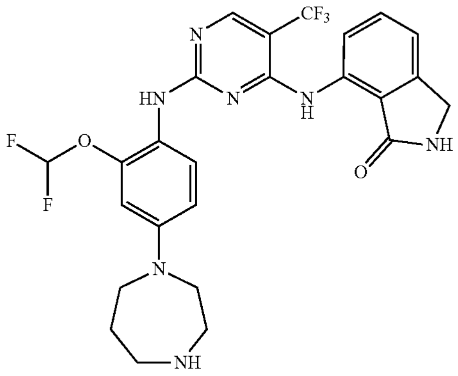 | 7-((2-((4-(1,4-diazepan-1-yl)-2-(difluoromethoxy)phenyl)amino)-5-chloropyrimidin-4-yl)amino)isoindolin-1-one |
| I-75 | 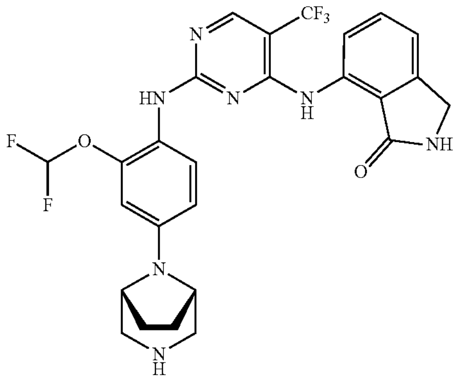 | 7-((2-((4-((1R,5S)-3,8-diazabicyclo[3.2.1]octan-8-yl)-2-(difluoromethoxy)phenyl)amino)-5-chloropyrimidin-4-yl)amino)isoindolin-1-one |
| I-76 | 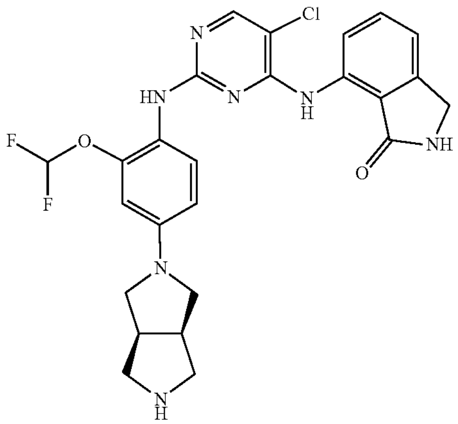 [SMILES: O=C1NCc2cccc(Nc3nc(Nc4ccc(N5C[C@H]6CNC[C@H]6C5)cc4OC(F)F)ncc3Cl)c21] | 7-((5-chloro-2-((2-(difluoromethoxy)-4-((3aR,6aS)-hexahydropyrrolo[3,4-c]pyrrol-2(1H)-yl)phenyl)amino)pyrimidin-4-yl)amino)isoindolin-1-one |

-continued
| Compound I.D. | Structure | Compound Name |
|---|---|---|
| I-77 | 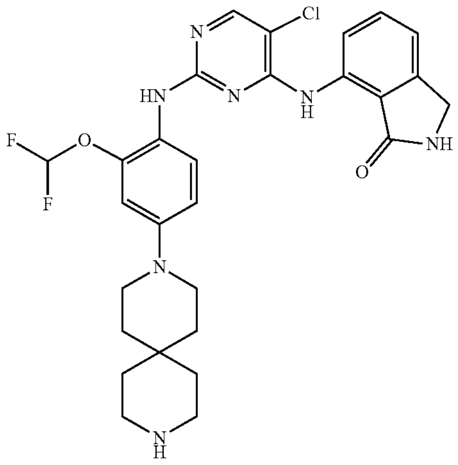 [SMILES: O=C1NCc2cccc(Nc3nc(Nc4ccc(N5CCC6(CCNCC6)CC5)cc4OC(F)F)ncc3Cl)c21] | 7-((5-chloro-2-((2-(difluoromethoxy)-4-(3,9-diazaspiro[5.5]undecan-3-yl)phenyl)amino)pyrimidin-4-yl)amino)isoindolin-1-one |
| I-78 | 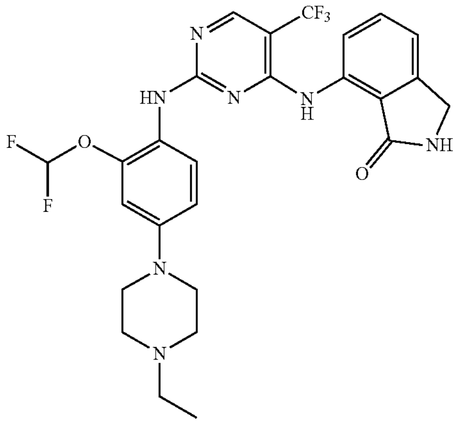 [SMILES: CCN1CCN(c2ccc(Nc3ncc(C(F)(F)F)c(Nc4cccc5c4C(=O)NC5)n3)c(OC(F)F)c2)CC1] | 7-((2-((2-(difluoromethoxy)-4-(4-ethylpiperazin-1-yl)phenyl)amino)-5-(trifluoromethyl)pyrimidin-4-yl)amino)isoindolin-1-one |
| I-79 | 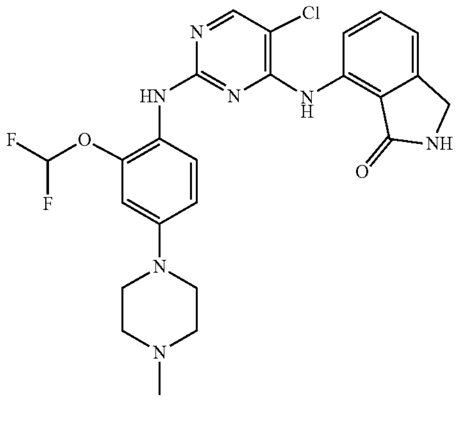 | 7-((2-((2-(difluoromethoxy)-4-(4-methylpiperazin-1-yl)phenyl)amino)-5-(trifluoromethyl)pyrimidin-4-yl)amino)isoindolin-1-one |

-continued

| Compound I.D. | Structure | Compound Name |
| --- | --- | --- |
| I-80 | 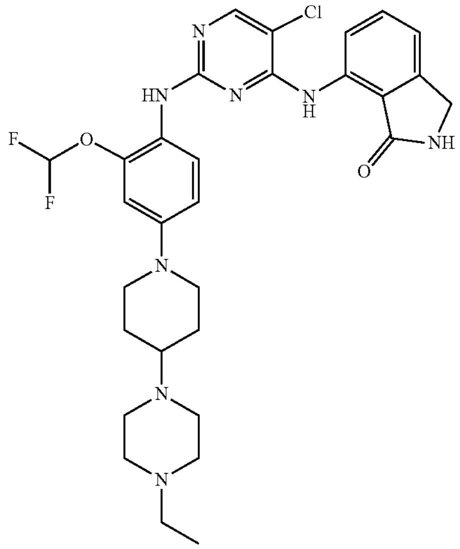 | 7-((5-chloro-2-((2-(difluoromethoxy)-4-(4-(4-ethylpiperazin-1-yl)piperidin-1-yl)phenyl)amino)pyrimidin-4-yl)amino)isoindolin-1-one |
| I-81 | 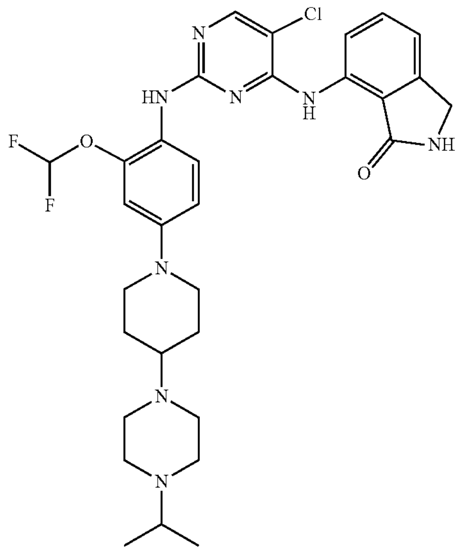 | 7-((5-chloro-2-((2-(difluoromethoxy)-4-(4-(4-isopropylpiperazin-1-yl)piperidin-1-yl)phenyl)amino)pyrimidin-4-yl)amino)isoindolin-1-one |
| I-82 | 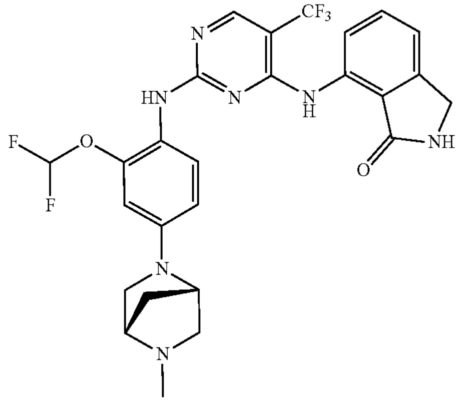 [SMILES: CN1C[C@@H]2C[C@H]1CN2c1ccc(Nc2ncc(C(F)(F)F)c(Nc3cccc4c3C(=O)NC4)n2)c(OC(F)F)c1] | 7-((2-((2-(difluoromethoxy)-4-((1S,4S)-5-methyl-2,5-diazabicyclo[2.2.1]heptan-2-yl)phenyl)amino)-5-(trifluoromethyl)pyrimidin-4-yl)amino)isoindolin-1-one |

-continued

| Compound I.D. | Structure | Compound Name |
|---|---|---|
| I-83 | 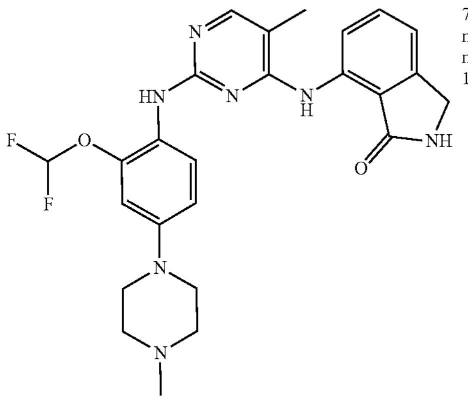 | 7-((2-((2-(difluoromethoxy)-4-(4-methylpiperazin-1-yl)phenyl)amino)-5-methylpyrimidin-4-yl)amino)isoindolin-1-one |
| I-84 | 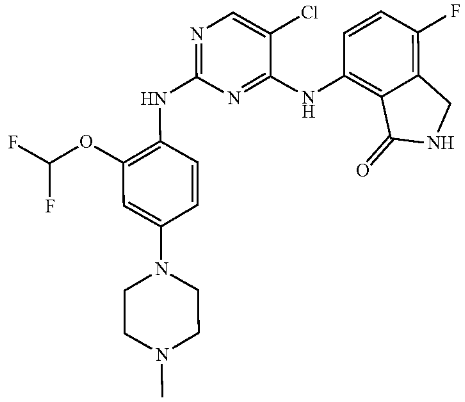 [SMILES: CN1CCN(c2ccc(Nc3ncc(Cl)c(Nc4ccc(F)c5c4C(=O)NC5)n3)c(OC(F)F)c2)CC1] | 7-((5-chloro-2-((2-(difluoromethoxy)-4-(4-methylpiperazin-1-yl)phenyl)amino)pyrimidin-4-yl)amino)-4-fluoroisoindolin-1-one and |
| I-85 | 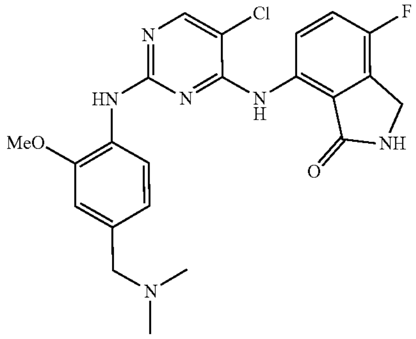 [SMILES: COc1cc(CN(C)C)ccc1Nc1ncc(Cl)c(Nc2ccc(F)c3c2C(=O)NC3)n1] | 7-((5-chloro-2-((4-((dimethylamino)methyl)-2-methoxyphenyl)amino)pyrimidin-4-yl)amino)-4-fluoroisoindolin-1-one |

or a pharmaceutically acceptable salt and/or solvate thereof.

15. A pharmaceutical composition comprising one or more compounds of claim 1 and a pharmaceutically acceptable carrier and/or diluent.

16. A method of treating a disease, disorder or condition that is treatable by inhibiting NUAK2 and/or NUAK1 comprising administering a therapeutically effective amount of one or more compounds of claim 1, to a subject in need thereof.

17. The method of claim 16, wherein the disease, disorder or condition that is treatable by inhibiting NUAK2 and/or NUAK1 is cancer and/or fibrosis.

18. The method of claim 17, wherein the cancer is selected from one or more of breast cancer, colon cancer, bladder cancer, skin cancer, head and neck cancer, liver cancer, lung cancer, pancreatic cancer, ovarian cancer, prostate cancer, bone cancer and glioblastoma, or wherein the fibrosis is one or more of liver fibrosis, lung fibrosis or kidney fibrosis.

19. A method of treating a disease, disorder or condition by inhibiting localization of YAP/TAZ to the nucleus of a cell comprising administering an effective amount of one of more compounds of claim 1, to a subject in need thereof.

20. A process for preparing a compound of claim 1 comprising:

(a) reacting a substituted dichloropyrimidine of Formula A, wherein $R^1$ is as defined in Formula I or a protected version thereof, with an 7-amino isoindolin-1-one of Formula B, wherein $R^2$ is as defined in Formula I or protected version thereof, under basic conditions to provide compounds of Formula D:

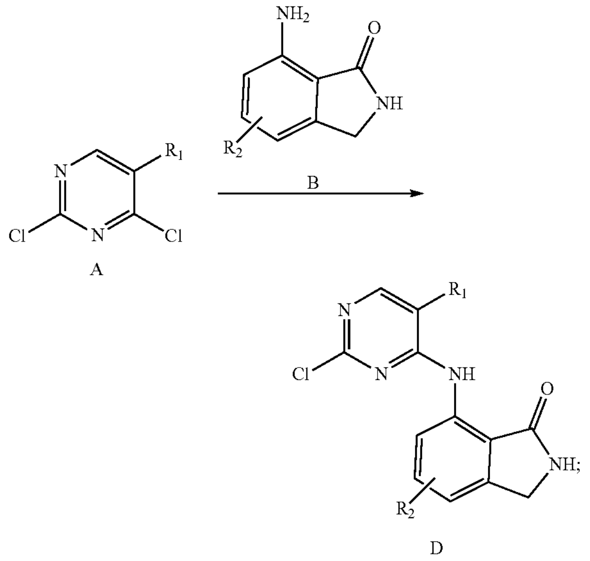
A
B
D
(b) reacting compounds of Formula D with anilines of Formula E, wherein $R^3$, $R^4$, X, Y and Z are as defined in Formula I or protected versions thereof, under acidic or basic conditions to provide, after removal of any protecting groups if needed, compounds of Formula I:
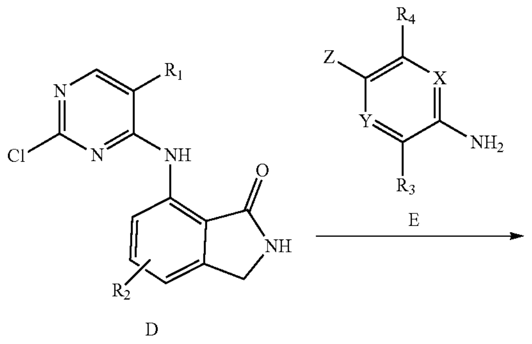
D
E
Formula I.
* * * * *